United States Patent
Coy et al.

(10) Patent No.: US 7,355,025 B2
(45) Date of Patent: Apr. 8, 2008

(54) MARKER MOLECULES ASSOCIATED WITH LUNG TUMORS

(75) Inventors: Johannes Coy, Dossenheim (DE); Rainer Hipfel, Balingen (DE); Birgit Wasser, Kornwestheim (DE)

(73) Assignee: MTM Laboratories, AG, Heidelberg (DE)

( * ) Notice: Subject to any disclaimer, the term of this patent is extended or adjusted under 35 U.S.C. 154(b) by 440 days.

(21) Appl. No.: 10/515,477

(22) PCT Filed: May 16, 2003

(86) PCT No.: PCT/EP03/50175

§ 371 (c)(1),
(2), (4) Date: Nov. 19, 2004

(87) PCT Pub. No.: WO03/097871

PCT Pub. Date: Nov. 27, 2003

(65) Prior Publication Data

US 2005/0176930 A1    Aug. 11, 2005

(30) Foreign Application Priority Data

May 21, 2002   (EP) .................................. 02010275

(51) Int. Cl.
*C07H 21/04*    (2006.01)
(52) U.S. Cl. ............. 536/23.5; 435/252.3; 435/254.11; 435/320.1; 435/325; 530/350
(58) Field of Classification Search ................ 536/23.1, 536/23.5; 530/350; 435/252.3, 254.11, 435/320.1, 325
See application file for complete search history.

(56) References Cited

U.S. PATENT DOCUMENTS

| | | | |
|---|---|---|---|
| 4,281,061 | A | 7/1981 | Zuk et al. |
| 6,033,847 | A | 3/2000 | Sherr et al. |
| 6,316,208 | B1 | 11/2001 | Roberts et al. |
| 6,436,703 | B1 | 8/2002 | Tang et al. |
| 2002/0061567 | A1 | 5/2002 | Tang et al. |
| 2002/0146757 | A1 | 10/2002 | Tang et al. |
| 2003/0049617 | A1 | 3/2003 | Chen et al. |
| 2003/0087370 | A1 | 5/2003 | Tang et al. |
| 2003/0092112 | A1 | 5/2003 | Tang et al. |
| 2003/0096279 | A1 | 5/2003 | Tang et al. |
| 2003/0157482 | A1 | 8/2003 | Keesee et al. |
| 2003/0180722 | A1 | 9/2003 | Godbole et al. |

FOREIGN PATENT DOCUMENTS

| | | |
|---|---|---|
| WO | WO 01/61055 | 8/2001 |
| WO | WO 01/75067 | 10/2001 |

OTHER PUBLICATIONS

Srebrow et al (J. Cell Sci., 119:2635-2641, 2006).*
Kirschbaum-Slager et al (Gen. Mol. Res., 3(4):512-520, 2004).*
Kalnina et al (Gen. Chrom. Can., 42:342-357, 2005).*
Harrington et al (Nat. Biotech., 19:440-445, 2001).*
Harrington et al, GenBankTM Accession No. BG181290, pp. 1-2, 2001.*
NCI-CGAP, GenBankTM Accession No. AW189129, pp. 1-2, 1999.*
Verma et al. (Nature 1997, 389: 239-242).*
Amalfitano et al. (Current Gene Therapy 2002, 2: 111-133).*
Patterson, Department of Health and Human Services memorandum, Jan. 2003, pp. 1-3.*
Pandha et al. (Current Opinion in Investigational Drugs 2000; 1 (1): 122-134).*
Ferrari et al. (Clin. Exp. Immunol. 2003; 132: 1-8).*
Arakawa, et al., "Mus musculus adult male liver tumor cDNA, RIKEN full-length enriched library . . . ", EMBL Online, Oct. 21, 2001, accession No. BB653919, XP002219900, abstract.
NCI-MGC: "602891694F1 NCI_CGAP_Lu29 Mus musculus cDNA clone IMAGE:50367110 5', mRNA sequence", EMBL Online, Jun. 28, 2001, accession No. Bi107698, XP002219901, abstract.
Tracey A: "Human DNA sequence from clone RP11-425D10 on chromosome 6", EMBL Online, Mar. 1, 2001, accession No. AL359711, XP002219902, abstract.
Drmanac et al., "DNA encoding novel human diagnostic protein #5135", EMBL Online, Feb. 13, 2002, accession No. AAS69331, XP002219903, abstract.
He, et al., "Expression, Deletion And Mutation of p16 Gene in Human Gastric Cancer" *World J. of Gastroenterology* 7(4): 515-521 (2001).
Myung, et al., "Loss Of p16 And p27 Is Associated With Progression Of Human Gastric Cancer" *Cancer Letters* 153:129-136 (2000).
Nakao et al., "Induction of p16 During Immortalization HPV 16 and 18 and Not During Malignant Transformation" *British J of Cancer* 75(10):1410-1416, 1997.
O'Nions, et al., "p73 Is Over-Expressed In Vulval Cancer Principally As The Δ2 Isoform" *British J. Cancer* 85(10):1551-1556 (Nov. 2001).
Sano et al., "Expression Status of p16 Protein Is Associated With Human Papillomavirus Oncogenic Potential In Cervical and Genital lesions" *American J. Pathology* 153(6):1741, 1998.
Sano, et al., "Overexpression Of P16 And P14ARF Is Associated With Human Papillomavirus Infection In Cervical Squamous Cell Carcinoma And Dysplasia" *Pathology.Int.* 52:375-383 (May 2002).
Sherr, "The Ink4a/Arf Network In Tumor Suppression" *Nature Reviews Mol. Cell Bio* 2:731-737, (2001).

(Continued)

*Primary Examiner*—Stephen L. Rawlings
*Assistant Examiner*—Brad Duffy
(74) *Attorney, Agent, or Firm*—Howrey LLP; Viola T. Kung

(57) ABSTRACT

The present invention relates to nucleic acids and polypeptides associated with lung cancer. The invention is more specifically related to a nucleic acids and the polypeptides transcribed thereof, the expression of which is significantly altered in association with lung cancer. The invention relates to a series of differentially spliced transcripts of the gene disclosed herein, that are associated with tumors of the respiratory tract. Furthermore the present invention provides a method for early diagnosis, prognosis and monitoring of the disease course and for therapy and vaccination of cell proliferative disorders such as e.g. lung tumors.

12 Claims, 51 Drawing Sheets

OTHER PUBLICATIONS

Takeuchi, et al., "Altered p16/MTSi/CDKN2 and Cycling D1/PRAD-1 Gene Expression Is Associated With The Prognosis of Squamous Cell Carcinoma of the Esophagus" *Clinical Cancer Research* 3:2229-2236, (1997).

Tsujie, et al., "Expression of Tumor Suppressor Gene p16INK4 Products in Primary Gastric Cancer" *Oncology* 58:126-136 (2000).

NCI-CGAP: 7q79d11.x1 NCI_CGAP_LU24 *Homo sapiens* cDNA clone IMAGE: 3704516 3', mRNA sequence, XP002261497, abstract, Apr. 2, 2001.

* cited by examiner

FIGURE 1: LUMA1 mRNA variant 1

```
   1 ATGGAAATCACCACTCTGAGAGCCCAACTCACAGACTTGGAAGAAGTGAATCTGAATCTC
     M  E  I  T  T  L  R  A  Q  L  T  D  L  E  E  V  N  L  N  L

61 AAGAAGCAGATTAGAAAAGAAGTCCAAGAAGAATATGAAGCATTAGTCCGAGCTTTGTTT
     K  K  Q  I  R  K  E  V  Q  E  E  Y  E  A  L  V  R  A  L  F

121 GAGACCTGTTTACACATAAAAGAGAAGCTGGATGATAATCAGCTTAATTTGATCCAGAAA
     E  T  C  L  H  I  K  E  K  L  D  D  N  Q  L  N  L  I  Q  K

181 GTGTGTGAGCTCATCGGTGAAGTGAGAACAGAAGGGATTGACAATATGAAGGACCTAAAG
     V  C  E  L  I  G  E  V  R  T  E  G  I  D  N  M  K  D  L  K

241 AAAAAATGGTGCTCTGCCAGCCCCGATGAAGGAATGAAAGAAAACCCAGCCAAACAGGAA
     K  K  W  C  S  A  S  P  D  E  G  M  K  E  N  P  A  K  Q  E

301 CAGCTGTGGGCCTTGGAGCAGGACAACTGCAGCCTGGCCAACCTGGTGTGCAAAGTGAGG
     Q  L  W  A  L  E  Q  D  N  C  S  L  A  N  L  V  C  K  V  R

361 AGCCTGGGCCGCTGGAGGCTGGCTGTGCAGCAGGCGTGCTTCCAGGCCCAGCTGAGCAGG
     S  L  G  R  W  R  L  A  V  Q  Q  A  C  F  Q  A  Q  L  S  R

421 ACAGAGAAGGAATCTATTCAAAGTAAAAAAGAGTATTTGCGCATCAAGCTGATGGCAGAG
     T  E  K  E  S  I  Q  S  K  K  E  Y  L  R  I  K  L  M  A  E

481 CGAGAAGTGGGTTTATTTCGTCAGCAGGTCCTGGCTCTCAGGCAGGCCCTGGCCAGGGCA
     R  E  V  G  L  F  R  Q  Q  V  L  A  L  R  Q  A  L  A  R  A

541 CAGGCTGACAGCGCGAGGATGTGGAAGCAGCAGGACAGCCAGGCTCAACTGCTGAAGGAG
     Q  A  D  S  A  R  M  W  K  Q  Q  D  S  Q  A  Q  L  L  K  E

601 TTAGAACATAGAGTGACCCAGGAAGCTCTCACCCAGCAGCAGCTGCATTTTATGAAAACA
     L  E  H  R  V  T  Q  E  A  L  T  Q  Q  Q  L  H  F  M  K  T

661 TCCAGGATGGAGAAGCTCTTGGAAGATGTGGGGCAAAAAGAACAGCAACTGCAGCTCCTT
     S  R  M  E  K  L  L  E  D  V  G  Q  K  E  Q  Q  L  Q  L  L

721 AGCAAAGAGGCTGAGAGGGCTTCTAAGCTGGGCCAACTGCAGCAGAAAAAAATGAAGAGG
     S  K  E  A  E  R  A  S  K  L  G  Q  L  Q  Q  K  K  M  K  R

781 GACCTCCACCAGATGAGAAGCCGGCTTGCCCAGGAGCGCAGTGTGAAGCTGGATGCTCTC
     D  L  H  Q  M  R  S  R  L  A  Q  E  R  S  V  K  L  D  A  L

841 CAGCGTGCAGAGGAGCTGCAGGGTCAGCTTCACGATGCCCAGCGGTCAGCTGTCCCCATG
     Q  R  A  E  E  L  Q  G  Q  L  H  D  A  Q  R  S  A  V  P  M

901 GGCTCGTCAGGCGACCTTATATCCCAGGCTCAATACTCCCCAACTTCTGCTTCCACATCA
     G  S  S  G  D  L  I  S  Q  A  Q  Y  S  P  T  S  A  S  T  S

961 TCCAGATACTCCCAGCAACGCTTTTTAAAGACTAATCTCAAAGGCAGTAAAATAACAAGA
     S  R  Y  S  Q  Q  R  F  L  K  T  N  L  K  G  S  K  I  T  R

1021 TGGATTCAAAGGCCACAGACTGTACCTATTAAACACAAAAAAAGAACTGACGATGTTTTC
     W  I  Q  R  P  Q  T  V  P  I  K  H  K  K  R  T  D  D  V  F

1081 CTACCCAATATGGCAGAAAATGTTCAACTGACAGCTTTTCAGGTTCAAACAGCTCCATCC
     L  P  N  M  A  E  N  V  Q  L  T  A  F  Q  V  Q  T  A  P  S

1141 AGATTCCCATTTAGAGCTGACTGGTGATGATATCTTCTTTTTCCAACCTTTATTCTATG
```

```
    R  F  P  F  R  A  D  W  *
1201 AGTATTTGAATGAATAAAAATGACTCCAAATGCCATTAAATCTCTTACTTAATTTTA
```

FIGURE 2: LUMA1 mRNA variant 2

```
   1 ATGGAAATCACCACTCTGAGAGCCCAACTCACAGACTTGGAAGAAGTGAATCTGAATCTC
     M  E  I  T  T  L  R  A  Q  L  T  D  L  E  E  V  N  L  N  L

61 AAGAAGCAGATTAGAAAAGAAGTCCAAGAAGAATATGAAGCATTAGTCCGAGCTTTGTTT
     K  K  Q  I  R  K  E  V  Q  E  E  Y  E  A  L  V  R  A  L  F

121 GAGACCTGTTTACACATAAAAGAGAAGCTGGATGATAATCAGCTTAATTTGATCCAGAAA
     E  T  C  L  H  I  K  E  K  L  D  D  N  Q  L  N  L  I  Q  K

181 GTGTGTGAGCTCATCGGTGAAGTGAGAACAGAAGGGATTGACAATATGAAGGACCTAAAG
     V  C  E  L  I  G  E  V  R  T  E  G  I  D  N  M  K  D  L  K

241 AAAAAATGGTGCTCTGCCAGCCCCGATGAAGGAATGAAAGAAAACCCAGCCAAACAGGAA
     K  K  W  C  S  A  S  P  D  E  G  M  K  E  N  P  A  K  Q  E

301 CAGCTGTGGGCCTTGGAGCAGGACAACTGCAGCCTGGCCAACCTGGTGTGCAAAGTGAGG
     Q  L  W  A  L  E  Q  D  N  C  S  L  A  N  L  V  C  K  V  R

361 AGCCTGGGCCGCTGGAGGCTGGCTGTGCAGCAGGCGTGCTTCCAGGCCCAGCTGAGCAGG
     S  L  G  R  W  R  L  A  V  Q  Q  A  C  F  Q  A  Q  L  S  R

421 ACAGAGAAGGAATCTATTCAAAGTAAAAAGGAGTATTTGCGCATCAAGCTGATGGCAGAG
     T  E  K  E  S  I  Q  S  K  K  E  Y  L  R  I  K  L  M  A  E

481 CGAGAAGTGGGGTTTATTTCGTCAGCAGGTCCTGGCTCTCAGGCAGGCCCTGGCCAGGGCA
     R  E  V  G  L  F  R  Q  Q  V  L  A  L  R  Q  A  L  A  R  A

541 CAGGCTGACAGCGCGAGGATGTGGAAGCAGCAGGACAGCCAGGCTCAACTGCTGAAGGAG
     Q  A  D  S  A  R  M  W  K  Q  Q  D  S  Q  A  Q  L  L  K  E

601 TTAGAACATAGAGTGACCCAGGAAGCTCTCACCCAGCAGCAGCTGCATTTTATGAAAACA
     L  E  H  R  V  T  Q  E  A  L  T  Q  Q  Q  L  H  F  M  K  T

661 TCCAGGATGGAGAAGCTCTTGGAAGATGTGGGGCAAAAAGAACAGCAACTGCAGCTCCTT
     S  R  M  E  K  L  L  E  D  V  G  Q  K  E  Q  Q  L  Q  L  L

721 AGCAAAGAGGCTGAGAGGGCTTCTAAGCTGGGCCAACTGCAGCAGAAAAAAATGAAGAGG
     S  K  E  A  E  R  A  S  K  L  G  Q  L  Q  Q  K  K  M  K  R

781 GACCTCCACCAGATGAGAAGCCGGCTTGCCCAGGAGCGCAGTGTGAAGCTGGATGCTCTC
     D  L  H  Q  M  R  S  R  L  A  Q  E  R  S  V  K  L  D  A  L

841 CAGCGTGCAGAGGAGCTGCAGGGTCAGCTTCACGATGCCCAGCGGTCAGCTGTCCCCATG
     Q  R  A  E  E  L  Q  G  Q  L  H  D  A  Q  R  S  A  V  P  M

901 GGCTCGTCAGGCGATACTCCCAGCAACGCTTTTTAAAGACTAATCTCAAAGGCAGTAAAA
     G  S  S  G  D  T  P  S  N  A  F  *

961 TAACAAGATGGATTCAAAGGCCACAGACTGTACCTATTAAACACAAAAAAAGAACTGACG

1021 ATGTTTTCCTACCCAATATGGCAGAAAATGTTCAACTGACAGCTTTTCAGGTTCAAACAG

1081 CTCCATCCAGATTCCCATTTAGAGCTGACTGGTGATGATATCTTCTTTTTCCAACCTTTA
```

1141 TTTCTATGAGTATTTGAATGAATAAAAATGACTCCAAATGCCATTAAATCTCTTACTTAA

1201 TTTTA

FIGURE 3: LUMA1 mRNA variant 3

```
   1 ATGGAAATCACCACTCTGAGAGCCCAACTCACAGACTTGGAAGAAGTGAATCTGAATCTC
     M   E   I   T   T   L   R   A   Q   L   T   D   L   E   E   V   N   L   N   L

61 AAGAAGCAGATTAGAAAAGAAGTCCAAGAAGAATATGAAGCATTAGTCCGAGCTTTGTTT
     K   K   Q   I   R   K   E   V   Q   E   E   Y   E   A   L   V   R   A   L   F

121 GAGACCTGTTTACACATAAAAGAGAAGCTGGATGATAATCAGCTTAATTTGATCCAGAAA
     E   T   C   L   H   I   K   E   K   L   D   D   N   Q   L   N   L   I   Q   K

181 GTGTGTGAGCTCATCGGTGAAGTGAGAACAGAAGGGATTGACAATATGAAGGACCTAAAG
     V   C   E   L   I   G   E   V   R   T   E   G   I   D   N   M   K   D   L   K

241 AAAAAATGGTGCTCTGCCAGCCCCGATGAAGGAATGAAAGAAAACCCAGCCAAAGAACAG
     K   K   W   C   S   A   S   P   D   E   G   M   K   E   N   P   A   K   E   Q

301 CTGTGGGCCTTGGAGCAGGACAACTGCAGCCTGGCCAACCTGGTGTGCAAAGTGAGGAGC
     L   W   A   L   E   Q   D   N   C   S   L   A   N   L   V   C   K   V   R   S

361 CTGGGCCGCTGGAGGCTGGCTGTGCAGCAGGCGTGCTTCCAGGCCCAGCTGAGCAGGACA
     L   G   R   W   R   L   A   V   Q   Q   A   C   F   Q   A   Q   L   S   R   T

421 GAGAAGGAATCTATTCAAAGTAAAAAAGAGTATTTGCGCATCAAGCTGATGGCAGAGCGA
     E   K   E   S   I   Q   S   K   K   E   Y   L   R   I   K   L   M   A   E   R

481 GAAGTGGGTTTATTTCGTCAGCAGGTCCTGGCTCTCAGGCAGGCCCTGGCCAGGGCACAG
     E   V   G   L   F   R   Q   Q   V   L   A   L   R   Q   A   L   A   R   A   Q

541 GCTGACAGCGCGAGGATGTGGAAGCAGCAGGACAGCCAGGCTCAACTGCTGAAGGAGTTA
     A   D   S   A   R   M   W   K   Q   Q   D   S   Q   A   Q   L   L   K   E   L

601 GAACATAGAGTGACCCAGGAAGCTCTCACCCAGCAGCAGCTGCATTTTATGAAAACATCC
     E   H   R   V   T   Q   E   A   L   T   Q   Q   Q   L   H   F   M   K   T   S

661 AGGATGGAGAAGCTCTTGGAAGATGTGGGGCAAAAAGAACAGCAACTGCAGCTCCTTAGC
     R   M   E   K   L   L   E   D   V   G   Q   K   E   Q   Q   L   Q   L   L   S

721 AAAGAGGCTGAGAGGGCTTCTAAGCTGGGCCAACTGCAGCAGAAAAAAATGAAGAGGGAC
     K   E   A   E   R   A   S   K   L   G   Q   L   Q   Q   K   K   M   K   R   D

781 CTCCACCAGATGAGAAGCCGGCTTGCCCAGGAGCGCAGTGTGAAGCTGGATGCTCTCCAG
     L   H   Q   M   R   S   R   L   A   Q   E   R   S   V   K   L   D   A   L   Q

841 CGTGCAGAGGAGCTGCAGGGTCAGCTTCACGATGCCCAGCGGTCAGCTGTCCCCATGGGC
     R   A   E   E   L   Q   G   Q   L   H   D   A   Q   R   S   A   V   P   M   G

901 TCGTCAGGCGACCTTATATCCCAGGCTCAATACTCCCCAACTTCTGCTTCCACATCATCC
     S   S   G   D   L   I   S   Q   A   Q   Y   S   P   T   S   A   S   T   S   S

961 AGATACTCCCAGCAACGCTTTTTAAAGACTAATCTCAAAGGCAGTAAAATAACAAGATGG
     R   Y   S   Q   Q   R   F   L   K   T   N   L   K   G   S   K   I   T   R   W

1021 ATTCAAAGGCCACAGACTGTACCTATTAAACACAAAAAAAGAACTGACGATGTTTTCCTA
     I   Q   R   P   Q   T   V   P   I   K   H   K   K   R   T   D   D   V   F   L

1081 CCCAATATGGCAGAAAATGTTCAACTGACAGCTTTTCAGGTTCAAACAGCTCCATCCAGA
```

```
         P  N  M  A  E  N  V  Q  L  T  A  F  Q  V  Q  T  A  P  S  R
1141 TTCCCATTTAGAGCTGACTGGTGATGATATCTTCTTTTTCCAACCTTTATTTCTATGAGT
     F  P  F  R  A  D  W  *

1201 ATTTGAATGAATAAAAATGACTCCAAATGCAAAAAAAAAAAAAAA
```

FIGURE 4: LUMA1 mRNA variant 4

```
  1 ATTAGTCCGAGCTTTGTTTGAGACCTGTTTACACATAAAAGAGAAGCTGGATGATAATCA
    L  V  R  A  L  F  E  T  C  L  H  I  K  E  K  L  D  D  N  Q

61 GCTTAATTTGATCCAGAAAGTGTGTGAGCTCATCGGTGAAGTGAGAACAGAAGGGATTGA
    L  N  L  I  Q  K  V  C  E  L  I  G  E  V  R  T  E  G  I  D

121 CAATATGAAGGACCTAAAGAAAAAATGGTGCTCTGCCAGCCCCGATGAAGGAATGAAAGA
    N  M  K  D  L  K  K  K  W  C  S  A  S  P  D  E  G  M  K  E

181 AAACCCAGCCAAAGAATCTATTCAAAGTAAAAAAGAGTATTTGCGCATCAAGCTGATGGC
    N  P  A  K  E  S  I  Q  S  K  K  E  Y  L  R  I  K  L  M  A

241 AGAGCGAGAAGTGGGTTTATTTCGTCAGCAGGTCCTGGCTCTCAGGCAGGCCCTGGCCAG
    E  R  E  V  G  L  F  R  Q  Q  V  L  A  L  R  Q  A  L  A  R

301 GGCACAGGCTGACAGCGCGAGGATGTGGAAGCAGCAGGACAGCCAGGCTCAACTGCTGAA
    A  Q  A  D  S  A  R  M  W  K  Q  Q  D  S  Q  A  Q  L  L  K

361 GGAGTTAGAACATAGAGTGACCCAGGAAGCTCTCACCCAGCAGCAGCTGCATTTTATGAA
    E  L  E  H  R  V  T  Q  E  A  L  T  Q  Q  Q  L  H  F  M  K

421 AACATCCAGGATGGAGAAGCTCTTGGAAGATGTGGGGCAAAAAGAACAGCAACTGCAGCT
    T  S  R  M  E  K  L  L  E  D  V  G  Q  K  E  Q  Q  L  Q  L

481 CCTTAGCAAAGAGGCTGAGAGGGCTTCTAA
    L  S  K  E  A  E  R  A  S
```

FIGURE 5: LUMA1 mRNA variant 5

```
  1 ATCGGTGAAGTGAGAACAGAAGGGATTGACAATATGAAGGACCTAAAGAAAAAATGGTGC
    I  G  E  V  R  T  E  G  I  D  N  M  K  D  L  K  K  K  W  C

61 TCTGCCAGCCCCGATGAAGGAATGAAAGAAAACCCAGCCAAAGCTCAACTGCTGAAGGAG
    S  A  S  P  D  E  G  M  K  E  N  P  A  K  A  Q  L  L  K  E

121 TTAGAACATAGAGTGACCCAGGAAGCTCTCACCCAGCAGCAGCTGCATTTTATGAAAACA
    L  E  H  R  V  T  Q  E  A  L  T  Q  Q  Q  L  H  F  M  K  T

181 TCCAGGATGGAGAAGCTCTTGGAAGATGTGGGGCAAAAAGAACAGCAACTGCAGCTCCTT
    S  R  M  E  K  L  L  E  D  V  G  Q  K  E  Q  Q  L  Q  L  L

241 AGCAAAGAGGCTGAGAGGGCTTCTAAGCTGGGCCAACTGCAGCAGAAAAAAATGAAGAGG
    S  K  E  A  E  R  A  S  K  L  G  Q  L  Q  Q  K  K  M  K  R

301 GACCTCCACCAGATGAGAAGCCGGCTTGCCCAGGAGCGCAGTGTGAAGCTGGATGCTCTC
    D  L  H  Q  M  R  S  R  L  A  Q  E  R  S  V  K  L  D  A  L

361 CAGCGTGCAGAGGAGCTGCAGGGTCAGCTTCACGATGCCCAGCGGTCAGCTGTCCCCATG
    Q  R  A  E  E  L  Q  G  Q  L  H  D  A  Q  R  S  A  V  P  M
```

```
421 GGCTCGTCAGGCGACCTTATATCCCAGGCTCAATACTCCCCAACTTCTGCTTCCACATCA
     G  S  S  G  D  L  I  S  Q  A  Q  Y  S  P  T  S  A  S  T  S

481 TCCAGATACTCCCAGCAACGCTTTTTAAAGACTAA
     S  R  Y  S  Q  Q  R  F  L  K  T
```

FIGURE 6: LUMA1 mRNA variant 6

```
  1 ATCGGTGAAGTGAGAACAGAAGGGATTGACAATATGAAGGACCTAAAGAAAAAATGGTGC
     I  G  E  V  R  T  E  G  I  D  N  M  K  D  L  K  K  K  W  C

61 TCTGCCAGCCCCGATGAAGGAATGAAAGAAAACCCAGCCAAAATGAGAAGCCGGCTTGCC
     S  A  S  P  D  E  G  M  K  E  N  P  A  K  M  R  S  R  L  A

121 CAGGAGCGCAGTGTGAAGCTGGATGCTCTCCAGCGTGCAGAGGAGCTGCAGGGTCAGCTT
     Q  E  R  S  V  K  L  D  A  L  Q  R  A  E  E  L  Q  G  Q  L

181 CACGATGCCCAGCGGTCAGCTGTCCCCATGGGCTCGTCAGGCGACCTTATATCCCAGGCT
     H  D  A  Q  R  S  A  V  P  M  G  S  S  G  D  L  I  S  Q  A

241 CAATACTCCCCAACTTCTGCTTCCACATCATCCAGATACTCCCAGCAACGCTTTTTAAAG
     Q  Y  S  P  T  S  A  S  T  S  S  R  Y  S  Q  Q  R  F  L  K

301 ACTAA
     T
```

FIGURE 7: LUMA1 mRNA variant 7

Protein 1

A:

```
  g caa tgc gtg cta tgg gtc ctt ttt tct aac act tgc aga aga ttt cag      49
    Gln Cys Val Leu Trp Val Leu Phe Ser Asn Thr Cys Arg Arg Phe Gln
    1              5                  10                 15 ccc cgg cca cga tgt ttg ctg tca gcg gat gga aaa gtc ttc ctc aat        97
  Pro Arg Pro Arg Cys Leu Leu Ser Ala Asp Gly Lys Val Phe Leu Asn
                20                 25                 30 tta tgg ttc ata ccc cat tct tct gaa gtg ctg gtt atg ttc aaa act      145
  Leu Trp Phe Ile Pro His Ser Ser Glu Val Leu Val Met Phe Lys Thr
          35                 40                 45 ctg cca gaa aag gca gct ttt aaa gcc tta aag cga act cta caa ctg      193
  Leu Pro Glu Lys Ala Ala Phe Lys Ala Leu Lys Arg Thr Leu Gln Leu
      50                 55                 60 ata gct cct ctg cat gat atc gtg gcc tac ctt gtc agt ttt gct aag      241
  Ile Ala Pro Leu His Asp Ile Val Ala Tyr Leu Val Ser Phe Ala Lys
  65                 70                 75                 80 ctt ggc aat tgt cca gca tgt ttt gaa ttt cct cga agt ccc aac cct      289
  Leu Gly Asn Cys Pro Ala Cys Phe Glu Phe Pro Arg Ser Pro Asn Pro
                  85                 90                 95 ttg aga ggt gac tgg gga gga act gag ggc att ggg tct gag ctt caa      337
  Leu Arg Gly Asp Trp Gly Gly Thr Glu Gly Ile Gly Ser Glu Leu Gln
```

```
              100                 105                 110
gag ctg cag aac atg att gac agc ctc cag agc ccc caa gac cct atc         385
Glu Leu Gln Asn Met Ile Asp Ser Leu Gln Ser Pro Gln Asp Pro Ile
        115                 120                 125 cgg gtg gcc cag gca ctc ctc ctc cgg agg gag gtt ata ttt ttg cag         433
Arg Val Ala Gln Ala Leu Leu Leu Arg Arg Glu Val Ile Phe Leu Gln
    130                 135                 140 ttt gac gct gca gta agg cat ctc atc cga aga aca ttt ttg gca gct         481
Phe Asp Ala Ala Val Arg His Leu Ile Arg Arg Thr Phe Leu Ala Ala
145                 150                 155                 160 gga aat gtt cct gcc tac cag tct gtc aca gac ggc atg tgc cat ggg         529
Gly Asn Val Pro Ala Tyr Gln Ser Val Thr Asp Gly Met Cys His Gly
                165                 170                 175 cta cca gca ctg agc aac tct ctc agg aag agc att ttt gcc tca cag         577
Leu Pro Ala Leu Ser Asn Ser Leu Arg Lys Ser Ile Phe Ala Ser Gln
            180                 185                 190 ctc agc ctg ccc cag cca ctg gat cca cgg agc ctc cag gca ttt gag         625
Leu Ser Leu Pro Gln Pro Leu Asp Pro Arg Ser Leu Gln Ala Phe Glu
        195                 200                 205 ctg ttt cct tgg aga gca ttt ctg gaa gat gga gga cca ttc cca gtt         673
Leu Phe Pro Trp Arg Ala Phe Leu Glu Asp Gly Gly Pro Phe Pro Val
    210                 215                 220 atg agt aac agc cca gat acc cta gaa tat aat atg cag gta gga             718
Met Ser Asn Ser Pro Asp Thr Leu Glu Tyr Asn Met Gln Val Gly
225                 230                 235 taggtcttct ccattgttgc agagagaact gagcgcagac tgcaaagatg gttgccattg       778
ggttcacagg tcagatcctc ctactctcac ccacgatgaa taatgtgtga gataagcagg       838
gtgtttgatt ttgaggctgt aaacccaggg tcacgaggtg agtcacattt tcttatgata       898
gaagggaagc atgctctcaa ctggcatggg cctggttgt agactcagct gcagttttcg        958
taacagtagt gatctgggag aatggccagt catctccagt catgggctgg gcctcttaga       1018
gaaactccca ggctggcagc tcagagatgt gtgactcctg acctgtccat aaacagttgt      1078
gggaagggaa ctttttaaag caggactcgt agggagaatt tcttttcatt gttttctttt      1138
ttgctgttaa cttccttttaa atagtttgat tcttttcatt attaaatgtt ttccctgat     1198 tatttaagta aatattgttt ttatttaaaa aatagaaagc ttagaaagt attaagaaca      1258 acatgaaaat caaccataaa taacgcttca aaacaatatg gaggtgggga gtgggtggga     1318
tggggtagca ctggccacag gttaatggtt gttggggctg ggtgatggga acttttctgt      1378
ttgatttcta tatattcaaa attatccata agtagaacag gttttttaag taaaatagta     1438
aaagtggtct taaaaaatta accatatggc tgggtgtggt ggctcatgcc tgtaatctca     1498
gcactttggg aggccaaggt gggcagatct cttgagctca ggagttcaag accagcctgg    1558
```

```
gcaacaaggt gaaagcctgt gtctactgaa aatgcaaaaa ttagctgggt gtggtggcac      1618
acgcctgtag tcccagctac tcagaaggct aaggcatgag aatcacctga acccaggaga      1678
cggaggttgc agtgagctga gatcgtacca ctgcactcca gcctggtgac agtgtaagac      1738
tctcttaaaa aataaaataa aataaaataa aataaaaaat caaccatagt tccacaacta      1798
agagacaatt acagttcaca ttttatttcc ctggtatttt ccctctgcat atgtgtgttt      1858
atatctgtac ttttaaggga aaattgatat cacactatac attcaccatg tacagatctg      1918
ctgtaagggc tggaaacttg gcattttcat acagagccaa aatttgatgt gctcaaagaa      1978
aactttaagt tagaaatgtt actctggttt ttatgaattt tctagcagtt gagggaatgg      2038
gttcttgtaa atacagttac tcctagtttt cttcctgaaa accatatgta aaatatatat      2098
atggtcttca aatggaaggt ttttttgttt tttttttagct gtgcctctgt gggctgagtg      2158
accgtgaccg caaggtggct catggagaac tggtgggtgt gcaactgcta ctggaagatg      2218
ttctgagtag ctatcatgtg accatggagg ccccccaaag acagcaagcc acactgggca      2278
aaaatacaca gccagattgg tccaaagtgc caggattcag aagtcagttc cgaagcagcc      2338
caaagacctc tgagctgctg gagggcctgt gcgatgcggt gatgtcctttt gctttgctga      2398
gatcatttct gatactgtgg aagcagctgg aagtgctaaa ggagcactgg ggccgactca      2458
agctgcaagg ccaggatatc aactctgtct ctctccacaa acggttttca gagctctatg      2518
aaactgacgt tctctacccc agcatgaaag ctatagccag gcagatgggg aaagaagatg      2578
aatttgaagg atttatagta aataatcagt ctgttcttcc ccccagtgga gcctcagaag      2638
ttgaaataaa aactcaccaa cttcaaaaac ttctggaaaa ttgtgaaatt caaatgatcc      2698
aagaggtact aagaaaagtt aacagagaaa tgacactggt tttatcagaa aagtgcaagg      2758
aggagtgttc tctccctaca gctgtactgg gacagtggca atgtgtcttc tggcctttat      2818
ttcctaaagg aaaagcaaaa acagatttat atgtttatta tggaaagtag tcaattgtta      2878
aagaaacata gaatcccatt ttcaaaacca ggacttggca gtaaatagca tctctggaaa      2938
caccaagtca tgaaagaaaa cttttcagtc tcaagaccac aaatagttga aaaatttata      2998
cagagattaa tgtagaatta tcaggatgat ggagtagaga tcactttcag gaaagatcac      3058
cttgaggcct gcctccttc cctgggttgt gatgtgatgg caagagaatg cagcaacttt       3118
gagacctact ccatgtgcta tgagcatgtg ttgcatcatg ctaggcagag gctcagccag      3178
aaagagcaag aattagatgc tacacaaaga ggccagggtc cacctgaaga cagtgctggc      3238
cagattgcag agctcagtca tgatatgatc atggaaatca ccactctgag agcccaactc      3298
acagacttgg aagaagtgaa tctgaatctc aagaagcaga ttagaaaaga agtccaagaa      3358
gaatatgaag cattagtccg agctttgttt gagacctgtt tacacataaa agagaagctg      3418
```

```
gatgataatc agcttaattt gatccagaaa gtgtgtgagc tcatcggtga agtgagaaca    3478
gaagggattg acaatatgaa ggacctaaag aaaaatggt gctctgccag ccccgatgaa     3538
ggaatgaaag aaaacccagc caaacaggaa cagctgtggg ccttggagca ggacaactgc    3598
agcctggcca acctggtgtg caaagtgagg agcctgggcc gctggaggct ggctgtgcag    3658
caggcgtgct tccaggccca gctgagcagg acagagaagg aatctattca aagtaaaaaa    3718
gagtatttgc gcatcaagct gatggcagag cgagaagtgg gtttatttcg tcagcaggtc    3778
ctggctctca ggcaggccct ggccagggca caggctgaca gcgcgaggat gtggaagcag    3838
caggacagcc aggctcaact gctgaaggag ttagaacata gagtgaccca ggaagctctc    3898
acccagcagc agctgcattt tatgaaaaca tccaggatgg agaagctctt ggaagatgtg    3958
gggcaaaaag aacagcaact gcagctcctt agcaaagagg ctgagagggc ttctaagctg    4018
ggccaactgc agcagaaaaa aatgaagagg gacctccacc agatgagaag ccggcttgcc    4078
caggagcgca gtgtgaagct ggatgctctc cagcgtgcag aggagctgca gggtcagctt    4138
cacgatgccc agcggtcagc tgtccccatg ggctcgtcag gcgaccttat atcccaggct    4198
caatactccc caacttctgc ttccacatca tccagatact cccagcaacg cttttttaaag   4258
actaatctca aaggcagtaa aataacaaga tggattcaaa ggccacagac taagcccttt    4318
tcaaaaagaa gcaaagttca ctttgtatgt gtgggatcac aagggctttc aagaatcact    4378
tcatctccat ttcaccctga aagctgcaat accatggggg tgttggtgat cgtgacttgt    4438
tgaaaaggct gctaagcaga taagtgcatt agtgaagatt tattatattt gagagattca    4498
aaaggtgat aggctaaagc taattgatga acattgccct accaaataaa taaaccctac     4558
agtgaagtgt cttgtgggcc cattggccca gtggctatgt acaatacggg aaccccaagc    4618
aaaaaacctc aaggccaggg aaggtacaca gttagctgga acttcagatc tcaggtctga    4678
cttcttaagc aaggcctatg agacaagtca gataaatact cattgaagag gaatttatac    4738
atggctgaaa tgtaagaaca cagttaattt tctaaaaatt agccctgcac taacacaaat    4798
gataaaaaat taaggaattt ttagattact tgaagtatga gctgtgtttt cttccttaac    4858
tggaaatggc tttccactga tggattcatt cttgaccaat tcccttaggg acaatggcaa    4918
aatacagaca agaaggcata ctatatggcc taacccagac tgaatcaatg atcttggtct    4978
cattaataac agtgactttt tatgatgcta taacaagaat tattcaccat gttcttaaca    5038
ccaatatcta cttatattac aggtacctat taaacacaaa aaaagaactg acgatgtttt    5098
cctacccaat atggcagaaa atgttcaact gacagctttt caggttcaaa cagctccatc    5158
cagattccca tttagagctg actgg                                          5183
```

B:

| | | | | | | | | | | | | | | |
|---|---|---|---|---|---|---|---|---|---|---|---|---|---|---|
|Gln|Cys|Val|Leu|Trp|Val|Leu|Phe|Ser|Asn|Thr|Cys|Arg|Arg|Phe|Gln
1| | | |5| | | | |10| | | | |15

Gln Cys Val Leu Trp Val Leu Phe Ser Asn Thr Cys Arg Arg Phe Gln
1               5                   10                  15

Pro Arg Pro Arg Cys Leu Leu Ser Ala Asp Gly Lys Val Phe Leu Asn
            20                  25                  30

Leu Trp Phe Ile Pro His Ser Ser Glu Val Leu Val Met Phe Lys Thr
            35              40                  45

Leu Pro Glu Lys Ala Ala Phe Lys Ala Leu Lys Arg Thr Leu Gln Leu
    50              55                  60

Ile Ala Pro Leu His Asp Ile Val Ala Tyr Leu Val Ser Phe Ala Lys
65              70                  75                  80

Leu Gly Asn Cys Pro Ala Cys Phe Glu Phe Pro Arg Ser Pro Asn Pro
            85                  90                  95

Leu Arg Gly Asp Trp Gly Gly Thr Glu Gly Ile Gly Ser Glu Leu Gln
            100                 105                 110

Glu Leu Gln Asn Met Ile Asp Ser Leu Gln Ser Pro Gln Asp Pro Ile
            115             120                 125

Arg Val Ala Gln Ala Leu Leu Leu Arg Arg Glu Val Ile Phe Leu Gln
    130                 135                 140

Phe Asp Ala Ala Val Arg His Leu Ile Arg Arg Thr Phe Leu Ala Ala
145                 150                 155                 160

Gly Asn Val Pro Ala Tyr Gln Ser Val Thr Asp Gly Met Cys His Gly
            165             170                 175

Leu Pro Ala Leu Ser Asn Ser Leu Arg Lys Ser Ile Phe Ala Ser Gln
            180                 185                 190

Leu Ser Leu Pro Gln Pro Leu Asp Pro Arg Ser Leu Gln Ala Phe Glu
    195                 200                 205

Leu Phe Pro Trp Arg Ala Phe Leu Glu Asp Gly Gly Pro Phe Pro Val
    210                 215                 220

Met Ser Asn Ser Pro Asp Thr Leu Glu Tyr Asn Met Gln Val Gly
225                 230                 235

FIGURE 8: LUMA1 mRNA variant 8

Protein 2

A:

| | | | | |
|---|---|---|---|---|
| gcaatgcgtg | ctatgggtcc | ttttttctaa | cacttgcaga | agatttcagc | cccggccacg | 60 |
| atgtttgctg | tcagcggatg | gaaaagtctt | cctcaattta | tggttcatac | cccattcttc | 120 |
| tgaagtgctg | gttatgttca | aaactctgcc | agaaaaggca | gcttttaaag | ccttaaagcg | 180 |
| aactctacaa | ctgatagctc | ctctgcatga | tatcgtggcc | taccttgtca | gttttgctaa | 240 |
| gcttggcaat | tgtccagcat | gttttgaatt | tcctcgaagt | cccaaccctt | tgagaggtga | 300 |
| ctggggagga | actgagggca | ttgggtctga | gcttcaagag | ctgcagaaca | tgattgacag | 360 |
| cctccagagc | ccccaagacc | ctatccgggt | ggcccaggca | ctcctcctcc | ggagggaggt | 420 |
| tatatttttg | cagtttgacg | ctgcagtaag | gcatctcatc | cgaagaacat | ttttggcagc | 480 |
| tggaaatgtt | cctgcctacc | agtctgtcac | agacggcatg | tgccatgggc | taccagcact | 540 |
| gagcaactct | ctcaggaaga | gcattttgc | ctcacagctc | agcctgcccc | agccactgga | 600 |
| tccacggagc | ctccaggcat | ttgagctgtt | tccttggaga | gcatttctgg | aagatggagg | 660 |
| accattccca | gttatgagta | acagcccaga | taccctagaa | tataatatgc | aggtaggata | 720 |
| ggtcttctcc | attgttgcag | agagaactga | gcgcagactg | caaagatggt | tgccattggg | 780 |
| ttcacaggtc | agatcctcct | actctcaccc | acgatgaata | atgtgtgaga | taagcagggt | 840 |
| gtttgatttt | gaggctgtaa | acccagggtc | acgaggtgag | tcacattttc | ttatgataga | 900 |
| agggaagcat | gctctcaact | ggcatgggcc | tgggttgtag | actcagctgc | agttttcgta | 960 |
| acagtagtga | tctgggagaa | tggccagtca | tctccagtca | tgggctgggc | ctcttagaga | 1020 |
| aactcccagg | ctggcagctc | agagatgtgt | gactcctgac | ctgtccataa | acagttgtgg | 1080 |
| gaagggaact | ttttaaagca | ggactcgtag | ggagaatttc | ttttcattgt | tttctttttt | 1140 |
| gctgttaact | tcctttaaat | agtttgattc | ttttcattat | taaatgtttt | cccctgatta | 1200 |
| tttaagtaaa | tattgttttt | atttaaaaaa | tagaaagctt | agaaaagtat | taagaacaac | 1260 |
| atgaaaatca | accataaata | acgcttcaaa | acaatatgga | ggtgggagt | gggtgggatg | 1320 |
| gggtagcact | ggccacaggt | taatggttgt | tggggctggg | tgatgggaac | ttttctgttt | 1380 |
| gatttctata | tattcaaaat | tatccataag | tagaacaggt | ttttaagta | aaatagtaaa | 1440 |
| agtggtctta | aaaattaac | catatggctg | ggtgtggtgg | ctcatgcctg | taatctcagc | 1500 |
| actttgggag | gccaaggtgg | gcagatctct | tgagctcagg | agttcaagac | cagcctggc | 1560 |
| aacaaggtga | aagcctgtgt | ctactgaaaa | tgcaaaaatt | agctgggtgt | ggtggcacac | 1620 |
| gcctgtagtc | ccagctactc | agaaggctaa | ggcatgagaa | tcacctgaac | ccaggagacg | 1680 |

```
gaggttgcag tgagctgaga tcgtaccact gcactccagc ctggtgacag tgtaagactc    1740
tcttaaaaaa taaaataaaa taaaataaaa taaaaaatca accatagttc cacaactaag    1800
agacaattac agttcacatt ttatttccct ggtatttcc  ctctgcatat gtgtgtttat    1860
atctgtactt ttaagggaaa attgatatca cactatacat tcaccatgta cagatctgct    1920
gtaagggctg gaaacttggc attttcatac agagccaaaa tttgatgtgc tcaaagaaaa    1980
ctttaagtta gaaatgttac tctggttttt atgaattttc tagcagttga gggaatgggt    2040
tcttgtaaat acagttactc ctagttttct tcctgaaaac catatgtaaa atatatatat    2100
ggtcttcaaa tggaaggttt ttttgttttt ttttagctgt gcctctgtgg gctgagtgac    2160
cgtgaccgca aggtggctca tggagaactg gtgggtgtgc aactgctact ggaagatgtt    2220
ctgagtagct atcatgtgac c atg gag gcc ccc caa aga cag caa gcc aca    2271
                        Met Glu Ala Pro Gln Arg Gln Gln Ala Thr
                         1               5                   10 ctg ggc aaa aat aca cag cca gat tgg tcc aaa gtg cca gga ttc aga    2319
Leu Gly Lys Asn Thr Gln Pro Asp Trp Ser Lys Val Pro Gly Phe Arg
            15                  20                  25 agt cag ttc cga agc agc cca aag acc tct gag ctg ctg gag ggc ctg    2367
Ser Gln Phe Arg Ser Ser Pro Lys Thr Ser Glu Leu Leu Glu Gly Leu
            30                  35                  40 tgc gat gcg gtg atg tcc ttt gct ttg ctg aga tca ttt ctg ata ctg    2415
Cys Asp Ala Val Met Ser Phe Ala Leu Leu Arg Ser Phe Leu Ile Leu
        45                  50                  55 tgg aag cag ctg gaa gtg cta aag gag cac tgg ggc cga ctc aag ctg    2463
Trp Lys Gln Leu Glu Val Leu Lys Glu His Trp Gly Arg Leu Lys Leu
    60                  65                  70 caa ggc cag gat atc aac tct gtc tct ctc cac aaa cgg ttt tca gag    2511
Gln Gly Gln Asp Ile Asn Ser Val Ser Leu His Lys Arg Phe Ser Glu
75                  80                  85                  90 ctc tat gaa act gac gtt ctc tac ccc agc atg aaa gct ata gcc agg    2559
Leu Tyr Glu Thr Asp Val Leu Tyr Pro Ser Met Lys Ala Ile Ala Arg
                95                  100                 105 cag atg ggg aaa gaa gat gaa ttt gaa gga ttt ata gta aat aat cag    2607
Gln Met Gly Lys Glu Asp Glu Phe Glu Gly Phe Ile Val Asn Asn Gln
            110                 115                 120 tct gtt ctt ccc ccc agt gga gcc tca gaa gtt gaa ata aaa act cac    2655
Ser Val Leu Pro Pro Ser Gly Ala Ser Glu Val Glu Ile Lys Thr His
            125                 130                 135 caa ctt caa aaa ctt ctg gaa aat tgt gaa att caa atg atc caa gag    2703
Gln Leu Gln Lys Leu Leu Glu Asn Cys Glu Ile Gln Met Ile Gln Glu
        140                 145                 150 gta cta aga aaa gtt aac aga gaa atg aca ctg gtt tta tca gaa aag    2751
Val Leu Arg Lys Val Asn Arg Glu Met Thr Leu Val Leu Ser Glu Lys
155                 160                 165                 170
```

| | | | | | | | | | | | | | |
|---|---|---|---|---|---|---|---|---|---|---|---|---|---|
| tgc | aag | gag | gag | tgt | tct | ctc | cct | aca | gat | ctc | tgg | aaa | cac caa gtc | 2799 |
| Cys | Lys | Glu | Glu | Cys | Ser | Leu | Pro | Thr | Asp | Leu | Trp | Lys | His Gln Val | |
| | | | 175 | | | | 180 | | | | | 185 | | |
| atg | aaa | gaa | aac | ttt | tca | gtc | tca | aga | cca | caa | ata | gtt | gaa aaa ttt | 2847 |
| Met | Lys | Glu | Asn | Phe | Ser | Val | Ser | Arg | Pro | Gln | Ile | Val | Glu Lys Phe | |
| | | | 190 | | | | 195 | | | | | 200 | | |
| ata | cag | aga | tta | atg | tagaattatc | aggatgatgg | agtagagatc | actttcagga | | | | | | 2902 |
| Ile | Gln | Arg | Leu | Met | | | | | | | | | | |
| | | | 205 | | | | | | | | | | | |

| | | | | |
|---|---|---|---|---|
| aagatcacct | tgaggcctgc | ctcctttccc | tgggttgtga | tgtgatggca agagaatgca | 2962 |
| gcaactttga | gacctactcc | atgtgctatg | agcatgtgtt | gcatcatgct aggcagaggc | 3022 |
| tcagccagaa | agagcaagaa | ttagatgcta | cacaagagg | ccagggtcca cctgaagaca | 3082 |
| gtgctggcca | gattgcagag | ctcagtcatg | atatgatcat | ggaaatcacc actctgagag | 3142 |
| cccaactcac | agacttggaa | gaagtgaatc | tgaatctcaa | gaagcagatt agaaaagaag | 3202 |
| tccaagaaga | atatgaagca | ttagtccgag | ctttgtttga | gacctgttta cacataaaag | 3262 |
| agaagctgga | tgataatcag | cttaatttga | tccagaaagt | gtgtgagctc atcggtgaag | 3322 |
| tgagaacaga | agggattgac | aatatgaagg | acctaaagaa | aaaatggtgc tctgccagcc | 3382 |
| ccgatgaagg | aatgaaagaa | aacccagcca | acaggaaca | gctgtgggcc ttggagcagg | 3442 |
| acaactgcag | cctggccaac | ctggtgtgca | aagtgaggag | cctgggccgc tggaggctgg | 3502 |
| ctgtgcagca | ggcgtgcttc | caggcccagc | tgagcaggac | agagaaggaa tctattcaaa | 3562 |
| gtaaaaaaga | gtatttgcgc | atcaagctga | tggcagagcg | agaagtgggt ttatttcgtc | 3622 |
| agcaggtcct | ggctctcagg | caggccctgg | ccagggcaca | ggctgacagc gcgaggatgt | 3682 |
| ggaagcagca | ggacagccag | gctcaactgc | tgaaggagtt | agaacataga gtgacccagg | 3742 |
| aagctctcac | ccagcagcag | ctgcatttta | tgaaaacatc | caggatggag aagctcttgg | 3802 |
| aagatgtggg | gcaaaaagaa | cagcaactgc | agctccttag | caaagaggct gagagggctt | 3862 |
| ctaagctggg | ccaactgcag | cagaaaaaa | tgaagaggga | cctccaccag atgagaagcc | 3922 |
| ggcttgccca | ggagcgcagt | gtgaagctgg | atgctctcca | gcgtgcagag gagctgcagg | 3982 |
| gtcagcttca | cgatgcccag | cggtcagctg | tccccatggg | ctcgtcaggc gaccttatat | 4042 |
| cccaggctca | atactcccca | acttctgctt | ccacatcatc | cagatactcc cagcaacgct | 4102 |
| ttttaaagac | taatctcaaa | ggcagtaaaa | taacaagatg | gattcaaagg ccacagacta | 4162 |
| agccctttc | aaaagaagc | aaagttcact | ttgtatgtgt | gggatcacaa gggctttcaa | 4222 |
| gaatcacttc | atctccattt | caccctgaaa | gctgcaatac | catgggggtg ttggtgatcg | 4282 |
| tgacttgttg | aaaaggctgc | taagcagata | agtgcattag | tgaagattta ttatatttga | 4342 |
| gagattcaaa | agggtgatag | gctaaagcta | attgatgaac | attgccctac caaataaata | 4402 |

```
aaccctacag tgaagtgtct tgtgggccca ttggcccagt ggctatgtac aatacgggaa    4462
ccccaagcaa aaaacctcaa ggccagggaa ggtacacagt tagctggaac ttcagatctc    4522
aggtctgact tcttaagcaa ggcctatgag acaagtcaga taaatactca ttgaagagga    4582
atttatacat ggctgaaatg taagaacaca gttaattttc taaaaattag ccctgcacta    4642
acacaaatga taaaaaatta aggaattttt agattacttg aagtatgagc tgtgttttct    4702
tccttaactg gaaatggctt tccactgatg gattcattct tgaccaattc cctttaggac    4762
aatggcaaaa tacagacaag aaggcatact atatggccta acccagactg aatcaatgat    4822
cttggtctca ttaataacag tgacttttta tgatgctata acaagaatta ttcaccatgt    4882
tcttaacacc aatatctact tatattacag gtacctatta aacacaaaaa aagaactgac    4942
gatgttttcc tacccaatat ggcagaaaat gttcaactga cagcttttca ggttcaaaca    5002
gctccatcca gattcccatt tagagctgac tgg                                 5035
```

B:

```
Met Glu Ala Pro Gln Arg Gln Gln Ala Thr Leu Gly Lys Asn Thr Gln
1               5                   10                  15

Pro Asp Trp Ser Lys Val Pro Gly Phe Arg Ser Gln Phe Arg Ser Ser
            20                  25                  30

Pro Lys Thr Ser Glu Leu Leu Glu Gly Leu Cys Asp Ala Val Met Ser
            35                  40                  45

Phe Ala Leu Leu Arg Ser Phe Leu Ile Leu Trp Lys Gln Leu Glu Val
        50                  55                  60

Leu Lys Glu His Trp Gly Arg Leu Lys Leu Gln Gly Gln Asp Ile Asn
65                  70                  75                  80

Ser Val Ser Leu His Lys Arg Phe Ser Glu Leu Tyr Glu Thr Asp Val
                85                  90                  95

Leu Tyr Pro Ser Met Lys Ala Ile Ala Arg Gln Met Gly Lys Glu Asp
                100                 105                 110

Glu Phe Glu Gly Phe Ile Val Asn Asn Gln Ser Val Leu Pro Pro Ser
        115                 120                 125

Gly Ala Ser Glu Val Glu Ile Lys Thr His Gln Leu Gln Lys Leu Leu
        130                 135                 140

Glu Asn Cys Glu Ile Gln Met Ile Gln Glu Val Leu Arg Lys Val Asn
145                 150                 155                 160

Arg Glu Met Thr Leu Val Leu Ser Glu Lys Cys Lys Glu Glu Cys Ser
                165                 170                 175

Leu Pro Thr Asp Leu Trp Lys His Gln Val Met Lys Glu Asn Phe Ser
                180                 185                 190

Val Ser Arg Pro Gln Ile Val Glu Lys Phe Ile Gln Arg Leu Met
```

FIGURE 9: LUMA1 mRNA variant 9

Protein 3

A:

| | | | | | |
|---|---|---|---|---|---|
| gcaatgcgtg | ctatgggtcc | tttttctaa | cacttgcaga | agatttcagc | cccggccacg | 60 |
| atgtttgctg | tcagcggatg | gaaaagtctt | cctcaattta | tggttcatac | cccattcttc | 120 |
| tgaagtgctg | gttatgttca | aaactctgcc | agaaaaggca | gcttttaaag | ccttaaagcg | 180 |
| aactctacaa | ctgatagctc | ctctgcatga | tatcgtggcc | taccttgtca | gttttgctaa | 240 |
| gcttggcaat | tgtccagcat | gttttgaatt | tcctcgaagt | cccaaccctt | tgagaggtga | 300 |
| ctggggagga | actgagggca | ttgggtctga | gcttcaagag | ctgcagaaca | tgattgacag | 360 |
| cctccagagc | ccccaagacc | ctatccgggt | ggcccaggca | ctcctcctcc | ggagggaggt | 420 |
| tatattttg | cagtttgacg | ctgcagtaag | gcatctcatc | cgaagaacat | ttttggcagc | 480 |
| tggaaatgtt | cctgcctacc | agtctgtcac | agacggcatg | tgccatgggc | taccagcact | 540 |
| gagcaactct | ctcaggaaga | gcattttgc | ctcacagctc | agcctgcccc | agccactgga | 600 |
| tccacggagc | ctccaggcat | ttgagctgtt | tccttggaga | gcatttctgg | aagatggagg | 660 |
| accattccca | gttatgagta | acagcccaga | taccctagaa | tataatatgc | aggtaggata | 720 |
| ggtcttctcc | attgttgcag | agagaactga | gcgcagactg | caaagatggt | tgccattggg | 780 |
| ttcacaggtc | agatcctcct | actctcaccc | acgatgaata | atgtgtgaga | taagcagggt | 840 |
| gtttgatttt | gaggctgtaa | acccagggtc | acgaggtgag | tcacattttc | ttatgataga | 900 |
| agggaagcat | gctctcaact | ggcatgggcc | tgggttgtag | actcagctgc | agttttcgta | 960 |
| acagtagtga | tctgggagaa | tggccagtca | tctccagtca | tgggctgggc | ctcttagaga | 1020 |
| aactcccagg | ctggcagctc | agagatgtgt | gactcctgac | ctgtccataa | acagttgtgg | 1080 |
| gaagggaact | ttttaaagca | ggactcgtag | ggagaatttc | tttcattgt | ttcttttttt | 1140 |
| gctgttaact | tcctttaaat | agtttgattc | ttttcattat | taaatgtttt | ccctgatta | 1200 |
| tttaagtaaa | tattgttttt | atttaaaaaa | tagaaagctt | agaaagtat | taagaacaac | 1260 |
| atgaaaatca | accataaata | acgcttcaaa | acaatatgga | ggtggggagt | gggtgggatg | 1320 |
| gggtagcact | ggccacaggt | taatggttgt | tggggctggg | tgatgggaac | ttttctgttt | 1380 |
| gattctata | tattcaaaat | tatccataag | tagaacaggt | ttttaagta | aaatagtaaa | 1440 |
| agtggtctta | aaaattaac | catatggctg | ggtgtggtgg | ctcatgcctg | taatctcagc | 1500 |
| actttgggag | gccaaggtgg | gcagatctct | tgagctcagg | agttcaagac | cagcctgggc | 1560 |

```
aacaaggtga aagcctgtgt ctactgaaaa tgcaaaaatt agctgggtgt ggtggcacac    1620
gcctgtagtc ccagctactc agaaggctaa ggcatgagaa tcacctgaac ccaggagacg    1680
gaggttgcag tgagctgaga tcgtaccact gcactccagc ctggtgacag tgtaagactc    1740
tcttaaaaaa taaaataaaa taaaataaaa taaaaaatca accatagttc cacaactaag    1800
agacaattac agttcacatt ttatttccct ggtattttcc ctctgcatat gtgtgtttat    1860
atctgtactt ttaagggaaa attgatatca cactatacat tcaccatgta cagatctgct    1920
gtaagggctg gaaacttggc attttcatac agagccaaaa tttgatgtgc tcaaagaaaa    1980
ctttaagtta gaaatgttac tctggttttt atgaattttc tagcagttga gggaatgggt    2040
tcttgtaaat acagttactc ctagttttct tcctgaaaac catatgtaaa atatatatat    2100
ggtcttcaaa tggaaggttt ttttgttttt ttttagctgt gcctctgtgg gctgagtgac    2160
cgtgaccgca aggtggctca tggagaactg gtgggtgtgc aactgctact ggaagatgtt    2220
ctgagtagct atcatgtgac c atg gag gcc ccc caa aga cag caa gcc aca       2271
                         Met Glu Ala Pro Gln Arg Gln Gln Ala Thr
                           1               5                  10 ctg ggc aaa aat aca cag cca gat tgg tcc aaa gtg cca gga ttc aga       2319
Leu Gly Lys Asn Thr Gln Pro Asp Trp Ser Lys Val Pro Gly Phe Arg
                15                  20                  25 agt cag ttc cga agc agc cca aag acc tct gag ctg ctg gag ggc ctg       2367
Ser Gln Phe Arg Ser Ser Pro Lys Thr Ser Glu Leu Leu Glu Gly Leu
            30                  35                  40 tgc gat gcg gtg atg tcc ttt gct ttg ctg aga tca ttt ctg ata ctg       2415
Cys Asp Ala Val Met Ser Phe Ala Leu Leu Arg Ser Phe Leu Ile Leu
        45                  50                  55 tgg aag cag ctg gaa gtg cta aag gag cac tgg ggc cga ctc aag ctg       2463
Trp Lys Gln Leu Glu Val Leu Lys Glu His Trp Gly Arg Leu Lys Leu
    60                  65                  70 caa ggc cag gat atc aac tct gtc tct ctc cac aaa cgg ttt tca gag       2511
Gln Gly Gln Asp Ile Asn Ser Val Ser Leu His Lys Arg Phe Ser Glu
75                  80                  85                  90 ctc tat gaa act gac gtt ctc tac ccc agc atg aaa gct ata gcc agg       2559
Leu Tyr Glu Thr Asp Val Leu Tyr Pro Ser Met Lys Ala Ile Ala Arg
                95                  100                 105 cag atg ggg aaa gaa gat gaa ttt gaa gga ttt ata gta aat aat cag       2607
Gln Met Gly Lys Glu Asp Glu Phe Glu Gly Phe Ile Val Asn Asn Gln
            110                 115                 120 tct gtt ctt ccc ccc agt gga gcc tca gaa gtt gaa ata aaa act cac       2655
Ser Val Leu Pro Pro Ser Gly Ala Ser Glu Val Glu Ile Lys Thr His
        125                 130                 135 caa ctt caa aaa ctt ctg gaa aat tgt gaa att caa atg atc caa gag       2703
Gln Leu Gln Lys Leu Leu Glu Asn Cys Glu Ile Gln Met Ile Gln Glu
    140                 145                 150
```

```
gta cta aga aaa gtt aac aga gaa atg aca ctg gtt tta tca gaa aag      2751
Val Leu Arg Lys Val Asn Arg Glu Met Thr Leu Val Leu Ser Glu Lys
155                 160                 165                 170 tgc aag gag gag tgt tct ctc cct aca gat ctc tgg aaa cac caa gtc      2799
Cys Lys Glu Glu Cys Ser Leu Pro Thr Asp Leu Trp Lys His Gln Val
            175                 180                 185 atg aaa gaa aac ttt tca gtc tca aga cca caa ata gtt gaa aaa ttt      2847
Met Lys Glu Asn Phe Ser Val Ser Arg Pro Gln Ile Val Glu Lys Phe
        190                 195                 200 ata cag aga tta atg gag aat tat cag gat gat gga gta gag atc act      2895
Ile Gln Arg Leu Met Glu Asn Tyr Gln Asp Asp Gly Val Glu Ile Thr
    205                 210                 215 ttc agg aaa gat cac ctt gag gcc tgc ctc ctt tcc ctg ggt tgt gat      2943
Phe Arg Lys Asp His Leu Glu Ala Cys Leu Leu Ser Leu Gly Cys Asp
220                 225                 230 gtg atg gca aga gaa tgc agc aac ttt gag acc tac tcc atg tgc tat      2991
Val Met Ala Arg Glu Cys Ser Asn Phe Glu Thr Tyr Ser Met Cys Tyr
235                 240                 245                 250 gag cat gtg ttg cat cat gct agg cag agg ctc agc cag aaa gag caa      3039
Glu His Val Leu His His Ala Arg Gln Arg Leu Ser Gln Lys Glu Gln
            255                 260                 265 gaa tta gat gct aca caa aga ggc cag ggt cca cct gaa gac agt gct      3087
Glu Leu Asp Ala Thr Gln Arg Gly Gln Gly Pro Pro Glu Asp Ser Ala
        270                 275                 280 ggc cag att gca gag ctc agt cat gat atg atc atg gaa atc acc act      3135
Gly Gln Ile Ala Glu Leu Ser His Asp Met Ile Met Glu Ile Thr Thr
    285                 290                 295 ctg aga gcc caa ctc aca gac ttg gaa gaa gtg aat ctg aat ctc aag      3183
Leu Arg Ala Gln Leu Thr Asp Leu Glu Glu Val Asn Leu Asn Leu Lys
300                 305                 310 aag cag att aga aaa gaa gtc caa gaa gaa tat gaa gca tta gtc cga      3231
Lys Gln Ile Arg Lys Glu Val Gln Glu Glu Tyr Glu Ala Leu Val Arg
315                 320                 325                 330 gct ttg ttt gag acc tgt tta cac ata aaa gag aag ctg gat gat aat      3279
Ala Leu Phe Glu Thr Cys Leu His Ile Lys Glu Lys Leu Asp Asp Asn
            335                 340                 345 cag ctt aat ttg atc cag aaa gtg tgt gag ctc atc ggt gaa gtg aga      3327
Gln Leu Asn Leu Ile Gln Lys Val Cys Glu Leu Ile Gly Glu Val Arg
        350                 355                 360 aca gaa ggg att gac aat atg aag gac cta aag aaa aaa tgg tgc tct      3375
Thr Glu Gly Ile Asp Asn Met Lys Asp Leu Lys Lys Lys Trp Cys Ser
    365                 370                 375 gcc agc ccc gat gaa gga atg aaa gaa aac cca gcc aaa cag gaa cag      3423
Ala Ser Pro Asp Glu Gly Met Lys Glu Asn Pro Ala Lys Gln Glu Gln
380                 385                 390 ctg tgg gcc ttg gag cag gac aac tgc agc ctg gcc aac ctg gtg tgc      3471
Leu Trp Ala Leu Glu Gln Asp Asn Cys Ser Leu Ala Asn Leu Val Cys
```

```
      395                      400                      405                      410
aaa gtg agg agc ctg ggc cgc tgg agg ctg gct gtg cag cag gcg tgc                3519
Lys Val Arg Ser Leu Gly Arg Trp Arg Leu Ala Val Gln Gln Ala Cys
                415                      420                      425 ttc cag gcc cag ctg agc agg aca gag aag gaa tct att caa agt aaa                3567
Phe Gln Ala Gln Leu Ser Arg Thr Glu Lys Glu Ser Ile Gln Ser Lys
                430                      435                      440 aaa gag tat ttg cgc atc aag ctg atg gca gag cga gaa gtg ggt tta                3615
Lys Glu Tyr Leu Arg Ile Lys Leu Met Ala Glu Arg Glu Val Gly Leu
                445                      450                      455 ttt cgt cag cag gtc ctg gct ctc agg cag gcc ctg gcc agg gca cag                3663
Phe Arg Gln Gln Val Leu Ala Leu Arg Gln Ala Leu Ala Arg Ala Gln
    460                      465                      470 gct gac agc gcg agg atg tgg aag cag cag gac agc cag gct caa ctg                3711
Ala Asp Ser Ala Arg Met Trp Lys Gln Gln Asp Ser Gln Ala Gln Leu
475                      480                      485                      490 ctg aag gag tta gaa cat aga gtg acc cag gaa gct ctc acc cag cag                3759
Leu Lys Glu Leu Glu His Arg Val Thr Gln Glu Ala Leu Thr Gln Gln
                495                      500                      505 cag ctg cat ttt atg aaa aca tcc agg atg gag aag ctc ttg gaa gat                3807
Gln Leu His Phe Met Lys Thr Ser Arg Met Glu Lys Leu Leu Glu Asp
                510                      515                      520 gtg ggg caa aaa gaa cag caa ctg cag ctc ctt agc aaa gag gct gag                3855
Val Gly Gln Lys Glu Gln Gln Leu Gln Leu Leu Ser Lys Glu Ala Glu
                525                      530                      535 agg gct tct aag ctg ggc caa ctg cag cag aaa aaa atg aag agg gac                3903
Arg Ala Ser Lys Leu Gly Gln Leu Gln Gln Lys Lys Met Lys Arg Asp
                540                      545                      550 ctc cac cag atg aga agc cgg ctt gcc cag gag cgc agt gtg aag ctg                3951
Leu His Gln Met Arg Ser Arg Leu Ala Gln Glu Arg Ser Val Lys Leu
555                      560                      565                      570 gat gct ctc cag cgt gca gag gag ctg cag ggt cag ctt cac gat gcc                3999
Asp Ala Leu Gln Arg Ala Glu Glu Leu Gln Gly Gln Leu His Asp Ala
                575                      580                      585 cag cgg tca gct gtc ccc atg ggc tcg tca ggc gac ctt ata tcc cag                4047
Gln Arg Ser Ala Val Pro Met Gly Ser Ser Gly Asp Leu Ile Ser Gln
                590                      595                      600 gct caa tac tcc cca act tct gct tcc aca tca tcc aga tac tcc cag                4095
Ala Gln Tyr Ser Pro Thr Ser Ala Ser Thr Ser Ser Arg Tyr Ser Gln
                605                      610                      615 caa cgc ttt tta aag act aat ctc aaa ggc agt aaa ata aca aga tgg                4143
Gln Arg Phe Leu Lys Thr Asn Leu Lys Gly Ser Lys Ile Thr Arg Trp
                620                      625                      630 att caa agg cca cag act aag ccc ttt tca aaa aga agc aaa gtt cac                4191
Ile Gln Arg Pro Gln Thr Lys Pro Phe Ser Lys Arg Ser Lys Val His
635                      640                      645                      650
```

| | | | | | | | | | | | | | | |
|---|---|---|---|---|---|---|---|---|---|---|---|---|---|---|
| ttt | gta | tgt | gtg | gga | tca | caa | ggg | ctt | tca | aga | atc | act | tca tct cca | 4239 |
| Phe | Val | Cys | Val | Gly | Ser | Gln | Gly | Leu | Ser | Arg | Ile | Thr | Ser Ser Pro | |
| | | | | 655 | | | | | 660 | | | | 665 | |

| | | | | | | | | | | | | | | |
|---|---|---|---|---|---|---|---|---|---|---|---|---|---|---|
| ttt | cac | cct | gaa | agc | tgc | aat | acc | atg | ggg | gtg | ttg | gtg | atc gtg act | 4287 |
| Phe | His | Pro | Glu | Ser | Cys | Asn | Thr | Met | Gly | Val | Leu | Val | Ile Val Thr | |
| | | | 670 | | | | | 675 | | | | | 680 | | tgt tgaaaggct gctaagcaga taagtgcatt agtgaagatt tattatattt         4340
Cys gagagattca aaagggtgat aggctaaagc taattgatga acattgccct accaaataaa 4400
taaaccctac agtgaagtgt cttgtgggcc cattggccca gtggctatgt acaatacggg 4460
aaccccaagc aaaaacctc aaggccaggg aaggtacaca gttagctgga acttcagatc  4520
tcaggtctga cttcttaagc aaggcctatg agacaagtca gataaatact cattgaagag 4580
gaatttatac atggctgaaa tgtaagaaca cagttaattt tctaaaaatt agccctgcac 4640
taacacaaat gataaaaaat taaggaattt ttagattact tgaagtatga gctgtgtttt 4700
cttccttaac tggaaatggc tttccactga tggattcatt cttgaccaat tccctttagg 4760
acaatggcaa aatacagaca agaaggcata ctatatggcc taacccagac tgaatcaatg 4820
atcttggtct cattaataac agtgactttt tatgatgcta taacaagaat tattcaccat 4880
gttcttaaca ccaatatcta cttatattac aggtacctat taaacacaaa aaaagaactg 4940
acgatgtttt cctacccaat atggcagaaa atgttcaact gacagctttt caggttcaaa 5000
cagctccatc cagattccca tttagagctg actgg                            5035

B:

| | | | | | | | | | | | | | | |
|---|---|---|---|---|---|---|---|---|---|---|---|---|---|---|
| Met | Glu | Ala | Pro | Gln | Arg | Gln | Gln | Ala | Thr | Leu | Gly | Lys | Asn | Thr Gln |
| 1 | | | | 5 | | | | | 10 | | | | 15 | |

| | | | | | | | | | | | |
|---|---|---|---|---|---|---|---|---|---|---|---|
| Pro | Asp | Trp | Ser | Lys | Val | Pro | Gly | Phe | Arg | Ser Gln Phe Arg Ser Ser |
| | | | 20 | | | | 25 | | | 30 |

Pro Lys Thr Ser Glu Leu Leu Glu Gly Leu Cys Asp Ala Val Met Ser
         35              40              45

Phe Ala Leu Leu Arg Ser Phe Leu Ile Leu Trp Lys Gln Leu Glu Val
50                  55              60

Leu Lys Glu His Trp Gly Arg Leu Lys Leu Gln Gly Gln Asp Ile Asn
65              70              75              80

Ser Val Ser Leu His Lys Arg Phe Ser Glu Leu Tyr Glu Thr Asp Val
                85              90              95

Leu Tyr Pro Ser Met Lys Ala Ile Ala Arg Gln Met Gly Lys Glu Asp
             100             105             110

Glu Phe Glu Gly Phe Ile Val Asn Asn Gln Ser Val Leu Pro Pro Ser
         115             120             125

```
Gly Ala Ser Glu Val Glu Ile Lys Thr His Gln Leu Gln Lys Leu Leu
    130                 135                 140

Glu Asn Cys Glu Ile Gln Met Ile Gln Glu Val Leu Arg Lys Val Asn
145                 150                 155                 160

Arg Glu Met Thr Leu Val Leu Ser Glu Lys Cys Lys Glu Glu Cys Ser
                165                 170                 175

Leu Pro Thr Asp Leu Trp Lys His Gln Val Met Lys Glu Asn Phe Ser
                180                 185                 190

Val Ser Arg Pro Gln Ile Val Glu Lys Phe Ile Gln Arg Leu Met Glu
            195                 200                 205

Asn Tyr Gln Asp Asp Gly Val Glu Ile Thr Phe Arg Lys Asp His Leu
        210                 215                 220

Glu Ala Cys Leu Leu Ser Leu Gly Cys Asp Val Met Ala Arg Glu Cys
225                 230                 235                 240

Ser Asn Phe Glu Thr Tyr Ser Met Cys Tyr Glu His Val Leu His His
                245                 250                 255

Ala Arg Gln Arg Leu Ser Gln Lys Glu Gln Glu Leu Asp Ala Thr Gln
            260                 265                 270

Arg Gly Gln Gly Pro Pro Glu Asp Ser Ala Gly Gln Ile Ala Glu Leu
        275                 280                 285

Ser His Asp Met Ile Met Glu Ile Thr Thr Leu Arg Ala Gln Leu Thr
    290                 295                 300

Asp Leu Glu Glu Val Asn Leu Asn Leu Lys Lys Gln Ile Arg Lys Glu
305                 310                 315                 320

Val Gln Glu Glu Tyr Glu Ala Leu Val Arg Ala Leu Phe Glu Thr Cys
                325                 330                 335

Leu His Ile Lys Glu Lys Leu Asp Asp Asn Gln Leu Asn Leu Ile Gln
            340                 345                 350

Lys Val Cys Glu Leu Ile Gly Glu Val Arg Thr Glu Gly Ile Asp Asn
        355                 360                 365

Met Lys Asp Leu Lys Lys Lys Trp Cys Ser Ala Ser Pro Asp Glu Gly
    370                 375                 380

Met Lys Glu Asn Pro Ala Lys Gln Glu Gln Leu Trp Ala Leu Glu Gln
385                 390                 395                 400

Asp Asn Cys Ser Leu Ala Asn Leu Val Cys Lys Val Arg Ser Leu Gly
                405                 410                 415

Arg Trp Arg Leu Ala Val Gln Gln Ala Cys Phe Gln Ala Gln Leu Ser
            420                 425                 430

Arg Thr Glu Lys Glu Ser Ile Gln Ser Lys Lys Glu Tyr Leu Arg Ile
        435                 440                 445
```

```
Lys Leu Met Ala Glu Arg Glu Val Gly Leu Phe Arg Gln Gln Val Leu
    450                 455                 460

Ala Leu Arg Gln Ala Leu Ala Arg Ala Gln Ala Asp Ser Ala Arg Met
465                 470                 475                 480

Trp Lys Gln Gln Asp Ser Gln Ala Gln Leu Leu Lys Glu Leu Glu His
                485                 490                 495

Arg Val Thr Gln Glu Ala Leu Thr Gln Gln Leu His Phe Met Lys
            500                 505                 510

Thr Ser Arg Met Glu Lys Leu Leu Glu Asp Val Gly Gln Lys Glu Gln
        515                 520                 525

Gln Leu Gln Leu Leu Ser Lys Glu Ala Glu Arg Ala Ser Lys Leu Gly
    530                 535                 540

Gln Leu Gln Gln Lys Lys Met Lys Arg Asp Leu His Gln Met Arg Ser
545                 550                 555                 560

Arg Leu Ala Gln Glu Arg Ser Val Lys Leu Asp Ala Leu Gln Arg Ala
                565                 570                 575

Glu Glu Leu Gln Gly Gln Leu His Asp Ala Gln Arg Ser Ala Val Pro
            580                 585                 590

Met Gly Ser Ser Gly Asp Leu Ile Ser Gln Ala Gln Tyr Ser Pro Thr
        595                 600                 605

Ser Ala Ser Thr Ser Ser Arg Tyr Ser Gln Gln Arg Phe Leu Lys Thr
    610                 615                 620

Asn Leu Lys Gly Ser Lys Ile Thr Arg Trp Ile Gln Arg Pro Gln Thr
625                 630                 635                 640

Lys Pro Phe Ser Lys Arg Ser Lys Val His Phe Val Cys Val Gly Ser
                645                 650                 655

Gln Gly Leu Ser Arg Ile Thr Ser Ser Pro Phe His Pro Glu Ser Cys
            660                 665                 670

Asn Thr Met Gly Val Leu Val Ile Val Thr Cys
        675                 680
```

FIGURE 10: LUMA1 mRNA variant 10

Protein 4

A:

```
gcaatgcgtg ctatgggtcc ttttttctaa cacttgcaga agatttcagc cccggccacg    60
atgtttgctg tcagcggatg gaaagtctt cctcaattta tggttcatac cccattcttc    120
tgaagtgctg gttatgttca aactctgcc agaaaaggca gcttttaaag ccttaaagcg    180
aactctacaa ctgatagctc ctctgcatga tatcgtggcc taccttgtca gttttgctaa    240
```

| | | | | |
|---|---|---|---|---|
| gcttggcaat | tgtccagcat | gttttgaatt | tcctcgaagt | cccaacccttt tgagaggtga | 300 |
| ctggggagga | actgagggca | ttgggtctga | gcttcaagag | ctgcagaaca tgattgacag | 360 |
| cctccagagc | ccccaagacc | ctatccgggt | ggcccaggca | ctcctcctcc ggagggaggt | 420 |
| tatattttg | cagtttgacg | ctgcagtaag | gcatctcatc | cgaagaacat ttttggcagc | 480 |
| tggaaatgtt | cctgcctacc | agtctgtcac | agacggcatg | tgccatgggc taccagcact | 540 |
| gagcaactct | ctcaggaaga | gcattttgc | ctcacagctc | agcctgcccc agccactgga | 600 |
| tccacggagc | ctccaggcat | ttgagctgtt | tccttggaga | gcatttctgg aagatggagg | 660 |
| accattccca | gttatgagta | acagcccaga | taccctagaa | tataatatgc aggtaggata | 720 |
| ggtcttctcc | attgttgcag | agagaactga | gcgcagactg | caaagatggt tgccattggg | 780 |
| ttcacaggtc | agatcctcct | actctcaccc | acgatgaata | atgtgtgaga taagcagggt | 840 |
| gtttgatttt | gaggctgtaa | acccagggtc | acgaggtgag | tcacattttc ttatgataga | 900 |
| agggaagcat | gctctcaact | ggcatgggcc | tgggttgtag | actcagctgc agttttcgta | 960 |
| acagtagtga | tctgggagaa | tggccagtca | tctccagtca | tgggctgggc ctcttagaga | 1020 |
| aactcccagg | ctggcagctc | agagatgtgt | gactcctgac | ctgtccataa acagttgtgg | 1080 |
| gaagggaact | ttttaaagca | ggactcgtag | ggagaatttc | ttttcattgt ttctttttt | 1140 |
| gctgttaact | tcctttaaat | agtttgattc | ttttcattat | taaatgtttt ccctgatta | 1200 |
| tttaagtaaa | tattgttttt | atttaaaaaa | tagaaagctt | agaaagtat taagaacaac | 1260 |
| atgaaaatca | accataaata | acgcttcaaa | acaatatgga | ggtggggagt gggtgggatg | 1320 |
| gggtagcact | ggccacaggt | taatggttgt | tggggctggg | tgatgggaac ttttctgttt | 1380 |
| gatttctata | tattcaaaat | tatccataag | tagaacaggt | ttttaagta aatagtaaa | 1440 |
| agtggtctta | aaaaattaac | catatggctg | ggtgtggtgg | ctcatgcctg taatctcagc | 1500 |
| actttgggag | gccaaggtgg | gcagatctct | tgagctcagg | agttcaagac cagcctgggc | 1560 |
| aacaaggtga | aagcctgtgt | ctactgaaaa | tgcaaaaatt | agctgggtgt ggtggcacac | 1620 |
| gcctgtagtc | ccagctactc | agaaggctaa | ggcatgagaa | tcacctgaac ccaggagacg | 1680 |
| gaggttgcag | tgagctgaga | tcgtaccact | gcactccagc | ctggtgacag tgtaagactc | 1740 |
| tcttaaaaaa | taaataaaa | taaaataaaa | taaaaaatca | accatagttc cacaactaag | 1800 |
| agacaattac | agttcacatt | ttatttccct | ggtattttcc | ctctgcatat gtgtgtttat | 1860 |
| atctgtactt | ttaagggaaa | attgatatca | cactatacat | tcaccatgta cagatctgct | 1920 |
| gtaagggctg | gaaacttggc | attttcatac | agagccaaaa | tttgatgtgc tcaaagaaaa | 1980 |
| ctttaagtta | gaaatgttac | tctggttttt | atgaattttc | tagcagttga gggaatgggt | 2040 |
| tcttgtaaat | acagttactc | ctagttttct | tcctgaaaac | catatgtaaa atatatatat | 2100 |

```
ggtcttcaaa tggaaggttt ttttgttttt ttttagctgt gcctctgtgg gctgagtgac   2160
cgtgaccgca aggtggctca tggagaactg gtgggtgtgc aactgctact ggaagatgtt   2220
ctgagtagct atcatgtgac catggaggcc ccccaaagac agcaagccac actgggcaaa   2280
aatacacagc cagattggtc caaagtgcca ggattcagaa gtcagttccg aagcagccca   2340
aagacctctg agctgctgga gggcctgtgc gatgcggtga tgtcctttgc tttgctgaga   2400
tcatttctga tactgtggaa gcagctggaa gtgctaaagg agcactgggg ccgactcaag   2460
ctgcaaggcc aggatatcaa ctctgtctct ctccacaaac ggttttcaga gctctatgaa   2520
actgacgttc tctacccag catgaaagct atagccaggc agatggggaa agaagatgaa   2580
tttgaaggat ttatagtaaa taatcagtct gttcttcccc ccagtggagc ctcagaagtt   2640
gaaataaaaa ctcaccaact tcaaaaactt ctggaaaatt gtgaaattca aatgatccaa   2700
gaggtactaa gaaaagttaa cagagaaatg acactggttt tatcagaaaa gtgcaaggag   2760
gagtgttctc tccctacaga tctctggaaa caccaagtca tgaaagaaaa cttttcagtc   2820
tcaagaccac aaatagttga aaaatttata cagagattaa tgtagaatta tcaggatgat   2880
ggagtagaga tcactttcag gaaagatcac cttgaggcct gcctcctttc cctgggttgt   2940 gatgtg atg gca aga gaa tgc agc aac ttt gag acc tac tcc atg tgc       2988
       Met Ala Arg Glu Cys Ser Asn Phe Glu Thr Tyr Ser Met Cys
       1               5                   10 tat gag cat gtg ttg cat cat gct agg cag agg ctc agc cag aaa gag      3036
Tyr Glu His Val Leu His His Ala Arg Gln Arg Leu Ser Gln Lys Glu
15              20                  25                  30 caa gaa tta gat gct aca caa aga ggc cag ggt cca cct gaa gac agt      3084
Gln Glu Leu Asp Ala Thr Gln Arg Gly Gln Gly Pro Pro Glu Asp Ser
                35                  40                  45 gct ggc cag att gca gag ctc agt cat gat atg atc atg gaa atc acc      3132
Ala Gly Gln Ile Ala Glu Leu Ser His Asp Met Ile Met Glu Ile Thr
            50                  55                  60 act ctg aga gcc caa ctc aca gac ttg gaa gaa gtg aat ctg aat ctc      3180
Thr Leu Arg Ala Gln Leu Thr Asp Leu Glu Glu Val Asn Leu Asn Leu
65                  70                  75 aag aag cag att aga aaa gaa gtc caa gaa gaa tat gaa gca tta gtc      3228
Lys Lys Gln Ile Arg Lys Glu Val Gln Glu Glu Tyr Glu Ala Leu Val
    80                  85                  90 cga gct ttg ttt gag acc tgt tta cac ata aaa gag aag ctg gat gat      3276
Arg Ala Leu Phe Glu Thr Cys Leu His Ile Lys Glu Lys Leu Asp Asp
95                  100                 105                 110 aat cag ctt aat ttg atc cag aaa gtg tgt gag ctc atc ggt gaa gtg      3324
Asn Gln Leu Asn Leu Ile Gln Lys Val Cys Glu Leu Ile Gly Glu Val
                115                 120                 125 aga aca gaa ggg att gac aat atg aag gac cta aag aaa aaa tgg tgc      3372
Arg Thr Glu Gly Ile Asp Asn Met Lys Asp Leu Lys Lys Lys Trp Cys
```

|     |     |     |     |     |     |     |     |     |     |     |     |     |     |     |     |
|-----|-----|-----|-----|-----|-----|-----|-----|-----|-----|-----|-----|-----|-----|-----|-----|
|     |     |     |     | 130 |     |     |     | 135 |     |     |     | 140 |     |     |     |
| tct | gcc | agc | ccc | gat | gaa | gga | atg | aaa | gaa | aac | cca | gcc | aaa | cag | gaa | 3420
| Ser | Ala | Ser | Pro | Asp | Glu | Gly | Met | Lys | Glu | Asn | Pro | Ala | Lys | Gln | Glu |
|     |     | 145 |     |     |     |     | 150 |     |     |     |     | 155 |     |     |     |
| cag | ctg | tgg | gcc | ttg | gag | cag | gac | aac | tgc | agc | ctg | gcc | aac | ctg | gtg | 3468
| Gln | Leu | Trp | Ala | Leu | Glu | Gln | Asp | Asn | Cys | Ser | Leu | Ala | Asn | Leu | Val |
|     | 160 |     |     |     |     | 165 |     |     |     |     | 170 |     |     |     |     |
| tgc | aaa | gtg | agg | agc | ctg | ggc | cgc | tgg | agg | ctg | gct | gtg | cag | cag | gcg | 3516
| Cys | Lys | Val | Arg | Ser | Leu | Gly | Arg | Trp | Arg | Leu | Ala | Val | Gln | Gln | Ala |
| 175 |     |     |     |     | 180 |     |     |     |     | 185 |     |     |     |     | 190 |
| tgc | ttc | cag | gcc | cag | ctg | agc | agg | aca | gag | aag | gaa | tct | att | caa | agt | 3564
| Cys | Phe | Gln | Ala | Gln | Leu | Ser | Arg | Thr | Glu | Lys | Glu | Ser | Ile | Gln | Ser |
|     |     |     |     | 195 |     |     |     |     | 200 |     |     |     |     | 205 |     |
| aaa | aaa | gag | tat | ttg | cgc | atc | aag | ctg | atg | gca | gag | cga | gaa | gtg | ggt | 3612
| Lys | Lys | Glu | Tyr | Leu | Arg | Ile | Lys | Leu | Met | Ala | Glu | Arg | Glu | Val | Gly |
|     |     |     | 210 |     |     |     |     | 215 |     |     |     |     | 220 |     |     |
| tta | ttt | cgt | cag | cag | gtc | ctg | gct | ctc | agg | cag | gcc | ctg | gcc | agg | gca | 3660
| Leu | Phe | Arg | Gln | Gln | Val | Leu | Ala | Leu | Arg | Gln | Ala | Leu | Ala | Arg | Ala |
|     |     | 225 |     |     |     |     | 230 |     |     |     |     | 235 |     |     |     |
| cag | gct | gac | agc | gcg | agg | atg | tgg | aag | cag | cag | gac | agc | cag | gct | caa | 3708
| Gln | Ala | Asp | Ser | Ala | Arg | Met | Trp | Lys | Gln | Gln | Asp | Ser | Gln | Ala | Gln |
|     | 240 |     |     |     |     | 245 |     |     |     |     | 250 |     |     |     |     |
| ctg | ctg | aag | gag | tta | gaa | cat | aga | gtg | acc | cag | gaa | gct | ctc | acc | cag | 3756
| Leu | Leu | Lys | Glu | Leu | Glu | His | Arg | Val | Thr | Gln | Glu | Ala | Leu | Thr | Gln |
| 255 |     |     |     |     | 260 |     |     |     |     | 265 |     |     |     |     | 270 |
| cag | cag | ctg | cat | ttt | atg | aaa | aca | tcc | agg | atg | gag | aag | ctc | ttg | gaa | 3804
| Gln | Gln | Leu | His | Phe | Met | Lys | Thr | Ser | Arg | Met | Glu | Lys | Leu | Leu | Glu |
|     |     |     |     | 275 |     |     |     |     | 280 |     |     |     |     | 285 |     |
| gat | gtg | ggg | caa | aaa | gaa | cag | caa | ctg | cag | ctc | ctt | agc | aaa | gag | gct | 3852
| Asp | Val | Gly | Gln | Lys | Glu | Gln | Gln | Leu | Gln | Leu | Leu | Ser | Lys | Glu | Ala |
|     |     |     | 290 |     |     |     |     | 295 |     |     |     |     | 300 |     |     |
| gag | agg | gct | tct | aag | ctg | ggc | caa | ctg | cag | cag | aaa | aaa | atg | aag | agg | 3900
| Glu | Arg | Ala | Ser | Lys | Leu | Gly | Gln | Leu | Gln | Gln | Lys | Lys | Met | Lys | Arg |
|     |     | 305 |     |     |     |     | 310 |     |     |     |     | 315 |     |     |     |
| gac | ctc | cac | cag | atg | aga | agc | cgg | ctt | gcc | cag | gag | cgc | agt | gtg | aag | 3948
| Asp | Leu | His | Gln | Met | Arg | Ser | Arg | Leu | Ala | Gln | Glu | Arg | Ser | Val | Lys |
|     | 320 |     |     |     |     | 325 |     |     |     |     | 330 |     |     |     |     |
| ctg | gat | gct | ctc | cag | cgt | gca | gag | gag | ctg | cag | ggt | cag | ctt | cac | gat | 3996
| Leu | Asp | Ala | Leu | Gln | Arg | Ala | Glu | Glu | Leu | Gln | Gly | Gln | Leu | His | Asp |
| 335 |     |     |     |     | 340 |     |     |     |     | 345 |     |     |     |     | 350 |
| gcc | cag | cgg | tca | gct | gtc | ccc | atg | ggc | tcg | tca | ggc | gac | ctt | ata | tcc | 4044
| Ala | Gln | Arg | Ser | Ala | Val | Pro | Met | Gly | Ser | Ser | Gly | Asp | Leu | Ile | Ser |
|     |     |     |     | 355 |     |     |     |     | 360 |     |     |     |     | 365 |     |
| cag | gct | caa | tac | tcc | cca | act | tct | gct | tcc | aca | tca | tcc | aga | tac | tcc | 4092
| Gln | Ala | Gln | Tyr | Ser | Pro | Thr | Ser | Ala | Ser | Thr | Ser | Ser | Arg | Tyr | Ser |
|     |     |     | 370 |     |     |     |     | 375 |     |     |     |     | 380 |     |     |

| | | | | | | | | | | | | | | |
|---|---|---|---|---|---|---|---|---|---|---|---|---|---|---|
| cag | caa | cgc | ttt | tta | aag | act | aat | ctc | aaa | ggc | agt | aaa | ata | aca | aga | 4140 |
| Gln | Gln | Arg | Phe | Leu | Lys | Thr | Asn | Leu | Lys | Gly | Ser | Lys | Ile | Thr | Arg | |
| | | 385 | | | | | 390 | | | | | 395 | | | | |
| tgg | att | caa | agg | cca | cag | act | aag | ccc | ttt | tca | aaa | aga | agc | aaa | gtt | 4188 |
| Trp | Ile | Gln | Arg | Pro | Gln | Thr | Lys | Pro | Phe | Ser | Lys | Arg | Ser | Lys | Val | |
| | 400 | | | | | 405 | | | | | 410 | | | | | |
| cac | ttt | gta | tgt | gtg | gga | tca | caa | ggg | ctt | tca | aga | atc | act | tca | tct | 4236 |
| His | Phe | Val | Cys | Val | Gly | Ser | Gln | Gly | Leu | Ser | Arg | Ile | Thr | Ser | Ser | |
| 415 | | | | 420 | | | | | 425 | | | | | 430 | | |
| cca | ttt | cac | cct | gaa | agc | tgc | aat | acc | atg | ggg | gtg | ttg | gtg | atc | gtg | 4284 |
| Pro | Phe | His | Pro | Glu | Ser | Cys | Asn | Thr | Met | Gly | Val | Leu | Val | Ile | Val | |
| | | | | 435 | | | | | 440 | | | | | 445 | | |
| act | tgt | tgaaaaggct | | gctaagcaga | | taagtgcatt | | agtgaagatt | | tattatattt | | | | | | 4340 |
| Thr | Cys | | | | | | | | | | | | | | | |

| | | |
|---|---|---|
| gagagattca aaagggtgat aggctaaagc taattgatga acattgccct accaaataaa | 4400 |
| taaaccctac agtgaagtgt cttgtgggcc cattggccca gtggctatgt acaatacggg | 4460 |
| aaccccaagc aaaaaacctc aaggccaggg aaggtacaca gttagctgga acttcagatc | 4520 |
| tcaggtctga cttcttaagc aaggcctatg agacaagtca gataaatact cattgaagag | 4580 |
| gaattatac atggctgaaa tgtaagaaca cagttaattt tctaaaaatt agccctgcac | 4640 |
| taacacaaat gataaaaaat taaggaattt ttagattact tgaagtatga gctgtgtttt | 4700 |
| cttccttaac tggaaatggc tttccactga tggattcatt cttgaccaat tccctttagg | 4760 |
| acaatggcaa aatacagaca agaaggcata ctatatggcc taacccagac tgaatcaatg | 4820 |
| atcttggtct cattaataac agtgactttt tatgatgcta taacaagaat tattcaccat | 4880 |
| gttcttaaca ccaatatcta cttatattac aggtacctat taaacacaaa aaaagaactg | 4940 |
| acgatgtttt cctacccaat atggcagaaa atgttcaact gacagctttt caggttcaaa | 5000 |
| cagctccatc cagattccca tttagagctg actgg | 5035 |

B:

| | | | | | | | | | | | | | | |
|---|---|---|---|---|---|---|---|---|---|---|---|---|---|---|
| Met | Ala | Arg | Glu | Cys | Ser | Asn | Phe | Glu | Thr | Tyr | Ser | Met | Cys | Tyr | Glu |
| 1 | | | | 5 | | | | | 10 | | | | | 15 | |
| His | Val | Leu | His | His | Ala | Arg | Gln | Arg | Leu | Ser | Gln | Lys | Glu | Gln | Glu |
| | | | 20 | | | | | 25 | | | | | 30 | | |
| Leu | Asp | Ala | Thr | Gln | Arg | Gly | Gln | Gly | Pro | Pro | Glu | Asp | Ser | Ala | Gly |
| | | | 35 | | | | 40 | | | | | 45 | | | |
| Gln | Ile | Ala | Glu | Leu | Ser | His | Asp | Met | Ile | Met | Glu | Ile | Thr | Thr | Leu |
| | | | 50 | | | | 55 | | | | | 60 | | | |
| Arg | Ala | Gln | Leu | Thr | Asp | Leu | Glu | Glu | Val | Asn | Leu | Asn | Leu | Lys | Lys |
| 65 | | | | | 70 | | | | | 75 | | | | | 80 |
| Gln | Ile | Arg | Lys | Glu | Val | Gln | Glu | Glu | Tyr | Glu | Ala | Leu | Val | Arg | Ala |

```
                          85                    90                       95
       Leu Phe Glu Thr Cys Leu His Ile Lys Glu Lys Leu Asp Asp Asn Gln
                   100               105               110

Leu Asn Leu Ile Gln Lys Val Cys Glu Leu Ile Gly Glu Val Arg Thr
                   115               120               125

Glu Gly Ile Asp Asn Met Lys Asp Leu Lys Lys Lys Trp Cys Ser Ala
                   130               135               140

Ser Pro Asp Glu Gly Met Lys Glu Asn Pro Ala Lys Gln Glu Gln Leu
       145               150               155                       160

Trp Ala Leu Glu Gln Asp Asn Cys Ser Leu Ala Asn Leu Val Cys Lys
                             165               170               175

Val Arg Ser Leu Gly Arg Trp Arg Leu Ala Val Gln Gln Ala Cys Phe
                             180               185               190

Gln Ala Gln Leu Ser Arg Thr Glu Lys Glu Ser Ile Gln Ser Lys Lys
                   195               200               205

Glu Tyr Leu Arg Ile Lys Leu Met Ala Glu Arg Glu Val Gly Leu Phe
                   210               215               220

Arg Gln Gln Val Leu Ala Leu Arg Gln Ala Leu Ala Arg Ala Gln Ala
       225               230               235                       240

Asp Ser Ala Arg Met Trp Lys Gln Gln Asp Ser Gln Ala Gln Leu Leu
                             245               250               255

Lys Glu Leu Glu His Arg Val Thr Gln Glu Ala Leu Thr Gln Gln Gln
                             260               265               270

Leu His Phe Met Lys Thr Ser Arg Met Glu Lys Leu Leu Glu Asp Val
                   275               280               285

Gly Gln Lys Glu Gln Gln Leu Gln Leu Leu Ser Lys Glu Ala Glu Arg
                   290               295               300

Ala Ser Lys Leu Gly Gln Leu Gln Gln Lys Lys Met Lys Arg Asp Leu
       305               310               315                       320

His Gln Met Arg Ser Arg Leu Ala Gln Glu Arg Ser Val Lys Leu Asp
                             325               330               335

Ala Leu Gln Arg Ala Glu Glu Leu Gln Gly Gln Leu His Asp Ala Gln
                             340               345               350

Arg Ser Ala Val Pro Met Gly Ser Ser Gly Asp Leu Ile Ser Gln Ala
                   355               360               365

Gln Tyr Ser Pro Thr Ser Ala Ser Thr Ser Ser Arg Tyr Ser Gln Gln
                   370               375               380

Arg Phe Leu Lys Thr Asn Leu Lys Gly Ser Lys Ile Thr Arg Trp Ile
       385               390               395                       400

Gln Arg Pro Gln Thr Lys Pro Phe Ser Lys Arg Ser Lys Val His Phe
                             405               410               415
```

Val Cys Val Gly Ser Gln Gly Leu Ser Arg Ile Thr Ser Ser Pro Phe
            420                 425                 430

His Pro Glu Ser Cys Asn Thr Met Gly Val Leu Val Ile Val Thr Cys
            435                 440                 445

FIGURE 11: LUMA1 HUMAN GENOMIC SEQUENCE

```
00001   TCCCGTCAGT GAAGGTCCAC TGCAGGAACA CCAAGGAGTG TGCTTTCACT
00051   TTTGGTGAGC AACCCTCCTT AGGGTGCATT TTTTTTTCTT GAGTTTTTTG
00101   GTCGCTTTTG TTATTTTGTA CTGGTTTTGT TTGTTCTGT TTTGTTGTT
00151   ACTTTGGGGA GTTTTGTTGT TGTTTCTTGT TTTCTTTTGA TGCCAGTTAA
00201   GGTGCATTCC AGGCCAGACG CGGTGGCTCA CGCCTGTAAT CCCAGCACTT
00251   TGGGAGGCTG AGGTGGGTGG ATCACCTGAG GTCGGAAGTT CCAGACCAAC
00301   CTGACCAACA TGGAGAAACC CCGTCTCTAC TAAAAATACA AAATTAGCCA
00351   AGTGTGGTGG AGCATGCCTG TAATCCCAGG TACTCGGGAG GCTGAGGCAG
00401   GAGCATTGCC TGAACCCGGG AGGTGGAGGT TGCGGTGAGC CAAGATCGCT
00451   CCAGCCTGGG CAACAAGGGC AAAACTCTGT CTCAGACTAA ATAAATAAAT
00501   AAAATAAAAT GCATTCCAAA AAGAAAAGG GATGTTTGGG CTGAGGTGTC
00551   AAGGGGAGGC CAGTTTGGAA ATGGAGGCCA AGACAGTTGA AGTATTTTC
00601   TCTAACTGAA AAGGGCCTAT GTAGTGGCTT TTCTGGGGTC ACTTATTCAC
00651   CAGTCAGTGT CTGGCACTGT TCTGGGACCT TTGAATTGTC CTTAAATTCT
00701   TCTGCCCACA TTTATTTAGC AGAATGTTCA CTCTCTTCAT TAGGTTTAAA
00751   ATAGAAGTGA AATTCAATAC TGATCTATAA GAAACTATTT TGTAGTAGCA
00801   GTTTGAAACT CCTAAATTGT TTTTCTCACA CACACACACA CACACACACA
00851   CACACACACA CACACACACA TTTTCTCATG CTTCTAGATT GCAGAGCTCA
00901   GTCATGATAT GATCATGGAA ATCACCACTC TGAGAGCCCA ACTCACAGAC
00951   TTGGAAGAAG TGAATCTGAA TCTCAAGAAG CAGATTAGAA AAGAAGTCCA    EX1
01001   AGAAGAATAT GAAGCATTAG TCCGAGCTTT GTTTGAGACC TGTTTACACA
01051   TAAAAGTAAG TGTCCCGTGT TGAACATCTG GCCACCCAT TGGGTAGCCG
01101   AGTGTAACGG ATTCCCATGG TGGCTGCACA CCCAGGGATC GATGACAGAA
01151   TAATGGGCTT TGTAGTAACA AGAGATTGTT AGGCCCAAGA ATTTTCTAGC
01201   TCTAAGCTTT CACTGCAGAA AGAGAGTCAG CAATGGGTTG TCATTAACCA
01251   CGATAGACAC TGAATTTGGG GATAATATAG AAGTCTATCT TTTACCCTCT
```

```
01301  ATTGACAGTT GCTATTGTCA CTGTCTGATT GCTGTTGGGA GGACAGAGTG
01351  TTCTGCTCCC CACAGTCCCT CACCTCCCCA GTTTCTATCA CCATTTTATC
01401  TGTTAGTGTG ACTTTCCAGA CTACAGTGCC TGGGCCAGGC CGGACCTTAC
01451  GTAGGTAGCA GCAGGTGCCT CTGGAGAACT CCCTGGACAC ATTCAGAATT
01501  TGAATCAGCT TCCACATTTT TTTCCAACCC TCAAAATGCC TGCCAGCCTC
01551  ACTCTCACAT TCAATGTCAG CAAACTGCTG ACCTGTCAGC AAAGACCCAT
01601  TGCAGAAGTG ATGGGGTACG CATGCACCCG CAGCACTGTG GAAGCCAATC
01651  GCTTTCATGT GATGTTTGCA CAGCCATAAG ATAGATGCCC CAAGCCTAAA
01701  ATGGGCCATC AGGGAGACTG GTCCAGCTGA CTCACCAGTG TGAATTTCAG
01751  TGCAACCTAC CACCTGCAAG TCCACAGCTT CCCCCAACCC TGTCCCCTTC
01801  CCTGCTATTG GATACACCCC AAAGCCAGCC CCGTTTGGGT CCTTGAGTCT
01851  CTCCCCAGGG ATTGCAGAAT GGCCCTGAGG GTTGTTAGGT TAACAGGAGC
01901  TTCCACCAGT ACTCACCTTG GCCTGGTCAT TCCAGCGAGA ATTTCCTCTT
01951  ACTTGCAGTG TAAATGCTTA CACATATTAA GGGATCGAAC CCAAAATGTA
02001  TTAGGTCTGG TGCTGCAGGA GAAGGATGGG CAGACAGTGA CAGCTGGAAT
02051  TTGCTAAGCC ATCTTTCAGG TGTGAGATTG TTGAGAAATG TCTTAAGTTC
02101  CTTTTAGCTT CTGCCAGATT CCCAGTTAAA AAGTAGATTC TCTCTGTTTC
02151  CCAGGCTGAA GTAGTTCCAC CAAGCCTCCT ACAGTAGGGA ATCCCTGTTA
02201  TATTCCAGGG TCCCACGAAG TTGCTAAAGC TTGTGTTGTG TGGCCAGAGC
02251  CAGGCTTCCC TCCGTGGCTC CCAGCTGGGC ACCCTCCTCC TGCCTTCCTC
02301  TCCAGGGAAG TGGTTTAGAA GTGAGAGGAC ACCCCTACCC TACCTCTCAC
02351  CCCAGAGACA CTGGGTGTCT TAGTCTGCTC AGGCTGCCAT AACAAAATAT
02401  GATAGGCTGC ACAGCTTAAA CAACAGAAAG TATATTTCTC ACAGTTCTGG
02451  AAGCCAGAAG TCTGAGATCA GGGTGCCAGT GTGGTCTGCT TCTGGCTGAG
02501  GGCATGCTTC CTGGCTTGCA GGTGGCTGCC TTCTCACTGT CCTCACATGG
02551  GAGAGAGGGA GAAAAGAAA GGTCTCTCTC TCTCCCTCTT CCTATAAGGC
02601  CACAGTCTAT TGCAATAGAG CCTCACCCTT ATATCCTCAT TTTAATCTTA
02651  ATTACCTCCT AAAGATCCTA TCTCTAGATA CTGTCACATT GCTGGTTAGG
02701  GTTTCAACAT ATGAATCTGA GGAAGACACA ATTCAGTCCA TAGCACTGGG
02751  TCTTCAGTCG TACTTACCAT TGATCAGGCT GTTTCCTCAC AAGCCATTTA
02801  GCCAGAAGCC ATTCAGAACG GAATATTTCC TAATGGGGTT TCTGCTAGAT
```

```
02851  CCTAAATAGG AAGGCAGCCA GCCTGACTCC CTCCTCCACT TTATCTATAT
02901  TTAACAGAGC TCCTCAGGAG TGGCTCATCT ACAGTGTCTT GTCTGCTCAC
02951  ATTCTACTGT GAGTCAACAT AGCAGCAAAA ATCTTTGGTT CAGCTTCCCA
03001  AGTAACTCTT ACCAGGGGCA GTTGGTCAG  CAGGTTTTCT ACCTGTGTGA
03051  CCTTCCACTA TCCTCCTGGC TCAGCTTGCC TTGGTGTTGA CAAGGAAGGC
03101  ACAATCTAAG ATGTGCTGGT GTCCAGAAGA TGAAGCCCTG TGAATAAAAG
03151  ACAGCACTCA GGGGGCTGCT AAGTGTGACT TCCTTATAGT ACATGTCAGA
03201  ATAATTGTCT GAGGAGGTGA TATCTTAATG TGAAATTACT TACAAAAGTT
03251  AAGTTGTAGA AGGCAAAATG GCTTTCTTC  AACTACCCTT CACACTACCC
03301  AAATCCATTT TACTTCCTTG ACTTGATTCT GCAATTTGCA G̲G̲A̲G̲A̲A̲G̲C̲T̲G̲
03351  G̲A̲T̲G̲A̲T̲A̲A̲T̲C̲ A̲G̲C̲T̲T̲A̲A̲T̲T̲T̲ G̲A̲T̲C̲C̲A̲G̲A̲A̲A̲ G̲T̲G̲T̲G̲T̲G̲A̲G̲C̲ T̲C̲A̲T̲C̲G̲G̲T̲G̲A̲ EX2
03401  A̲G̲T̲G̲A̲G̲A̲A̲C̲A̲ G̲A̲A̲G̲G̲G̲A̲T̲T̲G̲ A̲C̲A̲A̲T̲A̲T̲G̲A̲A̲ G̲G̲A̲C̲C̲T̲A̲A̲A̲G̲ A̲A̲A̲A̲A̲A̲T̲G̲G̲T̲
03451  G̲C̲T̲C̲T̲G̲C̲C̲A̲G̲ C̲C̲C̲C̲G̲A̲T̲G̲A̲A̲ G̲G̲A̲A̲T̲G̲A̲A̲A̲G̲ A̲A̲A̲A̲C̲C̲C̲A̲G̲C̲ C̲A̲A̲A̲GTATGT
03501  GATTTCATTT AGCAATGGGA TATCAGCGTT TCATCCTAGC ATCTGACTCT
03551  ACCATTCACC CTGTTAGCAT TCCAGCCTGA TTTCCCTGAG AAAGCATTGC
03601  ATCAGGCATT TTAAAGGGGG CACAGGGACG CACTGCACAA TTGTGTCATC
03651  TTCTGGAAGG CATGTTTCTG ATGTTAGGGT TTGTGCCCTT CCTATGAAAA
                                                  >     >
03701  TGTTGGGGGC AGCCTTTCCT GAAAATGAGC CTTCTTAGC̲A̲ G̲G̲A̲A̲C̲A̲G̲C̲T̲G̲
03751  T̲G̲G̲G̲C̲C̲T̲T̲G̲G̲ A̲G̲C̲A̲G̲G̲A̲C̲A̲A̲ C̲T̲G̲C̲A̲G̲C̲C̲T̲G̲ G̲C̲C̲A̲A̲C̲C̲T̲G̲G̲ T̲G̲T̲G̲C̲A̲A̲A̲G̲T̲ EX3
03801  G̲A̲G̲G̲A̲G̲C̲C̲T̲G̲ G̲G̲C̲C̲G̲C̲T̲G̲G̲A̲ G̲G̲C̲T̲G̲G̲C̲T̲G̲T̲ G̲C̲A̲G̲C̲A̲G̲G̲C̲G̲ T̲G̲C̲T̲T̲C̲C̲A̲G̲G̲
03851  C̲C̲C̲A̲G̲C̲T̲G̲A̲G̲ C̲A̲G̲G̲A̲C̲A̲G̲A̲G̲ A̲A̲G̲GTGAGCT CTGGTGGGGG AGACCCAGAC
03901  AGTCCCCAGG ATGGCTGATC CAAGCCTCC  ATGGCTGCAG CTGCCATGGT
03951  GTCACTGTAG CTGTGAGTGG CACTGGTGTC AGGTGGTAGG GCCAACCATC
04001  CTGAAGGACC CGACGGTTGG CGATTTTCC  TGGGAACAGG CCATGTGAGA
04051  ACTTCAGGAG AAACAGAAAG GGGGCAGAAG CAAAGGGGGC AACAAAAAAC
04101  AGATCAGAGA ATTCAGCATA AGGGAAGGAA GTGAAAAGAT GGAGGAAAGG
04151  CTTCACCAAG GCCTGAGGC  TGCTTTGTCA AATACCGCA  TATCTTTGGG
04201  TTTCATACAT GAGTATCTGA GGAAAATGAA GTCACAAAAT AATAAGTGAG
04251  AAATCTGCTT TAAGGTAAAT TGAGTCCAAA GCTCATATTG ATAGCTATTT
04301  GGAAACTTTC ACATCCTGTT TCTGAAAGTA TTTACTCTCA TATGTTACCC
04351  TCTTCTGAAT TAAAATCATG GAAGCAGGCT GGACATGGTG GCTCATGCCT
```

```
04401  GTAATCCCAG CACTTTGAGA GACCAAGGTG GGCAGATCAC CTGAGGTCAG
04451  GAGTTTGAGA GCAGCCTGGC CAACATGATG AAGCCCAATC TCTACTAAAA
04501  ATACAAAAAA ATTAGCCGGG TGTGGTGGTG GCACCTGTA  GTCTCAGCTA
04551  CTCAGGAGGC TGAGGCAGGA GAATTGCTTG AACCTGGGAG GTAGAGGTTG
04601  CAGTGAGCCA AGATTGTACC ACTGTACTCC AGGCTGGGTT GACAGAGAAA
04651  GACTCCATCT CTAAATAAAT AAATAATAAA ATAAAATAAA ATCATGGAAG
04701  CAGTGAGTAG CAGGAGCTCC CTTCTACCGG AAGTTTGAAA GAAGAATGGA
04751  TGGGAAAGTG GTTTAGATAC TGCTTTTGAA ACTAAACATC TGGAAAGGAA
04801  ACCTATTTCC TATCTTACTG TGTTTGGGAT ATTTACAG GA ATCTATTCAA
04851  AGTAAAAAAG AGTATTTGCG CATCAAGCTG ATGGCAGAGC GAGAAGTGGG  EX4
04901  TTTATTTCGT CAGCAGGTCC TGGCTCTCAG GCAGCCCTG  GCCAGGGCAC
04951  AGGCTGACAG CGCGAGGATG TGGAAGCAGC AGGACAGCCA GGTATCTGAA
05001  CCTCAGAGCC TCTTCCTCAT TCCCTTTGCA GTTAACTCTG CAAAGCTGAA
05051  CGTGGCCACC ACACTTGGTG CTGTGGCTGT CAGGAGCAGT CACCAGAGCA
05101  CCACAGCCTG AAGCCACACA GATGGCACAG CCAGGAAAAG ATAGCCTGGA
05151  CTTGGGCTTC CCTTCTCCTC CCTCCTCTCC AGCCCAGAAA CCAAGGGCGG
05201  TGGCCAAAAG GCTATTGTTC TTACTCATGT GGCTGAGAAA ATATTACTCC
05251  TAAGCAAGAT CATTATCACA TACGTGTGTG TGTGTGTGTG TGTGTGTGTC
05301  CATTTCTCTG AGGATCTTTT TGCTAGAGGC TGTCCTGGGA TCCTGGGATC
05351  TAGGCCTCTG CCTTGAACAC AGGCTTTCAT GGGGCAAGCA CGCTTCCAGT
05401  TGACAACAAT CCTTGGCAAG TAGAGTGTGG TCCAGCCTTG TAGTATTATC
05451  CCCCATGCGA GACTGTATCC TTTCCCAGTG ATCCATACTG TGTCTCACTT
05501  TCAGAAGTTA CTGCTGCGCG ATAGGGGCCG GCACCAAAAT AAAGGCATTC
05551  TAAGCCTAAG CATTTCCTTA CTGTGCCAAC CCTCTGGGCA TGAATGAAGC
05601  AGGGGGACTC TAGGTTTAGA GTGAGAACAG CTGAGTTAAA GTAACAGCCT
05651  GGGAAAGCTA GGCGTATTTA AGCATGAAA  TTTAATTTGT TCATCTTGGA
05701  CCCTAATTCC TCCATGATTC TGCATCAGAT GAGTTAACTA TGTAAAGTAC
05751  ATTATAAACT GTAAAGTCAT CATACAGATA TGAATAATAA TTAAGTATTG
05801  ACCATCTAGT ACTTAGGATA ATACTTATTA GAAAAACTTT GGAACAGAAC
05851  GAAATTATTT CTACCCTTAT CCTTCTTTAA CTATCTAGAG TCTGACTTCC
05901  CCAGATTTTT GGAAGGGAAA ACAGAGCCTA AATCAGAACC TCCTTTCTTC
```

05951 GCCCATTGTG TGTATGGCAT GGCCCCATCT CCTTGGTGTT AAACGCTTCC

06001 ACGGCTACCT CCTGACAAAG GCTCCACGAC AATGTAAATG TTGTTTGTGC

06051 TAGATATGAT TATCTGGTTA GTAAGCTAAC ATACATATTA TCAAATCTGG

06101 GTATTAAAAG ACCAAATTAT TTGCCCTGGC ACTGCTGTAC AGTGGCGTGA

06151 TCGCATGCCT GGCTTTTGGT GTCTGTTCTG CTTCCCTCTG ACTGTCACTG

06201 CAGGGCTCAC AGTGTAAACG CCAGGCTAGG CTAGATCCTG GTGCTCTGGC

06251 TAGCACAGGA CAGAATCATT GGGCCGCATT TTCTAGAGCC CAGGAATACA

06301 CCATGTAGTT GTGTCCCTGA GCCCCAAAGG AGGGGATGGT TATTATGCTT

06351 TCCAACCTCT TCCCCCCTTC TGCTGGGAAG AAAGGCTCCC TGCCTTCTCC

06401 TTTCTTTTGG CGTTTTCCTG CCACAGGCTC AACTGCTGAA GGAGTTAGAA

06451 CATAGAGTGA CCCAGGAAGC TCTCACCCAG CAGCAGCTGC ATTTTATGAA

06501 AACATCCAGG ATGGAGAAGC TCTTGGAAGA TGTGGGGCAA AAAGAACAGC          EX5

06551 AACTGCAGCT CCTTAGCAAA GAGGCTGAGA GGGCTTCTAA GCTGGGCCAA

06601 CTGCAGCAGA AAAAAATGAA GAGGGACCTC CACCAGGTAA ACCTCAGTAA

06651 GAGGGAGTGT CCAACCAGAG TGCACCTGGT GCCCCAGCGA GGGCTGCTGC

06701 ATCCTTCCCC TGCGTGCCCA TGCCTCTCTC CTGTCCCCCA CAACAGTATT

06751 TCTCAACCTC TGTCACTTAT AGGCAGCCCA GGAGAATGGT AGCAACTCTC

06801 CCCACAGTGT CTCCCCACAC CACAGGGATT GCTGGGCAGG CCATGGTGGC

06851 TTGGCTGCCT CAGGGCTCAG AATCTCAGCA CCCCTGTAAC CTACTGGAAA

06901 AACCTGTTTC TACCCAGCTC TCATCTTTGA ACTAGGAATC TTTTAGAAAA

06951 TTCCAAGCAG TAACCTGGAA AAGCAGCAAG TGTTAATGGA GGCTATGACA

07001 AGAAGATTTT ATTCAAGTGT TCAGGAACT GCAGAGACAA AAATGAAAGG

07051 CAAAAGTGGT TTGCAGATCC AATGTATTTT GTTAACTACA CCTAACAACA

07101 AAGAAATAGA AGAGAATAAT ACTAGAATGT AGATGTGGAT TAATACAAGT

07151 TTCAACAAAG CAGAAAACAA TGTAATTCAA TAAAAAAGGA AAAAGTAATT

07201 TCCAAAGCAG GCACCTCACA CATATCCATT GAATGAGCAA ATCACTGAAC

07251 TCATTCATCA GAGATAGAAG GAGATGGAAA TTGAAAGACA AATTATTGGT

07301 CAAGTGTTTC TTTTTTTTT TTCTTTTTTT GAGACAGAGT CTCACTCTGT

07351 CACCCAGACT GGAGTGCAGT GGCGTAATCT TGGCTCACTG CAACCTCCAC

07401 CTCCCAGATT CAAGTGATTC TCCCACCTCA GCCTCCTTTG TAGCTGGGGC

07451 TACAGGCATG AGCCACTATG CCCAGCTAAT TTTTGTATTT TTAGTAGAGA

| | | | | | |
|---|---|---|---|---|---|
| 07501 | CGGGGTTTTA | CCACGTTGGC | CAGGCTGGTC | TCGAACTCCT | GATCTCAGGT |
| 07551 | GATCCGCCTG | CCTTGGCCTC | CCAAAGTGCT | GGGATTACAG | GCGTGAGCCA |
| 07601 | CCGCACCCGG | CCCCTGGTCA | ATTAAGTGCT | CAAGGAAGAG | ATCAATAAGG |
| 07651 | AGAATTCTAT | CTACAAAAAT | GACAAAAAAA | GATTAAAATT | TGAATTGAGT |
| 07701 | TAAAGAAAAT | ATATAGAAAT | GGGGGGAGAA | AATGAGTAGC | TTTAGAATAA |
| 07751 | AAATTAGAAT | TTCATATTTA | TTGCCTGAAA | AGTAAACAAA | AATATGACTC |
| 07801 | AACCTATAAG | AAAACTTTGG | CATCCCAATT | TTGTGTTACA | AATCATGCTT |
| 07851 | TTCTAAAAGC | CACCACAAAA | ACAGGGAAGT | TCGTAGATTC | ATTTCTTCAA |
| 07901 | GGTTTTCTCT | AGTTAATTAT | TTGTTTCATG | GCAGATATTC | TAGAGGTGGT |
| 07951 | CAAAACAAAT | ATTTGAGGT | TTCTCTCAAC | AAATGTGCAC | TTTACCATAT |
| 08001 | GTACGTATAA | GCCATTGGCC | CTTTGTAGAG | TACACCTCCA | GCTCTCCTGA |
| 08051 | CAGCTCAAGT | GTCCCTGCGC | CTACCTACTC | TAAACAGCAA | TCCTCAGCCA |
| 08101 | GCAAGACCCG | AGCCCCCCAC | CCTCACCCCC | CGGCCCCTTC | CAGCCAGAAG |
| 08151 | TGGCTTCTTT | AATCTATCTC | CGGCCTCTGA | CTCCATGGGC | AGATAATTCA |
| 08201 | CTGTCTGACC | TCGGAGAGCC | TCAGTGTCCT | AACCTGCTGC | CTGCGCCTGG |
| 08251 | TTGAGGTCAC | TTATAGTAGG | GGTTCCAAC | CCCCAGGCTG | TGGACCGGCA |
| 08301 | GGGGTCCATA | GCCTGTGAAA | CTGGGCTGCA | CAGCAGAAGA | TGAGCAGTTG |
| 08351 | GCAGCATAAC | TGCCTGAGCT | CCGCCTCTTG | TCAGACCAAC | GGAGGCCTTT |
| 08401 | GATTCTCATA | GGAGCACAAA | CCCTATTGTG | AACTGCACAT | GTGAGGGATC |
| 08451 | TAGGTTGCCT | GCTCCTTATG | AGAATCTAGC | TAGTGCCTGA | TGATCTGAGG |
| 08501 | TAGAACAGCT | TCATCCTGAA | ACCATTGTC | CCCACCCGGT | GGAAAAACTG |
| 08551 | TCTTCCATGA | AACCGGTACC | TGGTGCCAAA | AAGGTTGGGG | ACCAGTGATT |
| 08601 | TAGAGCACAG | GCCCTGGAGT | GGAACTGAGT | GGTTCATACC | GCTGGCCCTC |
| 08651 | CAGCGGTGTG | GCTTTGGGCA | AGGTCTGTGG | CTTCTCTATG | CTTTGATTTC |
| 08701 | TTCATCATTA | CAATGGAAAC | AATGTACTCA | CTTCACTGAA | TTTGGGGGAT |
| 08751 | GATTAAATTA | GGGAATTAGG | TAATTTAAAT | AAAGCCCTTA | AAACCAGGCC |
| 08801 | TAAAACAGGC | ATGCCTGTAG | TCCCAGCTAC | TTGGGAGGCT | GAGGCAGGAG |
| 08851 | GATCGCTTGA | GCCCAGGAGT | TCAAGCCTGC | AGTAAACTAA | GATTATGCCA |
| 08901 | CTATACTCCA | GCCTGGGTGA | AGAGTAAGA | CCCTGTCTCT | AAAAAATAAA |
| 08951 | ATTAAAAAAT | AAAAGTAAA | AAATTAACAA | AAATAAACAG | GCCAGGCACG |
| 09001 | GTGGCTCACT | CCTATAATGC | CAGCACTTTG | GGAGGCCAAG | GTGGGAGGAT |

```
09051  TGCTTGGGCA ACATGGTGAA ACCCTGTTTC TACAAAAAAT ACAAAAATTA
09101  GCCAGGGATG GTGGTGTGCA TCTGTGGTCC CAGCTACTCA GAGGGCTGAG
09151  GTGGGAGGAC CACTTGAACC TGGTTGCAGT GAGCCAAGAT TGTGCCAATG
09201  CACTCCAGCC TGCATGACAG AGACTTTGTC TCAAAACAAA CAACAGCAAA
09251  ATCACGGTGT GATACATAGC TCTCAGTAAA TGTTGGCTGT TTATATTTTT
09301  GTTGGGAATG TGAAGGTAGA CAGCCTTGGA AACAGGTAGG TAGACCTGGA
09351  CTCAAATCCT GGCTGTGTGG CCTTGGGCAA GTCACTTCAC CAGCCTCTGT
09401  GACATTGGGG TGAGTGACCT AACACAAGGA GGTCCTGAGG AAGCACGCTT
09451  CCTTGCTGGT GTTTCTTAGG TTTCCTAGTG CCAGCCTGGC TCAGGAAATC
09501  TTGATATGTT TCCTTGGCAC CAGCCCGTAG GGAATGAGGA TCCTACACAA
09551  ATCCCTACAG TATGGAGAGG GGCTTTGGAC CTACTTTATA TTAGGAAGTT
09601  TTCCTAACTC TGGAGCTCTG GTAATCTTCT GAAATTTAAA CTATGCTTGG
09651  GGGCCCCCCG ACATAAGGAA GAGCCCACTT TAACATTTAG GGCAATACTA
09701  TGCAGGGGCC TTCTGGCTGG GTCTGTATAG GCGGAGTGGG ATGTACAATA
09751  CACATGGCTG AATGCTTGAG ATTAGCACGT GTATTCATTT CCTAGAGTTA
09801  CCTTAATAAA TTATCACAAA CTGGGTGGCT TAATAGAATA AAAACGTATT
09851  CCTTCACAGC TCGGGAGGCC AGAAGCCTGA AACTAATGTG CTGGCAAGGC
09901  TGGTTCCTTT TGGAGGCTCT GAGGAAGAAT CTGTTCCATG TCTCTTCTTA
09951  GTCACATTTT GGTCTCTGGC ATTCCTCGGC TTGTAGTTAC CTCACTCCAA
10001  TCCTGCCTCT GTCATCATGG AGCCTTCTTC CTATGTGCTC CTCTGAGTTT
10051  CTGTATCCTT ATCCTATCTT CTTTGTAAGG ACAACAGTCA TTAGATTCAG
10101  GGCTCACCTA AATCCAGTAT GACCTCATCC TAACAAGTCC ATCTACGAAG
10151  ACCCTATTTC CAAATAAGGT CACATTCTGA GGTTCCAGGT AGACATGAAA
10201  TTTGGGGGGT ACTCTTCAAA CCACTATAGT ATATATTACT TTTCTACAAG
10251  TAAAAACAAT TAGGAGATTA TAAATTGAAA AAGCAAAACC ACCTGTCATC
10301  TGTGCAGATG AGATACACTT TGGACCTGGG CACTGCCTGG CTGGGGAGTG
10351  TGGGCTAGCC GTGCACGGGG AGAGCCATAT AAGTCAATAC AAAGGTTGCT
10401  TCTGGAGATG GGCTTGTCAG AACAGGGCAT TCCCGGCAGA TGCTGAGCTG
10451  AGAGCAGAGA TTTAGGAGAT AGATAAGTCT TTCCTCTGTT TGAAACTGTC
10501  CAGGGGCTCT GACAGGTCCT CACTGTAGAT GCAGTGGCTA GGCCTCCAAG
10551  GCCCTGTGTG CACTGGGCCC TCCCTCCCCT CTTCCTCTAC TTATCTGATG
```

| | | | | |
|---|---|---|---|---|
| 10601 | AAATAAACAT | GAAAGATATA | ACCTTGTGAA | TAAGTTCCTA | GCTATTATAA |
| 10651 | GGTATAAGGG | ATTCCACGGA | CTGTTCCTTT | TTGGTTAAGT | TCTTGGTCTT |
| 10701 | CCTGAAGTTC | TTGATTCTCA | GAAGGCTGAG | TTCAGCCTAA | TCAGGACTTT |
| 10751 | AAGAGCCAGT | TCTCTTTGCA | GGGTAGCCTG | GGACACCCAT | TCTCCCTAGG |
| 10801 | AACCCCCTGT | GAACTGAGGA | AATGAAAGTG | AGCACAAAGA | ATCTCTGCTT |
| 10851 | CTCATTTTCC | CCTCAG<u>ATGA</u> | <u>GAAGCCGGCT</u> | <u>TGCCCAGGAG</u> | <u>CGCAGTGTGA</u> |
| 10901 | <u>AGCTGGATGC</u> | <u>TCTCCAGCGT</u> | <u>GCAGAGGAGC</u> | <u>TGCAGGGTCA</u> | <u>GCTTCACGAT</u> |
| 10951 | <u>GCCCAGCGGT</u> | <u>CAGCTGTCCC</u> | <u>CATGGGCTCG</u> | <u>TCAGGCGG</u>TA | AGGATAACCC |
| 11001 | CTGCTCTGGC | TAGAAAACCC | TCCCAGTCTC | TGGGGTCTGA | ACTGAGGAGG |
| 11051 | GTCTCAGAGA | CTCAGGGGGG | ACCGAATCAG | TAACTATCCA | GTGGTTATTG |
| 11101 | AGTGGGTCCT | CCACAATGTT | TGTTGAATGA | CACATAAACG | GATAAACCTT |
| 11151 | AATTCTGATT | TACAGTCAAA | ACTTCCTACT | TTAGTACCTT | GGAGTACTGA |
| 11201 | CATCCAACAC | TAAAAGGTTT | CAGTCATAAA | AAACTGGTCT | TGGCTGGACA |
| 11251 | CGGTGGCTCA | CGCCTGTAAT | CCCAGCACTT | TGGGAGGCCG | AGGTGGGCGG |
| 11301 | ATCACGAGGT | CAGGAGATTG | GGACTATCCT | GGCCAATATG | GTGAAACCCC |
| 11351 | GTCTCTACTA | AAGATACAAA | AATTAGCTGG | GTGTGGTGAC | ACACACCTGT |
| 11401 | AATTCCAGCT | ACTCAGGAGG | CTGAGGCAGG | AGAATTGCTT | GAACCTGGGA |
| 11451 | GTTGGAGGTT | GCAGTGAGCT | GAGATGGTGC | CATTGCACTC | CAGCCTGATG |
| 11501 | ACAGAGCGAG | ACTCTGTCAC | ACACACACAC | ACACACACAC | ACACACACAC |
| 11551 | ACACACACAA | AAAAAAAAAA | AAAAAACTG | GTCCCAGAAC | CAGTTCATTG |
| 11601 | GATTTTGAGA | CATCTTAATG | CTTGGGGGTT | TGGGGTGTCC | TTGAAAATAA |
| 11651 | TCAAAATAGC | TCTCTGAGCA | GTGCAGGCAG | CATGGAGCTG | AGACCAGACC |
| 11701 | CCAGGATGTC | TCTAAACCAG | CTTCCTCCTC | TATAAGATGA | GGACTAAATA |
| 11751 | CATTCTAAGT | TCTCTTCTAG | ATCTATTAGA | AATATCACCA | AATATCACTA |
| 11801 | ACCATGATTG | GCCTGTTGTT | ATGATTGGCC | ATGTCTCTTC | TTTCCTGTTC |
| 11851 | TGTACATAGC | CTGATAGTTG | AGTATATGGG | CTTTGGAGTG | AAACAGCCAG |
| 11901 | AATTCAGGCT | CTGGCTCTGT | CACTGCTAGC | CACATGACCT | TAGACAGACC |
| 11951 | TTAATTAGCC | TCTCCGTAAA | ATGGGAATAC | TCACCTCAAA | GGCTTGCTCT |
| 12001 | GAGATTAAAT | GAAATAATTC | CTGTCTTGAC | ACCTTAGTAT | AGTGGCACTT |
| 12051 | AGTAATTGTG | CAAGTGTTGG | TTACTATACT | TGCATACATG | TGTTTAGCCC |
| 12101 | TTTATCTGTG | TTTCCTTTTG | GCTACCTTCC | AGCGTGAATG | AGCTGAGCAA |

EX6 (at row 10901)

```
12151  ACAGCCTTTC AGGAGCACAG AGTCACAGAT GAAATTACTT TGGGTTTACT
12201  AAGAGCAGAG CTGGACTTGG CAGTAAAGCT CACAGGGCCC TCCTTCCTGC
12251  TTCTGGGTTG CTGCCTGGAC CTGACATTGG GAGCTGGTGT CCCCTGCCCC
12301  AGCTACTGGT TATTGCTGCT GCCCCAGCCC AACATAAAG GGCATCAAGA
12351  GCACACAAGG GCCCTACTTT GGCACCTGAC CCTATGCAGT TCGGTACCTT
12401  ACACTGTCTT CTCCATGTGC CAGGGGATTT TTTCCTTCTC TCCCTTTCAC
12451  CTCTGCCTGC AGCTTAGCCA AGCATCTTTC TAATCCCTTC CTGGGATAAT
12501  GCGTCCTAGT GAACTGCCAT CCACATCCTC CAACACCTGC CTATTGTGAA
12551  GGAGAACCAG AATGAGGCAC GAGGCAGGTG GGGGAGACCC TAATTCCCAG
12601  GATTGGGGTG GGAGCAGGAG TGGGAAGCAA ACTTCTTTCC CAGGAAGTAG
12651  AGGTAGACGT TACTCCCGGG CCTCAGCCCT CTTCTGTTTC CCTGTGCAGG
12701  GAGAGGAGGG GTTTGAGGGC ACAGTCAGCT ATCACCATAC TGTTAATGCT
12751  AAGCAGTAAA AGTCAGCCAT ATTCCCACTC CTCCTTCCTC CGCTGTTGCC
12801  CAACTGGAGT CTCAAAGTGA CCCAGGGGTC TTCTGCAGCA GCAGCCATGG
12851  CAGCATTCCT GCCTCCCATG TTGGAAGCAT AGGTGCACTC AAAGGGCGAG
12901  CTCTCTTTCC TTGCCATTAA CGTGATTCCC CTAGGATTTT GCAACTCCTG
12951  AGAAATGAAG ATTTTTTTCT AAATCAATTA TTTTAGACAT GCTTAAGAAA
13001  AAATGAAATC ACTTGGCTCA TAAAACTGTA AAATGTTGAG AGGAGGCCTG
13051  GCTAAAGGTA GCTTCATCAA GGTTTGACCT AGTTCATGAG GACTGCTTTC
13101  ACTCTCTCCA TCTCTGGCTC TGAGGAGGCT GGGAGCAGAA AGGAAGCAAG
13151  GCTCTTTGGA AGCAAGATGG CAGCCACCTC CGTAGCTTCC GTCTCTGTTC
13201  ATGCTCAGCA TGGCAGGAGC AGGGTATGGA GATGGGACAG TCAAAAAGAA
13251  TTGGGCTCTG CCTGGACTGA CTTGGGTCAT GTTGCCAATT TTGAACAAAT
13301  TAGTGGAGCC ACAGACTAAG ATGTCTGGTT GGCTTAGGCC CAGCTTACCT
13351  GCTTCTCCAC TGGAGCTGAG GGTTGGGTCA GCTCGCTGTC TCCTCCTCTC
13401  TGCAGCAACT GTTTTAAATC TGCCTTGTCT CCTCAGATCT TCATACGCTC
13451  CCCCCAACAC CTCATCCTTT CATCTCCCAC TTCACAGAGA AATTAGAAAC
13501  CCTCAGACAG GAATGCCATC TTCTCCCTGT CTCCCAGCCT ACCTACATCT
13551  GTACTCTGCT GCTTCTCCTT CCCTCCTGTG AACATGGAAA GGATGTCCCT
13601  TTTCTTCCCC AGGGCAATCC CTATGTAAAG GGCCCATCTG CTGCTACCTT
13651  CTCAGGGGCC TTGAACTAGC TGCTTCTTTT CTACATACTT GGATTTCCCA
```

```
13701  TCCATGCATC CCTCTAATCT TGCAACCAAC AATTACTTAT TGATCATGTA
13751  TGTGCCAGGA TCATAAAATC CACTGTAAAA TAGCTCCCCC CGCCCCCACT
13801  GCCTTGACAA CATATTCCTT CCCCTGCTGC TGGTCTTTCT CTTCCCAGTC
13851  AGACTTCTTA AAAGAGCTGC CTATACTCAC TTTCGTGATT CACCTCACTT
13901  AATTTCTCTC AGGTTTTGCC ATTCTCAACT TGTGGCTTCC AAATGTTCCT
13951  CACTACCTCA TGGTCCAATA TGATGCTTAC GCTTTCTGGC AATAGGAAG
14001  GAGGAAGGCA ACAAAAAGGG CCCACCCCTC CCTTGAAGCT TGAAGAATGC
14051  TTCCTGGAAG TCACTTGTGA CACTTCTGCG TACATTCCAT TGGCCAGCAC
14101  TTAGCCCCAA GACCACACAA AGGAGACTGT GAAATGTAGT TTTTATTCTA
14151  GGATGCCGTG AACAAAAAAT GTGAGGTCTA TTTCTAAGAA GAGAGGAGAG
14201  ATTTGCAATT GGGGGCCAAG AATAGGTCTC TGCACCACCA CCAGCAATCT
14251  GATTTTTCTT ACCACCATTT CATTGCAGTT GCTCTTGCCA AGATCACCTT
14301  CACTTCTGTC TCCAAGTCCA AAGGACACTG AGTTCTCACT GATTTCATGT
14351  CTCAGCAGCA TTTGAAACAG CTGACCACAC CCTTCTCCTA ATTATTCTCC
14401  TGGCACTGCT CCTTGTGGTT TTCCTCTTCC TCTGGCTGCT TTTTCTATCT
14451  CCTCCTTTTC TAGTTCCTCC TACTGTATCC AACCTCTAAA CACTGAAGTT
14501  GTTCAGGGAT CTTTCTGGCC CCTTCTTCTC TCACCTCACA TTGTCTCCAA
14551  ATAATTGCAT ATTTCCCACA GCTTTAATCA TTGTTTGCTA AGTCTACATC
14601  TGCAGCTCAA AACTCTCCTC TGAGCTGTAG ACCCCTATAT CCAGTGACCC
14651  ATATGTCCAG TGAATAATGT CTACGTTCAC GTGTCTCAGG CTCACAAGTT
14701  CAACAGGAAT GGAACCCGTC TTCCTATCCT TCTCCCTTCC TACTTTTGGG
14751  GTGGGGGAGA TGCTCTTTCA GCAAATGGTA GTGCCAAATA TCCAGTTGCT
14801  TAAGCCAGAA ATTTGGGAGC TATTCTTTGT CACCCTGCAA ATCTGGTTAA
14851  TTCTCAACTC CTACTAATTT AAGTAGCTCT CAGTCTATCC GCTTCTACCT
14901  ACCACAGTCC AAGTCTCTTG TCACCTCCTT CACTTTTACT TGGTCATGCG
14951  ACTATTGGGC AAAAAACTCT CTCCAAGTTT TGACACATTT GCTCAAAATT
15001  GATGAAGCTG AAAAATAAGC TGAGTTAGAT GCCAATTTTA AGCCCTAAAT
15051  TTTATGAATT AAATCTAGAT ACAGGAATTT GAGGTTATAG TGAGCTACGA
15101  TCGTGCCACT GCACTCCAGC CTGGGCAACA GAGTGAGGCC CCCACTCTCA
15151  AAAAAATAAA AAATCAAAAT AATCTAGGTT TATCCATTGC AACCAGAGAT
                                             >
15201  ATAATTTAAC ATTTTTAACT TTATAGACCT TATATCCCAG GCTCAATACT
                                    >
```

```
15251 CCCCAACTTC TGCTTCCACA TCATCCAGAT ACTCCCAGCA ACGCTTTTTA EX7
15301 AAGACTAATC TCAAAGGCAG TAAAATAACA AGATGGATTC AAAGGCCACA
15351 GACTGTAAGT AATAATAAGA TTGATTACAT GCATTAAACA ATAAAGCCTT
15401 ACAATTTGAT TTCATGGTTT TTGGGTCACT TCAGACTTAC ATTAGAAAAA
15451 TTATATATCA GGAGCTTATG TAGATGCCTT GAATCTGGAT AAGAAAATTC
15501 TGATGTTGAA ATAATCCTAT AACAGCACCT TCTAAATTAC AAGTCAATAA
15551 ATGGGTGTGG AATCAGTACC AACACCTTGC TGTGTTCCAT CTCTGAATTT
15601 CTTTTTTCCC CCAATCATCT TCAACAATTA ACTAGCAGCA TCAGACTCCT
15651 TATCTGAGTT CCCCAACAGA GCAGAAATAA GTTTCGGAAG TCATTTTAAA
15701 ACACGTGAGA AATCTACCCT CCAAGAAAAT TCCTGGGATG CAGATTAGCA
15751 TGTATTTGAA GAACTCGTAA AATGTTTCAG TTTTTAGTTT ATGTAAAACA
15801 ACATATACTT CCTCTTCCAC TGCCTCCTCT CTACTGCTTT AATAAGTATT
15851 TTACTCTTTG CTGCATTTTC TTTCAGAATC CCTTCTAGAG ATTCACATAT
15901 CTAATCAACA CATTTAGGAA TTCCTGGCTG GGCACGGTGG CTCACACCTG
15951 TAATCCCAGC ACTTTGGGAG GCCGAGGCAG GCAGATCACC TGAGGCCAGA
16001 AGTTTGAGAC CAGCCTGGCC AACATGGTGA AACACTGTCT CTATGAAAAA
16051 TACAAAAATT AGCTGGGCAT AGTGGCGGGC GCCTGTAATC CCAGCTACTC
16101 GGGAGGCTGA GGAAGGAGAA TCGCTTGAAC CTGGGAGGCA GAGGTTGCAG
16151 TGAGCTGAGA TTGCGCCATT GCACTCCAGC CTGGGCAACA AGAGTGAGAC
16201 TTCATCTCAA AAAAAAAAA AAAAATTATT TCCCATTACC TGATGAAAAA
16251 TTAAGAGGAA AATATTTAAT CATTCCTTCA GAGAAAAGTA TGCCATTCCA
16301 AGTCATTCGA TGGTGTAATT CCGCAGCTGA TGGTCTAGTT ATAAGGATCA
16351 AAAGTTTCAA GATTTCTAAA CATGCAGTTA AGAAGGGGA AAGACAGGTT
16401 GGGAAGATAC CCAAACACCA TCTTGACCAA GTGAGGGCCA CATTACTAAT
16451 GTCCACCATT TGCTTGACTC ACCAATCTCT GTGCAGTCAT CTTTCTTGAA
                                                >
16501 AATGTGAAAT TGTATTATAT GTCTATGTTT CCGCAAAAGC CCTTTTCAAA
16551 AAGAAGCAAA GTTCACTTTG TATGTGTGGG ATCACAAGGG CTTTCAAGAA
16601 TCACTTCATC TCCATTTCAC CCTGAAAGCT GCAATACCAT GGGGGTGTTG
16651 GTGATCGTGA CTTGTTGAAA AGGCTGCTAA GCAGATAAGT GCATTAGTGA
16701 AGATTTATTA TATTTGAGAG ATTCAAAAGG GTGATAGGCT AAAGCTAATT
16751 GATGAACATT GCCCTACCAA ATAAATAAAC CCTACAGTGA AGTGTCTTGT
```

```
16801  GGGCCCATTG GCCCAGTGGC TATGTACAAT ACGGGAACCC CAAGCAAAAA
16851  ACCTCAAGGC CAGGGAAGGT ACACAGTTAG CTGGAACTTC AGATCTCAGG
16901  TCTGACTTCT TAAGCAAGGC CTATGAGACA AGTCAGATAA ATACTCATTG
16951  AAGAGGAATT TATACATGGC TGAAATGTAA GAACACAGTT AATTTTCTAA
17001  AAATTAGCCC TGCACTAACA CAAATGATAA AAAATTAAGG AATTTTTAGA
17051  TTACTTGAAG TATGAGCTGT GTTTCTTCC  TTAACTGGAA ATGGCTTTCC
17101  ACTGATGGAT TCATTCTTGA CCAATTCCCT TTAGGACAAT GGCAAAATAC
17151  AGACAAGAAG GCATACTATA TGGCCTAACC CAGACTGAAT CAATGATCTT
17201  GGTCTCATTA ATAACAGTGA CTTTTTATGA TGCTATAACA AGAATTATTC
17251  ACCATGTTCT TAACACCAAT ATCTACTTAT ATTACAGGTA CCTATTAAAC
17301  ACAAAAAAAG AACTGACGAT GTTTTCCTAC CCAATATGGC AGAAAATGTT
17351  CAACTGACAG CTTTTCAGGT TCAAACAGCT CCATCCAGAT TCCCATTTAG  EX8
17401  AGCTGACTGG TGATGATATC TTCTTTTTCC AACCTTTATT TCTATGAGTA
17451  TTTGAATGAA TAAAAATGAC TCCAAATGCC ATTAAATCTC TTACTTAATT   AAAAAAAAAAA
17501  TTATGTATGA AATTCTCTTA TCTGTACTTG GAAGACAGGG TTGAAGGACT   AAAAAAAAAAAA
17551  AAGATGATTA CATCTTGAAC CAACCCCAGG TGAAGTAGGG GTTGGTCCCA
17601  GACTTTAAAA CCTAAGCATT GATTTGCATT TCTACAAGCT AGCCTTTGCC
17651  TCTGGTCAGC CAGCAGCCTC TGAATACGAA TTCTAGAGTT AGTGGGTAAG
17701  CAGGAAAGCT AAGATGGAGG CCCTTGCTTC TAAGCAGTGT TTACTAACAA
17751  GTGAAAAACC AAAGTATGTT AATAGAGATT AACACAAATG AACGTAAAG
17801  CATTTGTTTC ACTTCTTAGA AAACAAATTT GCCATCCTCT ATTAACAATC
17851  TTTTCATTCT TCCTACAAAT GCCAAATACT TCCTCAGACT TTAGTATAAA
17901  GTCCTAATCC AAGTCCTTTG TTCAGACAAG AAAATCTGTC TTGTGTAAAG
17951  CAATTAATAA ACAGATGAAT GGAACAGACA AACATATTTA CATGCATAAA
18001  TTTAAATACG ATGTATGTGG CTTTTCAAAC TAAAGAGAAC ATGGAGGCTA
18051  TTTGGAATAA ATTAAATCAT CACCTTACCC CATACACTAT AAATCCCAAA
18101  TGGATTAAAG ATCTAAATGC ACATACGTAC ACATGCATAC AGACACACAT
18151  GCCACACATG CACAAACTGA TTTTTTAAAC AGAATATAAA AGCCAATAGG
18201  AAAATTGGTA ACTTTGGTAT CAGAACTAAA ACTTCAGTAT GATAAAATAC
18251  TGTATCAGTT ATCAACTTAT ATCTCAGCTC CAAATTCATT CTTTATTGTC
```

| | |
|---|---|
| 18301 | TGTTCTGCAA TAACAAATAT GGACCCTATA AATATTTCCT CTTTGCCAAC |
| 18351 | TGGCAAGAAG TTAAGCTCTC AGTAGAGGGT GCTGGAGGGA CCCTGTAGGA |
| 18401 | GGTGGCAGGG TTTTTTTCCA GGTTACCTTG TGCTCCTCTA GGCAGGCTCT |
| 18451 | TGCAGTGTGC ATGGCTTCTG CAGCACCAGG TTCTTGTAGT ATATACAGTT |
| 18501 | TCTGTGGTGC CTGGCTCCAG TGATGCATGT AGCTCCATGG TAGAGTGCCA |
| 18551 | CTTGCATGGC ACCTCCTGTG ACGGGTCCCC TCCAGCACCC CTTTGAATAG |
| 18601 | CTTTGCAGTC TCTGTGAATT TCTCAGCCAT CCAATAAGCT TTGGCCAGAT |
| 18651 | CCTCTCCAAT GAGGTCTGGA TCTCAGCCCT GAAGGGTAGT GGCTGGTCCC |
| 18701 | TACATCCGCT ATCCTTGTAT TCTTTAGAGT CTCTTTATT GCTTACAAGC |
| 18751 | AGTATGCCAA TCTTTTGTTA TAGTTAATAA TTCTTTATAT CAAACTTTCC |
| 18801 | CTGTTTGAAT TACTGTGTGC TTTCTGTCTC CTGAATGGCC CATGACTGAT |
| 18851 | ATAGAACTGG TACCAGGAGC AGGGTGTTCC CAGAGGATAG ACCTGCTATG |
| 18901 | GTTTGAATGT CTGTCCTCTC CAAAACTCAT GTTAAAATTT AATCCCCAAT |
| 18951 | GTGGCAGTAC TGAAAGGTGA GACCTTTAAG AGGTGATTGG GTCATGAGGA |
| 19001 | CTCTGCCCTT ATGAATGGAT CGATCCATTC ATGGATTAAT GGATCGATCC |
| 19051 | ATTCATGGAT TAATGGATTT GTGGGTTGTT AAATTAATGG ACTATCATGG |
| 19101 | GAGTGGGACT GGTGGCTTTA TAAGAAAGGA AGACTTGGGT AGCATGCTCA |
| 19151 | GCTCCCTCAC CATGTGATAC CCTGTGCTGC CTCAGGTCTC TATGGAGGGT |
| 19201 | CCCCACCAGC AAGAAGGCTC TTACCAGATG TGCCTCCTCA ACCTTAGACT |
| 19251 | TCCCAGCCTC CATAACTTTA AGAAATAAAT TCCTTTTCTT CCCAAATTTC |
| 19301 | CCCATTTCAG GTATTATGTT ATAAACAACA GAAAATGTAC TGAAACAGAA |
| 19351 | CACAGATGGA ACTTGGGATT TGGTTGGTTG CAACCTTAGG CTTGAATACA |
| 19401 | GTGCTGAGCC AACAGGAAAT TGGAATGTTA GTATTCTTTG CATGCAGTGG |
| 19451 | CATCACAATC ACGTTACTAC CTGTGGCCGA TTGTGCTAAA GTACCTGCTG |
| 19501 | AAGCATGTGC CTTTAGGAGC CTAAATTGCT ACTACATTGA CTATAATGGT |
| 19551 | AGTCATGCTG ACTACAGAAA CTGTGGTGTG AGGTGGATTT TTTTGAATGC |
| 19601 | ACTTCAGCAC TTCTGGAAGA AAATGACAAG TCATGACCTT TAATTCTAGG |
| 19651 | CTTAATTCAT CGTCTGAAAC CAGAGAGCTT CCATGATACC CCTAAAAGTA |
| 19701 | TCTCTTATTT CTCATAGTCA CAGGGATAAT ATTGCTAAAA ATCAAGCACA |
| 19751 | AGTTTTTATT AGGGGCATGC TAAATTACAG TGACAGTTGT ATTTATAAGC |
| 19801 | TCATCAAGCT TCTCATTGCC ATTGAGATGG GCCCTGTGAT TTCAATGAAG |

```
19851  AAAATGCAAT TCCAAAGTGG AAGAGCGAAG TGGCAGGCTT TAACTGGCAA

19901  AAGACAAGGC GGGCACATCC ATTATAAAGG GCAATAGGGA TGTATCAGTA

19951  GTCAGAATCC CTTGGCCTGC AGAGATCTTT GGTAGTTAAT GTGTCCCCAG

20001  GTATGAAATC ATAGATTGCT TAATGTATAT AACAGAAATT GCTTAATGTA
```

FIGURE 12: LUMA1 mouse mRNA

```
  1    GTTGCAGAGCTCAGTCATGACATGATCATGGAAATCACTGCTTTGAGGGCCCAGCTCACA
       V  A  E  L  S  H  D  M  I  M  E  I  T  A  L  R  A  Q  L  T

61    GACCTGGAAGAGGAGAATCTGAATCTGAAAATCCAGATTAGAAAAGAGGTCCAGGAAGAG
       D  L  E  E  E  N  L  N  L  K  I  Q  I  R  K  E  V  Q  E  E

121    TACAGAGAATTAGTGCAGGCGTTGTTTCTGACCTGCTTACGCATAAAGGAGAAGTTGGAT
       Y  R  E  L  V  Q  A  L  F  L  T  C  L  R  I  K  E  K  L  D

181    GAGAATCAGTTTAATTTGATCCAGAAAGTGTGTGAGCTCATCGGGGAAGTGAGAGCTGAA
       E  N  Q  F  N  L  I  Q  K  V  C  E  L  I  G  E  V  R  A  E

241    GGGATTGCCAACGTGAAACAGCTAAAGAAAACCTGGGGCTCTGCCAGACCTGATGAAGAA
       G  I  A  N  V  K  Q  L  K  K  T  W  G  S  A  R  P  D  E  E

301    ACAAAAGAGAACACAGCCAAGGAGCAGCTGTGTGCCTTGGAGCAGGAACACAGCAGCACC
       T  K  E  N  T  A  K  E  Q  L  C  A  L  E  Q  E  H  S  S  T

361    CTGGCTGCTCTACTGTGCAAAGCGCGGAGCCTGGGCCGCTGGCGGCTGGCTGTGCAGCAG
       L  A  A  L  L  C  K  A  R  S  L  G  R  W  R  L  A  V  Q  Q

421    GCACACCTCAGAGGGCAGCTGAGCAGGGCAGAGATGGAATCTATTCTCAGTAAAAAGGAG
       A  H  L  R  G  Q  L  S  R  A  E  M  E  S  I  L  S  K  K  E

481    TGCTTGAGAATCAAGCTAATGGCAGAGCAAGAAGCGGCTTTACTCCATCAACAGCTCCTG
       C  L  R  I  K  L  M  A  E  Q  E  A  A  L  L  H  Q  Q  L  L

541    GCTGCAAGGCAAGCCCTGACCAAAGCTCAGACTGACAACAGGAAGCTGTGGCGGCAGAAT
       A  A  R  Q  A  L  T  K  A  Q  T  D  N  R  K  L  W  R  Q  N

601    GATACTCAGGCTCAACTGCTGAGGGAGTTGGAACACAGAGTGACTCAAGACTCTGTCACT
       D  T  Q  A  Q  L  L  R  E  L  E  H  R  V  T  Q  D  S  V  T

661    CGGCAGCAGCTGGATATCATAAAAACATCTGGCATGGAGAAGCTCCTAAAAGATGTGGAG
       R  Q  Q  L  D  I  I  K  T  S  G  M  E  K  L  L  K  D  V  E

721    CAAAAAGAGCAAAAACTACAGCTCCTGACAGAAGAGGCTGAGCGGGCTTCGAAACGAGGC
       Q  K  E  Q  K  L  Q  L  L  T  E  E  A  E  R  A  S  K  R  G

781    CAGCTGCAGCAAAAGAAGATGGACAGAGACCTGAAGCAGATGAGAAACCGGCTTGCTCAG
       Q  L  Q  Q  K  K  M  D  R  D  L  K  Q  M  R  N  R  L  A  Q

841    GAGCGCAGCGTGAAGCTGGATGCCTTCCAGCGAGTGCAGGAGCTGCAGAGTCAGCTTTAT
       E  R  S  V  K  L  D  A  F  Q  R  V  Q  E  L  Q  S  Q  L  Y

901    GACATCCAGTGGCCCTCTGTCCAGATGGGCTCCCCAGTCGGGCTCAGATCCCAGACCCAC
       D  I  Q  W  P  S  V  Q  M  G  S  P  V  G  L  R  S  Q  T  H

961    TGCTCCCTAAGCTCTGCTTCAACATTATCCAGACACCCTCACCACCATTTTTCAAAGACT
       C  S  L  S  S  A  S  T  L  S  R  H  P  H  H  H  F  S  K  T
```

```
1021 CATTTTGTGGGCAGTAAAATGACAAGAAGGATTCAAAGACCAAAGACTGTGCCAGTCAAA
      H   F   V   G   S   K   M   T   R   R   I   Q   R   P   K   T   V   P   V   K

1081 CACAACAGAAGGATTGAGGATGGTTCTCTACCCAGTGTGAAAGAAAATGTTCAACTTACA
      H   N   R   R   I   E   D   G   S   L   P   S   V   K   E   N   V   Q   L   T

1141 ACTTTTCAAGCCCAACAGCTCCATCTGGGATTCATTTAGACCTGAAAAGCTTTCTTCCTA
      T   F   Q   A   Q   Q   L   H   L   G   F   I   *

1201 GTGTGTGGCAGTTGGTCTGAGATGACTCATCTTGAGTGTCCCTCCACATGAAGCAGCTTT

GT
```

FIGURE 13: SEQUENCE COMPARISON HUMAN AND MOUSE LUMA1 mRNA
PERCENT IDENTITY: 79.394

```
  1 ATGGAAATCACCACTCTGAGAGCCCAACTCACAGACTTGGAAGAAGTGAA  50
    ||||||||||  ||  ||||  |||||  ||||||||| ||||||  | |||
 28 ATGGAAATCACTGCTTTGAGGGCCCAGCTCACAGACCTGGAAGAGGAGAA  77

51 TCTGAATCTCAAGAAGCAGATTAGAAAAGAAGTCCAAGAAGAATATGAAG 100
    |||||||||  ||  |  |||||||||||||  ||||| ||||||  ||   ||
 78 TCTGAATCTGAAAATCCAGATTAGAAAAGAGGTCCAGGAAGAGTACAGAG 127

101 CATTAGTCCGAGCTTTGTTTGAGACCTGTTTACACATAAAAGAGAAGCTG 150
    ||||||  |   ||  ||||||  ||||||  ||||  ||||||  ||||||  ||
128 AATTAGTGCAGGCGTTGTTTCTGACCTGCTTACGCATAAAGGAGAAGTTG 177

151 GATGATAATCAGCTTAATTTGATCCAGAAAGTGTGTGAGCTCATCGGTGA 200
    |||||  ||||||  |||||||||||||||||||||||||||||||||||||||||  ||
178 GATGAGAATCAGTTTAATTTGATCCAGAAAGTGTGTGAGCTCATCGGGGA 227

201 AGTGAGAACAGAAGGGATTGACAATATGAAGGACCTAAAGAAAAAATGGT 250
    |||||||  |  ||||||||||||  ||||  |  ||||||||||||||  |||
228 AGTGAGAGCTGAAGGGATTGCCAACGTGAAACAGCTAAAGAAAACCTGGG 277

251 GCTCTGCCAGCCCCGATGAAGGAATGAAAGAAAACCCAGCCAAACAGGAA 300
    ||||||||||  ||  |||||||  ||  |||||  |||  ||||||   ||||
278 GCTCTGCCAGACCTGATGAAGAAACAAAAGAGAACACAGCCA...AGGAG 324

301 CAGCTGTGGGCCTTGGAGCAGG...ACAACTGCAGCCTGGCCAACCTGGT 347
    ||||||||  ||||||||||||||||  |||  |  |||  ||||||   ||  |
325 CAGCTGTGTGCCTTGGAGCAGGAACACAGCAGCACCCTGGCTGCTCTACT 374

348 GTGCAAAGTGAGGAGCCTGGGCCGCTGGAGGCTGGCTGTGCAGCAGGCGT 397
    |||||||  |  ||||||||||||||||||||  ||||||||||||||||||||||
375 GTGCAAAGCGCGGAGCCTGGGCCGCTGGCGGCTGGCTGTGCAGCAGGCAC 424

398 GCTTCCAGGCCCAGCTGAGCAGGACAGAGAAGGAATCTATTCAAAGTAAA 447
    |  ||  |  |||||||||||||||  ||||||  |||||||||||  ||||||
425 ACCTCAGAGGGCAGCTGAGCAGGGCAGAGATGGAATCTATTCTCAGTAAA 474

448 AAAGAGTATTTGCGCATCAAGCTGATGGCAGAGCGAGAAGTGGGTTTATT 497
    ||  ||||  |||  |  ||||||||||  ||||||||||  ||||| ||  |||| |
475 AAGGAGTGCTTGAGAATCAAGCTAATGGCAGAGCAAGAAGCGGCTTTACT 524

498 TCGTCAGCAGGTCCTGGCTCTCAGGCAGGCCCTGGCCAGGGCACAGGCTG 547
```

```
              | ||| ||| ||||||||   ||||| |||||| ||| || ||| |||
     525 CCATCAACAGCTCCTGGCTGCAAGGCAAGCCCTGACCAAAGCTCAGACTG 574
     548 ACAGCGCGAGGATGTGGAAGCAGCAGGACAGCCAGGCTCAACTGCTGAAG 597
              ||| | || | ||||| |||| | || | |||||||||||||||| |
     575 ACAACAGGAAGCTGTGGCGGCAGAATGATACTCAGGCTCAACTGCTGAGG 624

598 GAGTTAGAACATAGAGTGACCCAGGAAGCTCTCACCCAGCAGCAGCTGCA 647
         ||||| ||||| |||||||| || ||  || |||| | |||||||||| |
     625 GAGTTGGAACACAGAGTGACTCAAGACTCTGTCACTCGGCAGCAGCTGGA 674

648 TTTTATGAAAACATCCAGGATGGAGAAGCTCTTGGAAGATGTGGGCAAA 697
         | | || ||||||||  | |||||||||||| | ||||||||| |||||
     675 TATCATAAAAACATCTGGCATGGAGAAGCTCCTAAAAGATGTGGAGCAAA 724

698 AAGAACAGCAACTGCAGCTCCTTAGCAAAGAGGCTGAGAGGGCTTCTAAG 747
         |||| ||  |||| |||||||| |   |||||||||||| |||||| ||
     725 AAGAGCAAAAACTACAGCTCCTGACAGAAGAGGCTGAGCGGGCTTCGAAA 774

748 CTGGGCCAACTGCAGCAGAAAAAAATGAAGAGGGACCTCCACCAGATGAG 797
         |  |||||  |||||||| || || ||| | || ||||| | ||||||||
     775 CGAGGCCAGCTGCAGCAAAAGAAGATGGACAGAGACCTGAAGCAGATGAG 824

798 AAGCCGGCTTGCCCAGGAGCGCAGTGTGAAGCTGGATGCTCTCCAGCGTG 847
         || ||||||||  ||||||||||| |||||||||||||||  ||||| |
     825 AAACCGGCTTGCTCAGGAGCGCAGCGTGAAGCTGGATGCCTTCCAGCGAG 874

848 CAGAGGAGCTGCAGGGTCAGCTTCACGATGCCCAGCGGTCAGCTGTCCCC 897
         ||||||||||| |||||||| || | ||   |||| || | ||||||
     875 TGCAGGAGCTGCAGAGTCAGCTTTATGACATCCAGTGGCCCTCTGTCCAG 924

898 ATGGGCTCGTCAGGCGACCTTATATCCCAGGCTCAATACTCCCCAACTTC 947
         |||||||  ||| ||  || | |||||| | || | |||||  ||   ||
     925 ATGGGCTCCCCAGTCGGGCTCAGATCCCAGACCCACTGCTCCCTAAGCTC 974

948 TGCTTCCACATCATCCAGATACTCCCAGCAACGCTTTTAAAGACTAATC 997
         ||||||| |||| |||||| || || | ||| | |||||||||| ||
     975 TGCTTCAACATTATCCAGACACCCTCACCACCATTTTCAAAGACTCATT 1024

998 TCAAAGGCAGTAAAATAACAAGATGGATTCAAAGGCCACAGACTGTACCT 1047
         |    |||||||||| |||||| |||||||||| || |||||||| ||
    1025 TTGTGGGCAGTAAAATGACAAGAAGGATTCAAAGACCAAAGACTGTGCCA 1074

1048 ATTAAACACAAAAAAAGAACTGACGATGTTTTCCTACCCAATATGGCAGA 1097
         | |||||||| | ||| | ||| || ||||||| | ||||||| ||
    1075 GTCAAACACAACAGAAGGATTGAGGATGGTTCTCTACCCAGTGTGAAAGA 1124

1098 AAATGTTCAACTGACAGCTTTTCAGGTTCAAACAGCTCCATCCAGATTCC 1147
         |||||||||||| ||| ||||||| | | |||||||||||||| |  |
    1125 AAATGTTCAACTTACAACTTTTCAAG.CCCAACAGCTCCATCTGGGAT.T 1172

1148 CATTTAGAGCTGA 1160
         ||||||||| ||||
    1173 CATTTAGACCTGA 1185
```

Figure 14:

Figure 14:
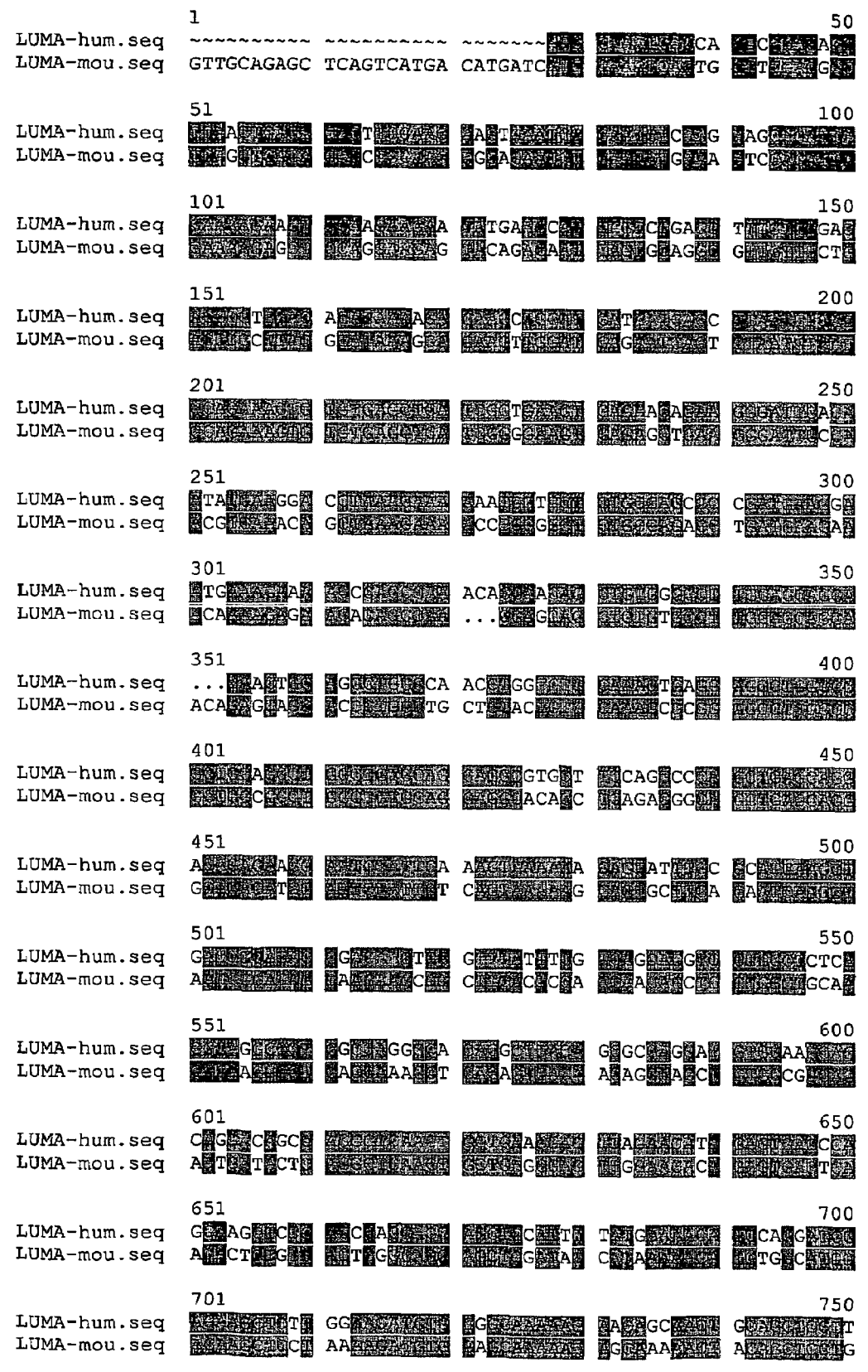

The figure shows a sequence alignment between LUMA-hum.seq and LUMA-mou.seq from position 1 to 750, with most nucleotides obscured by dark highlighting indicating conserved/matched regions.

```
              751                                                        800
LUMA-hum.seq  ▓GCA▓▓▓▓▓ ▓▓▓A▓▓▓▓ ▓▓▓T▓G▓TG ▓▓▓▓A▓▓▓ ▓▓G▓A▓▓
LUMA-mou.seq  ▓CAG▓▓▓▓▓ ▓▓▓C▓▓▓▓ ▓▓G▓A▓GA ▓▓▓G▓▓▓▓ ▓▓A▓G▓▓

801                                                        850
LUMA-hum.seq  A▓▓A▓G▓G ▓▓▓CC▓C▓ ▓▓▓▓▓▓▓G ▓▓▓▓▓▓▓C ▓▓▓▓▓▓▓▓
LUMA-mou.seq  G▓▓G▓C▓A ▓▓▓GA▓G▓ ▓▓▓▓▓▓▓A ▓▓▓▓▓▓▓T ▓▓▓▓▓▓▓▓

851                                                        900
LUMA-hum.seq  ▓T▓▓▓▓▓▓ ▓▓▓▓TC▓ ▓▓▓T▓CAG ▓▓▓▓▓▓▓▓ ▓G▓▓▓▓▓▓
LUMA-mou.seq  ▓C▓▓▓▓▓▓ ▓▓▓▓CT▓ ▓▓▓A▓TGC ▓▓▓▓▓▓▓▓ ▓A▓▓▓▓▓▓

901                                                        950
LUMA-hum.seq  C▓C▓TGC▓ ▓C▓T▓AG▓ ▓▓▓CC▓▓▓ ▓▓▓GT▓▓ G▓AC▓T▓T
LUMA-mou.seq  T▓T▓CAT▓ ▓T▓C▓CT▓ ▓▓▓AG▓▓▓ ▓▓▓CC▓▓ T▓GG▓C▓G 951                                                       1000
LUMA-hum.seq  ▓▓▓▓▓GT ▓A▓A▓▓▓ C▓CT▓▓▓ ▓▓C▓▓▓C▓ ▓▓▓▓▓T▓T
LUMA-mou.seq  ▓▓▓▓▓A▓C ▓C▓G▓▓▓ T▓GC▓▓▓ ▓▓A▓CA▓T▓ ▓▓▓▓▓C▓C 1001                                                      1050
LUMA-hum.seq  ▓C▓AGC▓A▓G C▓▓▓T▓▓▓ ▓▓▓A▓C▓CA AA▓▓▓▓▓▓ ▓▓A▓A▓▓
LUMA-mou.seq  ▓T▓CC▓C▓A T▓▓▓C▓▓▓ ▓▓C▓T▓TG TG▓▓▓▓▓▓ ▓G▓▓▓▓▓

1051                                                      1100
LUMA-hum.seq  T▓▓▓▓▓▓ ▓G▓C▓▓▓ ▓▓A▓TA▓T ▓▓▓▓▓A▓ A▓▓A▓C▓
LUMA-mou.seq  A▓▓▓▓▓▓ ▓A▓▓A▓▓ ▓▓G▓AG▓C ▓▓▓▓▓C▓ G▓▓G▓T▓

1101                                                      1150
LUMA-hum.seq  C▓▓T▓TC ▓▓▓▓A▓A ▓GC▓▓▓▓ ▓▓▓▓▓G ▓G▓▓▓▓
LUMA-mou.seq  G▓▓G▓CT ▓▓▓G▓G ▓AA▓▓▓▓ ▓▓▓▓▓T ▓A▓▓▓▓

1151                                                      1200
LUMA-hum.seq  ▓G▓TT▓▓A▓ ▓▓▓▓▓▓C A▓AT▓C▓C▓ ▓▓▓G▓▓▓▓ CTGGTG▓T▓A
LUMA-mou.seq  ▓A▓CC▓▓.▓ ▓▓▓▓▓▓T G▓GA▓T▓.▓ ▓▓▓▓C▓▓▓ .....A▓A▓C 1201                                                      1250
LUMA-hum.seq  ▓A▓▓T▓T▓T T▓CCAACCTT TA▓TC▓A▓ ▓TATT▓▓A ▓G▓ATAAA▓A
LUMA-mou.seq  ▓T▓▓▓▓C▓A G▓GTG.TGGC AG▓▓GG▓C▓ ▓▓A...▓▓C ▓C▓TCTTG▓G 1251                          1287
LUMA-hum.seq  ▓▓A▓T▓CAA▓ TGCC▓TTA▓A TC▓CT▓ACTT AATTTTA
LUMA-mou.seq  ▓T▓C▓TCC▓ CATG▓AGC▓G CT▓TG▓~~~ ~~~~~~~
```

Figure 15:

```
              1                                                          50
LUMA-hum.pep  ~~  T          V     K       EA  R    E    H
LUMA-mou.pep  MI  A          E     I       RE  Q    L    R 51                                                        100
LUMA-hum.pep      D  L              T  D M D    K C  S    GM   P
LUMA-mou.pep      E  F              A  A V Q    T G  R    ET   T 101                                                       150
LUMA-hum.pep  Q   W     D  N.CS  N V   V        CFQA     T K    Q
LUMA-mou.pep  .   C     E  HSST  A L   A        HLRG     A M    L 151                                                       200
LUMA-hum.pep      Y        R VG FR    V  L      AR  A SARM   K  Q  S
LUMA-mou.pep      C        Q AA LH    L  A      TK  T NRKL   R  N  T 201                                                       250
LUMA-hum.pep   K           EAL Q    HF  M   R       E  G    Q    SK
LUMA-mou.pep   R           DSV R    DI  I   G       K  E    K    TE 251                                                       300
LUMA-hum.pep    L         K  H    S           L  AE    G  H A RSA
LUMA-mou.pep    R         D  K    N           F  VQ    S  Y I WPS 301                                                       350
LUMA-hum.pep   P    SGD  I    AQY  PT    S    YSQQR   L   NLK     I  W      Q
LUMA-mou.pep   Q    PVG  R    THC  LS    L    HPHHH   S   HFV     M  R      K 351                                                   391
LUMA-hum.pep    I   KK  TD    VF   NMA         A   V  T  APSR   PFRAD W
LUMA-mou.pep    V   NR  IE    GS   SVK         T   A  Q  LHLG   I~~~~  ~
```

Figure 16:

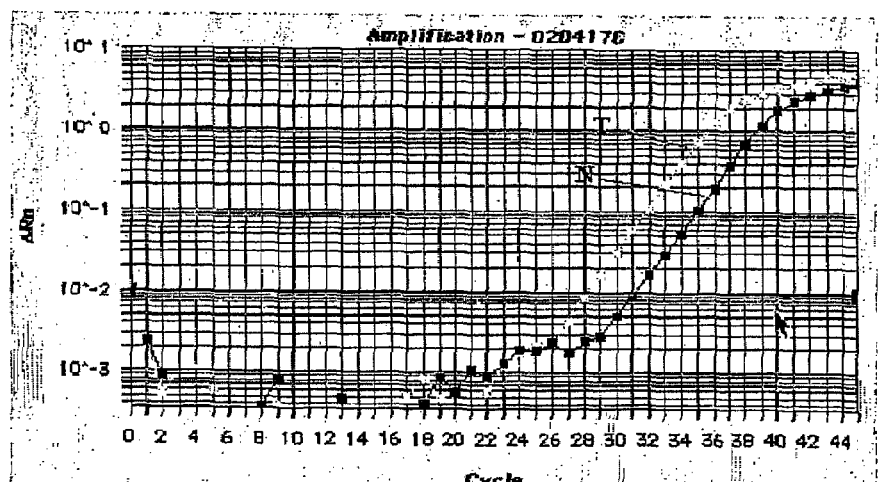

Lung adenocarcinoma N1/T1

N : normal tissue
T : tumor tissue

Lung adenocarcinoma N2/T2

N : normal tissue
T : tumor tissue

Lung adenocarcinoma N3/T3

N : normal tissue
T : tumor tissue

Lung adenocarcinoma N4/T4

N : normal tissue

T : tumor tissue

Lung adenocarcinoma N5/T5

N : normal tissue

T : tumor tissue

N : normal tissue
T : tumor tissue (lung adenocarcinoma)

N : normal tissue
T : tumor tissue (lung adenocarcinoma)

differential expression of the long and short exon 7 variant in normal tissues as determined by Real time PCR

Figure 24:
A:
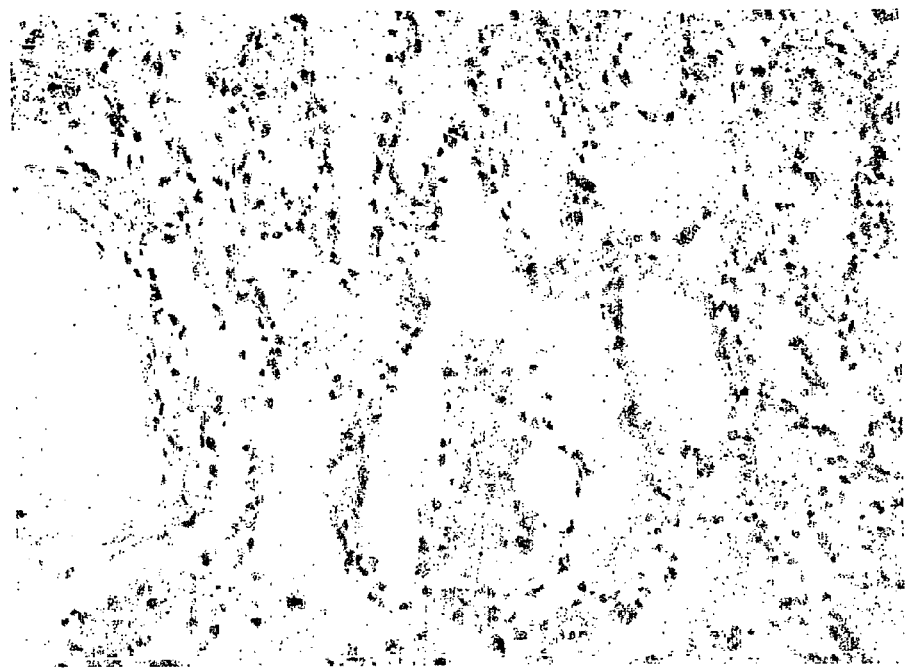
B:
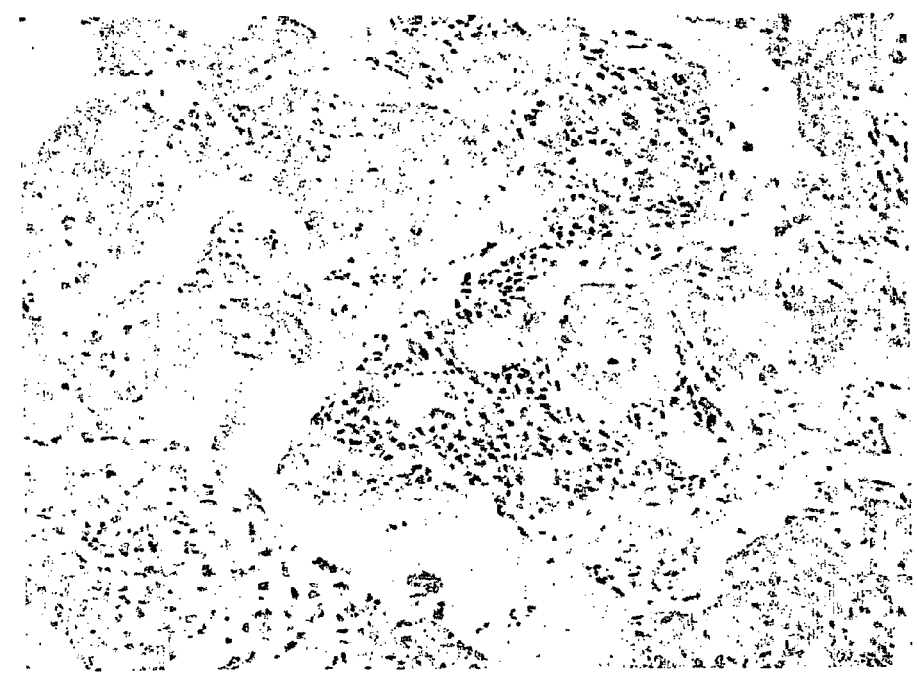

Figure 25:
A:
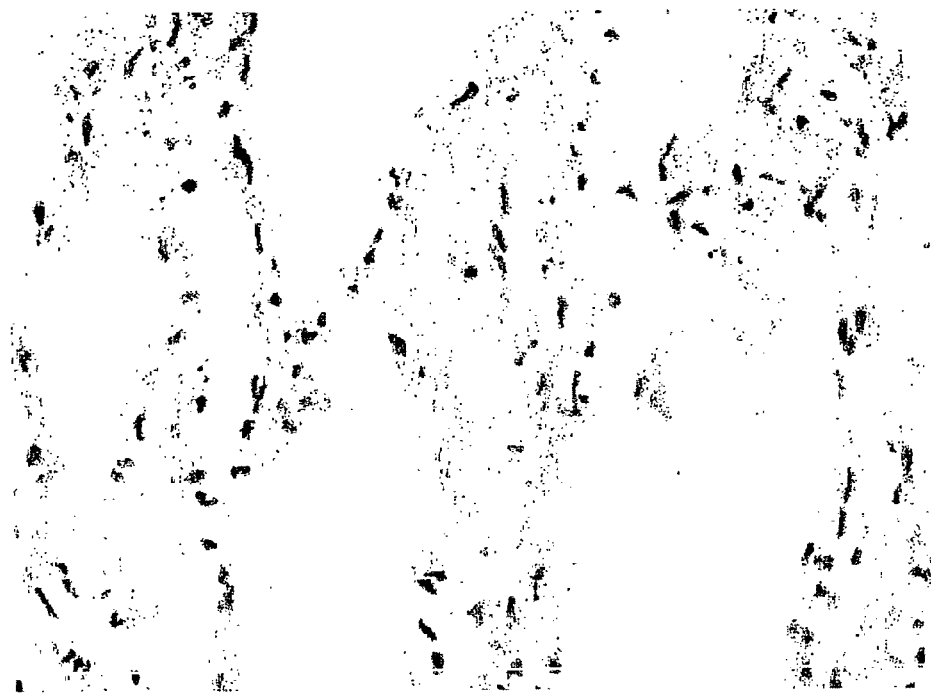
B:
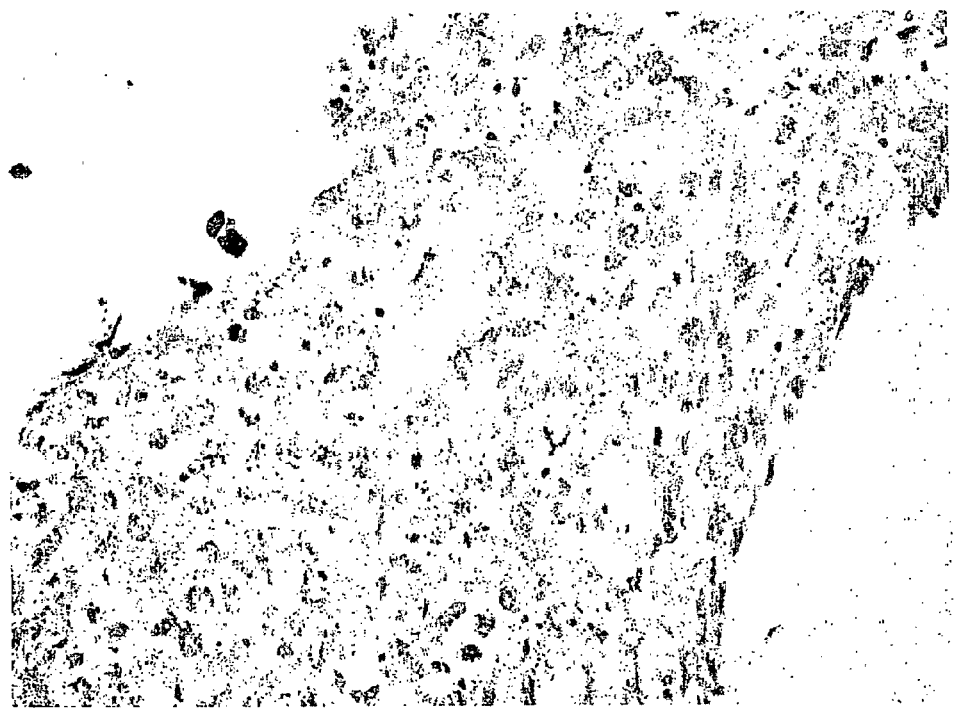

Figure 26:
A:
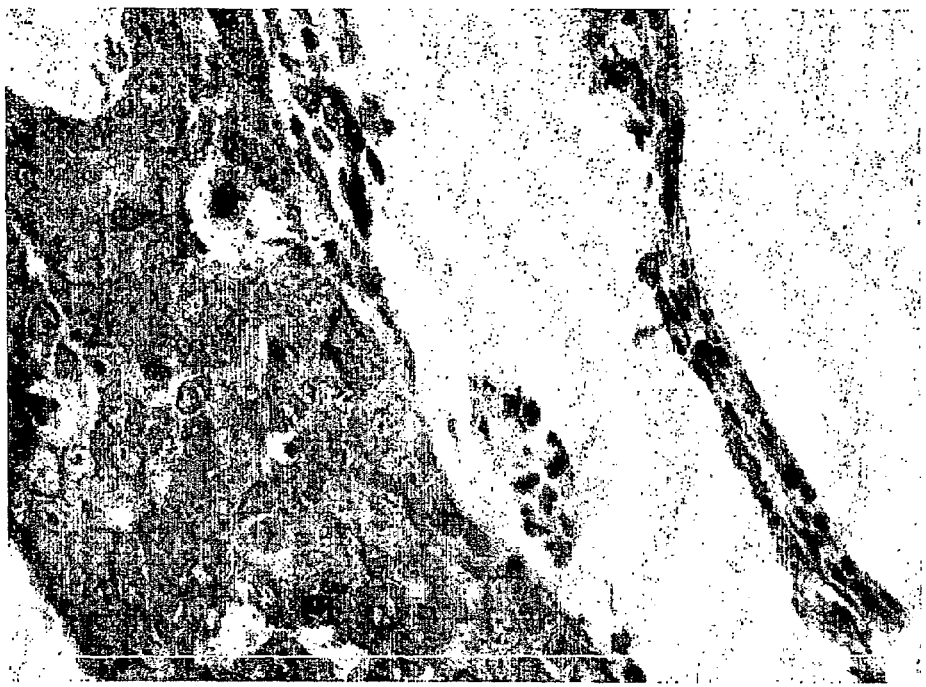
B:
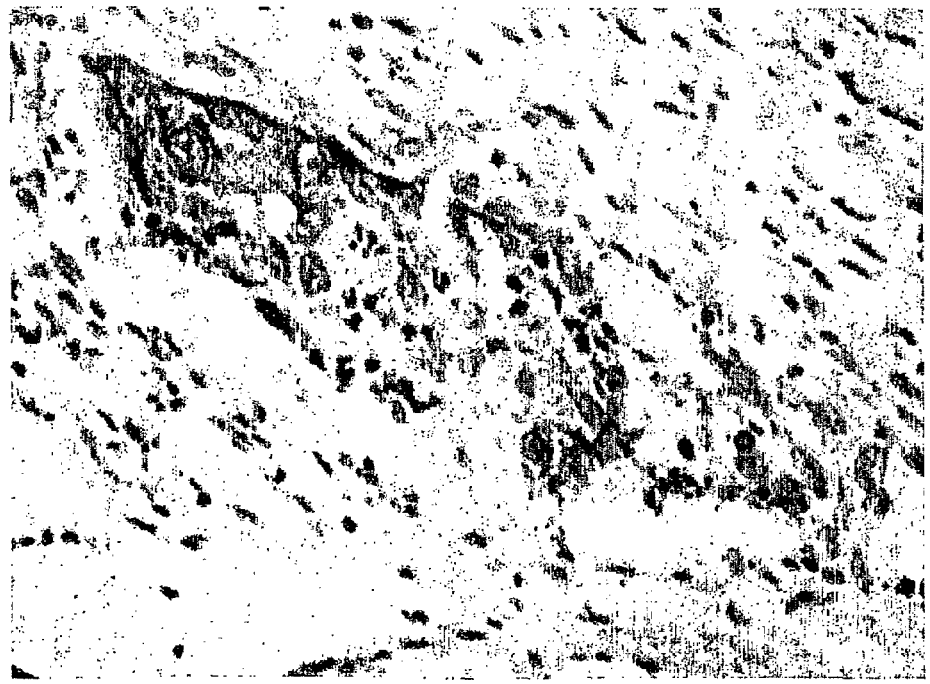

SEQUENCE LISTING

<160> NUMBER OF SEQ ID NOS: 38

<210> SEQ ID NO 1
<211> LENGTH: 1257
<212> TYPE: DNA
<213> ORGANISM: Homo sapiens

<400> SEQUENCE: 1

```
atggaaatca ccactctgag agcccaactc acagacttgg aagaagtgaa tctgaatctc      60
aagaagcaga ttagaaaaga agtccaagaa gaatatgaag cattagtccg agctttgttt     120
gagacctgtt tacacataaa agagaagctg gatgataatc agcttaattt gatccagaaa     180
gtgtgtgagc tcatcggtga agtgagaaca gaagggattg acaatatgaa ggacctaaag     240
aaaaaatggt gctctgccag ccccgatgaa ggaatgaaag aaaacccagc caaacaggaa     300
cagctgtggg ccttggagca ggacaactgc agcctggcca acctggtgtg caaagtgagg     360
agcctgggcc gctggaggct ggctgtgcag caggcgtgct tccaggccca gctgagcagg     420
acagagaagg aatctattca agtaaaaaaa gagtatttgc gcatcaagct gatggcagag     480
cgagaagtgg gtttatttcg tcagcaggtc ctggctctca ggcaggccct ggccagggca     540
caggctgaca gcgcgaggat gtggaagcag caggacagcc aggctcaact gctgaaggag     600
ttagaacata gagtgaccca ggaagctctc acccagcagc agctgcattt tatgaaaaca     660
tccaggatgg agaagctctt ggaagatgtg gggcaaaaag aacagcaact gcagctcctt     720
agcaaagagg ctgagagggc ttctaagctg gccaactgc agcagaaaaa aatgaagagg     780
gacctccacc agatgagaag ccggcttgcc caggagcgca gtgtgaagct ggatgctctc     840
cagcgtgcag aggagctgca gggtcagctt cacgatgccc agcggtcagc tgtccccatg     900
ggctcgtcag cgaccttat atcccaggct caatactccc caacttctgc ttccacatca     960
tccagatact cccagcaacg cttttttaaag actaatctca aaggcagtaa ataacaaga    1020
tggattcaaa ggccacagac tgtacctatt aaacacaaaa aaagaactga cgatgttttc    1080
ctacccaata tggcagaaaa tgttcaactg acagcttttc aggttcaaac agctccatcc    1140
agattcccat ttagagctga ctggtgatga tatcttcttt ttccaacctt tatttctatg    1200
agtatttgaa tgaataaaaa tgactccaaa tgccattaaa tctcttactt aattta       1257
```

<210> SEQ ID NO 2
<211> LENGTH: 388
<212> TYPE: PRT
<213> ORGANISM: Homo sapiens

<400> SEQUENCE: 2

```
Met Glu Ile Thr Thr Leu Arg Ala Gln Leu Thr Asp Leu Glu Glu Val
1               5                   10                  15
Asn Leu Asn Leu Lys Lys Gln Ile Arg Lys Glu Val Gln Glu Glu Tyr
                20                  25                  30
Glu Ala Leu Val Arg Ala Leu Phe Glu Thr Cys Leu His Ile Lys Glu
            35                  40                  45
Lys Leu Asp Asp Asn Gln Leu Asn Leu Ile Gln Lys Val Cys Glu Leu
        50                  55                  60
Ile Gly Glu Val Arg Thr Glu Gly Ile Asp Asn Met Lys Asp Leu Lys
65                  70                  75                  80
Lys Lys Trp Cys Ser Ala Ser Pro Asp Glu Gly Met Lys Glu Asn Pro
                85                  90                  95
```

```
Ala Lys Gln Glu Gln Leu Trp Ala Leu Glu Gln Asp Asn Cys Ser Leu
            100                 105                 110
Ala Asn Leu Val Cys Lys Val Arg Ser Leu Gly Arg Trp Arg Leu Ala
            115                 120                 125
Val Gln Gln Ala Cys Phe Gln Ala Gln Leu Ser Arg Thr Glu Lys Glu
        130                 135                 140
Ser Ile Gln Ser Lys Lys Glu Tyr Leu Arg Ile Lys Leu Met Ala Glu
145                 150                 155                 160
Arg Glu Val Gly Leu Phe Arg Gln Gln Val Leu Ala Leu Arg Gln Ala
                165                 170                 175
Leu Ala Arg Ala Gln Ala Asp Ser Ala Arg Met Trp Lys Gln Gln Asp
            180                 185                 190
Ser Gln Ala Gln Leu Leu Lys Glu Leu Glu His Arg Val Thr Gln Glu
        195                 200                 205
Ala Leu Thr Gln Gln Gln Leu His Phe Met Lys Thr Ser Arg Met Glu
    210                 215                 220
Lys Leu Leu Glu Asp Val Gly Gln Lys Glu Gln Gln Leu Gln Leu Leu
225                 230                 235                 240
Ser Lys Glu Ala Glu Arg Ala Ser Lys Leu Gly Leu Gln Gln Lys
                245                 250                 255
Lys Met Lys Arg Asp Leu His Gln Met Arg Ser Arg Leu Ala Gln Glu
            260                 265                 270
Arg Ser Val Lys Leu Asp Ala Leu Gln Arg Ala Glu Glu Leu Gln Gly
        275                 280                 285
Gln Leu His Asp Ala Gln Arg Ser Ala Val Pro Met Gly Ser Ser Gly
    290                 295                 300
Asp Leu Ile Ser Gln Ala Gln Tyr Ser Pro Thr Ser Ala Ser Thr Ser
305                 310                 315                 320
Ser Arg Tyr Ser Gln Gln Arg Phe Leu Lys Thr Asn Leu Lys Gly Ser
                325                 330                 335
Lys Ile Thr Arg Trp Ile Gln Arg Pro Gln Thr Val Pro Ile Lys His
            340                 345                 350
Lys Lys Arg Thr Asp Asp Val Phe Leu Pro Asn Met Ala Glu Asn Val
        355                 360                 365
Gln Leu Thr Ala Phe Gln Val Gln Thr Ala Pro Ser Arg Phe Pro Phe
    370                 375                 380
Arg Ala Asp Trp
385

<210> SEQ ID NO 3
<211> LENGTH: 1205
<212> TYPE: DNA
<213> ORGANISM: Homo sapiens

<400> SEQUENCE: 3
atggaaatca ccactctgag agcccaactc acagacttgg aagaagtgaa tctgaatctc      60
aagaagcaga ttagaaaaga gtccaagaa gaatatgaag cattagtccg agctttgttt     120
gagacctgtt tacacataaa agagaagctg atgataatc agcttaattt gatccagaaa      180
gtgtgtgagc tcatcggtga agtgagaaca gaagggattg acaatatgaa ggacctaaag     240
aaaaaatggt gctctgccag ccccgatgaa ggaatgaaag aaaacccagc caaacaggaa     300
cagctgtggg ccttggagca ggacaactgc agcctggcca acctggtgtg caaagtgagg     360
agcctgggcc gctggaggct ggctgtgcag caggcgtgct tccaggccca gctgagcagg     420
```

```
acagagaagg aatctattca aagtaaaaaa gagtatttgc gcatcaagct gatggcagag    480
cgagaagtgg gtttatttcg tcagcaggtc ctggctctca ggcaggccct ggccagggca    540
caggctgaca gcgcgaggat gtggaagcag caggacagcc aggctcaact gctgaaggag    600
ttagaacata gagtgaccca ggaagctctc acccagcagc agctgcattt tatgaaaaca    660
tccaggatgg agaagctctt ggaagatgtg gggcaaaaag aacagcaact gcagctcctt    720
agcaaagagg ctgagagggc ttctaagctg gccaactgc agcagaaaaa aatgaagagg     780
gacctccacc agatgagaag ccggcttgcc caggagcgca gtgtgaagct ggatgctctc    840
cagcgtgcag aggagctgca gggtcagctt cacgatgccc agcggtcagc tgtccccatg    900
ggctcgtcag gcgatactcc cagcaacgct ttttaaagac taatctcaaa ggcagtaaaa    960
taacaagatg gattcaaagg ccacagactg tacctattaa acacaaaaaa agaactgacg   1020
atgttttcct acccaatatg gcagaaaatg ttcaactgac agcttttcag gttcaaacag   1080
ctccatccag attcccattt agagctgact ggtgatgata tcttcttttt ccaacctttta  1140 tttctatgag tatttgaatg aataaaaatg actccaaatg ccattaaatc tcttacttaa   1200
tttta                                                              1205
```

<210> SEQ ID NO 4
<211> LENGTH: 311
<212> TYPE: PRT
<213> ORGANISM: Homo sapiens

<400> SEQUENCE: 4

```
Met Glu Ile Thr Thr Leu Arg Ala Gln Leu Thr Asp Leu Glu Glu Val
1               5                   10                  15

Asn Leu Asn Leu Lys Lys Gln Ile Arg Lys Glu Val Gln Glu Glu Tyr
            20                  25                  30

Glu Ala Leu Val Arg Ala Leu Phe Glu Thr Cys Leu His Ile Lys Glu
        35                  40                  45

Lys Leu Asp Asp Asn Gln Leu Asn Leu Ile Gln Lys Val Cys Glu Leu
    50                  55                  60

Ile Gly Glu Val Arg Thr Glu Gly Ile Asp Asn Met Lys Asp Leu Lys
65                  70                  75                  80

Lys Lys Trp Cys Ser Ala Ser Pro Asp Glu Gly Met Lys Glu Asn Pro
                85                  90                  95

Ala Lys Gln Glu Gln Leu Trp Ala Leu Glu Gln Asp Asn Cys Ser Leu
            100                 105                 110

Ala Asn Leu Val Cys Lys Val Arg Ser Leu Gly Arg Trp Arg Leu Ala
        115                 120                 125

Val Gln Gln Ala Cys Phe Gln Ala Gln Leu Ser Arg Thr Glu Lys Glu
    130                 135                 140

Ser Ile Gln Ser Lys Lys Glu Tyr Leu Arg Ile Lys Leu Met Ala Glu
145                 150                 155                 160

Arg Glu Val Gly Leu Phe Arg Gln Gln Val Leu Ala Leu Arg Gln Ala
                165                 170                 175

Leu Ala Arg Ala Gln Ala Asp Ser Ala Arg Met Trp Lys Gln Gln Asp
            180                 185                 190

Ser Gln Ala Gln Leu Leu Lys Glu Leu Glu His Arg Val Thr Gln Glu
        195                 200                 205

Ala Leu Thr Gln Gln Gln Leu His Phe Met Lys Thr Ser Arg Met Glu
    210                 215                 220
```

```
Lys Leu Leu Glu Asp Val Gly Gln Lys Glu Gln Gln Leu Gln Leu Leu
225                 230                 235                 240

Ser Lys Glu Ala Glu Arg Ala Ser Lys Leu Gly Gln Leu Gln Leu Lys
                245                 250                 255

Lys Met Lys Arg Asp Leu His Gln Met Arg Ser Arg Leu Ala Gln Glu
            260                 265                 270

Arg Ser Val Lys Leu Asp Ala Leu Gln Arg Ala Glu Glu Leu Gln Gly
        275                 280                 285

Gln Leu His Asp Ala Gln Arg Ser Ala Val Pro Met Gly Ser Ser Gly
    290                 295                 300

Asp Thr Pro Ser Asn Ala Phe
305                 310

<210> SEQ ID NO 5
<211> LENGTH: 1245
<212> TYPE: DNA
<213> ORGANISM: Homo sapiens

<400> SEQUENCE: 5
atggaaatca ccactctgag agcccaactc acagacttgg aagaagtgaa tctgaatctc     60
aagaagcaga ttagaaaaga gtccaagaa gaatatgaag cattagtccg agctttgttt    120
gagacctgtt tacacataaa agagaagctg atgataatc agcttaattt gatccagaaa    180
gtgtgtgagc tcatcggtga agtgagaaca aagggattg acaatatgaa ggacctaaag    240
aaaaaatggt gctctgccag ccccgatgaa ggaatgaaag aaaacccagc caaagaacag    300
ctgtgggcct tggagcagga caactgcagc ctggccaacc tggtgtgcaa agtgaggagc    360
ctgggccgct ggaggctggc tgtgcagcag gcgtgcttcc aggcccagct gagcaggaca    420
gagaaggaat ctattcaaag taaaaagag tatttgcgca tcaagctgat ggcagagcga    480
gaagtgggtt tatttcgtca gcaggtcctg gctctcaggc aggccctggc cagggcacag    540
gctgacagcg cgaggatgtg aagcagcag acagccagg ctcaactgct gaaggagtta    600
gaacatagag tgacccagga agctctcacc cagcagcagc tgcattttat gaaaacatcc    660
aggatggaga agctcttgga agatgtgggg caaaagaac agcaactgca gctccttagc    720
aaagaggctg agagggcttc taagctgggc caactgcagc agaaaaaaat gaagagggac    780
ctccaccaga tgagaagccg gcttgcccag gagcgcagtg tgaagctgga tgctctccag    840
cgtgcagagg agctgcaggg tcagcttcac gatgcccagc ggtcagctgt ccccatgggc    900
tcgtcaggcg accttatatc ccaggctcaa tactccccaa cttctgcttc cacatcatcc    960
agatactccc agcaacgctt tttaaagact aatctcaaag gcagtaaaat aacaagatgg   1020
attcaaaggc cacagactgt acctattaaa cacaaaaaaa gaactgacga tgttttccta   1080
cccaatatgg cagaaaatgt tcaactgaca gcttttcagg ttcaaacagc tccatccaga   1140
ttcccatta gagctgactg gtgatgatat cttcttttc aacctttat ttctatgagt   1200
atttgaatga ataaaaatga ctccaaatgc aaaaaaaaa aaaaa                    1245

<210> SEQ ID NO 6
<211> LENGTH: 387
<212> TYPE: PRT
<213> ORGANISM: Homo sapiens

<400> SEQUENCE: 6

Met Glu Ile Thr Thr Leu Arg Ala Gln Leu Thr Asp Leu Glu Glu Val
1               5                   10                  15
```

-continued

```
Asn Leu Asn Leu Lys Lys Gln Ile Arg Lys Glu Val Gln Glu Glu Tyr
             20                  25                  30
Glu Ala Leu Val Arg Ala Leu Phe Glu Thr Cys Leu His Ile Lys Glu
         35                  40                  45
Lys Leu Asp Asp Asn Gln Leu Asn Leu Ile Gln Lys Val Cys Glu Leu
     50                  55                  60
Ile Gly Glu Val Arg Thr Glu Gly Ile Asp Asn Met Lys Asp Leu Lys
 65                  70                  75                  80
Lys Lys Trp Cys Ser Ala Ser Pro Asp Glu Gly Met Lys Glu Asn Pro
                 85                  90                  95
Ala Lys Glu Gln Leu Trp Ala Leu Glu Gln Asp Asn Cys Ser Leu Ala
            100                 105                 110
Asn Leu Val Cys Lys Val Arg Ser Leu Gly Arg Trp Arg Leu Ala Val
        115                 120                 125
Gln Gln Ala Cys Phe Gln Ala Gln Leu Ser Arg Thr Glu Lys Glu Ser
    130                 135                 140
Ile Gln Ser Lys Lys Glu Tyr Leu Arg Ile Lys Leu Met Ala Glu Arg
145                 150                 155                 160
Glu Val Gly Leu Phe Arg Gln Gln Val Leu Ala Leu Arg Gln Ala Leu
                165                 170                 175
Ala Arg Ala Gln Ala Asp Ser Ala Arg Met Trp Lys Gln Gln Asp Ser
            180                 185                 190
Gln Ala Gln Leu Leu Lys Glu Leu Glu His Arg Val Thr Gln Glu Ala
        195                 200                 205
Leu Thr Gln Gln Gln Leu His Phe Met Lys Thr Ser Arg Met Glu Lys
    210                 215                 220
Leu Leu Glu Asp Val Gly Gln Lys Glu Gln Gln Leu Gln Leu Leu Ser
225                 230                 235                 240
Lys Glu Ala Glu Arg Ala Ser Lys Leu Gly Gln Leu Gln Gln Lys Lys
                245                 250                 255
Met Lys Arg Asp Leu His Gln Met Arg Ser Arg Leu Ala Gln Glu Arg
            260                 265                 270
Ser Val Lys Leu Asp Ala Leu Gln Arg Ala Glu Glu Leu Gln Gly Gln
        275                 280                 285
Leu His Asp Ala Gln Arg Ser Ala Val Pro Met Gly Ser Ser Gly Asp
    290                 295                 300
Leu Ile Ser Gln Ala Gln Tyr Ser Pro Thr Ser Ala Ser Thr Ser Ser
305                 310                 315                 320
Arg Tyr Ser Gln Gln Arg Phe Leu Lys Thr Asn Leu Lys Gly Ser Lys
                325                 330                 335
Ile Thr Arg Trp Ile Gln Arg Pro Gln Thr Val Pro Ile Lys His Lys
            340                 345                 350
Lys Arg Thr Asp Asp Val Phe Leu Pro Asn Met Ala Glu Asn Val Gln
        355                 360                 365
Leu Thr Ala Phe Gln Val Gln Thr Ala Pro Ser Arg Phe Pro Phe Arg
    370                 375                 380
Ala Asp Trp
385

<210> SEQ ID NO 7
<211> LENGTH: 510
<212> TYPE: DNA
<213> ORGANISM: Homo sapiens

<400> SEQUENCE: 7
```

-continued

```
attagtccga gctttgtttg agacctgttt acacataaaa gagaagctgg atgataatca      60
gcttaatttg atccagaaag tgtgtgagct catcggtgaa gtgagaacag aagggattga     120
caatatgaag gacctaaaga aaaaatggtg ctctgccagc cccgatgaag gaatgaaaga     180
aaacccagcc aaagaatcta ttcaaagtaa aaaagagtat ttgcgcatca agctgatggc     240
agagcgagaa gtgggtttat tcgtcagca ggtcctggct ctcaggcagg ccctggccag      300
ggcacaggct gacagcgcga ggatgtggaa gcagcaggac agccaggctc aactgctgaa     360
ggagttagaa catagagtga cccaggaagc tctcacccag cagcagctgc attttatgaa     420
aacatccagg atggagaagc tcttggaaga tgtggggcaa aagaacagc aactgcagct      480 ccttagcaaa gaggctgaga gggcttctaa                                      510
```

<210> SEQ ID NO 8
<211> LENGTH: 169
<212> TYPE: PRT
<213> ORGANISM: Homo sapiens

<400> SEQUENCE: 8

```
Leu Val Arg Ala Leu Phe Glu Thr Cys Leu His Ile Lys Glu Lys Leu
1               5                   10                  15

Asp Asp Asn Gln Leu Asn Leu Ile Gln Lys Val Cys Glu Leu Ile Gly
            20                  25                  30

Glu Val Arg Thr Glu Gly Ile Asp Asn Met Lys Asp Leu Lys Lys Lys
        35                  40                  45

Trp Cys Ser Ala Ser Pro Asp Glu Gly Met Lys Glu Asn Pro Ala Lys
    50                  55                  60

Glu Ser Ile Gln Ser Lys Lys Glu Tyr Leu Arg Ile Lys Leu Met Ala
65                  70                  75                  80

Glu Arg Glu Val Gly Leu Phe Arg Gln Gln Val Leu Ala Leu Arg Gln
                85                  90                  95

Ala Leu Ala Arg Ala Gln Ala Asp Ser Ala Arg Met Trp Lys Gln Gln
            100                 105                 110

Asp Ser Gln Ala Gln Leu Leu Lys Glu Leu Glu His Arg Val Thr Gln
        115                 120                 125

Glu Ala Leu Thr Gln Gln Gln Leu His Phe Met Lys Thr Ser Arg Met
    130                 135                 140

Glu Lys Leu Leu Glu Asp Val Gly Gln Lys Glu Gln Gln Leu Gln Leu
145                 150                 155                 160

Leu Ser Lys Glu Ala Glu Arg Ala Ser
                165
```

<210> SEQ ID NO 9
<211> LENGTH: 515
<212> TYPE: DNA
<213> ORGANISM: Homo sapiens

<400> SEQUENCE: 9

```
atcggtgaag tgagaacaga agggattgac aatatgaagg acctaaagaa aaaatggtgc      60
tctgccagcc ccgatgaagg aatgaaagaa aacccagcca agctcaact gctgaaggag     120 ttagaacata gagtgaccca ggaagctctc acccagcagc agctgcattt tatgaaaaca     180
tccaggatgg agaagctctt ggaagatgtg gggcaaaaag aacagcaact gcagctcctt     240
agcaaagagg ctgagagggc ttctaagctg gccaactgc agcagaaaaa aatgaagagg      300
gacctccacc agatgagaag ccggcttgcc caggagcgca gtgtgaagct ggatgctctc     360
```

-continued

```
cagcgtgcag aggagctgca gggtcagctt cacgatgccc agcggtcagc tgtccccatg    420
ggctcgtcag gcgaccttat atcccaggct caatactccc caacttctgc ttccacatca    480
tccagatact cccagcaacg cttttttaaag actaa                              515
```

<210> SEQ ID NO 10
<211> LENGTH: 171
<212> TYPE: PRT
<213> ORGANISM: Homo sapiens

<400> SEQUENCE: 10

```
Ile Gly Glu Val Arg Thr Glu Gly Ile Asp Asn Met Lys Asp Leu Lys
1               5                   10                  15

Lys Lys Trp Cys Ser Ala Ser Pro Asp Glu Gly Met Lys Glu Asn Pro
            20                  25                  30

Ala Lys Ala Gln Leu Leu Lys Glu Leu Glu His Arg Val Thr Gln Glu
        35                  40                  45

Ala Leu Thr Gln Gln Leu His Phe Met Lys Thr Ser Arg Met Glu
    50                  55                  60

Lys Leu Leu Glu Asp Val Gly Gln Lys Glu Gln Leu Gln Leu Leu
65                  70                  75                  80

Ser Lys Glu Ala Glu Arg Ala Ser Lys Leu Gly Gln Leu Gln Lys
                85                  90                  95

Lys Met Lys Arg Asp Leu His Gln Met Arg Ser Arg Leu Ala Gln Glu
            100                 105                 110

Arg Ser Val Lys Leu Asp Ala Leu Gln Arg Ala Glu Glu Leu Gln Gly
        115                 120                 125

Gln Leu His Asp Ala Gln Arg Ser Ala Val Pro Met Gly Ser Ser Gly
    130                 135                 140

Asp Leu Ile Ser Gln Ala Gln Tyr Ser Pro Thr Ser Ala Ser Thr Ser
145                 150                 155                 160

Ser Arg Tyr Ser Gln Gln Arg Phe Leu Lys Thr
                165                 170
```

<210> SEQ ID NO 11
<211> LENGTH: 305
<212> TYPE: DNA
<213> ORGANISM: Homo sapiens

<400> SEQUENCE: 11

```
atcggtgaag tgagaacaga agggattgac aatatgaagg acctaaagaa aaaatggtgc     60
tctgccagcc ccgatgaagg aatgaaagaa aacccagcca aaatgagaag ccggcttgcc    120
caggagcgca gtgtgaagct ggatgctctc agcgtgcag aggagctgca gggtcagctt    180
cacgatgccc agcggtcagc tgtccccatg ggctcgtcag gcgaccttat atcccaggct    240
caatactccc caacttctgc ttccacatca tccagatact cccagcaacg cttttttaaag    300 actaa                                                                305
```

<210> SEQ ID NO 12
<211> LENGTH: 101
<212> TYPE: PRT
<213> ORGANISM: Homo sapiens

<400> SEQUENCE: 12

```
Ile Gly Glu Val Arg Thr Glu Gly Ile Asp Asn Met Lys Asp Leu Lys
1               5                   10                  15
```

```
Lys Lys Trp Cys Ser Ala Ser Pro Asp Glu Gly Met Lys Glu Asn Pro
            20                  25                  30
Ala Lys Met Arg Ser Arg Leu Ala Gln Glu Arg Ser Val Lys Leu Asp
        35                  40                  45
Ala Leu Gln Arg Ala Glu Glu Leu Gln Gly Gln Leu His Asp Ala Gln
    50                  55                  60
Arg Ser Ala Val Pro Met Gly Ser Ser Gly Asp Leu Ile Ser Gln Ala
65                  70                  75                  80
Gln Tyr Ser Pro Thr Ser Ala Ser Thr Ser Ser Arg Tyr Ser Gln Gln
                85                  90                  95
Arg Phe Leu Lys Thr
            100

<210> SEQ ID NO 13
<211> LENGTH: 5183
<212> TYPE: DNA
<213> ORGANISM: Homo sapiens

<400> SEQUENCE: 13
```

| | | | | | |
|---|---|---|---|---|---|
| gcaatgcgtg | ctatgggtcc | ttttttctaa | cacttgcaga | agatttcagc | cccggccacg | 60 |
| atgtttgctg | tcagcggatg | gaaaagtctt | cctcaattta | tggttcatac | cccattcttc | 120 |
| tgaagtgctg | gttatgttca | aaactctgcc | agaaaaggca | gcttttaaag | ccttaaagcg | 180 |
| aactctacaa | ctgatagctc | ctctgcatga | tatcgtggcc | taccttgtca | gttttgctaa | 240 |
| gcttggcaat | tgtccagcat | gttttgaatt | tcctcgaagt | cccaaccctt | tgagaggtga | 300 |
| ctggggagga | actgagggca | ttgggtctga | gcttcaagag | ctgcagaaca | tgattgacag | 360 |
| cctccagagc | ccccaagacc | ctatccgggt | ggcccaggca | ctcctcctcc | ggagggaggt | 420 |
| tatattttg | cagtttgacg | ctgcagtaag | gcatctcatc | cgaagaacat | ttttggcagc | 480 |
| tggaaatgtt | cctgcctacc | agtctgtcac | agacggcatg | tgccatgggc | taccagcact | 540 |
| gagcaactct | ctcaggaaga | gcattttgc | ctcacagctc | agcctgcccc | agccactgga | 600 |
| tccacggagc | ctccaggcat | ttgagctgtt | tccttggaga | gcatttctgg | aagatggagg | 660 |
| accattccca | gttatgagta | acagcccaga | taccctagaa | tataatatgc | aggtaggata | 720 |
| ggtcttctcc | attgttgcag | agagaactga | gcgcagactg | caaagatggt | tgccattggg | 780 |
| ttcacaggtc | agatcctcct | actctcaccc | acgatgaata | atgtgtgaga | taagcagggt | 840 |
| gtttgatttt | gaggctgtaa | acccagggtc | acgaggtgag | tcacatttc | ttatgataga | 900 |
| agggaagcat | gctctcaact | ggcatgggcc | tgggttgtag | actcagctgc | agttttcgta | 960 |
| acagtagtga | tctgggagaa | tggccagtca | tctccagtca | tgggctgggc | ctcttagaga | 1020 |
| aactcccagg | ctggcagctc | agagatgtgt | gactcctgac | ctgtccataa | acagttgtgg | 1080 |
| gaagggaact | ttttaaagca | ggactcgtag | ggagaatttc | ttttcattgt | tttctttttt | 1140 |
| gctgttaact | tcctttaaat | agtttgattc | ttttcattat | taaatgtttt | ccctgatta | 1200 |
| tttaagtaaa | tattgttttt | atttaaaaaa | tagaaagctt | agaaaagtat | taagaacaac | 1260 |
| atgaaaatca | accataaata | acgcttcaaa | acaatatgga | ggtggggagt | gggtgggatg | 1320 |
| gggtagcact | ggccacaggt | taatggttgt | tggggctggg | tgatgggaac | ttttctgttt | 1380 |
| gatttctata | tattcaaaat | tatccataag | tagaacaggt | ttttttaagta | aaatagtaaa | 1440 |
| agtggtctta | aaaaattaac | catatggctg | ggtgtggtgg | ctcatgcctg | taatctcagc | 1500 |
| actttgggag | gccaaggtgg | gcagatctct | tgagctcagg | agttcaagac | cagcctgggc | 1560 |
| aacaaggtga | aagcctgtgt | ctactgaaaa | tgcaaaaatt | agctgggtgt | ggtggcacac | 1620 |

```
gcctgtagtc ccagctactc agaaggctaa ggcatgagaa tcacctgaac ccaggagacg    1680
gaggttgcag tgagctgaga tcgtaccact gcactccagc ctggtgacag tgtaagactc    1740
tcttaaaaaa taaatataaa taaaataaaa taaaaaatca accatagttc cacaactaag    1800
agacaattac agttcacatt ttatttccct ggtattttcc ctctgcatat gtgtgtttat    1860
atctgtactt ttaagggaaa attgatatca cactatacat tcaccatgta cagatctgct    1920
gtaagggctg gaaacttggc attttcatac agagccaaaa tttgatgtgc tcaaagaaaa    1980
ctttaagtta gaaatgttac tctggttttt atgaattttc tagcagttga gggaatgggt    2040
tcttgtaaat acagttactc ctagttttct tcctgaaaac catatgtaaa atatatatat    2100
ggtcttcaaa tggaaggttt ttttgttttt ttttagctgt gcctctgtgg gctgagtgac    2160
cgtgaccgca aggtggctca tggagaactg gtgggtgtgc aactgctact ggaagatgtt    2220
ctgagtagct atcatgtgac catggaggcc ccccaaagac agcaagccac actgggcaaa    2280
aatacacagc cagattggtc caaagtgcca ggattcagaa gtcagttccg aagcagccca    2340
aagacctctg agctgctgga gggcctgtgc gatgcggtga tgtcctttgc tttgctgaga    2400
tcatttctga tactgtggaa gcagctggaa gtgctaaagg agcactgggg ccgactcaag    2460
ctgcaaggcc aggatatcaa ctctgtctct ctccacaaac ggttttcaga gctctatgaa    2520
actgacgttc tctacccag catgaaagct atagccaggc agatggggaa agaagatgaa    2580
tttgaaggat ttatagtaaa taatcagtct gttcttcccc ccagtggagc ctcagaagtt    2640
gaaataaaaa ctcaccaact tcaaaaactt ctggaaaatt gtgaaattca aatgatccaa    2700
gaggtactaa gaaagttaa cagagaaatg acactggttt tatcagaaaa gtgcaaggag    2760
gagtgttctc tccctacagc tgtactggga cagtggcaat gtgtcttctg gcctttattt    2820
cctaaaggaa aagcaaaaac agatttatat gtttattatg gaaagtagtc aattgttaaa    2880
gaaacataga atcccatttt caaaaccagg acttggcagt aaatagcatc tctgaaaaca    2940
ccaagtcatg aaagaaaact tttcagtctc aagaccacaa atagttgaaa aatttataca    3000
gagattaatg tagaattatc aggatgatgg agtagagatc actttcagga aagatcacct    3060
tgaggcctgc ctccttttccc tgggttgtga tgtgatggca agagaatgca gcaactttga    3120
gacctactcc atgtgctatg agcatgtgtt gcatcatgct aggcagaggc tcagccagaa    3180
agagcaagaa ttagatgcta cacaaagagg ccagggtcca cctgaagaca gtgctggcca    3240
gattgcagag ctcagtcatg atatgatcat ggaaatcacc actctgagag cccaactcac    3300
agacttggaa gaagtgaatc tgaatctcaa gaagcagatt agaaagaag tccaagaaga    3360 atatgaagca ttagtccgag cttgtttga gacctgttta cacataaaag agaagctgga    3420
tgataatcag cttaatttga tccagaaagt gtgtgagctc atcggtgaag tgagaacaga    3480
agggattgac aatatgaagg acctaaagaa aaaatggtgc tctgccagcc ccgatgaagg    3540
aatgaaagaa aacccagcca acaggaaca gctgtgggcc ttggagcagg acaactgcag    3600
cctggccaac ctggtgtgca agtgaggag cctgggccgc tggaggctgg ctgtgcagca    3660
ggcgtgcttc caggcccagc tgagcaggac agagaaggaa tctattcaaa gtaaaaaaga    3720
gtatttgcgc atcaagctga tggcagagcg agaagtgggt ttatttcgtc agcaggtcct    3780
ggctctcagg caggccctgg ccagggcaca ggctgacagc gcgaggatgt ggaagcagca    3840
ggacagccag gctcaactgc tgaaggagtt agaacataga gtgacccagg aagctctcac    3900
ccagcagcag ctgcatttta tgaaaacatc caggatggag aagctcttgg aagatgtggg    3960
```

-continued

```
gcaaaaagaa cagcaactgc agctccttag caaagaggct gagagggctt ctaagctggg      4020
ccaactgcag cagaaaaaaa tgaagaggga cctccaccag atgagaagcc ggcttgccca      4080
ggagcgcagt gtgaagctgg atgctctcca gcgtgcagag gagctgcagg gtcagcttca      4140
cgatgcccag cggtcagctg tccccatggg ctcgtcaggc gaccttatat cccaggctca      4200
atactcccca acttctgctt ccacatcatc cagatactcc cagcaacgct ttttaaagac      4260
taatctcaaa ggcagtaaaa taacaagatg gattcaaagg ccacagacta agcccttttc      4320
aaaaagaagc aaagttcact ttgtatgtgt gggatcacaa gggctttcaa gaatcacttc      4380
atctccattt caccctgaaa gctgcaatac catgggggtg ttggtgatcg tgacttgttg      4440
aaaaggctgc taagcagata agtgcattag tgaagattta ttatatttga gagattcaaa      4500
agggtgatag gctaaagcta attgatgaac attgccctac caaataaata aaccctacag      4560
tgaagtgtct tgtgggccca ttggcccagt ggctatgtac aatacgggaa ccccaagcaa      4620
aaaacctcaa ggccagggaa ggtacacagt tagctggaac ttcagatctc aggtctgact      4680
tcttaagcaa ggcctatgag acaagtcaga taaatactca ttgaagagga atttatacat      4740
ggctgaaatg taagaacaca gttaattttc taaaaattag ccctgcacta acacaaatga      4800
taaaaaatta aggaattttt agattacttg aagtatgagc tgtgttttct tccttaactg      4860
gaaatggctt tccactgatg gattcattct tgaccaattc cctttaggac aatggcaaaa      4920
tacagacaag aaggcatact atatggccta acccagactg aatcaatgat cttggtctca      4980
ttaataacag tgacttttta tgatgctata acaagaatta ttcaccatgt tcttaacacc      5040
aatatctact tatattacag gtacctatta aacacaaaaa aagaactgac gatgttttcc      5100
tacccaatat ggcagaaaat gttcaactga cagcttttca ggttcaaaca gctccatcca      5160
gattcccatt tagagctgac tgg                                              5183
```

<210> SEQ ID NO 14
<211> LENGTH: 239
<212> TYPE: PRT
<213> ORGANISM: Homo sapiens

<400> SEQUENCE: 14

```
Gln Cys Val Leu Trp Val Leu Phe Ser Asn Thr Cys Arg Arg Phe Gln
1               5                   10                  15

Pro Arg Pro Arg Cys Leu Leu Ser Ala Asp Gly Lys Val Phe Leu Asn
            20                  25                  30

Leu Trp Phe Ile Pro His Ser Ser Glu Val Leu Met Phe Lys Thr
        35                  40                  45

Leu Pro Glu Lys Ala Ala Phe Lys Ala Leu Lys Arg Thr Leu Gln Leu
    50                  55                  60

Ile Ala Pro Leu His Asp Ile Val Ala Tyr Leu Val Ser Phe Ala Lys
65                  70                  75                  80

Leu Gly Asn Cys Pro Ala Cys Phe Glu Phe Pro Arg Ser Pro Asn Pro
                85                  90                  95

Leu Arg Gly Asp Trp Gly Gly Thr Glu Gly Ile Gly Ser Glu Leu Gln
            100                 105                 110

Glu Leu Gln Asn Met Ile Asp Ser Leu Gln Ser Pro Gln Asp Pro Ile
        115                 120                 125

Arg Val Ala Gln Ala Leu Leu Leu Arg Arg Glu Val Ile Phe Leu Gln
    130                 135                 140

Phe Asp Ala Ala Val Arg His Leu Ile Arg Arg Thr Phe Leu Ala Ala
145                 150                 155                 160
```

```
Gly Asn Val Pro Ala Tyr Gln Ser Val Thr Asp Gly Met Cys His Gly
            165                 170                 175

Leu Pro Ala Leu Ser Asn Ser Leu Arg Lys Ser Ile Phe Ala Ser Gln
        180                 185                 190

Leu Ser Leu Pro Gln Pro Leu Asp Pro Arg Ser Leu Gln Ala Phe Glu
    195                 200                 205

Leu Phe Pro Trp Arg Ala Phe Leu Glu Asp Gly Gly Pro Phe Pro Val
210                 215                 220

Met Ser Asn Ser Pro Asp Thr Leu Glu Tyr Asn Met Gln Val Gly
225                 230                 235

<210> SEQ ID NO 15
<211> LENGTH: 5035
<212> TYPE: DNA
<213> ORGANISM: Homo sapiens

<400> SEQUENCE: 15
```

| | | | | | |
|---|---|---|---|---|---|
| gcaatgcgtg | ctatgggtcc | tttttctaa | cacttgcaga | agatttcagc | cccggccacg    60 |
| atgtttgctg | tcagcggatg | gaaaagtctt | cctcaattta | tggttcatac | cccattcttc   120 |
| tgaagtgctg | gttatgttca | aaactctgcc | agaaaaggca | gcttttaaag | ccttaaagcg   180 |
| aactctacaa | ctgatagctc | ctctgcatga | tatcgtggcc | taccttgtca | gttttgctaa   240 |
| gcttggcaat | tgtccagcat | gttttgaatt | tcctcgaagt | cccaacccct | tgagaggtga   300 |
| ctggggagga | actgagggca | ttgggtctga | gcttcaagag | ctgcagaaca | tgattgacag   360 |
| cctccagagc | ccccaagacc | ctatccgggt | ggcccaggca | ctcctcctcc | ggagggaggt   420 |
| tatattttg | cagtttgacg | ctgcagtaag | gcatctcatc | cgaagaacat | ttttggcagc   480 |
| tggaaatgtt | cctgcctacc | agtctgtcac | agacggcatg | tgccatgggc | taccagcact   540 |
| gagcaactct | ctcaggaaga | gcattttgc | ctcacagctc | agcctgcccc | agccactgga   600 |
| tccacggagc | ctccaggcat | tgagctgtt | tccttggaga | gcatttctgg | aagatggagg   660 |
| accattccca | gttatgagta | acagcccaga | taccctagaa | tataatatgc | aggtaggata   720 |
| ggtcttctcc | attgttgcag | agagaactga | gcgcagactg | caaagatggt | tgccattggg   780 |
| ttcacaggtc | agatcctcct | actctcaccc | acgatgaata | atgtgtgaga | taagcagggt   840 |
| gtttgatttt | gaggctgtaa | acccagggtc | acgaggtgag | tcacattttc | ttatgataga   900 |
| agggaagcat | gctctcaact | ggcatgggcc | tggttgtag | actcagctgc | agttttcgta   960 |
| acagtagtga | tctgggagaa | tggccagtca | tctccagtca | tgggctgggc | ctcttagaga  1020 |
| aactcccagg | ctggcagctc | agagatgtgt | gactcctgac | ctgtccataa | acagttgtgg  1080 |
| gaagggaact | ttaaagca | ggactcgtag | ggagaatttc | ttttcattgt | ttctttttt  1140 |
| gctgttaact | tcctttaaat | agtttgattc | ttttcattat | taaatgtttt | ccctgatta  1200 |
| tttaagtaaa | tattgttttt | atttaaaaaa | tagaaagctt | agaaaagtat | taagaacaac  1260 |
| atgaaaatca | accataaata | acgcttcaaa | acaatatgga | ggtggggagt | gggtgggatg  1320 |
| gggtagcact | ggccacaggt | taatggttgt | tgggctggg | tgatgggaac | ttttctgttt  1380 |
| gatttctata | tattcaaaat | tatccataag | tagaacaggt | tttttaagta | aaatagtaaa  1440 |
| agtggtctta | aaaaattaac | catatggctg | ggtgtggtgg | ctcatgcctg | taatctcagc  1500 |
| actttgggag | gccaaggtgg | gcagatctct | tgagctcagg | agttcaagac | cagcctgggc  1560 |
| aacaaggtga | aagcctgtgt | ctactgaaaa | tgcaaaaatt | agctgggtgt | ggtggcacac  1620 |
| gcctgtagtc | ccagctactc | agaaggctaa | ggcatgagaa | tcacctgaac | ccaggagacg  1680 |

-continued

```
gaggttgcag tgagctgaga tcgtaccact gcactccagc ctggtgacag tgtaagactc    1740
tcttaaaaaa taaaataaaa taaaataaaa taaaaaatca accatagttc cacaactaag    1800
agacaattac agttcacatt ttatttccct ggtattttcc ctctgcatat gtgtgtttat    1860
atctgtactt ttaagggaaa attgatatca cactatacat tcaccatgta cagatctgct    1920
gtaagggctg gaaacttggc attttcatac agagccaaaa tttgatgtgc tcaaagaaaa    1980
ctttaagtta gaaatgttac tctggttttt atgaattttc tagcagttga gggaatgggt    2040
tcttgtaaat acagttactc ctagttttct tcctgaaaac catatgtaaa atatatatat    2100
ggtcttcaaa tggaaggttt ttttgttttt ttttagctgt gcctctgtgg gctgagtgac    2160
cgtgaccgca aggtggctca tggagaactg gtgggtgtgc aactgctact ggaagatgtt    2220
ctgagtagct atcatgtgac catggaggcc ccccaaagac agcaagccac actgggcaaa    2280
aatacacagc cagattggtc caaagtgcca ggattcagaa gtcagttccg aagcagccca    2340
aagacctctg agctgctgga gggcctgtgc gatgcggtga tgtcctttgc tttgctgaga    2400
tcatttctga tactgtggaa gcagctggaa gtgctaaagg agcactgggg ccgactcaag    2460
ctgcaaggcc aggatatcaa ctctgtctct ctccacaaac ggttttcaga gctctatgaa    2520
actgacgttc tctaccccag catgaaagct atagccaggc agatggggaa agaagatgaa    2580
tttgaaggat ttatagtaaa taatcagtct gttcttcccc ccagtggagc ctcagaagtt    2640
gaaataaaaa ctcaccaact tcaaaaactt ctggaaaatt gtgaaattca aatgatccaa    2700
gaggtactaa gaaaagttaa cagagaaatg acactggttt tatcagaaaa gtgcaaggag    2760
gagtgttctc tccctacaga tctctggaaa caccaagtca tgaaagaaaa cttttcagtc    2820
tcaagaccac aaatagttga aaaatttata cagagattaa tgtagaatta tcaggatgat    2880
ggagtagaga tcactttcag gaaagatcac cttgaggcct gcctcctttc cctgggttgt    2940
gatgtgatgg caagagaatg cagcaacttt gagacctact ccatgtgcta tgagcatgtg    3000
ttgcatcatg ctaggcagag gctcagccag aaagagcaag aattagatgc tacacaaaga    3060
ggccagggtc cacctgaaga cagtgctggc cagattgcag agctcagtca tgatatgatc    3120
atggaaatca ccactctgag agcccaactc acagacttgg aagaagtgaa tctgaatctc    3180
aagaagcaga ttagaaaaga gtccaagaa gaatatgaag cattagtccg agctttgttt    3240
gagacctgtt tacacataaa agagaagctg gatgataatc agcttaattt gatccagaaa    3300
gtgtgtgagc tcatcggtga agtgagaaca gaagggattg acaatatgaa ggacctaaag    3360
aaaaaatggt gctctgccag ccccgatgaa ggaatgaaag aaaacccagc caaacaggaa    3420
cagctgtggg ccttggagca ggacaactgc agcctggcca acctggtgtg caaagtgagg    3480
agcctgggcc gctggaggct ggctgtgcag caggcgtgct tccaggccca gctgagcagg    3540
acagagaagg aatctattca aagtaaaaaa gagtatttgc gcatcaagct gatggcagag    3600
cgagaagtgg gtttatttcg tcagcaggtc ctggctctca ggcaggccct ggccagggca    3660
caggctgaca gcgcgaggat gtggaagcag caggacagcc aggctcaact gctgaaggag    3720
ttagaacata gagtgaccca ggaagctctc acccagcagc agctgcattt tatgaaaaca    3780
tccaggatgg agaagctctt ggaagatgtg gggcaaaaag aacagcaact gcagctcctt    3840
agcaaagagg ctgagagggc ttctaagctg gccaactgc agcagaaaaa aatgaagagg    3900
gacctccacc agatgagaag ccggcttgcc caggagcgca gtgtgaagct ggatgctctc    3960
cagcgtgcag aggagctgca gggtcagctt cacgatgccc agcggtcagc tgtccccatg    4020
```

```
ggctcgtcag gcgaccttat atcccaggct caatactccc caacttctgc ttccacatca    4080
tccagatact cccagcaacg cttttaaaag actaatctca aaggcagtaa ataacaaga     4140 tggattcaaa ggccacagac taagcccttt tcaaaaagaa gcaaagttca ctttgtatgt    4200
gtgggatcac aagggctttc aagaatcact tcatctccat ttcaccctga aagctgcaat    4260
accatggggg tgttggtgat cgtgacttgt tgaaaaggct gctaagcaga taagtgcatt    4320
agtgaagatt tattatattt gagagattca aaagggtgat aggctaaagc taattgatga    4380
acattgccct accaaataaa taaacccctac agtgaagtgt cttgtgggcc cattggccca   4440
gtggctatgt acaatacggg aaccccaagc aaaaaacctc aaggccaggg aaggtacaca    4500
gttagctgga acttcagatc tcaggtctga cttcttaagc aaggcctatg agacaagtca    4560
gataaatact cattgaagag gaatttatac atggctgaaa tgtaagaaca cagttaattt    4620
tctaaaaatt agccctgcac taacacaaat gataaaaaat taaggaattt ttagattact    4680
tgaagtatga gctgtgtttt cttccttaac tggaaatggc tttccactga tggattcatt    4740
cttgaccaat tccctttagg acaatggcaa aatacagaca agaaggcata ctatatggcc    4800
taacccagac tgaatcaatg atcttggtct cattaataac agtgactttt tatgatgcta    4860
taacaagaat tattcaccat gttcttaaca ccaatatcta cttatattac aggtacctat    4920
taaacacaaa aaaagaactg acgatgtttt cctacccaat atggcagaaa atgttcaact    4980
gacagctttt caggttcaaa cagctccatc cagattccca tttagagctg actgg         5035

<210> SEQ ID NO 16
<211> LENGTH: 207
<212> TYPE: PRT
<213> ORGANISM: Homo sapiens

<400> SEQUENCE: 16

Met Glu Ala Pro Gln Arg Gln Gln Ala Thr Leu Gly Lys Asn Thr Gln
1               5                   10                  15

Pro Asp Trp Ser Lys Val Pro Gly Phe Arg Ser Gln Phe Arg Ser Ser
            20                  25                  30

Pro Lys Thr Ser Glu Leu Leu Glu Gly Leu Cys Asp Ala Val Met Ser
        35                  40                  45

Phe Ala Leu Leu Arg Ser Phe Leu Ile Leu Trp Lys Gln Leu Glu Val
    50                  55                  60

Leu Lys Glu His Trp Gly Arg Leu Lys Leu Gln Gly Gln Asp Ile Asn
65                  70                  75                  80

Ser Val Ser Leu His Lys Arg Phe Ser Glu Leu Tyr Glu Thr Asp Val
                85                  90                  95

Leu Tyr Pro Ser Met Lys Ala Ile Ala Arg Gln Met Gly Lys Glu Asp
            100                 105                 110

Glu Phe Glu Gly Phe Ile Val Asn Asn Gln Ser Val Leu Pro Pro Ser
        115                 120                 125

Gly Ala Ser Glu Val Glu Ile Lys Thr His Gln Leu Gln Lys Leu Leu
    130                 135                 140

Glu Asn Cys Glu Ile Gln Met Ile Gln Glu Val Leu Arg Lys Val Asn
145                 150                 155                 160

Arg Glu Met Thr Leu Val Leu Ser Glu Lys Cys Lys Glu Glu Cys Ser
                165                 170                 175

Leu Pro Thr Asp Leu Trp Lys His Gln Val Met Lys Glu Asn Phe Ser
            180                 185                 190

Val Ser Arg Pro Gln Ile Val Glu Lys Phe Ile Gln Arg Leu Met
        195                 200                 205
```

<210> SEQ ID NO 17
<211> LENGTH: 5035
<212> TYPE: DNA
<213> ORGANISM: Homo sapiens

<400> SEQUENCE: 17

```
gcaatgcgtg ctatgggtcc ttttttctaa cacttgcaga agatttcagc cccggccacg    60
atgtttgctg tcagcggatg gaaaagtctt cctcaattta tggttcatac cccattcttc   120
tgaagtgctg gttatgttca aaactctgcc agaaaaggca gcttttaaag ccttaaagcg   180
aactctacaa ctgatagctc ctctgcatga tatcgtggcc taccttgtca gttttgctaa   240
gcttggcaat tgtccagcat gttttgaatt tcctcgaagt cccaacccctt tgagaggtga   300
ctggggagga actgagggca ttgggtctga gcttcaagag ctgcagaaca tgattgacag   360
cctccagagc ccccaagacc ctatccgggt ggcccaggca ctcctcctcc ggagggaggt   420
tatattttg cagtttgacg ctgcagtaag gcatctcatc cgaagaacat ttttggcagc   480
tggaaatgtt cctgcctacc agtctgtcac agacggcatg tgccatgggc taccagcact   540
gagcaactct ctcaggaaga gcattttgc ctcacagctc agcctgcccc agccactgga   600
tccacggagc ctccaggcat ttgagctgtt ccttggaga gcatttctgg aagatggagg   660
accattccca gttatgagta acagcccaga taccctagaa tataatatgc aggtaggata   720
ggtcttctcc attgttgcag agagaactga gcgcagactg caaagatggt tgccattggg   780
ttcacaggtc agatcctcct actctcaccc acgatgaata atgtgtgaga taagcagggt   840
gtttgatttt gaggctgtaa acccagggtc acgaggtgag tcacatttttc ttatgataga   900
agggaagcat gctctcaact ggcatgggcc tgggttgtag actcagctgc agttttcgta   960
acagtagtga tctgggagaa tggccagtca tctccagtca tgggctgggc ctcttagaga  1020
aactcccagg ctggcagctc agagatgtgt gactcctgac ctgtccataa acagttgtgg  1080
gaagggaact ttttaaagca ggactcgtag ggagaatttc ttttcattgt tttcttttt   1140
gctgttaact tcctttaaat agtttgattc ttttcattat taaatgtttt cccctgatta  1200
tttaagtaaa tattgttttt atttaaaaaa tagaaagctt agaaaagtat taagaacaac  1260
atgaaaatca accataaata acgcttcaaa acaatatgga ggtggggagt gggtgggatg  1320
gggtagcact ggccacaggt taatggttgt tgggctggg tgatgggaac ttttctgttt  1380
gatttctata tattcaaaat tatccataag tagaacaggt ttttaagta aaatagtaaa  1440
agtggtctta aaaaattaac catatggctg ggtgtggtgg ctcatgcctg taatctcagc  1500
actttgggag gccaaggtgg gcagatctct tgagctcagg agttcaagac cagcctgggc  1560
aacaaggtga agcctgtgt ctactgaaaa tgcaaaaatt agctgggtgt ggtggcacac  1620
gcctgtagtc ccagctactc agaaggctaa ggcatgagaa tcacctgaac ccaggagacg  1680
gaggttgcag tgagctgaga tcgtaccact gcactccagc ctggtgacag tgtaagactc  1740
tcttaaaaaa taaataaaa taaaataaaa taaaaaatca accatagttc acaactaag   1800
agacaattac agttcacatt ttatttccct ggtatttcc ctctgcatat gtgtgtttat  1860
atctgtactt ttaagggaaa attgatatca cactatacat tcaccatgta cagatctgct  1920
gtaagggctg gaaacttggc attttcatac agagccaaaa tttgatgtgc tcaaagaaaa  1980
ctttaagtta gaaatgttac tctggttttt atgaattttc tagcagttga gggaatgggt  2040
tcttgtaaat acagttactc ctagtttct tcctgaaaac catatgtaaa atatatatat  2100
```

```
ggtcttcaaa tggaaggttt ttttgttttt ttttagctgt gcctctgtgg gctgagtgac   2160
cgtgaccgca aggtggctca tggagaactg gtgggtgtgc aactgctact ggaagatgtt   2220
ctgagtagct atcatgtgac catggaggcc ccccaaagac agcaagccac actgggcaaa   2280
aatacacagc cagattggtc caaagtgcca ggattcagaa gtcagttccg aagcagccca   2340
aagacctctg agctgctgga gggcctgtgc gatgcggtga tgtcctttgc tttgctgaga   2400
tcatttctga tactgtggaa gcagctggaa gtgctaaagg agcactgggg ccgactcaag   2460
ctgcaaggcc aggatatcaa ctctgtctct ctccacaaac ggttttcaga gctctatgaa   2520
actgacgttc tctacccag catgaaagct atagccaggc agatggggaa agaagatgaa   2580
tttgaaggat ttatagtaaa taatcagtct gttcttcccc ccagtggagc ctcagaagtt   2640
gaaataaaaa ctcaccaact tcaaaaactt ctggaaaatt gtgaaattca aatgatccaa   2700
gaggtactaa gaaaagttaa cagagaaatg acactggttt tatcagaaaa gtgcaaggag   2760
gagtgttctc tccctacaga tctctggaaa caccaagtca tgaaagaaaa cttttcagtc   2820
tcaagaccac aaatagttga aaaatttata cagagattaa tggagaatta tcaggatgat   2880
ggagtagaga tcactttcag gaaagatcac cttgaggcct gcctcctttc cctgggttgt   2940
gatgtgatgg caagagaatg cagcaacttt gagacctact ccatgtgcta tgagcatgtg   3000
ttgcatcatg ctaggcagag gctcagccag aaagagcaag aattagatgc tacacaaaga   3060
ggccagggtc cacctgaaga cagtgctggc cagattgcag agctcagtca tgatatgatc   3120
atggaaatca ccactctgag agcccaactc acagacttgg aagaagtgaa tctgaatctc   3180
aagaagcaga ttagaaaaga agtccaagaa gaatatgaag cattagtccg agctttgttt   3240
gagacctgtt tacacataaa agagaagctg atgataatc agcttaattt gatccagaaa   3300
gtgtgtgagc tcatcggtga agtgagaaca gaagggattg acaatatgaa ggacctaaag   3360
aaaaaatggt gctctgccag ccccgatgaa ggaatgaaag aaaacccagc caaacaggaa   3420
cagctgtggg ccttggagca ggacaactgc agcctggcca acctggtgtg caaagtgagg   3480
agcctgggcc gctggaggct ggctgtgcag caggcgtgct tccaggccca gctgagcagg   3540
acagagaagg aatctattca aagtaaaaaa gagtatttgc gcatcaagct gatggcagag   3600
cgagaagtgg gtttatttcg tcagcaggtc ctggctctca ggcaggccct ggccagggca   3660
caggctgaca gcgcgaggat gtggaagcag caggacagcc aggctcaact gctgaaggag   3720
ttagaacata gagtgaccca ggaagctctc acccagcagc agctgcattt tatgaaaaca   3780
tccaggatgg agaagctctt ggaagatgtg gggcaaaaag aacagcaact gcagctcctt   3840
agcaaagagc tgagagggc ttctaagctg gccaactgc agcagaaaaa aatgaagagg   3900
gacctccacc agatgagaag ccggcttgcc caggagcgca gtgtgaagct ggatgctctc   3960
cagcgtgcag aggagctgca gggtcagctt cacgatgccc agcggtcagc tgtccccatg   4020
ggctcgtcag gcgaccttat atcccaggct caatactccc caacttctgc ttccacatca   4080
tccagatact cccagcaacg cttttttaaag actaatctca aaggcagtaa aataacaaga   4140
tggattcaaa ggccacagac taagcccttt tcaaaaagaa gcaaagttca ctttgtatgt   4200
gtgggatcac aagggctttc aagaatcact tcatctccat ttcaccctga agctgcaat   4260 accatggggg tgttggtgat cgtgacttgt tgaaaaggct gctaagcaga taagtgcatt   4320
agtgaagatt tattatattt gagagattca aaagggtgat aggctaaagc taattgatga   4380
acattgccct accaaataaa taaaccctac agtgaagtgt cttgtgggcc cattggccca   4440
```

```
gtggctatgt acaatacggg aaccccaagc aaaaaacctc aaggccaggg aaggtacaca    4500
gttagctgga acttcagatc tcaggtctga cttcttaagc aaggcctatg agacaagtca    4560
gataaatact cattgaagag gaatttatac atggctgaaa tgtaagaaca cagttaattt    4620
tctaaaaatt agccctgcac taacacaaat gataaaaaat taaggaattt ttagattact    4680
tgaagtatga gctgtgtttt cttccttaac tggaaatggc tttccactga tggattcatt    4740
cttgaccaat tcccttaggg acaatggcaa aatacagaca agaaggcata ctatatggcc    4800
taacccagac tgaatcaatg atcttggtct cattaataac agtgactttt tatgatgcta    4860
taacaagaat tattcaccat gttcttaaca ccaatatcta cttatattac aggtacctat    4920
taaacacaaa aaaagaactg acgatgtttt cctacccaat atggcagaaa atgttcaact    4980
gacagctttt caggttcaaa cagctccatc cagattccca tttagagctg actgg         5035
```

<210> SEQ ID NO 18
<211> LENGTH: 683
<212> TYPE: PRT
<213> ORGANISM: Homo sapiens

<400> SEQUENCE: 18

```
Met Glu Ala Pro Gln Arg Gln Gln Ala Thr Leu Gly Lys Asn Thr Gln
1               5                   10                  15

Pro Asp Trp Ser Lys Val Pro Gly Phe Arg Ser Gln Phe Arg Ser Ser
            20                  25                  30

Pro Lys Thr Ser Glu Leu Leu Glu Gly Leu Cys Asp Ala Val Met Ser
        35                  40                  45

Phe Ala Leu Leu Arg Ser Phe Leu Ile Leu Trp Lys Gln Leu Glu Val
    50                  55                  60

Leu Lys Glu His Trp Gly Arg Leu Lys Leu Gln Gly Gln Asp Ile Asn
65                  70                  75                  80

Ser Val Ser Leu His Lys Arg Phe Ser Glu Leu Tyr Glu Thr Asp Val
                85                  90                  95

Leu Tyr Pro Ser Met Lys Ala Ile Ala Arg Gln Met Gly Lys Glu Asp
            100                 105                 110

Glu Phe Glu Gly Phe Ile Val Asn Asn Gln Ser Val Leu Pro Pro Ser
        115                 120                 125

Gly Ala Ser Glu Val Glu Ile Lys Thr His Gln Leu Gln Lys Leu Leu
    130                 135                 140

Glu Asn Cys Glu Ile Gln Met Ile Gln Glu Val Leu Arg Lys Val Asn
145                 150                 155                 160

Arg Glu Met Thr Leu Val Leu Ser Glu Lys Cys Lys Glu Glu Cys Ser
                165                 170                 175

Leu Pro Thr Asp Leu Trp Lys His Gln Val Met Lys Glu Asn Phe Ser
            180                 185                 190

Val Ser Arg Pro Gln Ile Val Glu Lys Phe Ile Gln Arg Leu Met Glu
        195                 200                 205

Asn Tyr Gln Asp Asp Gly Val Glu Ile Thr Phe Arg Lys Asp His Leu
    210                 215                 220

Glu Ala Cys Leu Leu Ser Leu Gly Cys Asp Val Met Ala Arg Glu Cys
225                 230                 235                 240

Ser Asn Phe Glu Thr Tyr Ser Met Cys Tyr Glu His Val Leu His His
                245                 250                 255

Ala Arg Gln Arg Leu Ser Gln Lys Glu Gln Glu Leu Asp Ala Thr Gln
            260                 265                 270
```

-continued

```
Arg Gly Gln Gly Pro Pro Glu Asp Ser Ala Gly Gln Ile Ala Glu Leu
        275                 280                 285

Ser His Asp Met Ile Met Glu Ile Thr Thr Leu Arg Ala Gln Leu Thr
290                 295                 300

Asp Leu Glu Glu Val Asn Leu Asn Leu Lys Lys Gln Ile Arg Lys Glu
305                 310                 315                 320

Val Gln Glu Glu Tyr Glu Ala Leu Val Arg Ala Leu Phe Glu Thr Cys
                325                 330                 335

Leu His Ile Lys Glu Lys Leu Asp Asp Asn Gln Leu Asn Leu Ile Gln
            340                 345                 350

Lys Val Cys Glu Leu Ile Gly Glu Val Arg Thr Gly Ile Asp Asn
        355                 360                 365

Met Lys Asp Leu Lys Lys Lys Trp Cys Ser Ala Ser Pro Asp Glu Gly
        370                 375                 380

Met Lys Glu Asn Pro Ala Lys Gln Glu Gln Leu Trp Ala Leu Glu Gln
385                 390                 395                 400

Asp Asn Cys Ser Leu Ala Asn Leu Val Cys Lys Val Arg Ser Leu Gly
            405                 410                 415

Arg Trp Arg Leu Ala Val Gln Gln Ala Cys Phe Gln Ala Gln Leu Ser
        420                 425                 430

Arg Thr Glu Lys Glu Ser Ile Gln Ser Lys Lys Glu Tyr Leu Arg Ile
        435                 440                 445

Lys Leu Met Ala Glu Arg Glu Val Gly Leu Phe Arg Gln Gln Val Leu
    450                 455                 460

Ala Leu Arg Gln Ala Leu Ala Arg Ala Gln Ala Asp Ser Ala Arg Met
465                 470                 475                 480

Trp Lys Gln Gln Asp Ser Gln Ala Gln Leu Leu Lys Glu Leu Glu His
                485                 490                 495

Arg Val Thr Gln Glu Ala Leu Thr Gln Gln Leu His Phe Met Lys
            500                 505                 510

Thr Ser Arg Met Glu Lys Leu Leu Glu Asp Val Gly Gln Lys Glu Gln
        515                 520                 525

Gln Leu Gln Leu Leu Ser Lys Glu Ala Glu Arg Ala Ser Lys Leu Gly
    530                 535                 540

Gln Leu Gln Gln Lys Lys Met Lys Arg Asp Leu His Gln Met Arg Ser
545                 550                 555                 560

Arg Leu Ala Gln Glu Arg Ser Val Lys Leu Asp Ala Leu Gln Arg Ala
            565                 570                 575

Glu Glu Leu Gln Gly Gln Leu His Asp Ala Gln Arg Ser Ala Val Pro
            580                 585                 590

Met Gly Ser Ser Gly Asp Leu Ile Ser Gln Ala Gln Tyr Ser Pro Thr
        595                 600                 605

Ser Ala Ser Thr Ser Ser Arg Tyr Ser Gln Arg Phe Leu Lys Thr
610                 615                 620

Asn Leu Lys Gly Ser Lys Ile Thr Arg Trp Ile Gln Arg Pro Gln Thr
625                 630                 635                 640

Lys Pro Phe Ser Lys Arg Ser Lys Val His Phe Val Cys Val Gly Ser
            645                 650                 655

Gln Gly Leu Ser Arg Ile Thr Ser Ser Pro Phe His Pro Glu Ser Cys
        660                 665                 670

Asn Thr Met Gly Val Leu Val Ile Val Thr Cys
        675                 680
```

<210> SEQ ID NO 19
<211> LENGTH: 5035
<212> TYPE: DNA
<213> ORGANISM: Homo sapiens

<400> SEQUENCE: 19

```
gcaatgcgtg ctatgggtcc ttttttctaa cacttgcaga agatttcagc cccggccacg         60
atgtttgctg tcagcggatg gaaaagtctt cctcaattta tggttcatac cccattcttc        120
tgaagtgctg gttatgttca aaactctgcc agaaaaggca gcttttaaag ccttaaagcg        180
aactctacaa ctgatagctc ctctgcatga tatcgtggcc taccttgtca gttttgctaa        240
gcttggcaat tgtccagcat gttttgaatt tcctcgaagt cccaacccctt tgagaggtga       300
ctggggagga actgagggca ttgggtctga gcttcaagag ctgcagaaca tgattgacag        360
cctccagagc ccccaagacc ctatccgggt ggcccaggca ctcctcctcc ggagggaggt        420
tatattttg cagtttgacg ctgcagtaag gcatctcatc cgaagaacat ttttggcagc        480
tggaaatgtt cctgcctacc agtctgtcac agacggcatg tgccatgggc taccagcact        540
gagcaactct ctcaggaaga gcattttgc ctcacagctc agcctgcccc agccactgga        600
tccacggagc ctccaggcat tgagctgtt tccttggaga gcatttctgg aagatggagg        660
accattccca gttatgagta acagcccaga taccctagaa ataatatgc aggtaggata        720
ggtcttctcc attgttgcag agagaactga gcgcagactg caaagatggt tgccattggg        780
ttcacaggtc agatcctcct actctcaccc acgatgaata atgtgtgaga taagcagggt        840
gtttgatttt gaggctgtaa acccagggtc acgaggtgag tcacatttc ttatgataga        900
agggaagcat gctctcaact ggcatgggcc tgggttgtag actcagctgc agttttcgta        960
acagtagtga tctgggagaa tggccagtca tctccagtca tgggctgggc ctcttagaga       1020
aactcccagg ctggcagctc agagatgtgt gactcctgac ctgtccataa acagttgtgg       1080
gaagggaact ttttaaagca ggactcgtag ggagaatttc ttttcattgt tttcttttt        1140
gctgttaact tcctttaaat agtttgattc ttttcattat taaatgtttt ccctgatta        1200
tttaagtaaa tattgttttt atttaaaaaa tagaaagctt agaaaagtat taagaacaac       1260
atgaaaatca accataaata acgcttcaaa acaatatgga ggtggggagt gggtgggatg       1320
gggtagcact ggccacaggt taatggttgt tggggctggg tgatgggaac ttttctgttt       1380
gatttctata tattcaaaat tatccataag tagaacaggt tttttaagta aaatagtaaa       1440
agtggtctta aaaaattaac catatggctg ggtgtggtgg ctcatgcctg taatctcagc       1500
actttgggag gccaaggtgg gcagatctct tgagctcagg agttcaagac cagcctgggc       1560
aacaaggtga agcctgtgt ctactgaaaa tgcaaaaatt agctgggtgt ggtggcacac        1620
gcctgtagtc ccagctactc agaaggctaa ggcatgagaa tcacctgaac ccaggagacg       1680
gaggttgcag tgagctgaga tcgtaccact gcactccagc ctggtgacag tgtaagactc       1740
tcttaaaaaa taaataaaa taaaataaaa taaaaaatca accatagttc cacaactaag        1800
agacaattac agttcacatt ttatttccct ggtatttttcc ctctgcatat gtgtgtttat      1860
atctgtactt ttaagggaaa attgatatca cactatacat tcaccatgta cagatctgct       1920
gtaagggctg gaaacttggc attttcatac agagccaaaa tttgatgtgc tcaaagaaaa       1980
ctttaagtta gaaatgttac tctggttttt atgaattttc tagcagttga gggaatgggt       2040
tcttgtaaat acagttactc ctagtttct cctgaaaac catatgtaaa atatatatat         2100
ggtcttcaaa tggaaggttt tttgttttt ttttagctgt gcctctgtgg gctgagtgac        2160
```

```
cgtgaccgca aggtggctca tggagaactg gtgggtgtgc aactgctact ggaagatgtt    2220
ctgagtagct atcatgtgac catggaggcc ccccaaagac agcaagccac actgggcaaa    2280
aatacacagc cagattggtc caaagtgcca ggattcagaa gtcagttccg aagcagccca    2340
aagacctctg agctgctgga gggcctgtgc gatgcggtga tgtcctttgc tttgctgaga    2400
tcatttctga tactgtggaa gcagctggaa gtgctaaagg agcactgggg ccgactcaag    2460
ctgcaaggcc aggatatcaa ctctgtctct ctccacaaac ggttttcaga gctctatgaa    2520
actgacgttc tctacccag catgaaagct atagccaggc agatggggaa agaagatgaa    2580
tttgaaggat ttatagtaaa taatcagtct gttcttcccc ccagtggagc ctcagaagtt    2640
gaaataaaaa ctcaccaact tcaaaaactt ctggaaaatt gtgaaattca aatgatccaa    2700
gaggtactaa gaaaagttaa cagagaaatg acactggttt tatcagaaaa gtgcaaggag    2760
gagtgttctc tccctacaga tctctggaaa caccaagtca tgaaagaaaa cttttcagtc    2820
tcaagaccac aaatagttga aaatttata cagagattaa tggagaatta tcaggatgat    2880
ggagtagaga tcactttcag gaaagatcac cttgaggcct gcctcctttc cctgggttgt    2940
gatgtgatgg caagagaatg cagcaacttt gagacctact ccatgtgcta tgagcatgtg    3000
ttgcatcatg ctaggcagag gctcagccag aaagagcaag aattagatgc tacacaaaga    3060
ggccagggtc cacctgaaga cagtgctggc cagattgcag agctcagtca tgatatgatc    3120
atggaaatca ccactctgag agcccaactc acagacttgg aagaagtgaa tctgaatctc    3180
aagaagcaga ttagaaaaga agtccaagaa gaatatgaag cattagtccg agctttgttt    3240
gagacctgtt tacacataaa agagaagctg gatgataatc agcttaattt gatccagaaa    3300
gtgtgtgagc tcatcggtga agtgagaaca gaagggattg acaatatgaa ggacctaaag    3360
aaaaaatggt gctctgccag ccccgatgaa ggaatgaaag aaaacccagc caaacaggaa    3420
cagctgtggg ccttggagca ggacaactgc agcctggcca acctggtgtg caaagtgagg    3480
agcctgggcc gctggaggct ggctgtgcag caggcgtgct tccaggccca gctgagcagg    3540
acagagaagg aatctattca aagtaaaaaa gagtatttgc gcatcaagct gatggcagag    3600
cgagaagtgg gtttatttcg tcagcaggtc ctggctctca ggcaggccct ggccagggca    3660
caggctgaca gcgcgaggat gtggaagcag caggacagcc aggctcaact gctgaaggag    3720
ttagaacata gagtgaccca ggaagctctc acccagcagc agctgcattt tatgaaaaca    3780
tccaggatgg agaagctctt ggaagatgtg gggcaaaaag aacagcaact gcagctcctt    3840
agcaaagagg ctgagagggc ttctaagctg gccaactgc agcagaaaaa aatgaagagg    3900
gacctccacc agatgagaag ccggcttgcc caggagcgca gtgtgaagct ggatgctctc    3960
cagcgtgcag aggagctgca gggtcagctt cacgatgccc agcggtcagc tgtccccatg    4020
ggctcgtcag gcgaccttat atcccaggct caatactccc caacttctgc ttccacatca    4080
tccagatact cccagcaacg cttttttaaag actaatctca aaggcagtaa aataacaaga    4140
tggattcaaa ggccacagac taagcccttt tcaaaaagaa gcaaagttca ctttgtatgt    4200
gtgggatcac aagggctttc aagaatcact tcatctccat ttcaccctga agctgcaat    4260 accatggggg tgttggtgat cgtgacttgt tgaaaaggct gctaagcaga taagtgcatt    4320
agtgaagatt tattatattt gagagattca aagggtgat aggctaaagc taattgatga    4380
acattgccct accaaataaa taaaccctac agtgaagtgt cttgtgggcc cattggccca    4440
gtggctatgt acaatacggg aaccccaagc aaaaaacctc aaggcagggg aaggtacaca    4500
gttagctgga acttcagatc tcaggtctga cttcttaagc aaggcctatg agacaagtca    4560
```

```
gataaatact cattgaagag gaatttatac atggctgaaa tgtaagaaca cagttaattt    4620
tctaaaaatt agccctgcac taacacaaat gataaaaaat taaggaattt ttagattact    4680
tgaagtatga gctgtgtttt cttccttaac tggaaatggc tttccactga tggattcatt    4740
cttgaccaat tccctttagg acaatggcaa aatacagaca agaaggcata ctatatggcc    4800
taacccagac tgaatcaatg atcttggtct cattaataac agtgactttt tatgatgcta    4860
taacaagaat tattcaccat gttcttaaca ccaatatcta cttatattac aggtacctat    4920
taaacacaaa aaaagaactg acgatgtttt cctacccaat atggcagaaa atgttcaact    4980
gacagctttt caggttcaaa cagctccatc cagattccca tttagagctg actgg          5035
```

<210> SEQ ID NO 20
<211> LENGTH: 448
<212> TYPE: PRT
<213> ORGANISM: Homo sapiens

<400> SEQUENCE: 20

```
Met Ala Arg Glu Cys Ser Asn Phe Glu Thr Tyr Ser Met Cys Tyr Glu
1               5                   10                  15

His Val Leu His His Ala Arg Gln Arg Leu Ser Gln Lys Glu Gln Glu
            20                  25                  30

Leu Asp Ala Thr Gln Arg Gly Gln Gly Pro Pro Glu Asp Ser Ala Gly
        35                  40                  45

Gln Ile Ala Glu Leu Ser His Asp Met Ile Met Glu Ile Thr Thr Leu
    50                  55                  60

Arg Ala Gln Leu Thr Asp Leu Glu Glu Val Asn Leu Asn Leu Lys Lys
65                  70                  75                  80

Gln Ile Arg Lys Glu Val Gln Glu Glu Tyr Glu Ala Leu Val Arg Ala
                85                  90                  95

Leu Phe Glu Thr Cys Leu His Ile Lys Glu Lys Leu Asp Asp Asn Gln
            100                 105                 110

Leu Asn Leu Ile Gln Lys Val Cys Glu Leu Ile Gly Glu Val Arg Thr
        115                 120                 125

Glu Gly Ile Asp Asn Met Lys Asp Leu Lys Lys Lys Trp Cys Ser Ala
    130                 135                 140

Ser Pro Asp Glu Gly Met Lys Glu Asn Pro Ala Lys Gln Glu Gln Leu
145                 150                 155                 160

Trp Ala Leu Glu Gln Asp Asn Cys Ser Leu Ala Asn Leu Val Cys Lys
                165                 170                 175

Val Arg Ser Leu Gly Arg Trp Arg Leu Ala Val Gln Gln Ala Cys Phe
            180                 185                 190

Gln Ala Gln Leu Ser Arg Thr Glu Lys Glu Ser Ile Gln Ser Lys Lys
        195                 200                 205

Glu Tyr Leu Arg Ile Lys Leu Met Ala Glu Arg Glu Val Gly Leu Phe
    210                 215                 220

Arg Gln Gln Val Leu Ala Leu Arg Gln Ala Leu Ala Arg Ala Gln Ala
225                 230                 235                 240

Asp Ser Ala Arg Met Trp Lys Gln Asp Ser Gln Ala Gln Leu Leu
                245                 250                 255

Lys Glu Leu Glu His Arg Val Thr Gln Glu Ala Leu Thr Gln Gln
            260                 265                 270

Leu His Phe Met Lys Thr Ser Arg Met Glu Lys Leu Leu Glu Asp Val
        275                 280                 285
```

```
Gly Gln Lys Glu Gln Gln Leu Gln Leu Leu Ser Lys Glu Ala Glu Arg
    290                 295                 300
Ala Ser Lys Leu Gly Gln Leu Gln Gln Lys Lys Met Lys Arg Asp Leu
305                 310                 315                 320
His Gln Met Arg Ser Arg Leu Ala Gln Glu Arg Ser Val Lys Leu Asp
                325                 330                 335
Ala Leu Gln Arg Ala Glu Glu Leu Gln Gly Gln Leu His Asp Ala Gln
            340                 345                 350
Arg Ser Ala Val Pro Met Gly Ser Gly Asp Leu Ile Ser Gln Ala
        355                 360                 365
Gln Tyr Ser Pro Thr Ser Ala Ser Thr Ser Ser Arg Tyr Ser Gln Gln
    370                 375                 380
Arg Phe Leu Lys Thr Asn Leu Lys Gly Ser Lys Ile Thr Arg Trp Ile
385                 390                 395                 400
Gln Arg Pro Gln Thr Lys Pro Phe Ser Lys Arg Ser Lys Val His Phe
                405                 410                 415
Val Cys Val Gly Ser Gln Gly Leu Ser Arg Ile Thr Ser Ser Pro Phe
            420                 425                 430
His Pro Glu Ser Cys Asn Thr Met Gly Val Leu Val Ile Val Thr Cys
        435                 440                 445

<210> SEQ ID NO 21
<211> LENGTH: 20050
<212> TYPE: DNA
<213> ORGANISM: Homo sapiens

<400> SEQUENCE: 21
tcccgtcagt gaaggtccac tgcaggaaca ccaaggagtg tgctttcact tttggtgagc      60
aaccctcctt agggtgcatt tttttttctt gagtttttg gtcgcttttg ttattttgta     120
ctggttttgt tttgttctgt ttttgttgtt actttgggga gttttgttgt tgtttcttgt     180
tttcttttga tgccagttaa ggtgcattcc aggccagacg cggtggctca cgcctgtaat     240
cccagcactt tgggaggctg aggtgggtgg atcacctgag gtcggaagtt ccagaccaac     300
ctgaccaaca tggagaaacc ccgtctctac taaaaataca aaattagcca gtgtggtgg     360
agcatgcctg taatcccagg tactcggag gctgaggcag gagcattgcc tgaacccggg     420
aggtggaggt tgcggtgagc caagatcgct ccagcctggg caacaagggc aaaactctgt     480
ctcagactaa ataaataaat aaataaat gcattccaaa aagaaaagg gatgtttggg     540
ctgaggtgtc aagggaggc cagttggaa atggaggcca agacagttga gtattttc         600
tctaactgaa aagggcctat gtagtggctt ttctggggtc acttattcac cagtcagtgt     660
ctggcactgt tctgggacct ttgaattgtc cttaaattct tctgcccaca tttatttagc     720
agaatgttca ctctcttcat taggtttaaa atagaagtga aattcaatac tgatctataa     780
gaaactattt tgtagtagca gtttgaaact cctaaattgt ttttctcaca cacacaca     840
cacacacaca cacacacaca cacacacaca ttttctcatg cttctagatt gcagagctca     900
gtcatgatat gatcatggaa atcaccactc tgagagccca actcacagac ttggaagaag     960
tgaatctgaa tctcaagaag cagattagaa agaagtcca agaagaatat gaagcattag    1020
tccgagcttt gtttgagacc tgtttacaca taaagtaag tgtcccgtgt tgaacatctg    1080
ggccacccat tgggtagccg agtgtaacgg attcccatgg tggctgcaca cccagggatc    1140
gatgacagaa taatgggctt tgtagtaaca agagattgtt aggcccaaga attttctagc    1200
tctaagcttt cactgcagaa agagagtcag caatggggttg tcattaacca cgatagacac    1260
```

```
tgaatttggg dataatatag aagtctatct tttaccctct attgacagtt gctattgtca    1320
ctgtctgatt gctgttggga ggacagagtg ttctgctccc cacagtccct cacctcccca    1380
gtttctatca ccattttatc tgttagtgtg actttccaga ctacagtgcc tgggccaggc    1440
cggaccttac gtaggtagca gcaggtgcct ctggagaact ccctggacac attcagaatt    1500
tgaatcagct tccacatttt tttccaaccc tcaaaatgcc tgccagcctc actctcacat    1560
tcaatgtcag caaactgctg acctgtcagc aaagacccat gcagaagtg atggggtacg     1620
catgcacccg cagcactgtg gaagccaatc gctttcatgt gatgtttgca cagccataag    1680
atagatgccc caagcctaaa atgggccatc agggagactg gtccagctga ctcaccagtg    1740
tgaatttcag tgcaacctac cacctgcaag tccacagctt cccccaaccc tgtcccttc     1800
cctgctattg gatacacccc aaagccagcc ccgtttgggt ccttgagtct ctccccaggg    1860
attgcagaat ggccctgagg gttgttaggt aacaggagc ttccaccagt actcaccttg     1920
gcctggtcat tccagcgaga atttcctctt acttgcagtg taaatgctta cacatattaa    1980
gggatcgaac ccaaaatgta ttaggtctgg tgctgcagga aaggatggg cagacagtga     2040
cagctggaat ttgctaagcc atctttcagg tgtgagattg ttgagaaatg tcttaagttc    2100
cttttagctt ctgccagatt cccagttaaa aagtagattc tctctgtttc ccaggctgaa    2160
gtagttccac caagcctcct acagtaggga atccctgtta tattccaggg tcccacgaag    2220
ttgctaaagc ttgtgttgtg tggccagagc caggcttccc tccgtggctc ccagctgggc    2280
accctcctcc tgccttcctc tccagggaag tggtttagaa gtgagaggac accctaccc    2340
tacctctcac cccagagaca ctgggtgtct tagtctgctc aggctgccat aacaaaatat    2400
gataggctgc acagcttaaa aacagaaag tatatttctc acagttctgg aagccagaag    2460
tctgagatca gggtgccagt gtggtctgct tctggctgag ggcatgcttc ctggcttgca    2520
ggtggctgcc ttctcactgt cctcacatgg gagagaggga gaaaagaaa ggtctctctc     2580
tctccctctt cctataaggc cacagtctat tgcaatagag cctcacccctt atatcctcat   2640
tttaatctta attacctcct aaagatccta tctctagata ctgtcacatt gctggttagg    2700
gtttcaacat atgaatctga ggaagacaca attcagtcca tagcactggg tcttcagtcg    2760
tacttaccat tgatcaggct gttttcctcac aagccattta gccagaagcc attcagaacg   2820
gaatatttcc taatggggtt tctgctagat cctaaatagg aaggcagcca gcctgactcc    2880
ctcctccact ttatctatat ttaacagagc tcctcaggag tggctcatct acagtgtctt    2940
gtctgctcac attctactgt gagtcaacat agcagcaaaa atctttggtt cagcttccca    3000
agtaactctt accagggca gtttggtcag caggttttct acctgtgtga ccttccacta     3060
tcctcctggc tcagcttgcc ttggtgttga caaggaaggc acaatctaag atgtgctggt    3120
gtccagaaga tgaagccctg tgaataaaag acagcactca gggggctgct aagtgtgact    3180
tccttatagt acatgtcaga ataattgtct gaggaggtga tatcttaatg tgaaattact    3240
tacaaaagtt aagttgtaga aggcaaaatg gcttttcttc aactacccctt cacactaccc   3300
aaatccattt tacttccttg acttgattct gcaatttgca ggagaagctg gatgataatc    3360
agcttaattt gatccagaaa gtgtgtgagc tcatcggtga agtgagaaca gaagggattg    3420
acaatatgaa ggacctaaag aaaaaatggt gctctgccag ccccgatgaa ggaatgaaag    3480
aaaacccagc caaagtatgt gatttcattt agcaatggga tatcagcgtt tcatcctagc    3540
atctgactct accattcacc ctgttagcat tccagcctga tttccctgag aaagcattgc    3600
```

```
atcaggcatt taaaggggg cacagggacg cactgcacaa ttgtgtcatc ttctggaagg    3660
catgtttctg atgttagggt ttgtgccctt cctatgaaaa tgttgggggc agcctttcct    3720
gaaaatgagc cttcttagca ggaacagctg tgggccttgg agcaggacaa ctgcagcctg    3780
gccaacctgg tgtgcaaagt gaggagcctg gccgctgga ggctggctgt gcagcaggcg    3840
tgcttccagg cccagctgag caggacagag aaggtgagct ctggtggggg agacccagac    3900
agtccccagg atggctgatc ccaagcctcc atggctgcag ctgccatggt gtcactgtag    3960
ctgtgagtgg cactggtgtc aggtggtagg gccaaccatc ctgaaggacc cgacggttgg    4020 cgattttttcc tgggaacagg ccatgtgaga acttcaggag aaacagaaag ggggcagaag    4080 caaaggggc aacaaaaaac agatcagaga attcagcata agggaaggaa gtgaaaagat    4140
ggaggaaagg cttcaccaag gccttgaggc tgctttgtca aataccgca tatctttggg    4200 tttcatacat gagtatctga ggaaaatgaa gtcacaaaat aataagtgag aaatctgctt    4260
taaggtaaat tgagtccaaa gctcatattg atagctattt ggaaactttc acatcctgtt    4320
tctgaaagta tttactctca tatgttaccc cttctgaat taaaatcatg gaagcaggct    4380
ggacatggtg gctcatgcct gtaatcccag cactttgaga ccaaggtg ggcagatcac    4440 ctgaggtcag gagtttgaga gcagcctggc caacatgatg aagcccaatc tctactaaaa    4500
atacaaaaaa attagccggg tgtggtggtg ggcacctgta gtctcagcta ctcaggaggc    4560
tgaggcagga gaattgcttg aacctgggag gtagaggttg cagtgagcca agattgtacc    4620
actgtactcc aggctgggtt gacagagaaa gactccatct ctaaataaat aaataataaa    4680
ataaaataaa atcatggaag cagtgactag caggagctcc cttctaccgg aagtttgaaa    4740
gaagaatgga tgggaaagtg gtttagatac tgcttttgaa actaaacatc tggaaaggaa    4800 acctattcc tatcttactg tgtttgggat atttacagga atctattcaa agtaaaaaag    4860
agtatttgcg catcaagctg atggcagagc gagaagtggg tttatttcgt cagcaggtcc    4920
tggctctcag gcaggccctg ccagggcac aggctgacag cgcgaggatg tggaagcagc    4980
aggacagcca ggtatctgaa cctcagagcc tcttcctcat tcccttgca gttaactctg    5040 caaagctgaa cgtggccacc acacttggtg ctgtggctgt caggagcagt caccagagca    5100
ccacagcctg aagccacaca gatggcacag ccaggaaaag atagcctgga cttgggcttc    5160
ccttctcctc cctcctctcc agcccagaaa ccaagggcgg tggccaaaag gctattgttc    5220
ttactcatgt ggctgagaaa atattactcc taagcaagat cattatcaca tacgtgtgtg    5280
tgtgtgtgtg tgtgtgtgtc catttctctg aggatctttt tgctagaggc tgtcctggga    5340
tcctgggatc taggcctctg ccttgaacac aggctttcat ggggcaagca cgcttccagt    5400
tgacaacaat ccttggcaag tagagtgtgg tccagccttg tagtattatc ccccatgcga    5460
gactgtatcc tttcccagtg atccatactg tgtctcactt tcagaagtta ctgctgcgcg    5520
ataggggccg gcaccaaaat aaaggcattc taagcctaag catttcctta ctgtgccaac    5580
cctctgggca tgaatgaagc agggggactc taggtttaga gtgagaacag ctgagttaaa    5640
gtaacagcct gggaaagcta ggcgtattta aagcatgaaa tttaatttgt tcatcttgga    5700
ccctaattcc tccatgattc tgcatcagat gagttaacta tgtaaagtac attataaact    5760
gtaaagtcat catacagata tgaataataa ttaagtattg accatctagt acttaggata    5820
atacttatta gaaaaacttt ggaacagaac gaaattattt ctacccttat ccttctttaa    5880
ctatctagag tctgacttcc ccagattttt ggaagggaaa acagagccta aatcagaacc    5940 tccttttcttc gcccattgtg tgtatggcat ggccccatct ccttggtgtt aaacgcttcc    6000
```

```
acggctacct cctgacaaag gctccacgac aatgtaaatg ttgtttgtgc tagatatgat      6060
tatctggtta gtaagctaac atacatatta tcaaatctgg gtattaaaag accaaattat      6120
ttgccctggc actgctgtac agtggcgtga tcgcatgcct ggcttttggt gtctgttctg      6180
cttccctctg actgtcactg cagggctcac agtgtaaacg ccaggctagg ctagatcctg      6240
gtgctctggt tagcacagga cagaatcatt gggccgcatt ttctagagcc caggaataca      6300
ccatgtagtt gtgtccctga gccccaaagg aggggatggt tattatgctt tccaacctct      6360
tccccccttc tgctgggaag aaaggctccc tgccttctcc tttcttttgg cgttttcctg      6420
ccacaggctc aactgctgaa ggagttagaa catagagtga cccaggaagc tctcacccag      6480
cagcagctgc attttatgaa acatccagg atggagaagc tcttggaaga tgtggggcaa       6540
aaagaacagc aactgcagct ccttagcaaa gaggctgaga gggcttctaa gctgggccaa      6600
ctgcagcaga aaaaaatgaa gagggacctc caccaggtaa acctcagtaa gagggagtgt      6660
ccaaccagag tgcacctggt gccccagcga gggctgctgc atccttcccc tgcgtgccca      6720
tgcctctctc ctgtccccca caacagtatt tctcaacctc tgtcacttat aggcagccca      6780
ggagaatggt agcaactctc cccacagtgt ctccccacac cacagggatt gctgggcagg      6840
ccatggtggc ttggctgcct cagggctcag aatctcagca cccctgtaac ctactggaaa      6900
aacctgtttc tacccagctc tcatctttga actaggaatc ttttagaaaa ttccaagcag      6960
taacctggaa aagcagcaag tgttaatgga ggctatgaca agaagatttt attcaagtgt      7020
ttcaggaact gcagagacaa aaatgaaagg caaaagtggt ttgcagatcc aatgtatttt      7080
gttaactaca cctaacaaca aagaaataga agagaataat actagaatgt agatgtggat      7140
taatacaagt ttcaacaaag cagaaaacaa tgtaattcaa taaaaaagga aaagtaatt      7200
tccaaagcag gcacctcaca catatccatt gaatgagcaa atcactgaac tcattcatca      7260
gagatagaag gagatggaaa ttgaaagaca aattattggt caagtgtttc ttttttttt      7320
ttctttttt gagacagagt ctcactctgt cacccagact ggagtgcagt ggcgtaatct      7380
tggctcactg caacctccac ctcccagatt caagtgattc tcccacctca gcctcctttg      7440
tagctggggc tacaggcatg agccactatg cccagctaat ttttgtattt ttagtagaga      7500
cggggtttta ccacgttggc caggctggtc tcgaactcct gatctcaggt gatccgcctg      7560
ccttggcctc ccaaagtgct gggattacag gcgtgagcca ccgcacccgg cccctggtca      7620
attaagtgct caaggaagag atcaataagg agaattctat ctacaaaaat gacaaaaaaa      7680
gattaaaatt tgaattgagt taaagaaaat atatagaaat gggggagaa aatgagtagc       7740
tttagaataa aaattagaat ttcatattta ttgcctgaaa agtaaacaaa atatgactc       7800
aacctataag aaaactttgg catcccaatt ttgtgttaca aatcatgctt ttctaaaagc      7860
caccacaaaa acagggaagt tcgtagattc atttcttcaa ggttttctct agttaattat      7920
ttgtttcatg gcagatattc tagaggtggt caaaacaaat attttgaggt ttctctcaac      7980
aaatgtgcac tttaccatat gtacgtataa gccattggcc ctttgtagag tacacctcca      8040
gctctcctga cagctcaagt gtccctgcgc ctacctactc taaacagcaa tcctcagcca      8100
gcaagacccg agccccccac cctcacccc cggcccttc cagccagaag tggcttcttt         8160
aatctatctc cggcctctga ctccatgggc agataattca ctgtctgacc tcggagagcc      8220
tcagtgtcct aacctgctgc ctgcgcctgg ttgaggtcac ttatagtagg gtttccaac       8280
ccccaggctg tggaccggca ggggtccata gcctgtgaaa ctgggctgca cagcagaaga      8340
```

```
tgagcagttg gcagcataac tgcctgagct ccgcctcttg tcagaccaac ggaggccttt      8400
gattctcata ggagcacaaa ccctattgtg aactgcacat gtgagggatc taggttgcct      8460
gctccttatg agaatctagc tagtgcctga tgatctgagg tagaacagct tcatcctgaa      8520
accatttgtc cccacccggt ggaaaaactg tcttccatga aaccggtacc tggtgccaaa      8580
aaggttgggg accagtgatt tagagcacag gccctggagt ggaactgagt ggttcatacc      8640
gctggccctc cagcggtgtg gctttgggca aggtctgtgg cttctctatg ctttgatttc      8700
ttcatcatta caatggaaac aatgtactca cttcactgaa tttgggggat gattaaatta      8760
gggaattagg taatttaaat aaagccctta aaaccaggcc taaaacaggc atgcctgtag      8820
tcccagctac ttgggaggct gaggcaggag gatcgcttga gcccaggagt tcaagcctgc      8880
agtaaactaa gattatgcca ctatactcca gcctgggtga aagagtaaga ccctgtctct      8940
aaaaaataaa attaaaaaat aaaaagtaaa aaattaacaa aaataaacag gccaggcacg      9000
gtggctcact cctataatgc cagcactttg ggaggccaag gtgggaggat tgcttgggca      9060
acatggtgaa accctgtttc tacaaaaaat acaaaaatta gccagggatg gtggtgtgca      9120
tctgtggtcc cagctactca gagggctgag gtggggaggac cacttgaacc tggttgcagt      9180
gagccaagat tgtgccaatg cactccagcc tgcatgacag agactttgtc tcaaaacaaa      9240
caacagcaaa atcacggtgt gatacatagc tctcagtaaa tgttggctgt ttatattttt      9300
gttgggaatg tgaaggtaga cagccttgga aacaggtagg tagacctgga ctcaaatcct      9360
ggctgtgtgg ccttgggcaa gtcacttcac cagcctctgt gacattgggg tgagtgacct      9420
aacacaagga ggtcctgagg aagcacgctt ccttgctggt gtttcttagg tttcctagtg      9480
ccagcctggc tcaggaaatc ttgatatgtt tccttggcac cagcccgtag ggaatgagga      9540
tcctacacaa atccctacag tatggagagg ggctttggac ctactttata ttaggaagtt      9600
ttcctaactc tggagctctg gtaatcttct gaaatttaaa ctatgcttgg gggcccccg      9660 acataaggaa gagcccactt taacatttag ggcaatacta tgcaggggcc ttctggctgg      9720
gtctgtatag gcggagtggg atgtacaata cacatggctg aatgcttgag attagcacgt      9780
gtattcattt cctagagtta ccttaataaa ttatcacaaa ctgggtggct aatagaata      9840 aaaacgtatt ccttcacagc tcgggaggcc agaagcctga aactaatgtg ctggcaaggc      9900
tggttccttt tggaggctct gaggaagaat ctgttccatg tctcttctta gtcacatttt      9960
ggtctctggc attcctcggc ttgtagttac ctcactccaa tcctgcctct gtcatcatgg     10020
agccttcttc ctatgtgctc ctctgagttt ctgtatcctt atcctatctt ctttgtaagg     10080
acaacagtca ttagattcag ggctcaccta aatccagtat gacctcatcc taacaagtcc     10140
atctacgaag accctatttc caaataaggt cacattctga ggttccaggt agacatgaaa     10200 tttgggggt actcttcaaa ccactatagt atatattact tttctacaag taaaaacaat     10260
taggagatta taaattgaaa aagcaaaacc acctgtcatc tgtgcagatg agatacactt     10320
tggacctggg cactgcctgg ctggggagtg tgggctagcc gtgcacgggg agagccatat     10380
aagtcaatac aaaaggttgct tctggagatg ggcttgtcag aacagggcat tcccggcaga     10440
tgctgagctg agagcagaga tttaggagat agataagtct ttcctctgtt tgaaactgtc     10500
caggggctct gacaggtcct cactgtgagat gcagtggcta ggcctccaag gccctgtgtg     10560
cactgggccc tccctccccct cttcctctac ttatctgatg aaataaacat gaaagatata     10620
accttgtgaa taagttccta gctattataa ggtataaggg attccacgga ctgttccttt     10680
ttggttaagt tcttggtctt cctgaagttc ttgattctca gaaggctgag ttcagcctaa     10740
```

```
tcaggacttt aagagccagt tctctttgca gggtagcctg ggacacccat tctccctagg    10800
aaccccctgt gaactgagga aatgaaagtg agcacaaaga atctctgctt ctcattttcc    10860
cctcagatga aagccggct  tgcccaggag cgcagtgtga agctggatgc tctccagcgt    10920
gcagaggagc tgcagggtca gcttcacgat gcccagcggt cagctgtccc catgggctcg    10980
tcaggcggta aggataaccc ctgctctggc tagaaaaccc tcccagtctc tggggtctga    11040
actgaggagg gtctcagaga ctcagggggg accgaatcag taactatcca gtggttattg    11100
agtgggtcct ccacaatgtt tgttgaatga cacataaacg gataaacctt aattctgatt    11160
tacagtcaaa acttcctact ttagtacctt ggagtactga catccaacac taaaaggttt    11220
cagtcataaa aaactggtct tggctggaca cggtggctca cgcctgtaat cccagcactt    11280
tgggaggccg aggtgggcgg atcacgaggt caggagattg gactatcct  ggccaatatg    11340 gtgaaacccc gtctctacta aagatacaaa aattagctgg gtgtggtgac acacacctgt    11400
aattccagct actcaggagg ctgaggcagg agaattgctt gaacctggga gttggaggtt    11460
gcagtgagct gagatggtgc cattgcactc cagcctgatg acagagcgag actctgtcac    11520
acacacacac acacacacac acacacacac acacacacaa aaaaaaaaaa aaaaaaactg    11580
gtcccagaac cagttcattg gattttgaga catcttaatg cttgggggtt tggggtgtcc    11640
ttgaaaataa tcaaaatagc tctctgagca gtgcaggcag catggagctg agaccagacc    11700
ccaggatgtc tctaaaccag cttcctcctc tataagatga ggactaaata cattctaagt    11760
tctcttctag atctattaga aatatcacca aatatcacta accatgattg gcctgttgtt    11820
atgattggcc atgtctcttc tttcctgttc tgtacatagc ctgatagttg agtatatggg    11880 cttggagtg  aaacagccag aattcaggct ctggctctgt cactgctagc cacatgacct    11940
tagacagacc ttaattagcc tctccgtaaa atgggaatac tcacctcaaa ggcttgctct    12000
gagattaaat gaataattc  ctgtcttgac accttagtat agtggcactt agtaattgtg    12060
caagtgttgg ttactatact tgcatacatg tgtttagccc tttatctgtg tttccttttg    12120
gctaccttcc agcgtgaatg agctgagcaa acagcctttc aggagcacag agtcacagat    12180
gaaattactt tgggtttact aagagcagag ctggacttgg cagtaaagct cacagggccc    12240
tccttcctgc ttctgggttg ctgcctggac ctgacattgg gagctggtgt ccctgcccc    12300 agctactggt tattgctgct gccccagccc caacataaag ggcatcaaga gcacacaagg    12360
gccctacttt ggcacctgac cctatgcagt tcggtacctt acactgtctt ctccatgtgc    12420 cagggganttt tttccttctc tccctttcac ctctgcctgc agcttagcca agcatctttc    12480
taatcccttc ctgggataat gcgtcctagt gaactgccat ccacatcctc caacacctgc    12540
ctattgtgaa ggagaaccag aatgaggcac gaggcaggtg ggggagaccc taattcccag    12600
gattggggtg ggagcaggag tgggaagcaa acttcttttcc caggaagtag aggtagacgt    12660
tactcccggg cctcagccct cttctgtttc cctgtgcagg gagaggaggg gtttgagggc    12720
acagtcagct atcaccatac tgttaatgct aagcagtaaa agtcagccat attcccactc    12780
ctccttcctc cgctgttgcc caactggagt ctcaaagtga cccagggtc ttctgcagca    12840 gcagccatgg cagcattcct gcctcccatg ttggaagcat aggtgcactc aaagggcgag    12900
ctctcttccc ttgccattaa cgtgattccc ctaggatttt gcaactcctg agaaatgaag    12960 attttttttct aaatcaatta ttttagacat gcttaagaaa aaatgaaatc acttggctca    13020
taaaactgta aatgttgag  aggaggcctg gctaaaggta gcttcatcaa ggtttgacct    13080
```

```
agttcatgag gactgctttc actctctcca tctctggctc tgaggaggct gggagcagaa    13140
aggaagcaag gctctttgga agcaagatgg cagccacctc cgtagcttcc gtctctgttc    13200
atgctcagca tggcaggagc agggtatgga gatgggacag tcaaaaagaa ttgggctctg    13260
cctggactga cttgggtcat gttgccaatt ttgaacaaat tagtggagcc acagactaag    13320
atgtctggtt ggcttaggcc cagcttacct gcttctccac tggagctgag ggttgggtca    13380
gctcgctgtc tcctcctctc tgcagcaact gttttaaatc tgccttgtct cctcagatct    13440
tcatacgctc cccccaacac ctcatccttt catctcccac ttcacagaga aattagaaac    13500
cctcagacag gaatgccatc ttctccctgt ctcccagcct acctacatct gtactctgct    13560
gcttctcctt ccctcctgtg aacatggaaa ggatgtccct tttcttcccc agggcaatcc    13620
ctatgtaaag ggcccatctg ctgctacctt ctcaggggcc ttgaactagc tgcttctttt    13680
ctacatactt ggatttccca tccatgcatc cctctaatct tgcaaccaac aattacttat    13740
tgatcatgta tgtgccagga tcataaaatc cactgtaaaa tagctccccc cgcccccact    13800
gccttgacaa catattcctt cccctgctgc tggtctttct cttcccagtc agacttctta    13860
aaagagctgc ctatactcac tttcgtgatt caccccactt aatttctctc aggttttgcc    13920
attctcaact tgtggcttcc aaatgttcct cactacctca tggtccaata tgatgcttac    13980
gctttctggc aataggaag gaggaaggca acaaaaaggg cccacccctc ccttgaagct    14040
tgaagaatgc ttcctggaag tcacttgtga cacttctgcg tacattccat tggccagcac    14100
ttagccccaa gaccacacaa aggagactgt gaaatgtagt ttttattcta ggatgccgtg    14160
aacaaaaaat gtgaggtcta tttctaagaa gagaggagag atttgcaatt gggggccaag    14220
aataggtctc tgcaccacca ccagcaatct gattttcttt accacctttt cattgcagtt    14280
gctcttgcca agatcacctt cacttctgtc tccaagtcca aaggacactg agttctcact    14340
gatttcatgt ctcagcagca tttgaaacag ctgaccacac ccttctccta attattctcc    14400
tggcactgct ccttgtggtt ttcctcttcc tctggctgct ttttctatct cctccttttc    14460
tagttcctcc tactgtatcc aacctctaaa cactgaagtt gttcagggat ctttctggcc    14520
ccttcttctc tcacctcaca ttgtctccaa ataattgcat atttcccaca gctttaatca    14580
ttgtttgcta agtctacatc tgcagctcaa aactctcctc tgagctgtag acccctatat    14640
ccagtgaccc atatgtccag tgaataatgt ctacgttcac gtgtctcagg ctcacaagtt    14700
caacaggaat ggaaccccgtc ttcctatcct tctcccttcc tacttttggg gtgggggaga    14760
tgctctttca gcaaatggta gtgccaaata tccagttgct taagcagaa atttgggagc    14820 tattcttttgt caccctgcaa atctggttaa ttctcaactc ctactaattt aagtagctct    14880
cagtctatcc gcttctacct accacagtcc aagtctcttg tcacctcctt cacttttact    14940
tggtcatgcg actattgggc aaaaaactct ctccaagttt tgacacattt gctcaaaatt    15000
gatgaagctg aaaaataagc tgagttagat gccaatttta agccctaaat tttatgaatt    15060
aaatctagat acaggaattt gaggttatag tgagctacga tcgtgccact gcactccagc    15120
ctgggcaaca gagtgaggcc cccactctca aaaaataaa aaatcaaaat aatctaggtt    15180
tatccattgc aaccagagat ataatttaac atttttaact ttatagacct tatatcccag    15240
gctcaatact ccccaacttc tgcttccaca tcatccagat actcccagca acgcttttta    15300
aagactaatc tcaaaggcag taaaataaca agatggattc aaaggccaca gactgtaagt    15360
aataataaga ttgattacat gcattaaaca ataaagcctt acaatttgat ttcatggttt    15420
ttgggtcact tcagacttac attagaaaaa ttatatatca ggagcttatg tagatgcctt    15480
```

```
gaatctggat aagaaaattc tgatgttgaa ataatcctat aacagcacct tctaaattac    15540
aagtcaataa atgggtgtgg aatcagtacc aacaccttgc tgtgttccat ctctgaattt    15600
cttttttccc ccaatcatct tcaacaatta actagcagca tcagactcct tatctgagtt    15660
ccccaacaga gcagaaataa gtttcggaag tcattttaaa acacgtgaga atctaccct     15720 ccaagaaaat tcctgggatg cagattagca tgtatttgaa gaactcgtaa aatgtttcag    15780
tttttagttt atgtaaaaca acatatactt cctcttccac tgcctcctct ctactgcttt    15840
aataagtatt ttactctttg ctgcattttc tttcagaatc ccttctagag attcacatat    15900
ctaatcaaca catttaggaa ttcctggctg ggcacggtgg ctcacacctg taatcccagc    15960
actttgggag gccgaggcag gcagatcacc tgaggccaga gtttgagac cagcctggcc     16020 aacatggtga aacactgtct ctatgaaaaa tacaaaaatt agctgggcat agtggcgggc    16080
gcctgtaatc ccagctactc gggaggctga ggaaggagaa tcgcttgaac ctgggaggca    16140
gaggttgcag tgagctgaga ttgcgccatt gcactccagc ctgggcaaca agagtgagac    16200
ttcatctcaa aaaaaaaaa aaaaattatt tcccattacc tgatgaaaaa ttaagaggaa     16260
aatatttaat cattccttca gagaaaagta tgccattcca agtcattcga tggtgtaatt    16320
ccgcagctga tggtctagtt ataaggatca aaagtttcaa gatttctaaa catgcagtta    16380
agaaggggga aagacaggtt gggaagatac ccaaacacca tcttgaccaa gtgagggcca    16440
cattactaat gtccaccatt tgcttgactc accaatctct gtgcagtcat ctttcttgaa    16500
aatgtgaaat tgtattatat gtctatgttt ccgcaaaagc ccttttcaaa aagaagcaaa    16560
gttcactttg tatgtgtggg atcacaaggg ctttcaagaa tcacttcatc tccatttcac    16620
cctgaaagct gcaataccat gggggtgttg gtgatcgtga cttgttgaaa aggctgctaa    16680
gcagataagt gcattagtga agatttatta tatttgagag attcaaaagg gtgataggct    16740
aaagctaatt gatgaacatt gccctaccaa ataaataaac cctacagtga agtgtcttgt    16800
gggcccattg gcccagtggc tatgtacaat acgggaaccc caagcaaaaa acctcaaggc    16860
cagggaaggt acacagttag ctggaacttc agatctcagg tctgacttct taagcaaggc    16920
ctatgagaca agtcagataa atactcattg aagaggaatt tatacatggc tgaaatgtaa    16980
gaacacagtt aattttctaa aaattagccc tgcactaaca caaatgataa aaaattaagg    17040 aattttttaga ttacttgaag tatgagctgt gttttcttcc ttaactggaa atggctttcc    17100
actgatggat tcattcttga ccaattccct ttaggacaat ggcaaaatac agacaagaag    17160
gcatactata tggcctaacc cagactgaat caatgatctt ggtctcatta ataacagtga    17220 cttttttatga tgctataaca agaattattc accatgttct taacaccaat atctactta    17280 attacaggta cctattaaac acaaaaaaag aactgacgat gttttcctac ccaatatggc    17340
agaaaatgtt caactgacag cttttcaggt tcaaacagct ccatccagat tcccatttag    17400
agctgactgg tgatgatatc ttctttttcc aacctttatt tctatgagta tttgaatgaa    17460
taaaaatgac tccaaatgcc attaaatctc ttacttaatt ttatgtatga aattctctta    17520
tctgtacttg gaagacaggg ttgaaggact aagatgatta catcttgaac caaccccagg    17580
tgaagtaggg gttggtccca gactttaaaa cctaagcatt gatttgcatt tctacaagct    17640
agcctttgcc tctggtcagc cagcagcctc tgaatacgaa ttctagagtt agtgggtaag    17700
caggaaagct aagatggagg cccttgcttc taagcagtgt ttactaacaa gtgaaaaacc    17760
aaagtatgtt aatagagatt aacacaaatg aacgttaaag catttgtttc acttcttaga    17820
```

```
aaacaaattt gccatcctct attaacaatc ttttcattct tcctacaaat gccaaatact    17880
tcctcagact ttagtataaa gtcctaatcc aagtcctttg ttcagacaag aaaatctgtc    17940
ttgtgtaaag caattaataa acagatgaat ggaacagaca aacatattta catgcataaa    18000
tttaaatacg atgtatgtgg cttttcaaac taaagagaac atggaggcta tttggaataa    18060
attaaatcat caccttaccc catacactat aaatcccaaa tggattaaag atctaaatgc    18120
acatacgtac acatgcatac agacacacat gccacacatg cacaaactga tttttaaac    18180 agaatataaa agccaatagg aaaattggta actttggtat cagaactaaa acttcagtat    18240
gataaaatac tgtatcagtt atcaacttat atctcagctc caaattcatt ctttattgtc    18300
tgttctgcaa taacaaatat ggaccctata aatatttcct ctttgccaac tggcaagaag    18360
ttaagctctc agtagagggt gctggaggga ccctgtagga ggtggcaggg tttttttcca    18420
ggttaccttg tgctcctcta ggcaggctct tgcagtgtgc atggcttctg cagcaccagg    18480
ttcttgtagt atatacagtt tctgtggtgc ctggctccag tgatgcatgt agctccatgg    18540
tagagtgcca cttgcatggc acctcctgtg acgggtcccc tccagcaccc ctttgaatag    18600
ctttgcagtc tctgtgaatt tctcagccat ccaataagct ttggccagat cctctccaat    18660
gaggtctgga tctcagccct gaagggtagt ggctggtccc tacatccgct atccttgtat    18720
tctttagagt tctctttatt gcttacaagc agtatgccaa tcttttgtta tagttaataa    18780
ttctttatat caaactttcc ctgttgaat tactgtgtgc tttctgtctc ctgaatggcc    18840
catgactgat atagaactgg taccaggagc agggtgttcc cagaggatag acctgctatg    18900
gtttgaatgt ctgtcctctc caaaactcat gttaaaattt aatccccaat gtggcagtac    18960
tgaaaggtga dacctttaag aggtgattgg gtcatgagga ctctgccctt atgaatggat    19020
cgatccattc atggattaat ggatcgatcc attcatggat taatgatttt gtgggttgtt    19080
aaattaatgg actatcatgg gagtgggact ggtggcttta taagaaagga agacttgggg    19140
agcatgctca gctccctcac catgtgatac cctgtgctgc ctcaggtctc tatggagggt    19200
ccccaccagc aagaaggctc ttaccagatg tgcctcctca accttagact tcccagcctc    19260
cataacttta agaaataaat tccttttctt cccaaatttc cccatttcag gtattatgtt    19320
ataaacaaca gaaatgtac tgaaacagaa cacagatgga acttgggatt tggttggttg    19380
caaccttagg cttgaataca gtgctgagcc aacaggaaat tggaatgtta gtattctttg    19440
catgcagtgg catcacaatc acgttattac ctgtggccga ttgtgctaaa gtacctgctg    19500
aagcatgtgc ctttaggagc ctaaattgct actacattga ctataatggt agtcatgctg    19560
actacagaaa ctgtggtgtg aggtggattt ttttgaatgc acttcagcac ttctggaaga    19620
aaatgacaag tcatgacctt taattctagg cttaattcat cgtctgaaac cagagagctt    19680
ccatgatacc cctaaaagta tctcttattt ctcatagtca cagggataat attgctaaaa    19740
atcaagcaca agttttttatt aggggcatgc taaattacag tgacagttgt atttataagc    19800
tcatcaagct tctcattgcc attgagatgg gccctgtgat ttcaatgaag aaaatgcaat    19860
tccaaagtgg aagagcgaag tggcaggctt taactggcaa aagacaaggc gggcacatcc    19920
attataaagg gcaatagggga tgtatcagta gtcagaatcc cttggcctgc agagatcttt    19980
ggtagttaat gtgtccccag gtatgaaatc atagattgct taatgtatat aacagaaatt    20040
gcttaatgta                                                          20050
```

<210> SEQ ID NO 22
<211> LENGTH: 1262

<212> TYPE: DNA
<213> ORGANISM: Mus musculus

<400> SEQUENCE: 22

```
gttgcagagc tcagtcatga catgatcatg gaaatcactg ctttgagggc ccagctcaca      60
gacctggaag aggagaatct gaatctgaaa atccagatta gaaagaggt ccaggaagag      120
tacagagaat tagtgcaggc gttgtttctg acctgcttac gcataaagga gaagttggat     180
gagaatcagt ttaatttgat ccagaaagtg tgtgagctca tcggggaagt gagagctgaa     240
gggattgcca acgtgaaaca gctaaagaaa acctggggct ctgccagacc tgatgaagaa     300
acaaaagaga acacagccaa ggagcagctg tgtgccttgg agcaggaaca cagcagcacc     360
ctggctgctc tactgtgcaa agcgcggagc ctgggccgct ggcggctggc tgtgcagcag     420
gcacacctca gagggcagct gagcagggca gagatggaat ctattctcag taaaaaggag     480
tgcttgagaa tcaagctaat ggcagagcaa gaagcggctt tactccatca acagctcctg     540
gctgcaaggc aagccctgac caaagctcag actgacaaca ggaagctgtg gcggcagaat     600
gatactcagg ctcaactgct gagggagttg aacacagag tgactcaaga ctctgtcact      660
cggcagcagc tggatatcat aaaaacatct ggcatggaga agctcctaaa agatgtggag     720
caaaaagagc aaaaactaca gctcctgaca gaagaggctg agcgggcttc gaaacgaggc     780
cagctgcagc aaaagaagat ggacagagac ctgaagcaga tgagaaaccg gcttgctcag     840
gagcgcagcg tgaagctgga tgccttccag cgagtgcagg agctgcagag tcagctttat     900
gacatccagt ggccctctgt ccagatgggc tccccagtcg ggctcagatc ccagacccac     960
tgctccctaa gctctgcttc aacattatcc agacaccctc accaccattt ttcaaagact    1020
cattttgtgg gcagtaaaat gacaagaagg attcaaagac caaagactgt gccagtcaaa    1080
cacaacagaa ggattgagga tggttctcta cccagtgtga agaaaatgt tcaacttaca    1140
acttttcaag cccaacagct ccatctggga ttcatttaga cctgaaaagc tttcttccta    1200
gtgtgtggca gttggtctga tgactcat cttgagtgtc cctccacatg aagcagcttt     1260
gt                                                                    1262
```

<210> SEQ ID NO 23
<211> LENGTH: 392
<212> TYPE: PRT
<213> ORGANISM: Mus musculus

<400> SEQUENCE: 23

```
Val Ala Glu Leu Ser His Asp Met Ile Met Glu Ile Thr Ala Leu Arg
1               5                  10                  15

Ala Gln Leu Thr Asp Leu Glu Glu Glu Asn Leu Asn Leu Lys Ile Gln
            20                  25                  30

Ile Arg Lys Glu Val Gln Glu Glu Tyr Arg Glu Leu Val Gln Ala Leu
        35                  40                  45

Phe Leu Thr Cys Leu Arg Ile Lys Glu Lys Leu Asp Glu Asn Gln Phe
    50                  55                  60

Asn Leu Ile Gln Lys Val Cys Glu Leu Ile Gly Glu Val Arg Ala Glu
65                  70                  75                  80

Gly Ile Ala Asn Val Lys Gln Leu Lys Lys Thr Trp Gly Ser Ala Arg
                85                  90                  95

Pro Asp Glu Glu Thr Lys Glu Asn Thr Ala Lys Glu Gln Leu Cys Ala
            100                 105                 110

Leu Glu Gln Glu His Ser Ser Thr Leu Ala Ala Leu Leu Cys Lys Ala
```

115                 120                 125
Arg Ser Leu Gly Arg Trp Arg Leu Ala Val Gln Gln Ala His Leu Arg
    130                 135                 140

Gly Gln Leu Ser Arg Ala Glu Met Glu Ser Ile Leu Ser Lys Lys Glu
145                 150                 155                 160

Cys Leu Arg Ile Lys Leu Met Ala Glu Gln Glu Ala Ala Leu Leu His
                165                 170                 175

Gln Gln Leu Leu Ala Ala Arg Gln Ala Leu Thr Lys Ala Gln Thr Asp
            180                 185                 190

Asn Arg Lys Leu Trp Arg Gln Asn Asp Thr Gln Ala Gln Leu Leu Arg
        195                 200                 205

Glu Leu Glu His Arg Val Thr Gln Asp Ser Val Thr Arg Gln Gln Leu
    210                 215                 220

Asp Ile Ile Lys Thr Ser Gly Met Glu Lys Leu Leu Lys Asp Val Glu
225                 230                 235                 240

Gln Lys Glu Gln Lys Leu Gln Leu Leu Thr Glu Glu Ala Glu Arg Ala
                245                 250                 255

Ser Lys Arg Gly Gln Leu Gln Gln Lys Lys Met Asp Arg Asp Leu Lys
            260                 265                 270

Gln Met Arg Asn Arg Leu Ala Gln Glu Arg Ser Val Lys Leu Asp Ala
        275                 280                 285

Phe Gln Arg Val Gln Glu Leu Gln Ser Gln Leu Tyr Asp Ile Gln Trp
    290                 295                 300

Pro Ser Val Gln Met Gly Ser Pro Val Gly Leu Arg Ser Gln Thr His
305                 310                 315                 320

Cys Ser Leu Ser Ser Ala Ser Thr Leu Ser Arg His Pro His His His
                325                 330                 335

Phe Ser Lys Thr His Phe Val Gly Ser Lys Met Thr Arg Arg Ile Gln
            340                 345                 350

Arg Pro Lys Thr Val Pro Val Lys His Asn Arg Arg Ile Glu Asp Gly
        355                 360                 365

Ser Leu Pro Ser Val Lys Glu Asn Val Gln Leu Thr Thr Phe Gln Ala
    370                 375                 380

Gln Gln Leu His Leu Gly Phe Ile
385                 390

<210> SEQ ID NO 24
<211> LENGTH: 21
<212> TYPE: DNA
<213> ORGANISM: Artificial sequence
<220> FEATURE:
<223> OTHER INFORMATION: Primer

<400> SEQUENCE: 24
ctcgtcaggc gaccttatat c                                         21

<210> SEQ ID NO 25
<211> LENGTH: 22
<212> TYPE: DNA
<213> ORGANISM: Artificial sequence
<220> FEATURE:
<223> OTHER INFORMATION: Primer

<400> SEQUENCE: 25
tgtcagttga acattttctg cc                                        22

<210> SEQ ID NO 26

-continued

```
<211> LENGTH: 19
<212> TYPE: DNA
<213> ORGANISM: Artificial sequence
<220> FEATURE:
<223> OTHER INFORMATION: Primer

<400> SEQUENCE: 26
ctcgtcaggc gatactccc                                                19

<210> SEQ ID NO 27
<211> LENGTH: 21
<212> TYPE: DNA
<213> ORGANISM: Artificial sequence
<220> FEATURE:
<223> OTHER INFORMATION: Primer

<400> SEQUENCE: 27
caccagtcag ctctaaatgg g                                             21

<210> SEQ ID NO 28
<211> LENGTH: 22
<212> TYPE: DNA
<213> ORGANISM: Artificial sequence
<220> FEATURE:
<223> OTHER INFORMATION: Primer

<400> SEQUENCE: 28
cctaaaagcc accccacttc tc                                            22

<210> SEQ ID NO 29
<211> LENGTH: 22
<212> TYPE: DNA
<213> ORGANISM: Artificial sequence
<220> FEATURE:
<223> OTHER INFORMATION: Primer

<400> SEQUENCE: 29
atgctatcac ctcccctgtg tg                                            22

<210> SEQ ID NO 30
<211> LENGTH: 22
<212> TYPE: DNA
<213> ORGANISM: Artificial sequence
<220> FEATURE:
<223> OTHER INFORMATION: Primer

<400> SEQUENCE: 30
atggaaatca ccactctgag ag                                            22

<210> SEQ ID NO 31
<211> LENGTH: 22
<212> TYPE: DNA
<213> ORGANISM: Artificial sequence
<220> FEATURE:
<223> OTHER INFORMATION: Primer

<400> SEQUENCE: 31
ttgatccaga aagtgtgtga gc                                            22

<210> SEQ ID NO 32
<211> LENGTH: 21
<212> TYPE: DNA
<213> ORGANISM: Artificial sequence
<220> FEATURE:
<223> OTHER INFORMATION: Primer

<400> SEQUENCE: 32
```

-continued tgcagttggc ccagcttaga a            21

<210> SEQ ID NO 33
<211> LENGTH: 22
<212> TYPE: DNA
<213> ORGANISM: Artificial sequence
<220> FEATURE:
<223> OTHER INFORMATION: Primer

<400> SEQUENCE: 33
agtctttaaa aagcgttgct gg            22

<210> SEQ ID NO 34
<211> LENGTH: 45
<212> TYPE: DNA
<213> ORGANISM: Artificial sequence
<220> FEATURE:
<223> OTHER INFORMATION: Primer

<400> SEQUENCE: 34
ctaatacgac tcactatagg gcaagcagtg gtatcaacgc agagt            45

<210> SEQ ID NO 35
<211> LENGTH: 22
<212> TYPE: DNA
<213> ORGANISM: Artificial sequence
<220> FEATURE:
<223> OTHER INFORMATION: Primer

<400> SEQUENCE: 35
ctaatacgac tcactatagg gc            22

<210> SEQ ID NO 36
<211> LENGTH: 23
<212> TYPE: DNA
<213> ORGANISM: Artificial sequence
<220> FEATURE:
<223> OTHER INFORMATION: Primer

<400> SEQUENCE: 36
ggagatggag ctgtttgacc tga            23

<210> SEQ ID NO 37
<211> LENGTH: 23
<212> TYPE: DNA
<213> ORGANISM: Artificial sequence
<220> FEATURE:
<223> OTHER INFORMATION: Primer

<400> SEQUENCE: 37
aagcagtggt atcaacgcag agt            23

<210> SEQ ID NO 38
<211> LENGTH: 21
<212> TYPE: DNA
<213> ORGANISM: Artificial sequence
<220> FEATURE:
<223> OTHER INFORMATION: Primer

<400> SEQUENCE: 38
tgcagttggc ccagcttaga a            21

MARKER MOLECULES ASSOCIATED WITH LUNG TUMORS

This application is a National Stage of International Application PCT/EP03/50175, filed May 16, 2003, published Nov. 27, 2003, under PCT Article 21(2) in English; which claims the priority of EP 02010275.2, filed May 21, 2002.

FIELD OF THE INVENTION

The present invention relates to nucleic acids and polypeptides associated with lung cancer. The invention is more specifically related to a nucleic acids and the polypeptides transcribed thereof, the expression of which is significantly altered in association with lung cancer. The invention relates to a series of differentially spliced transcripts of the gene disclosed herein, that are associated with tumors of the respiratory tract. Furthermore the present invention provides a method for early diagnosis, prognosis and monitoring of the disease course and for therapy and vaccination of cell proliferative disorders such as e.g. lung tumors.

BACKGROUND OF THE INVENTION

In the developed countries death rates from cancer declined throughout the past decade. One exception from this decline in cancer caused death rates is lung cancer. Overall lung cancer is one of the few cancers in the world still showing increasing incidence. Lung cancer is the leading cause of cancer deaths in both men in women. Moreover the survival rate in lung cancer is poor up to now and despite the scientific and medical efforts in the field of lung cancer there was hardly any increase in the survival rate.

In lung tumors as in most other tumors, there is a strong correlation between the patients outcome following initial therapy and the stage at which the disease has been diagnosed. So the earlier the cancer could be detected, the better are the chances for the patient to survive. Thus sensitive testing methods are required for detecting the tumors in early stages.

The most promising methods for early diagnosis of tumors are those involving molecular markers characteristic for tumor cells.

Lung cancer is a quite heterogeneous disease. Multiple regulators of the cell growth can be involved in the genesis of cancer. These regulatory elements of the cell cycle can be either positive regulators, named oncogenes when mutated, so that a transformed state is reached, or negative regulators, named tumor suppressor genes. The number of factors known to be involved in the regulation of the cell cycle and potentially being candidates for the development of cancer exceeds 100 up to know and is still increasing.

The molecules being involved in the emergence of the cancerous state of a cell can be used to discriminate between cancer cells and normal tissue. Thus cancerous tissue can be detected by detecting molecules characteristic for the cancer cells. This turns out to be sophisticated due to the large number of molecules potentially being involved in causing cancer.

For improved diagnosis of tumors, there is a need for new marker molecules for use in diagnosis of cancers and especially of lung cancer, which enable for specific early detection and give the opportunity to treat the disorders at an early stage.

SUMMARY OF THE INVENTION

The present invention provides nucleic acids and polypeptides associated with lung cancer. According to the present invention these molecules may be used as molecular markers that allow for comprehensive detection of cell proliferative disorders such as e.g. lung tumors even at early stages.

The present invention thus provides polypeptides and nucleic acids, the expression of which is significantly altered associated with lung tumors, which allow for enhanced prognosis and diagnosis of diseases associated with abnormalities of the growth of cells. Furthermore the nucleic acids disclosed herein comprise transcripts arising from alternative splicing of genes, that do not occur in normal tissue in the extent they may be found in tumorous tissue.

In another aspect of the invention, the nucleic acids and/or polypeptides disclosed herein alone or in combination with other molecules may be used for therapy and/or vaccination of cell proliferative disorders such as e.g. lung tumors.

Yet another aspect of the present invention are pharmaceutical compositions containing polypeptides and/or polynucleotides disclosed herein alone or combination with one or more other therapeutic or diagnostic agents and/or carrier or adjuvant substances.

The present invention also provides kits such as diagnostic kits or research kits for the detection of the polynucleotides or polypeptides disclosed herein or comprising the polynucleotides or polypeptides disclosed herein or combinations thereof.

During the experiments leading to the present invention a gene was identified, the expression of which is associated with lung tumors. The present invention furthermore is based on the inventors findings shown in Examples 1 to 6, that the level of expression of nucleic acids as well as of polypeptides transcribed from the marker gene presented herein in FIG. 1-11 in samples allows to diagnose and grade cell proliferative disorders such as e.g. lung tumors, to predict the course of the disease and to follow up the disease after initial therapy.

The present invention thus provides novel nucleic acids and polypeptides associated with lung cancer.

BRIEF DESCRIPTION OF THE DRAWINGS

FIG. 1 depicts human LUMA1 mRNA variant 1 sequence (SEQ ID NO: 1) and the encoded LUMA1-protein isoform 1 Sequence (SEQ ID NO: 2).

FIG. 2 depicts human LUMA1 mRNA variant 2 sequence (SEQ ID NO: 3). Differential splicing of exon 7 leads to deletion of part of exon 7 which introduces a frameshift in the 3' sequence of the splice variant. Compared to mRNA variant 1, the encoded protein in variant 2 (SEQ ID NO: 4) is shorter than the one in mRNA variant 1. The frameshift leads to a protein isoform with a different carboxy terminal sequence. In addition the complete exon can be spliced out (not shown).

FIG. 3 depicts human LUMA1 mRNA variant 3 sequence (SEQ ID NOS: 5 and 6). This variant is characterized by a 3 bp deletion and a different polyadenylation site which leads to a shorter 3' sequence.

FIG. 4 depicts human LUMA1 mRNA variant 4 sequence (SEQ NOS: 7 and 8). This variant is characterized by a deletion of exon 3.

FIG. 5 depicts human LUMA1 mRNA variant 5 sequence (SEQ ID NOS: 9 and 10). This variant is characterized by a deletion of exon 3 and exon 4.

FIG. 6 depicts human LUMA1 mRNA variant 6 sequence (SEQ ID NOs: 11 and 12). This variant is characterized by a deletion of exon 3, 4 and 5.

FIG. 7A depicts human LUMA1 mRNA variant 7 sequence (SEQ ID NO: 13). FIG. 7B depicts protein 1 sequence (SEQ ID NO: 14). Protein 1 is encoded by an ORF located at the 5'-end of the mRNA.

FIG. 8A depicts human LUMA1 mRNA variant 8 sequence (SEQ ID NO: 15). FIG. 8B depicts protein 2 sequence (SEQ ID NO: 16). Protein 2 is encoded by an ORF beginning at base pair 2242. The open reading frame is terminated by a stop codon at bp 2863-65. This stop codon is absent in mRNA variant 9 encoding protein 3 (see FIG. 9).

FIG. 9A depicts human LUMA1 mRNA variant 9 sequence (SEQ ID NO: 17). FIG. 9B depicts protein 3 sequence (SEQ ID NO: 18). The N-terminal part of protein 3 is present in protein 2. Due to the absence of the stop codon at bp 2863-65, the open reading frame extends to bp 4290.

FIG. 10A depicts human LUMA1 mRNA variant 10 sequence (SEQ ID NO: 19). FIG. 10B depicts protein 4 sequence (SEQ ID NO: 20). Protein 4 is encoded by an ORF starting at bp 2866 due to the presence of a 5' stop codon at bp 2863-65. Protein 3 (FIG. 9) and protein 4 do harbour a different c-terminus compared to the protein depicted in FIG. 1 because of a differential splicing at exon 8 (exon T) which extends the exon to the 5' end leading to a frameshift.

FIG. 11 depicts genomic sequence of the human LUMA1 gene (SEQ ID NO: 21). LUMA1 exon sequences are underlined. The genomic sequence harbors LUMA1 exon 1 to exon 8. Two different splice acceptor sites are detectable at exon 3 leading to an additional codon which is indicated by (>). Exon 3 or exons 3 and 4 or exons 3, 4 and 5 are differentially spliced. In addition differential splicing of part of exon 7 has been detected. Whereas exon 3, exons 3 and 4, and exons 3, 4 and 5 deletions lead to an in frame deletion of internal LUMA1 amino acid sequences the differential splicing of part of exon 7 generates a frameshift. This frameshift generates to different carboxy-terminal LUMA1 protein isoforms. The two splice acceptor sites at exon 7 are indicated by (>). In addition two different polyadenylation sites of the LUMA1 gene are indicated.

FIG. 12 depicts mouse LUMA1 mRNA sequence (SEQ ID NOs: 22 and 23)

FIG. 13 shows nucleotide sequence comparison of human (nucleotides 1 to 1160 of SEQ ID NO: 1) and mouse LUMA1 (nucleotides 28 to 1185 of SEQ ID NO: 22) mRNA. Over the entire coding sequence, a strong sequence conservation during evolution is detectable.

FIG. 14 shows nucleotide sequence comparison of human and mouse LUMA1 mRNA (nucleotides 1 to 1160 of SEQ ID NO: 1 and nucleotides 28 to 1185 of SEQ ID NO: 22). Sequence blocks which are identical in human and mouse LUMA1 are boxed.

FIG. 15 shows amino acid sequence comparison of human and mouse LUMA1 protein. Sequence blocks which are identical in human (amino acids 1 to 391 of SEQW ID NO: 2) and mouse (amino acids 8 to 392 of SEQ ID NO: 23) LUMA1 are boxed. Highly conserved peptide sequences are present indicative for a highly conserved function during evolution.

FIG. 16-20 shows detection of the expression of LUMA1 in lung adenocarcinomas (FIG. 16: N1/T1; FIG. 17: N2/T2; FIG. 18: N3/T3; FIG. 19: N4/T4; FIG. 20: N5/T5) using the real time PCR technique (ABI TaqMan 7700). For amplification of the LUMA1 gene the following primers were used: LUMA1-A: CTCGTCAGGCGACCTTATATC (SEQ ID NO: 24); LUMA1-B: TGTCAGTTGAACATTTTCTGCC (SEQ ID NO: 25). For the analysis corresponding tumor and normal samples were used.

```
LUMA1-C:   CTCGTCAGGCGATACTCCC;      (SEQ ID NO: 26)
LUMA1-D:   CACCAGTCAGCTCTAAATGGG.    (SEQ ID NO: 27)
```

Figure 23:
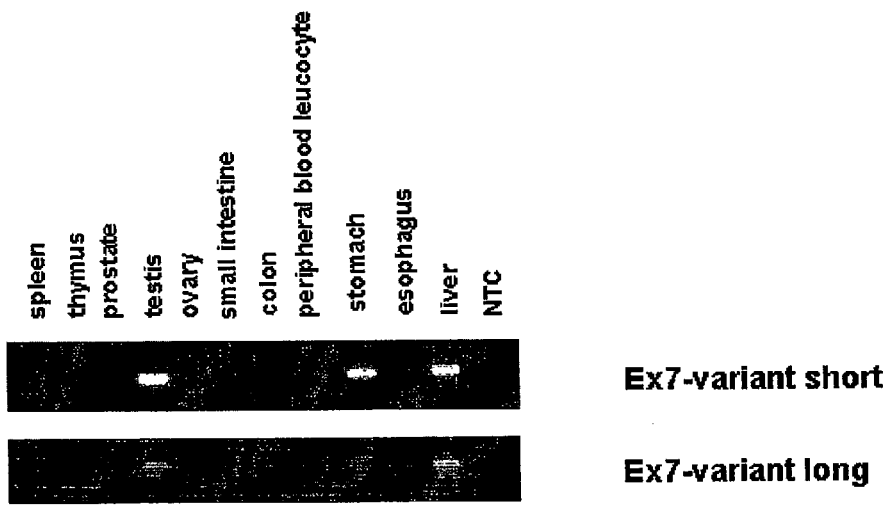

FIG. 23 shows gel electrophoresis of the endpoint PCR of the amplification of the two different LUMA1 exon 7 (exon S) transcripts in normal tissues. 11 normal tissue samples were tested for expression of the long variant of exon 7. Only in testis and liver an expression of this exon 7 splice variant has been detected. In addition, the expression of the short exon 7 splice variant could be observed in testis, liver and stomach. NTC=no template control.

FIG. 24B shows immunohistochemical analysis of lung adenocarcinoma, and FIG. 24A shows that corresponding normal tissue employing a primary antibody directed against LUMA exon 2. In the carcinoma tissue and in the corresponding normal lung tissue a cytoplasmic staining has been detected with the polyclonal antibody directed protein sequences of exon 2. No difference in the staining pattern between normal and tumor has been observed.

FIG. 25B shows immunohistochemical analysis of lung adenocarcinoma, and FIG. 25A shows the corresponding normal tissue employing a monoclonal primary antibody directed against LUMA exon 7. In the carcinoma of the presented sample a strong overexpression of the luma exon 7 (long transcript) proteinisoform is detectable. The tumor cells show a cytoplasmic staining pattern. In the corresponding normal lung tissue no staining has been detected with the exon 7 specific monoclonal antibody.

FIG. 26A shows immunohistochemical analysis of lung carcinoid, and FIG. 26B shows squamous cell carcinoma employing a monoclonal antibody directed against LUMA exon 7. In the carcinoid (A) and in the squamous cell carcinoma (B) a strong overexpression of the LUMA exon 7 (long transcript) proteinisoform has been detected. The tumor cells show a cytoplasmic staining pattern.

DETAILED DESCRIPTION OF THE INVENTION

In one aspect the method according to the present invention is especially useful for early detection of cell proliferative disorders such as e.g. lung tumors and for detection of disseminated tumor cells in the course of diagnosis of minimal residual disease.

In another aspect of the present invention, the nucleic acids or polypeptides disclosed herein may be used in the course of diagnosis of disorders associated with abnormal proliferation of cells in samples such as tumor resections, biopsies or the like. In this aspect the invention provides a method, which allows to build a strategy for the therapy of diseases according to their molecular properties. According to the present invention, the level of said polypeptides and/or nucleic acids can be used as a molecular marker for prognosis, monitoring and the design of a strategy of tumor therapeutics.

It is yet another aspect of the present invention to provide methods for identification of molecules binding to the nucleic acids and polypeptides of the present invention as well as of activators and inhibitors of the expression of the genes of the present invention. Also a method for the identification of drug candidates for the therapy of proliferative disorders is provided.

The present invention provides tumor associated nucleic acids and polypeptides characterized by the sequences given in FIG. 1-11.

Marker molecules as used in the present invention my comprise nucleic acids and polynucleotides. On the level of nucleic acids the marker molecules may be DNA or RNA comprising genomic DNA, cDNA, and RNA such as mRNA or hnRNA. In one preferred embodiment of the invention, nucleic acids arising from particular differential splicing events may be marker molecules.

Expression as used according to the present invention may comprise for example expression of proteins. The transcription to RNA and thus the level of mRNA may also be understood to be expression according to the present invention.

The expression of a compound is said to be significantly altered according to the present invention, if the level of expression differs by more than 30%. The alteration of the expression may comprise for example elevated expression or reduced expression of said compound. Another aspect of the altered expression may be an alteration in a way, that the compound is expressed under non wild-type circumstances. This may comprise, that the compound is for example expressed in situations that naturally suppress the expression, or is not expressed in situations that naturally induce the expression of the compound.

Alteration of the expression as used herein may also comprise an alteration in the transcription pattern of a gene. E.g. the alteration of the transcription pattern may comprise alternative splicing of the gene. The alterations in the transcription pattern may influence the polypeptides translated from the altered transcripts or may be restricted to untranslated regions. The alteration in the transcription pattern of a gene may comprise use of novel exons in the transcripts, deletions of exons in the transcripts or the variation in the ratios of different splicing variants in cells. Thus alterations in transcriptional patterns of genes as used herein may comprise the production of nucleic acids such as e.g. mRNA, cDNA etc. containing additional stretches of nucleic acid sequences compared to wild type nucleic acids occurring in control tissues. Alternatively the nucleic acids produced by alternative splicing patterns may produce nucleic acids missing stretches of nucleic acid sequences present in wild type polynucleotides. The presence of additional stretches may occur simultaneously with the absence of original sequence-stretches in single transcripts. Alterations in the expression of genes as used in the context of the present invention may also comprise an alteration in the level of expression of splicing variants of genes. This may include increased or decreased expression of particular splicing variants as well as expression of variants not present in wild type tissue or the absence of expression of splicing variants present in wild type tissue. In one embodiment, the alteration of the expression of the splicing variants may comprise the alteration of the ratios of different splicing variants in said tissue.

Nucleic acids as used in the context of the present invention are preferably polynucleotides or fragments thereof. Preferred polynucleotides comprise at least 20 consecutive nucleotides, preferably at least 30 consecutive nucleotides and more preferably at least 45 consecutive nucleotides, which are identical, share sequence homology or encode for identical, or homologous polypeptides, compared to the polypeptides associated with the proliferative disorders disclosed herein. The nucleic acids according to the present invention may also be complementary to any of said polynucleotides. Polynucleotides may for example include single-stranded (sense or antisense) or double-stranded molecules, and may be DNA (genomic, cDNA or synthetic) or RNA. RNA molecules comprise as well hnRNA (containing introns) as mRNA (not containing introns). According to the present invention the polynucleotides may also be linked to any other molecules, such as support materials or detection marker molecules, and may, but need not, contain additional coding or non-coding sequences.

The polynucleotides according to the present invention may be native sequences or variants thereof. The variants may contain one or more substitutions, additions, deletions and/or insertions such that the immunogenicity of the encoded polypeptide is not diminished, relative to the respective native proteins. The variants show preferably 70%, more preferably at least 80% and most preferably at least 90% of sequence identity to the native nucleic acid molecules used in the methods according to the present invention. Methods for determination of sequence similarity are known to those of skill in the art.

One example for detecting the similarity of sequences can be carried out using the FastA and/or BlastN bioinformatics software accessible on the HUSAR server of the DKFZ Heidelberg.

Furthermore nucleic acids according to the present invention are all polynucleotides, which hybridise to probes specific for the sequences disclosed herein under stringent conditions. Stringent conditions applied for the hybridisation reaction are known to those of ordinary skill in the art and may be applied as described in Sambrook et al. Molecular cloning: A Laboratory Manual, $2^{nd}$ Edition, 1989.

The present invention also provides polynucleotides, which due to the degeneracy of the genetic code encode the polypeptides natively encoded by the disclosed nucleic acids while not showing the percentage of sequence homology as described above within the nucleic acid sequence. Such nucleic acids might arise by changing the codons present in the disclosed sequences by degenerate codons and so preparing a synthetic nucleic acid.

The nucleotide sequences according to the present invention may be joined to a variety of other nucleic acid sequences using the known recombinant DNA techniques. The sequences may for example be cloned into any of a variety of cloning vectors, such as plasmids, phagemids, lambda phage derivatives and cosmids. Furthermore vectors such as expression vectors, replication vectors, probe generation vectors and sequencing vectors may be joined with the sequences disclosed herein. Sequences of special interest, that could be cloned to the nucleic acids according to the present invention are for example non coding sequences and regulatory sequences including promoters, enhancers and terminators.

In a preferred embodiment, polynucleotides may be formulated such that they are able to enter mammalian cells and to be expressed in said cells. Such formulations are especially useful for therapeutic purposes. The expression of nucleic acid sequences in target cells may be achieved by any method known to those skilled in the art. The nucleic acids may for example be joined to elements that are apt to enable their expression in a host cell. Such elements may comprise promoters or enhancers, such as CMV-, SV40-, RSV-, metallothionein I- or polyhedrin-promotors respectively CMV- or SV40-enhancers. Possible methods for the expression are for example incorporation of the polynucleotides into a viral vector including adenovirus, adeno-associated virus, retrovirus, vaccinia virus or pox virus. Viral vectors for the purpose of expression of nucleic acids in mammalian host cells may comprise pcDNA3, pMSX, pKCR, pEFBOS, cDM8, pCEV4 etc. These techniques are known to those skilled in the art.

Other formulations for administration in therapeutic purposes include colloidal dispersion systems such as for example macromolecule complexes, microspheres, beads, micelles and liposomes.

Generally, by means of conventional molecular biological processes it is possible (see, e.g., Sambrook et al., supra) to introduce different mutations into the nucleic acid molecules of the invention. As a result the inventive lung tumor associated polypeptides or polypeptids related thereto with possibly modified biological properties are synthesized. One possibility is the production of deletion mutants in which nucleic acid molecules are produced by continuous deletions from the 5'- or 3'-terminal of the coding DNA sequence and that lead to the synthesis of polypeptids that are shortened accordingly. Another possibility is the introduction of single-point mutation at positions where a modification of the amino aid sequence influences, e.g., the proliferation specific properties. By this method muteins can be produced, for example, that possess a modified Km-value or that are no longer subject to the regulation mechanisms that normally exist in the cell, e.g. with regard to allosteric regulation or covalent modification. Such muteins might also be valuable as therapeutically useful antagonists of the inventive lung tumor associated marker.

For the manipulation in prokaryotic cells by means of genetic engineering the nucleic acid molecules of the invention or parts of these molecules can be introduced into plasmids allowing a mutagenesis or a modification of a sequence by recombination of DNA sequences. By means of conventional methods (cf. Sambrook et al., supra), bases can be exchanged and natural or synthetic sequences can be added. In order to link the DNA fragments with each other adapters or linkers can be added to the fragments. Furthermore, manipulations can be performed that provide suitable cleavage sites or that remove superfluous DNA or cleavage sites. If insertions, deletions or substitutions are possible, in vitro mutagenesis, primer repair, restriction or ligation can be performed. As analysis method usually sequence analysis, restriction analysis and other biochemical or molecular biological methods are used.

The polypeptides encoded by the various variants of the nucleic acid molecules of the invention show certain common characteristics, such as activity in the regulation of cell proliferation and differentiation, molecular weight, immunological reactivity or conformation or physical properties like the electrophoretical mobilty, chromatographic behavior, sedimentation coefficients, solubility, spectroscopic properties, stability, pH optimum, temperature optimum.

The invention furthermore relates to vectors containing the inventive lung tumor associated nucleic acid molecules. Preferably, they are plasmids, cosmids, viruses, bacteriophages and other vectors usually used in the field of genetic engineering. Vectors suitable for use in the present invention include, but are not limited to the T7-based dual expression vectors (expression in prokaryotes and in eucaryotes) for expression in mammalian cells and baculovirus-derived vectors for expression in insect cells. Preferably, the nucleic acid molecule of the invention is operatively linked to the regulatory elements in the recombinant vector of the invention that guarantee the transcription and synthesis of an mRNA in prokaryotic and/or eukaryotic cells that can be translated. The nucleotide sequence to be transcribed can be operably linked to a promoter like a T7, metallothionein I or polyhedrin promoter.

In a further embodiment, the present invention relates to recombinant host cells transiently or stably containing the nucleic acid molecules or vectors of the invention. A host cell is understood to be an organism that is capable to take up in vitro recombinant DNA and, if the case may be, to synthesize the polypeptids encoded by the nucleic acid molecules of the invention. Preferably, these cells are prokaryotic or eukaryotic cells, for example mammalian cells, bacterial cells, insect cells or yeast cells. The host cells of the invention are preferably characterized by the fact that the introduced nucleic acid molecule of the invention either is heterologous with regard to the transformed cell, i.e. that it does not naturally occur in these cells, or is localized at a place in the genome different from that of the corresponding naturally occurring sequence.

A further embodiment of the invention relates to a polypeptide exhibiting a biological property of the inventive lung tumor associated marker and being encoded by the nucleic acid molecules of the invention, as well as to methods for their production whereby, e.g., a host cell of the invention is cultivated under conditions allowing the synthesis of the polypeptide and the polypeptide is subsequently isolated from the cultivated cells and/or the culture medium. Isolation and purification of the recombinantly produced polypeptide may be carried out by conventional means including preparative chromatography and affinity and immunological separations using, e.g., an antibody directed against the inventive lung tumor associated marker proteins, or, e.g., can be substantially purified by the one-step method described in Smith and Johnson, Gene 67; 31-40 (1988). These polypeptides, however, not only comprise recombinantly produced polypeptides but include isolated naturally occurring polypeptides, synthetically produced polypeptides, or polypeptides produced by a combination of these methods. Means for preparing such polypeptides or related polypeptides are well understood in the art. These polypeptides are preferably in a substantially purified form.

The production of a polypeptide according to the present invention may for example be carried out in a cell free in vitro transcription and/or translation system. Such systems are known to those of ordinary skill in the art. One example may comprise an intro translation system as provided by Roche molecular Biochemicals' Rapid translation System.

Polypeptides as used in the present invention comprise at least an immunogenic portion of the inventive lung tumor associated marker proteins disclosed herein. The polypeptides may be of any length. Immunogenic portion as used above is a portion of a protein, that is recognized by a B-cell and/or T-cell surface antigen receptor. The immunogenic portions comprise at least 10 amino acid residues, more preferably at least 20 amino acid residues of the protein associated with a lung tumor. In a preferred embodiment of the present invention, particular domains of the proteins, such as for example transmembrane domains or N-terminal leader sequences have been deleted. The immunogenic portions according to the present invention react with antisera or specific antibodies in the same or nearly same intensity as the native full length proteins.

The immunogenic portions are generally identified using the techniques well known in the art. Possible techniques are for example screening of the polypeptides for the ability to react with antigen-specific antibodies, antisera and/or T-cell lines or clones.

The polypeptides associated with lung tumors according to the present invention comprise also variants of the native proteins. These variants may differ from the native protein in one or more alterations such as substitutions, deletions, additions and/or insertions. The immunoreactivity of the variants according to the present invention is not substantially diminished compared to the native proteins. In a preferred embodiment of the invention the immunoreactivity is diminished less than 50% in a more preferred embodiment the immunoreactivity is diminished less than 20% compared to the native polypeptides.

In a preferred embodiment variants may be deficient in one or more portions, such as for example N-terminal leader sequences, transmembrane domains or small N- and/or C-terminal sequences. The variants exhibit 70%, more preferably at least 90% and most preferably at least 95% identity to the polypeptides disclosed according to the present invention.

The variants of the present invention are preferably conservative substitutions, so that the amino acids changed are substituted for amino acids with similar properties. The properties concerned may include polarity, charge, solubility, hydrophobicity, hydrophilicity and/or amphipathic nature of the amino acid residues. The variants disclosed herein may also comprise additional terminal leader sequences, linkers or sequences, which enable synthesis, purification or stability of the polypeptides in an easier or more comfortable way.

The polypeptides according to the present invention comprise also polypeptides that are fusion or chimeric polypeptides comprising the amino acid sequence encoded by the nucleic acid sequence of the inventive lung tumor associated marker disclosed herein. The polypeptides may be fused to any suitable amino acid sequences. These sequences may for example comprise antigenic fragments, receptors, enzymes, toxins, chelating epitopes, etc. In a preferred embodiment of the present invention the amino acid sequences, that are fused to the disclosed polypeptides are tags useful in the purification or recovery of the polypeptides such as e.g. his-tags or myc-tags. The amino acid sequences fused together may be directly linked or may be separated by any linker or spacer sequences suitable in the particular purpose.

The polypeptides and polynucleotides according to the present invention are isolated. This means that the molecules are removed from their original environment. Naturally occurring proteins are isolated if they are separated from some or all of the materials, which coexist in the natural environment. Polynucleotides are isolated for example if they are cloned into vectors.

Furthermore, the present invention provides binding agents such as antibodies and antigen-binding fragments, that specifically bind to the proteins associated with a lung tumors disclosed herein.

The term binding agent comprises a variety of substances such as oligopeptides, antibodies, peptdiomimetic molecules comprising antigen binding oligopeptides, nucleic acids, carbohydrates, organic compounds, etc. Antibody according to the present invention preferably relates to antibodies which consist essentially of pooled monoclonal antibodies with different epitopic specificities, as well as distinct monoclonal antibody preparations. Monoclonal antibodies are made from an antigen containing fragments of the polypeptides of the invention by methods well known to those skilled in the art (see, e.g., Köhler et al., Nature 256 (1975), 495). As used herein, the term "antibody" (Ab) or "monoclonal antibody" (Mab) is meant to include intact molecules as well as antibody fragments (such as, for example, Fab and F(ab') 2 fragments) which are capable of specifically binding to protein. Fab and f(ab')2 fragments lack the Fc fragment of intact antibody, clear more rapidly from the circulation, and may have less non-specific tissue binding than an intact antibody. (Wahl et al., J. Nucl. Med. 24: 316-325 (1983)). Thus, these fragments are preferred, as well as the products of a FAB or other immunoglobulin expression library. Moreover, antibodies of the present invention include chimerical, single chain, and humanized antibodies.

Binding agents according to the present invention may for example be employed for the inhibition of the activity of the inventive lung tumor associated marker polypeptides disclosed herein. In this respect the term "binding agents" relates to agents specifically binding to the polypeptides transcribed from the novel lung tumor associated nucleic acids and thus inhibiting the activity of said polypeptide. Such binding agents may for example comprise nucleic acids (DNA, RNA, PNA etc.), polypeptides (antibodies, receptors, antigenic fragments, oligopeptides), carbohydrates, lipids, organic or inorganic compounds (metal-ions, sulfur compounds, boranes, silicates, reducing agents, oxidizing agents). The binding agents may preferably interact with the polypeptide by binding to epitopes, that are essential for the biological activity. The interaction may be reversible or irreversibly. The binding may be non-covalent or even covalent binding to the polypeptide. Furthermore the binding agents may introduce alterations to the polypeptide, that alter or diminish the biological activity of the inventive polypeptide.

For certain purposes, e.g. diagnostic methods, the antibody or binding agent of the present invention may be detectably labelled, for example, with a radioisotope, a bioluminescent compound, a chemiluminescent compound, a fluorescent compound, a metal chelate, or an enzyme. The nucleic acid of the present invention may be detectably labelled, for example, with a radioisotope, a bioluminescent compound, a chemiluminescent compound, a fluorescent compound, a metal chelate, biotin, digoxygenin, or an enzyme. Furthermore any method suitable for the detection of the intermolecular interaction may be employed.

The antibody or antigen-binding agent is said to react specifically, if it reacts at a detectable level with a protein disclosed herein, and does not significantly react with other proteins. The antibodies according to the present invention may be monoclonal or polyclonal antibodies. Other molecules capable of binding specifically may be for example antigen-binding fragments of antibodies such as Fab fragments, RNA molecules or polypeptides. According to the present invention binding agents may be used isolated or in combination. By means of combination it is possible to achieve a higher degree of sensitivity.

The antibodies useful for the methods according to the present invention may comprise further binding sites for either therapeutic agents or other polypeptides or may be coupled to said therapeutic agents or polypeptides. Therapeutic agents may comprise drugs, toxins, radio-nuclides and derivatives thereof. The agents may be coupled to the binding agents either directly or indirectly for example by a linker or carrier group. The linker group may for example function in order to enable the coupling reaction between binding agent and therapeutic or other agent or the linker may act as a spacer between the distinct parts of the fusion molecule. The linker may also be cleavable under certain circumstances, so as to release the bound agent under said conditions. The therapeutic agents may be covalently coupled to carrier groups directly or via a linker group. The agent may also be non-covalently coupled to the carrier. Carriers that can be used according to the present invention are for example albumins, polypeptides, polysaccharides or liposomes.

The antibody used according to the present invention may be coupled to one or more agents. The multiple agents coupled to one antibody may be all of the same species or may be several different agents bound to one antibody.

The invention also relates to a transgenic non-human animal such as transgenic mouse, rats, hamsters, dogs, monkeys, rabbits, pigs, *C. elegans* and fish such as torpedo fish comprising a nucleic acid molecule or vector of the invention, preferably wherein said nucleic acid molecule or vector may be stably integrated into the genome of said non-human animal, preferably such that the presence of said nucleic acid molecule or vector leads to the expression of the inventive lung tumor associated marker polypeptide (or related polypeptide) of the invention, or may otherwise be transiently expressed within the non-human animal. Said animal may have one or several copies of the same or different nucleic acid molecules encoding one or several forms of the inventive lung tumor associated marker polypeptide or mutant forms thereof. This animal has numerous utilities, including as a research model for the regulation of cell proliferation and differentiation and therefore, presents a novel and valuable animal in the development of therapies, treatment, etc. for diseases caused by deficiency or failure of the inventive lung tumor associated marker protein involved in the development of cell proliferative disorders, e.g., lung tumors. Accordingly, in this instance, the non-human mammal is preferably a laboratory animal such as a mouse or rat.

Preferably, the transgenic non-human animal of the invention further comprises at least one inactivated wild type allele of the corresponding gene encoding the inventive lung tumor associated polypeptide. This embodiment allows for example the study of the interaction of various mutant forms of the inventive lung tumor associated marker polypeptides on the onset of the clinical symptoms of disease associated with the regulation of cell proliferation and differentiation. All the applications that have been herein before discussed with regard to a transgenic animal also apply to animals carrying two, three or more transgenes. It might be also desirable to inactivate the inventive lung tumor associated marker protein expression or function at a certain stage of development and/or life of the transgenic animal. This can be achieved by using, for example, tissue specific, developmental and/or cell regulated and/or inducible promoters which drive the expression of, e.g., an antisense or ribozyme directed against the RNA transcript encoding the inventive lung tumor associated marker encoding mRNA; see also supra. A suitable inducible system is for example tetracycline-regulated gene expression as described, e.g., by Gossen and Bujard (Proc. Natl. Acad. Sci. 89 USA (1992), 5547-5551) and Gossen et al. (Trends Biotech. 12 (1994), 58-62). Similar, the expression of the mutant inventive lung tumor associated protein may be controlled by such regulatory elements.

Furthermore, the invention also relates to a transgenic mammalian cell which contains (preferably stably integrated into its genome or transiently introduced) a nucleic acid molecule according to the invention or part thereof, wherein the transcription and/or expression of the nucleic acid molecule or part thereof leads to reduction of the synthesis of an inventive lung tumor associated marker protein. In a preferred embodiment, the reduction is achieved by an antisense, sense, ribozyme, co-suppression and/or dominant mutant effect. "Antisense" and "antisense nucleotides" means DNA or RNA constructs which block the expression of the naturally occurring gene product. In another preferred embodiment the native nucleic acid sequence coding for the inventive lung tumor associated marker polypeptide may be altered or substituted by a variant of said nucleic acid sequence, e.g. by means of recombination, thus rendering the inventive lung tumor associated marker gene non functional. Thus an organism lacking the inventive lung tumor associated marker polypeptide activity may be produced according to knock out experiments.

The provision of the nucleic acid molecule according to the invention opens up the possibility to produce transgenic non-human animals with a reduced level of the inventive lung tumor associated marker protein as described above and, thus, with a defect in the regulation of cell proliferation and differentiation. Techniques how to achieve this are well known to the person skilled in the art. These include, for example, the expression of antisense-RNA, ribozymes, of molecules which combine antisense and ribozyme functions and/or of molecules which provide for a co-suppression effect. When using the antisense approach for reduction of the amount of the inventive lung tumor associated marker proteins in cells, the nucleic acid molecule encoding the antisense-RNA is preferably of homologous origin with respect to the animal species used for transformation. However, it is also possible to use nucleic acid molecules which display a high degree of homology to endogenously occurring nucleic acid molecules encoding an inventive lung tumor associated marker protein. In this case the homology is preferably higher than 80%, particularly higher than 90% and still more preferably higher than 95%. The reduction of the synthesis of a polypeptide according to the invention in the transgenic mammalian cells can result in an alteration in, e.g., degradation of endogenous proteins. In transgenic animals comprising such cells this can lead to various physiological, developmental and/or morphological changes.

Thus, the present invention also relates to transgenic non-human animals comprising the above-described transgenic cells. These may show, for example, a deficiency in regulation of cell proliferation and/or differentiation compared to wild type animals due to the stable or transient presence of a foreign DNA resulting in at least one of the following features:

(a) disruption of (an) endogenous gene(s) encoding the inventive lung tumor associated marker;

(b) expression of at least one antisense RNA and/or ribozyme against a transcript comprising a nucleic acid molecule of the invention;

(c) expression of a sense and/or non-translatable mRNA of the nucleic acid molecule of the invention;

(d) expression of an antibody of the invention;
(e) incorporation of a functional or non-functional copy of the regulatory sequence of the invention; or
(f) incorporation of a recombinant DNA molecule or vector of the invention.

Methods for the production of a transgenic non-human animal of the present invention, preferably transgenic mouse, are well known to the person skilled in the art. Such methods, e.g., comprise the introduction of a nucleic acid molecule or vector of the invention into a germ cell, an embryonic cell, stem cell or an egg or a cell derived therefrom. The non-human animal can be used in accordance with a screening method of the invention described herein and may be a non-transgenic healthy animal, or may have a disorder, preferably a disorder caused by at least one mutation in the inventive lung tumor associated marker protein. Such transgenic animals are well suited for, e.g., pharmacological studies of drugs in connection with mutant forms of the above described inventive lung tumor associated marker polypeptide. Production of transgenic embryos and screening of those can be performed, e.g., as described by A. L. Joyner Ed., Gene Targeting, A Practical Approach (1993), Oxford University Press. The DNA of the embryonal membranes of embryos can be analyzed using, e.g., Southern blots with an appropriate probe, amplification techniques based on nucleic acids (e.g. PCR) etc.; see supra.

Another aspect of the present invention is a pharmaceutical composition for use in the treatment of disorders associated with abnormal cell proliferation. The polypeptides, polynucleotides and binding agents (esp. antibodies) according to the present invention may be incorporated into pharmaceutical or immunogenic compositions.

The pharmaceutical compositions may be administered by any suitable way known to those of skill in the art. The administration may for example comprise injection, such as e.g., intracutaneous, intramuscular, intravenous or subcutaneous injection, intranasal administration for example by aspiration or oral administration. A suitable dosage to ensure the pharmaceutical benefit of the treatment should be chosen according the parameters, such as age, sex, body weight etc. of the patient, known to those of skill in the art.

The pharmaceutical compositions comprise said compounds and a physiologically acceptable carrier. The type of carrier to be employed in the pharmaceutical compositions of this invention, will vary depending on the mode of administration. For parenteral administration, such as subcutaneous injection, the carrier preferably comprises water, saline, alcohol, a lipid, a wax and/or a buffer. For oral administration, any of the above carriers or a solid carrier, such as mannitol, lactose, starch, magnesium stearate, sodium saccharine, talcum, cellulose, glucose, sucrose, and/or magnesium carbonate, may be employed. Biodegradable microspheres (e.g., polylactic glycolide) may also be employed as carriers for the pharmaceutical compositions of this invention. Suitable biodegradable microspheres are disclosed, for example, in U.S. Pat. Nos. 4,897,268 and 5,075,109.

A pharmaceutical composition or vaccine may for example contain DNA, that codes for one or more polypeptides according to the present invention. The DNA may be administered in a way that allows the polypeptides to be generated in situ. Suitable expression systems are known to those skilled in the art. In another embodiment of the invention the nucleic acids may be for example anti-sense constructs. Pharmaceutical compositions may also comprise nucleic acid molecules expressible in a mammalian or human host system comprising a viral or other expression system for example an adenoviral vector system.

The nucleic acid may also be administered as a naked nucleic acid. In this case appropriate physical delivery systems, which enhance the uptake of nucleic acid may be employed, such as coating the nucleic acid onto biodegradable beads, which are efficiently transported into the cells. Administration of naked nucleic acids may for example be useful for the purpose of transient expression within a host or host cell.

Alternatively the pharmaceutical compositions may comprise one or more polypeptides. The polypeptides incorporated into pharmaceutical compositions may be the inventive lung tumor associated polypeptide. Optionally the polypeptide may be administered in combination with one or more other known polypeptides such as for example enzymes, antibodies, regulatory factors, such as cyclins, cyclin-dependent kinases or CKIs, or toxins.

Polypeptides of the present invention or fragments thereof, that comprise an immunogenic portion of an inventive lung tumor associated protein, may be used in immunogenic compositions, wherein the polypeptide e.g. stimulates the patient's own immune response to tumor cells. A patient may be afflicted with disease, or may be free of detectable disease. Accordingly, the compounds disclosed herein may be used to treat cancer or to inhibit the development of cancer. The compounds may be administered either prior to or following a conventional treatment of tumors such as surgical removal of primary tumors, treatment by administration of radiotherapy, conventional chemotherapeutic methods or any other mode of treatment of the respective cancer or its precursors.

Immunogenic compositions such as vaccines may comprise one or more polypeptides and a non-specific immune-response enhancer, wherein the non-specific immune response enhancer is capable of eliciting or enhancing an immune response to an exogenous antigen. Any suitable immune-response enhancer may be employed in the vaccines of this invention. For example, an adjuvant may be included. Most adjuvants contain a substance designed to protect the antigen from rapid catabolism, such as aluminium hydroxide or mineral oil, and a non-specific stimulator of immune response, such as lipid A, *Bordetella pertussis* or *Mycobacterium tuberculosis*. Such adjuvants are commercially available as, for example, Freund's Incomplete Adjuvant and Complete Adjuvant (Difco Laboratories, Detroit, Mich.) and Merck Adjuvant 65 (Merck and Company, Inc., Rahway, N.J.).

Pharmaceutical compositions and vaccines may also contain other epitopes of tumor antigens, either incorporated into a fusion protein as described above (i.e., a single polypeptide that contains multiple epitopes) or present within a separate polypeptide.

Disorders characterized by abnormal cell proliferation, as used in the context of the present invention, may comprise for example neoplasms such as benign and malignant tumors, carcinomas, sarcomas, leukemias, lymhomas or dysplasias. Tumors may comprise tumors of the head and the neck, tumors of the respiratory tract, tumors of the gastrointestinal tract, tumors of the urinary system, tumors of the reproductive system, tumors of the endocrine system, tumors of the central and peripheral nervous system, tumors of the skin and its appendages, tumors of the soft tissues and bones, tumors of the lymphopoietic and hematopoietic system, breast cancer, colorectal cancer, anogenital cancer etc.

In one preferred embodiment of the invention, the disorders are lung tumors. Lung tumors according to the present invention comprise conditions of the respiratory tract characterized by abnormal growth properties of cells or tissues compared to the growth properties of normal control cells or tissues. The growth of the cells or tissues may be for example abnormally accelerated or may be regulated abnormally. Abnormal regulation as used above may comprise any form of presence or absence of non-wild type responses of the cells or tissues to naturally occurring growth regulating influences. The abnormalities in growth of the cells or tissues may be for example neoplastic or hyperplastic. In one preferred embodiment of the invention the lung tumors are cancers or precancerours conditions of the respiratory tract.

A sample according to the method of the present invention is any sample, that may contain cells, tissues or body liquids. Furthermore any sample potentially containing the marker molecules to be detected may be a sample according to the present invention. Such samples are e.g. blood, plasma, serum, swabs, washes, sputum, cell- and tissue-samples or biopsies.

Biopsies as used in the context of the present invention may comprise e.g. resection samples of tumors, tissue samples prepared by endoscopic means or needle biopsies. Furthermore any sample potentially containing the marker molecules to be detected may be a sample according to the present invention.

The method for detection of the level of the polynucleotides or polypeptides according to the present invention is any method, which is suited to detect very small amounts of specific molecules in samples. The detection reaction according to the present invention may be for example detection either on the level of nucleic acids or on the level of polypeptides. The detection may either be a detection of the level of polypeptides or nucleic acids in cells in total or in cell lysates or a detection of the level of polypeptides or nucleic acids in distinct subcellular regions. The methods for determining the subcellular distribution of compounds are known to those of skill in the art. In one embodiment of the invention the detection of the marker molecules may comprise the detection of particular splicing variants. In another embodiment of the present invention the detection method may comprise the detection of methylation of nucleic acid molecules in samples.

Applicable formats for the detection reaction according to the present invention may be blotting techniques, such as Western-Blot, Southern-blot, Northern-blot. The blotting techniques are known to those of ordinary skill in the art and may be performed for example as electro-blots, semidry-blots, vacuum-blots or dot-blots. Furthermore immunological methods for detection of molecules may be applied, such as for example immunoprecipitation or immunological assays, such as ELISA, RIA, lateral flow assays etc.

Methods for detection of methylation of nucleic acids are known to those of skill in the art and may comprise for example methods employing chemical pre-treatment of nucleic acids with e.g. sodium bisulphite, permanganate or hydrazine, and subsequent detection of the modification by means of specific restriction endonucleases or by means of specific probes e.g. in the course of an amplification reaction. The detection of methylation may furthermore be performed using methylation specific restriction endonucleases.

In one preferred embodiment of the invention, the detection of the level of marker molecules is carried out by detection of the level of nucleic acids coding for the marker molecules or fragments thereof present in the sample. The means for detection of nucleic acid molecules are known to those skilled in the art. The procedure for the detection of nucleic acids can for example be carried out by a binding reaction of the molecule to be detected to complementary nucleic acid probes, proteins with binding specificity for the nucleic acids or any other entities specifically recognizing and binding to aid nucleic acids. This method can be performed as well in vitro as directly in-situ for example in the course of a detecting staining reaction. Another way of detecting the marker molecules in a sample on the level of nucleic acids performed in the method according to the present invention is an amplification reaction of nucleic acids, which can be carried out in a quantitative manner such as for example PCR, LCR or NASBA.

In another preferred embodiment of the invention the detection of the level of marker molecules is carried out by determining the level of expression of a protein. The determination of the marker molecules on the protein level may for example be carried out in a reaction comprising a binding agent specific for the detection of the marker molecules. These binding agents may comprise for example antibodies and antigen-binding fragments, bifunctional hybrid antibodies, peptidomimetics containing minimal antigen-binding epitopes etc. The binding agents may be used in many different detection techniques for example in western-blot, ELISA, lateral flow assay, latex-agglutination, immunochromatographic strips or immuno-precipitation. Generally binding agent based detection may be carried out as well in vitro as directly in situ for example in the course of an immuno-cytochemical staining reaction. Any other method suitable for determining the amount of particular polypeptides in solutions of biological samples, such as biochemical, chemical, physical or physico-chemical methods, can be used according to the present invention.

In one preferred embodiment of the invention, the level of markers in significantly elevated compared to a non tumorous test sample. In this case the marker is overexpressed in the sample. In another preferred embodiment of the present invention the level of the marker is lowered compared to a non tumorous test sample. In a third embodiment there is no detectable expression of the marker at all in the test sample unlike in a control sample. In yet another embodiment there is detectable level of non wild-type marker molecules. Non wild-Type marker molecules may comprise any marker molecules that deviate in sequence or structure from the structure or sequence, that is functional in wild type tissue not affected by a cell proliferative disease. Wild type sequences or structures are the sequences or structures predominantly present in normal cells or tissues. In one preferred embodiment of the invention the level of particular splicing variants of the marker gene is altered in the test samples compared to the wild type tissue. This may lead to altered levels of splicing variants, new splicing variants, neo-peptides, altered ratios of different splicing variants of genes.

The detection of the level of molecular markers according to the present invention may be the detection of the level of single marker molecules in separated reaction mixtures as well as the detection of a combination of markers simultaneously. The combination may comprise the molecular markers disclosed herein and additionally further marker molecules useful for the detection of tumors.

The detection may be carried out in solution or using reagents fixed to a solid phase. The detection of one or more molecular markers may be performed in a single reaction mixture or in two or separate reaction mixtures. The detection reactions for several marker molecules may for example be performed simultaneously in multi-well reaction vessels. The markers characteristic for the lung tumors disclosed herein may be detected using reagents that specifically recognise these molecules. Simultaneously one or more further markers may be detected using reagents, that specifically recognize them. The detection reaction for each single marker may comprise one or more reactions with detecting agents either recognizing the initial marker molecules or preferably recognizing molecules used to recognize other molecules. Such reaction may e.g. comprise the use of primary and secondary and further antibodies. The detection reaction further may comprise a reporter reaction indicating the level of the inventive polypeptides associated with lung tumors. The reporter reaction may be for example a reaction producing a coloured compound, a bioluminescence reaction, a fluorescence reaction, generally a radiation emitting reaction etc.

In one preferred embodiment, the detection of tissues expressing marker gene products is carried out in form of molecular imaging procedures. The respective procedures are known to those of ordinary skill in the art. Imaging methods for use in the context of the present invention may for example comprise MRI, SPECT, PET and other methods suitable for in vivo imaging.

In one embodiment the method may be based on the enzymatic conversion of inert or labelled compounds to molecules detectable in the course of molecular imaging methods by the marker molecules. In another embodiment the molecular imaging method may be based on the use of compounds carrying a suitable label for in vivo molecular imaging, such as radio isotopes, metal ions etc., specifically binding to marker molecules in vivo.

In a preferred embodiment of the invention, these compounds are non-toxic compounds and may be eliminated from the circulation of organisms, such as humans, in a time span, that allows for performing the detection of label accumulated in tumor tissue overexpressing the respective marker gene. In another preferred embodiment of the invention compounds are used for molecular imaging, for which clearance from the circulation is not relevant for performing the molecular imaging reaction. This may be for example due to low background produced by the circulating molecules etc. The compounds for use in molecular imaging methods are administered in pharmaceutical acceptable form in compositions that may additionally comprise any other suitable substances, such as e.g. other diagnostically useful substances, therapeutically useful substances, carrier substances or the like.

The marker molecules disclosed according to the present invention may be used for diagnosis, monitoring of the disease course and prognosis in cell proliferative disorders such as e.g. lung tumors.

Diagnosis of disorders associated with the expression of the inventive gene as used herein may for example comprise the detection of cells or tissues affected by abnormal growth. In one preferred embodiment diagnosis means the primary detection of a disease in an organism or sample. According to the present invention the method for diagnosis of disorders such as tumors may be applied in routine screening tests for preventive aspects in order to detect said disease at an early stage of the onset of the disorder. In another preferred embodiment the diagnostic method may be used to determine the minimal residual disease of a tumor after primary therapy. In this respect the method of the invention may be applied to determine cells in body samples displaying abnormal expression of marker molecules according to the present invention, characteristic for lung tumors. Thus a spread of affected cells may be detected in body liquids.

In one embodiment of the invention, the methods disclosed herein may be used for the detection and identification of metastases. The method may be applied either for detection of metastases in body tissues or organs by the detection methods described herein, or the metastases may be diagnoses with respect to prognosis and prediction of disease course.

Monitoring of the disease course may comprise determining the levels of marker molecules at different time points, comparing the levels at the different time points and assessing a diagnosis about the progression of the disease over the covered period of time. Thus monitoring may enable for assessment of prognosis and/or for design of an adequate therapy for a particular patient.

Prognosis of the disease course of a cell proliferative disorders such as e.g. lung tumors according to the present invention may comprise determining the level of expression of one or more marker molecules, comparing the levels with data from subsequent studies in a database and prognosticating the disease course from said comparison. In a preferred embodiment the method may comprise the detection of the levels of a set of marker molecules, the distinct levels of which may characterize distinct stages in the course of the disease. In a further embodiment of the invention the combination of the levels of a combination of markers may be an indicator for the prognosis of the further disease course and may build the basis for design of an adequate therapy.

The present invention further provides kits for use in e.g. research or diagnostic methods. Such kits may contain two or more components for performing a scientific or diagnostic assay. Components may be compounds, reagents, containers and/or equipment. One component may be an antibody or fragment thereof that specifically binds to a polypeptide associated with lung tumors. Additionally the kit may contain reagents, buffers or others known in the art as necessary for performing the diagnostic assay. Alternatively the research kit or diagnostic kit may contain nucleotide probes or primers for the detection of DNA or RNA. Such a kit should contain appropriate additional reagents and buffers known in the art.

A kit according to present invention comprises:
  a) reagents for the detection of the molecular marker molecules,
  b) the reagents and buffers commonly used for carrying out the detection reaction, such as buffers, detection-markers, carrier substances and others, and
  c) a marker sample for carrying out a positive control reaction.

The reagent for the detection of the marker includes any agent capable of binding to the marker molecule. Such reagents may include proteins, polypeptides, nucleic acids, glycoproteins, proteoglycans, polysaccharides or lipids.

The sample for carrying out a positive control may comprise for example nucleic acids in applicable form, such as solution or salt, peptides in applicable form, tissue section samples or positive cells expressing the molecules associated with lung tumors.

In a preferred embodiment of the invention, the detection of the marker molecules is carried out on the level of polypeptides. In this embodiment, the binding agents may be for example antibodies specific for the marker molecules or fragments thereof.

In another embodiment of the test kit, the detection of the marker molecule is carried out on the nucleic acid level. In this embodiment of the invention the reagents for the detection may be for example nucleic acid probes or primers complementary to said marker molecule nucleic acids.

Another aspect of the present invention is to provide a method for therapy and/or vaccination. According to the present invention a therapy of cell proliferative disorders can be carried out using the inventive lung tumor associated polypeptides and/or polynucleotides. The therapy may be for example immunotherapy or somatic gene therapy.

The inventive lung tumor associated polypeptides and/or polynucleotides may according to the present invention be used for vaccination against cell proliferative disorders. Vaccination according to the present invention may comprise administering an immunogenic compound to an individual for the purpose of stimulating an immune response directed against said immunogenic compound and thus immunizing said individual against said immunogenic compound. Stimulating an immune response may comprise inducing the production of antibodies against said compound as well as stimulating cytotoxic T-cells. For the purpose of vaccination the polypeptides, nucleic acids and binding agents according to the present invention may be administered in a physiological acceptable form. The composition to be administered to individuals may comprise one or more antigenic components, physiologically acceptable carrier substances or buffer solutions, immunostimulants and/or adjuvants. Adjuvants may comprise for example Freund's incomplete adjuvant or Freund's complete adjuvant or other adjuvants known to those of skill in the art.

The composition may be administered in any applicable way such as e.g. intravenous, subcutaneous, intramuscular etc. The dosage of the composition depends on the particular case and purpose of the vaccination. It has to be adapted to parameters by the individual treated such as age, weight, sex etc. Furthermore the type of the immune response to be elicited has to be taken into account. In general it may be preferable if an individual receives 100 µg-1 g of a polypeptide according to the present invention or $10^6$-$10^{12}$ MOI of a recombinant nucleic acid, containing a nucleic acid according to the present invention in a form that may be expressed in situ.

Individuals for the purpose of vaccination may be any organisms containing the inventive lung tumor associated polypeptides and/or polynucleotides and being able to get affected by cell proliferative disorders.

Vaccination of individuals may be favourable e.g. in the case of altered, non wild-type sequences or structure of marker molecules associated with cell proliferative disorders.

Polypeptides disclosed herein may also be employed in adoptive immunotherapy for the treatment of cancer. Adoptive immunotherapy may be broadly classified into either active or passive immunotherapy. In active immunotherapy, treatment relies on the in vivo stimulation of the endogenous host immune system to react against tumors with the administration of immune response-modifying agents (for example, tumor vaccines, bacterial adjuvants, and/or cytokines).

In passive immunotherapy, treatment involves the delivery of biologic reagents with established tumor-immune reactivity (such as effector cells or antibodies) that can directly or indirectly mediate antitumor effects and does not necessarily depend on an intact host immune system. Examples of effector cells include T lymphocytes (for example, CD8+ cytotoxic T-lymphocyte, CD4+ T-helper, tumor-infiltrating lymphocytes), killer cells (such as Natural Killer cells, lymphokine-activated killer cells), B cells, or antigen presenting cells (such as dendritic cells and macrophages) expressing the disclosed antigens. The polypeptides disclosed herein may also be used to generate antibodies or anti-idiotypic antibodies (as in U.S. Pat. No. 4,918,164), for passive immunotherapy.

The predominant method of procuring adequate numbers of T-cells for adoptive immunotherapy is to grow immune T-cells in vitro. Culture conditions for expanding single antigen-specific T-cells to several billion in number with retention of antigen recognition in vivo are well known in the art. These in vitro culture conditions typically utilize intermittent stimulation with antigen, often in the presence of cytokines, such as IL-2, and non-dividing feeder cells. As noted above, the immunoreactive polypeptides described herein may be used to rapidly expand antigen-specific T cell cultures in order to generate sufficient number of cells for immunotherapy. In particular, antigen-presenting cells, such as dendritic, macrophage or B-cells, may be pulsed with immunoreactive polypeptides or transfected with a nucleic acid sequence(s), using standard techniques well known in the art. For example, antigen presenting cells may be transfected with a nucleic acid sequence, wherein said sequence contains a promoter region appropriate for increasing expression, and can be expressed as part of a recombinant virus or other expression system. For cultured T-cells to be effective in therapy, the cultured T-cells must be able to grow and distribute widely and to survive long term in vivo. Studies have demonstrated that cultured T-cells can be induced to grow in vivo and to survive long term in substantial numbers by repeated stimulation with antigen supplemented with IL-2 (see, for example, Cheever, M., et al, "Therapy With Cultured T Cells: Principles Revisited," Immunological Reviews, 157:177, 1997).

The polypeptides disclosed herein may also be employed to generate and/or isolate tumor-reactive T-cells, which can then be administered to the patient. In one technique, antigen-specific T-cell lines may be generated by in vivo immunization with short peptides corresponding to immunogenic portions of the disclosed polypeptides. The resulting antigen specific CD8+ CTL clones may be isolated from the patient, expanded using standard tissue culture techniques, and returned to the patient.

Alternatively, peptides corresponding to immunogenic portions of the polypeptides of the invention may be employed to generate tumor reactive T-cell subsets by selective in vitro stimulation and expansion of autologous T-cells to provide antigen-specific T-cells which may be subsequently transferred to the patient as described, for example, by Chang et al. (Crit. Rev. Oncol. Hematol., 22(3), 213, 1996). Cells of the immune system, such as T-cells, may be isolated from the peripheral blood of a patient, using a commercially available cell separation system, such as CellPro Incorporated's (Bothell, Wash.) CEPRATE™ system (see U.S. Pat. Nos. 5,240,856; 5,215,926; WO 89/06280; WO 91/16116 and WO 92/07243). The separated cells are stimulated with one or more of the immunoreactive polypeptides contained within a delivery vehicle, such as a microsphere, to provide antigen-specific T-cells. The population of tumor antigen-specific T-cells is then expanded using standard techniques and the cells are administered back to the patient.

In another embodiment, T-cell and/or antibody receptors specific for the polypeptides can be cloned, expanded, and transferred into other vectors or effector cells for use in adoptive immunotherapy.

In a further embodiment, syngeneic or autologous dendritic cells may be pulsed with peptides corresponding to at least an immunogenic portion of a polypeptide disclosed herein. The resulting antigen-specific dendritic cells may either be transferred into a patient, or employed to stimulate T-cells to provide antigen-specific T-cells, which may, in turn, be administered to a patient. The use of peptide-pulsed dendritic cells to generate antigen-specific T-cells and the subsequent use of such antigen-specific T-cells to eradicate tumors in a murine model has been demonstrated by Cheever et al, Immunological Reviews, 157:177, 1997.

Additionally, vectors expressing the disclosed nucleic acids may be introduced into stem cells taken from the patient and clonally propagated in vitro for autologous transplant back into the same patient.

Monoclonal antibodies of the present invention may also be used as therapeutic compounds in order to diminish or eliminate tumors. The antibodies may be used on their own (for instance, to inhibit metastases) or coupled to one or more therapeutic agents. Suitable agents in this regard include radio nuclides, differentiation inducers, drugs, toxins, and derivatives thereof. Preferred radio nuclides include 90Y, 123, I125, I131, I186Re, 188Re, 211At, and 212Bi. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, *Pseudomonas* exotoxin, *Shigella* toxin, and pokeweed antiviral protein.

In one embodiment of the invention, the therapy of disorders characterized by abnormal cell proliferation may comprise the administration of antisense construct or ribozymes. The methods for administration of ribozymes or antisense constructs are known to those of skill in the art. The administration may take place as administration of naked nucleic acids or as administration of nucleic acids that are suited for expression of the relevant active products in situ.

In another embodiment of the invention the treatment of disorders may comprise the administration of binding agents directed against the inventive lung tumor associated molecules. These binding agents may for example be coupled to other compounds such as toxins, enzymes, radio-isotopes etc.

In another embodiment of the invention, therapy of disorders associated with abnormal expression of the presented inventive lung tumor associated molecules may comprise the administration of antagonists or agonists of the inventive lung tumor associated molecules, of binding partners of the inventive lung tumor associated polypeptides of inhibitors or enhancer of the expression of the inventive lung tumor associated polypeptides or of drugs identifiable by assays involving the measurement of the activity of the inventive lung tumor associated polypeptides. The methods for identifying these substances are known to those of skill in the art.

An example for a method for identifying a binding partner of an inventive lung tumor associated polypeptides (or related polypeptide) and/or polynucleotide may comprise:
  (a) contacting the inventive lung tumor associated polypeptide of the invention with a compound to be screened; and
  (b) determining whether the compound affects an activity of the polypeptide.

The inventive lung tumor associated polypeptides may be used to screen for proteins or other compounds that bind to the inventive lung tumor associated polypeptides or for proteins or other compounds to which the inventive lung tumor associated polypeptide binds. The binding of the inventive lung tumor associated polypeptide and the molecule may activate (agonist), increase, inhibit (antagonist), or decrease activity of the inventive lung tumor associated polypeptide or the molecule bound. Examples of such molecules include antibodies, oligonucleotides, proteins (e.g., receptors), or small molecules.

Preferably, the molecule is closely related to the natural ligand of the inventive lung tumor associated polypeptide, e.g., a fragment of the ligand, or a natural substrate, a ligand, a structural or functional mimetic; see, e.g., Coligan, Current Protocols in Immunology 1(2) (1991); Chapter 5. Similarly, the molecule can be closely related to the natural receptor to which the inventive lung tumor associated polypeptide might bind, or at least, a fragment of the receptor capable of being bound by the inventive lung tumor associated polypeptide (e.g., active site). In either case, the molecule can be rationally designed using known techniques.

Preferably, the screening for these molecules involves producing appropriate cells which express the inventive lung tumor associated polypeptide, either as a secreted protein or on the cell membrane. Preferred cells include cells from mammals, yeast, *Drosophila*, or *E. coli*. Cells expressing the inventive lung tumor associated polypeptide (or cell membrane containing the expressed polypeptide) are then preferably contacted with a test compound potentially containing the molecule to observe binding, stimulation, or inhibition of activity of the inventive lung tumor associated polypeptide.

The assay may simply test binding of a candidate compound to the inventive lung tumor associated polypeptide, wherein binding is detected by a label, or in an assay involving competition with a labelled competitor. Further, the assay may test whether the candidate compound results in a signal generated by binding to the inventive lung tumor associated polypeptide.

Alternatively, the assay can be carried out using cell-free preparations, polypeptide/molecule affixed to a solid support, chemical libraries, or natural product mixtures. The assay may also simply comprise the steps of mixing a candidate compound with a solution containing the inventive lung tumor associated polypeptide, measuring the inventive lung tumor associated polypeptide/molecule activity or binding, and comparing the inventive lung tumor associated polypeptide/molecule activity or binding to a standard.

Preferably, an ELISA assay can measure the inventive lung tumor associated polypeptide level or activity in a sample (e.g., biological sample) using a monoclonal or polyclonal antibody. The antibody can measure the inventive lung tumor associated polypeptide level or activity by either binding, directly or indirectly, to the inventive lung tumor associated polypeptide or by competing with the inventive lung tumor associated polypeptide for a substrate. All of these above assays can be used as diagnostic or prognostic markers. The molecules discovered using these assays can be used to treat disease or to bring about a particular result in a patient (e.g., elimination of an epithelial tumor or stop of progression of tumor growth) by activating or inhibiting the inventive lung tumor associated molecule. Moreover, the assays can discover agents which may inhibit or enhance the production of the inventive lung tumor associated polypeptide from suitably manipulated cells or tissues.

Therefore, the invention includes a method of identifying compounds which bind to the inventive lung tumor associated polypeptide comprising the steps of: (a) incubating a candidate binding compound with a polypeptide of the invention (the inventive lung tumor associated polypeptide); and (b) determining if binding has occurred.

Moreover, the invention includes a method of identifying activators/agonists or inhibitors/antagonists of a the inventive lung tumor associated polypeptide comprising the steps of: (a) incubating a candidate compound with a polypeptide of the invention; b) assaying a biological activity, and (c) determining if a biological activity of the polypeptide of the invention has been altered.

In a further embodiment, the present invention relates to method of identifying and obtaining a drug candidate for therapy of a disorder characterized by abnormal cell proliferation comprising the steps of
  (a) contacting a lung tumor associated polypeptide of the present invention or a cell expressing said polypeptide in the presence of components capable of providing a detectable signal in response to altered regulation of cell proliferation or to altered cell differentiation, with said drug candidate to be screened under conditions to allow protein degradation, and
  (b) detecting presence or absence of a signal or increase of the signal generated from protein degradation, wherein the presence or increase of the signal is indicative for a putative drug.

Experiments using animals or isolated cells or cell lines may be used to examine the proliferative behavior of cells or tissues in dependence on the inventive lung tumor associated polypeptide action. The same procedures may be employed for the study of cell differentiation.

The drug candidate may be a single compound or a plurality of compounds. The term "plurality of compounds" in a method of the invention is to be understood as a plurality of substances which may or may not be identical.

Said compound or plurality of compounds may be chemically synthesized or microbiologically produced and/or comprised in, for example, samples, e.g., cell extracts from, e.g., plants, animals or microorganisms. Furthermore, said compound(s) may be known in the art but hitherto not known to be capable of suppressing or activating the inventive lung tumor associated polypeptides. The reaction mixture may be a cell free extract or may comprise a cell or tissue culture. Suitable set ups for the method of the invention are known to the person skilled in the art and are, for example, generally described in Alberts et al., Molecular Biology of the Cell, third edition (1994) and in the appended examples. The plurality of compounds may be, e.g., added to the reaction mixture, culture medium, injected into a cell or otherwise applied to the transgenic animal. The cell or tissue that may be employed in the method of the invention preferably is a host cell, mammalian cell or non-human transgenic animal of the invention described in the embodiments hereinbefore.

If a sample containing a compound or a plurality of compounds is identified in the method of the invention, then it is either possible to isolate the compound from the original sample identified as containing the compound capable of suppressing or activating the inventive lung tumor associated polypeptide, or one can further subdivide the original sample, for example, if it consists of a plurality of different compounds, so as to reduce the number of different substances per sample and repeat the method with the subdivisions of the original sample. Depending on the complexity of the samples, the steps described above can be performed several times, preferably until the sample identified according to the method of the invention only comprises a limited number of or only one substance(s). Preferably said sample comprises substances of similar chemical and/or physical properties, and most preferably said substances are identical.

Several methods are known to the person skilled in the art for producing and screening large libraries to identify compounds having specific affinity for a target. These methods include the phage-display method in which randomized peptides are displayed from phage and screened by affinity chromatography to an immobilized receptor; see, e.g., WO 91/17271, WO 92/01047, U.S. Pat. No. 5,223,409. In another approach, combinatorial libraries of polymers immobilized on a chip are synthesized using photolithography; see, e.g., U.S. Pat. No. 5,143,854, WO 90/15070 and WO 92/10092. The immobilized polymers are contacted with a labelled receptor and scanned for label to identify polymers binding to the receptor. The synthesis and screening of peptide libraries on continuous cellulose membrane supports that can be used for identifying binding ligands of the polypeptide of the invention and thus possible inhibitors and activators is described, for example, in Kramer, Methods Mol. Biol. 87 (1998), 25-39. This method can also be used, for example, for determining the binding sites and the recognition motifs in the polypeptide of the invention. In like manner, the substrate specificity of the DnaK chaperon was determined and the contact sites between human interleukin-6 and its receptor; see Rudiger, EMBO J. 16 (1997), 1501-1507 and Weiergraber, FEBS Lett. 379 (1996), 122-126, respectively. Furthermore, the above-mentioned methods can be used for the construction of binding supertopes derived from the polypeptide of the invention. A similar approach was successfully described for peptide antigens of the anti-p24 (HIV-1) monoclonal antibody; see Kramer, Cell 91 (1997), 799-809. A general route to fingerprint analyses of peptide-antibody interactions using the clustered amino acid peptide library was described in Kramer, Mol. Immunol. 32 (1995), 459-465. In addition, antagonists of the inventive lung tumor associated polypeptide of the invention can be derived and identified from monoclonal antibodies that specifically react with the polypeptide of the invention in accordance with the methods as described in Doring, Mol. Immunol. 31 (1994), 1059-1067.

More recently, WO 98/25146 described further methods for screening libraries of complexes for compounds having a desired property, especially, the capacity to agonize, bind to, or antagonize a polypeptide or its cellular receptor. The complexes in such libraries comprise a compound under test, a tag recording at least one step in synthesis of the compound, and a tether susceptible to modification by a reporter molecule. Modification of the tether is used to signify that a complex contains a compound having a desired property. The tag can be decoded to reveal at least one step in the synthesis of such a compound. Other methods for identifying compounds which interact with the polypeptides according to the invention or nucleic acid molecules encoding such molecules are, for example, the in vitro screening with the phage display system as well as filter binding assays or "real time" measuring of interaction using, for example, the BIAcore apparatus (Pharmacia).

All these methods can be used in accordance with the present invention to identify activators/agonists and inhibitors/antagonists of the lung tumor associated polypeptide or related polypeptide of the invention.

Various sources for the basic structure of such an activator or inhibitor can be employed and comprise, for example, mimetic analogues of the polypeptide of the invention. Mimetic analogues of the polypeptide of the invention or biologically active fragments thereof can be generated by, for example, substituting the amino acids that are expected to be essential for the biological activity with, e.g., stereoisomers, i.e. D-amino acids; see e.g., Tsukida, J. Med. Chem. 40 (1997), 3534-3541. Furthermore, in case fragments are used for the design of biologically active analogs promimetic components can be incorporated into a peptide to reestablish at least some of the conformational properties that may have been lost upon removal of part of the original polypeptide; see, e.g., Nachman, Regul. Pept. 57 (1995), 359-370. Furthermore, the lung tumor associated polypeptide of the invention can be used to identify synthetic chemical peptide mimetics that bind to or can function as a ligand, substrate, binding partner or the receptor of the polypeptide of the invention as effectively as does the natural polypeptide; see, e.g., Engleman, J. Clin. Invest. 99 (1997), 2284-2292. For example, folding simulations and computer redesign of structural motifs of the polypeptide of the invention can be performed using appropriate computer programs (Olszewski, Proteins 25 (1996), 286-299; Hoffman, Comput. Appl. Biosci. 11 (1995), 675-679). Computer modelling of protein folding can be used for the conformational and energetic analysis of detailed peptide and protein models (Monge, J. Mol. Biol. 247 (1995), 995-1012; Renouf, Adv. Exp. Med. Biol. 376 (1995), 37-45). In particular, the appropriate programs can be used for the identification of interactive sites of the inventive lung tumor associated polypeptide and its possible receptor, its ligand or other interacting proteins by computer assistant searches for complementary peptide sequences (Fassina, Immunomethods 5 (1994), 114-120. Further appropriate computer systems for the design of protein and peptides are described in the prior art, for example in Berry, Biochem. Soc. Trans. 22 (1994), 1033-1036; Wodak, Ann. N.Y. Acad. Sci. 501 (1987), 1-13; Pabo, Biochemistry 25 (1986), 5987-5991. The results obtained from the above-described computer analysis can be used for, e.g., the preparation of peptide mimetics of the protein of the invention or fragments thereof. Such pseudopeptide analogues of the natural amino acid sequence of the protein may very efficiently mimic the parent protein (Benkirane, J. Biol. Chem. 271 (1996), 33218-33224). For example, incorporation of easily available achiral *-amino acid residues into a protein of the invention or a fragment thereof results in the substitution of amide bonds by polymethylene units of an aliphatic chain, thereby providing a convenient strategy for constructing a peptide mimetic (Banerjee, Biopolymers 39 (1996), 769-777). Superactive peptidomimetic analogues of small peptide hormones in other systems are described in the prior art (Zhang, Biochem. Biophys. Res. Commun. 224 (1996), 327-331). Appropriate peptide mimetics of the protein of the present invention can also be identified by the synthesis of peptide mimetic combinatorial libraries through successive amide alkylation and testing the resulting compounds, e.g., for their binding and immunological properties. Methods for the generation and use of peptidomimetic combinatorial libraries are described in the prior art, for example in Ostresh, Methods in Enzymology 267 (1996), 220-234 and Dorner, Bioorg. Med. Chem. 4 (1996), 709-715. Furthermore, a three-dimensional and/or crystallographic structure of the polypeptide of the invention can be used for the design of peptide mimetic inhibitors of the biological activity of the polypeptide of the invention (Rose, Biochemistry 35 (1996), 12933-12944; Rutenber, Bioorg. Med. Chem. 4 (1996), 1545-1558).

The structure-based design and synthesis of low-molecular-weight synthetic molecules that mimic the activity of the native biological polypeptide is further described in, e.g., Dowd, Nature Biotechnol. 16 (1998), 190-195; Kieber-Emmons, Current Opinion Biotechnol. 8 (1997), 435-441; Moore, Proc. West Pharmacol. Soc. 40 (1997), 115-119; Mathews, Proc. West Pharmacol. Soc. 40 (1997), 121-125; Mukhija, European J. Biochem. 254 (1998), 433-438.

It is also well known to the person skilled in the art, that it is possible to design, synthesize and evaluate mimetics of small organic compounds that, for example, can act as a substrate or ligand to the lung tumor associated polypeptide of the invention or the related polypeptide. For example, it has been described that D-glucose mimetics of hapalosin exhibited similar efficiency as hapalosin in antagonizing multidrug resistance assistance-associated protein in cytotoxicity; see Dinh, J. Med. Chem. 41 (1998), 981-987.

The nucleic acid molecule of the invention can also serve as a target for activators and inhibitors. Activators may comprise, for example, proteins that bind to the mRNA of a gene encoding a the inventive lung tumor associated polypeptide, thereby stabilizing the native conformation of the mRNA and facilitating transcription and/or translation, e.g., in like manner as Tat protein acts on HIV-RNA. Furthermore, methods are described in the literature for identifying nucleic acid molecules such as an RNA fragment that mimics the structure of a defined or undefined target RNA molecule to which a compound binds inside of a cell resulting in retardation of cell growth or cell death; see, e.g., WO 98/18947 and references cited therein. These nucleic acid molecules can be used for identifying unknown compounds of pharmaceutical and/or agricultural interest, and for identifying unknown RNA targets for use in treating a disease. These methods and compositions can be used in screening for novel antibiotics, bacteriostatics, or modifications thereof or for identifying compounds useful to alter expression levels of proteins encoded by a nucleic acid molecule. Alternatively, for example, the conformational structure of the RNA fragment which mimics the binding site can be employed in rational drug design to modify known antibiotics to make them bind more avidly to the target. One such methodology is nuclear magnetic resonance (NMR), which is useful to identify drug and RNA conformational structures. Still other methods are, for example, the drug design methods as described in WO 95/35367, U.S. Pat. No. 5,322,933, where the crystal structure of the RNA fragment can be deduced and computer programs are utilized to design novel binding compounds which can act as antibiotics.

Some genetic changes lead to altered protein conformational states. For example, some mutant the inventive lung tumor associated polypetides may possess a tertiary structure that renders them far less capable of protein degradation. Restoring the normal or regulated conformation of mutated proteins is the most elegant and specific means to correct these molecular defects, although it may be difficult. Pharmacological manipulations thus may aim at restoration of wild-type conformation of the inventive lung tumor associated polypeptide. Thus, the nucleic acid molecules and encoded polypeptides of the present invention may also be used to design and/or identify molecules which are capable of activating the wild-type function of a the inventive lung tumor associated polypeptide or related polypepetide.

The compounds which can be tested and identified according to a method of the invention may be expression libraries, e.g., cDNA expression libraries, peptides, proteins, nucleic acids, antibodies, small organic compounds, hormones, peptidomimetics, PNAs or the like (Milner, Nature Medicine 1 (1995), 879-880; Hupp, Cell 83 (1995), 237-245; Gibbs, Cell 79 (1994), 193-198 and references cited supra). Furthermore, genes encoding a putative regulator of the inventive lung tumor associated polypeptide and/or which exert their effects up- or downstream the inventive lung tumor associated polypeptide may be identified using, for example, insertion mutagenesis using, for example, gene targeting vectors known in the art. Said compounds can also be functional derivatives or analogues of known inhibitors or activators. Such useful compounds can be for example transacting factors which bind to the inventive lung tumor associated polypeptide or regulatory sequences of the gene encoding it. Identification of transacting factors can be carried out using standard methods in the art (see, e.g., Sambrook, supra, and Ausubel, supra). To determine whether a protein binds to the protein itself or regulatory sequences, standard native gel-shift analyses can be carried out. In order to identify a transacting factor which binds to the protein or regulatory sequence, the protein or regulatory sequence can be used as an affinity reagent in standard protein purification methods, or as a probe for screening an expression library. The identification of nucleic acid molecules which encode polypeptides which interact with the inventive lung tumor associated polypeptides described above can also be achieved, for example, as described in Scofield (Science 274 (1996), 2063-2065) by use of the so-called yeast "two-hybrid system". In this system the polypeptide encoded by a nucleic acid molecule according to the invention or a smaller part thereof is linked to the DNA-binding domain of the GAL4 transcription factor. A yeast strain expressing this fusion polypeptide and comprising a lacZ reporter gene driven by an appropriate promoter, which is recognized by the GAL4 transcription factor, is transformed with a library of cDNAs which will express plant proteins or peptides thereof fused to an activation domain. Thus, if a peptide encoded by one of the cDNAs is able to interact with the fusion peptide comprising a peptide of an inventive lung tumor associated polypeptide, the complex is able to direct expression of the reporter gene. In this way the nucleic acid molecules according to the invention and the encoded peptide can be used to identify peptides and proteins interacting with the inventive lung tumor associated protein. It is apparent to the person skilled in the art that this and similar systems may then further be exploited for the identification of inhibitors of the binding of the inventive lung tumor associated proteins.

Once the transacting factor is identified, modulation of its binding to or regulation of expression of the inventive lung tumor associated polypeptide can be pursued, beginning with, for example, screening for inhibitors against the binding of the transacting factor to the protein of the present invention. Activation or repression of the inventive lung tumor associated proteins could then be achieved in animals by applying the transacting factor (or its inhibitor) or the gene encoding it, e.g. in an expression vector. In addition, if the active form of the transacting factor is a dimer, dominant-negative mutants of the transacting factor could be made in order to inhibit its activity. Furthermore, upon identification of the transacting factor, further components in the pathway leading to activation (e.g. signal transduction) or repression of a gene involved in the control of the inventive lung tumor associated polypeptide then can be identified. Modulation of the activities of these components can then be pursued, in order to develop additional drugs and methods for modulating the metabolism of protein degradation in animals. Thus, the present invention also relates to the use of the two-hybrid system as defined above for the identification of the inventive lung tumor associated polypeptide or activators or inhibitors of the inventive lung tumor associated polypeptide.

The compounds isolated by the above methods also serve as lead compounds for the development of analogue compounds. The analogues should have a stabilized electronic configuration and molecular conformation that allows key functional groups to be presented to the inventive lung tumor associated polypeptide or its possible receptor in substantially the same way as the lead compound. In particular, the analogue compounds have spatial electronic properties which are comparable to the binding region, but can be smaller molecules than the lead compound, frequently having a molecular weight below about 2 kD and preferably below about 1 kD. Identification of analogue compounds can be performed through use of techniques such as self-consistent field (SCF) analysis, configuration interaction (CI) analysis, and normal mode dynamics analysis. Computer programs for implementing these techniques are available; e.g., Rein, Computer-Assisted Modeling of Receptor-Ligand Interactions (Alan Liss, New York, 1989). Methods for the preparation of chemical derivatives and analogues are well known to those skilled in the art and are described in, for example, Beilstein, Handbook of Organic Chemistry, Springer edition New York Inc., 175 Fifth Avenue, New York, N.Y. 10010 U.S.A. and Organic Synthesis, Wiley, New York, USA. Furthermore, said derivatives and analogues can be tested for their effects according to methods known in the art; see also supra. Furthermore, peptidomimetics and/or computer aided design of appropriate derivatives and analogues can be used, for example, according to the methods described above.

In a preferred embodiment of the above-described methods of the invention, said cell is a cell of or, obtained by a method of the invention or is comprised in the above-described transgenic non-human animal.

Once the described compound has been identified and obtained, it is preferably provided in a therapeutically acceptable form.

The present invention provides methods for detection and treatment of disorders characterized by abnormal cell proliferation, such as e.g. cancers. In one aspect the present invention provides a method for the detection of disorders characterized by abnormal cell proliferation, such as e.g. cancers based on the determination of the presence or absence and/or the level of expression of the inventive lung tumor associated gene in biological samples. In a second aspect the present invention provides a method for treatment of disorders characterized by abnormal cell proliferation, such as e.g. cancers using the inventive lung tumor associated gene products as therapeutically active agents. The invention also provides for therapeutic methods based on the modulation of the activity of the inventive lung tumor associated polypeptide. It is one aspect of the invention to provide a method for rational tumor management based on the detection of the inventive lung tumor associated gene products in patient samples and the tailoring of a therapy correlated to the detected overexpression of said gene products. Furthermore the present invention provides for a research or diagnostic test kit for performing the reactions involved in the detection of the presence or absence and/or the level of overexpression of the inventive lung tumor associated gene. Finally the present invention relates to pharmaceutical compositions applicable in the treatment of disorders according to the present invention.

The following examples are given for the purpose of illustration only and are not intended to limit the scope of the invention disclosed herein.

EXAMPLES

Example 1

Real-time RT-PCR Analysis of LUMA1 Expression in Tumor Samples Including Colon Carcinoma, Carcinoma of the Stomach, Small Cell Lung Cancer and Lung Adenocarcinoma.

An upregulation of LUMA1 transcripts has been detected in 60% of tested lung adenocarcinomas, whereas no upregulation was found in colon carcinoma, carcinoma of the stomach and small cell lung cancer.

1.1. Theoretical Basis

Quantitative values were obtained from the threshold cycle number at which the increase in the signal associated with an exponential growth of PCR products started to be detected (using PE Biosystems analysis software), according to the manufacturer's manuals.

6.25 ng cDNA of oligo dT primed total RNA was added to each real time PCR. We quantified transcripts of the beta-actin gene (ACTB Actin, Primer Actin1—CCTAAAAGCCACCCCACTTCTC (SEQ ID NO: 28), Primer Actin2—ATGCTATCACCTCCCCTGTGTG (SEQ ID NO: 29)) encoding human actin, beta (ACTB) as the endogenous RNA control.

Final results, expressed as N-fold differences in target gene expression relative to the reference gene ACTB, termed 'Ntarget', were determined as follows:

$$N_{target} = 2^{(delta\ Ct_{sample} - delta\ Ct_{reference\ gene})}$$

where delta Ct values of the sample and reference were determined by subtracting the average Ct value of the WT1 gene from the average Ct value of the ACTB gene.

Primers for WT1 and ACTB gene were chosen with the assistance of the computer programs PRIMER (Husar program package, DKFZ Heidelberg) and Primer Express (Perkin-Elmer Applied Biosystems, Foster City, Calif.). The following nucleotide sequences of primers for the amplification of the LUMA1 gene were used: LUMA1-A: CTCGTCAGGCGACCTTATATC (SEQ ID NO: 24) and LUMA1-B: TGTCAGTTGAACATTTTCTGCC (SEQ ID NO: 25); LUMA1-C: CTCGTCAGGCGATACTCCC (SEQ ID NO: 26) and LUMA1-D: CACCAGTCAGCTCTAAATGGG (SEQ ID NO: 27).

1.2. RNA Extraction

Total RNA was extracted from tissue specimens by using the QIAamp RNA Mini Protocol (Qiagen, Hilden, Germany).

1.3. cDNA Synthesis

1 µg total RNA was DNAse I digested for 15 min at 25° C. in a final volume of 20 µl containing 1 µl DNAse I Amp Grade (1 Unit/µl; Invitrogen) and 2 µl DNAse Reaction Buffer (10×; Invitrogen). The reaction was stopped by adding 2 µl EDTA (25 mM; Invitrogen) and incubation for 10 min at 65° C. The reverse transcription was performed 2 h at 37° C. in a final volume of 40 µl containing 4 µl 10x RT buffer, 4 µl 5 mM dNTP, 1 µl RNAsin 40 U/µl Promega), 4 µl Oligo dT Primer 0,5 µg/ml and 2 µl Omniscript 4 U/µl (Qiagen, Hilden, Germany). Reverse transcriptase was inactivated by heating at 93° C. for 5 min and cooling at 4° C. for 5 min.

1.4. PCR Amplification

All PCR reactions were performed using a ABI Prism 7700 Sequence Detection System (Perkin-Elmer Applied Biosystems). PCR was performed using the SYBR® Green PCR Mix (Perkin-Elmer Applied Biosystems). The thermal cycling conditions comprised an initial denaturation step at 95° C. for 10 min and 40 cycles at 95° C. for 15 s and 60° C. for 1 min. Experiments were performed with duplicates for each data point.

As shown in FIG. 16-20, an enhanced expression of LUMA1 transcripts in lung adenocarcinomas has been detected. For amplification of the LUMA1 transcripts the following primers were used: LUMA1-A: CTCGTCAGGCGACCTTATATC (SEQ ID NO: 24) and LUMA1-B: TGTCAGTTGAACATTTTCTGCC. (SEQ ID NO: 25). The PCR with primer LUMA1-A and LUMA1-B amplified the splice variant which harboured the complete exon 7, whereas the primers LUMA1-C (CTCGTCAGGCGATACTCCC) SEQ ID NO: 26) and LUMA1-D (CACCAGTCAGCTCTAAATGGG, SEQ ID NO: 27) amplified the splice variant, which represented only part of exon 7. Using these primer combinations, an upregulation of both splice variants was observed in real time PCR experiments. In FIG. 16 the real time amplification of tumor 1 and corresponding normal sample 1 is shown (primer LUMA1-A and LUMA1-B). A threshold cycle difference of three was observed whereas with the reference primers for the ACTB gene no difference was detected (not shown). This indicates a 8-fold overexpression of the LUMA1 transcript in lung adenocarcinoma of one individual. In another individual, no differences between normal and lung adenocarcinoma tissue was observed (FIG. 14). One further individual showed a 13-fold overexpression in the tumor tissue (FIG. 15). More individuals were characterized by the absence of LUMA1 transcript in normal tissue and an strong upregulation in the tumor tissue (more than 4000-fold) (FIG. 16; 17).

The PCR products of the two different analysed exon 7 variants shown in FIG. 23 were obtained by the Real time PCR described above and were analyzed by gel electrophoresis.

Example 2

Cloning of Differentially Spliced LUMA1 Transcripts

Using primers specific for the LUMA1, transcript PCR was performed with random primed human cDNA derived from lung adenocarcinoma, colon carcinoma and fetal brain.

```
Forward primers:
LUMA1-C:  CTCGTCAGGC-
          GATACTCCC;

LUMA1-E:  ATGGAAATCACCACTCT-  (SEQ ID NO: 30)
          GAGAG;

LUMA1-F:  TTGATCCAGAAAGTGT-   (SEQ ID NO: 31)
          GTGAGC

Reverse primers:
LUMA1-G:  TGCAGTTGGCCCAGCT-   (SEQ ID NO: 32)
          TAGAA;

LUMA1-H:  AGTCTTTAAAAAGCGT-   (SEQ ID NO: 33)
          TGCTGG
```

The following primer combinations were used to amplify:

```
LUMA1-C + LUMA1-H; LUMA1-E + LUMA1-G; LUMA1-E +
LUMA1-H; LUMA1-F + LUMA1-G; LUMA1-F + LUMA1-H
```

The following PCR conditions used were to amplify the differentially spliced LUMA1 transcripts:

95° C. 1 min, (95° C. 30 sec, 60° C. 1 min, 68° C. 3,5 min)-34 cycles

The TaqAdvantage polymerase (Clontech) was used.

1 µl dNTP (20 mM), 0.5 µl 50×TaqAdvantageII (Clontech), 2.5 µl 10×Buffer, 3 µl cDNA (100 ng), 1.5 µl (Primer forward, 10 µm), 1.5 µl (Primer reverse, 10 µm), 15 µl H$_2$O.

Figure 17:
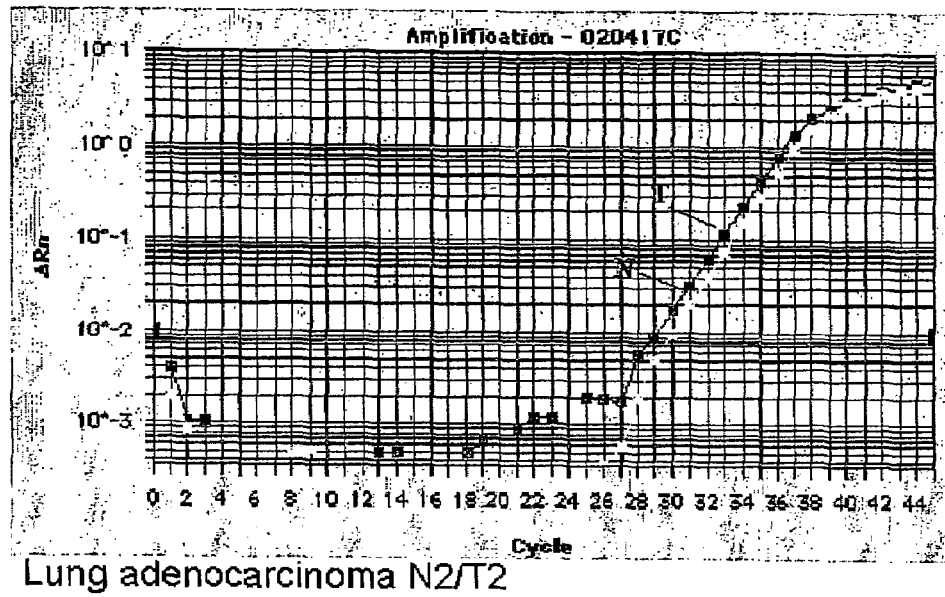
Figure 18:
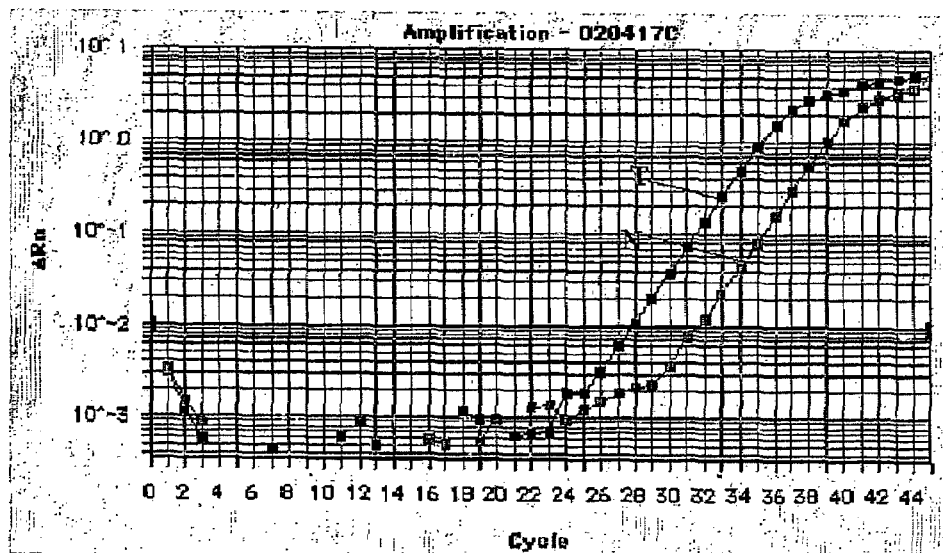
Figure 19:
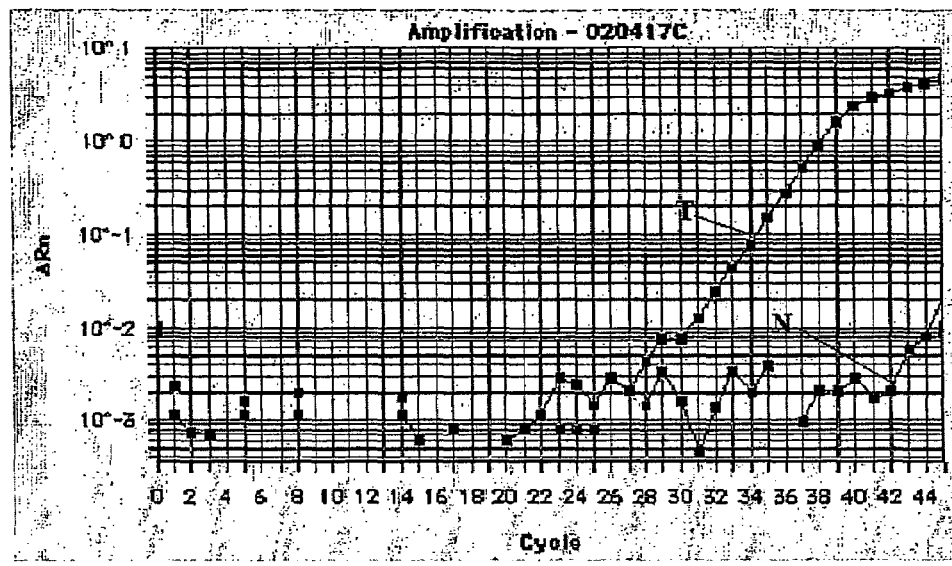
Figure 20:
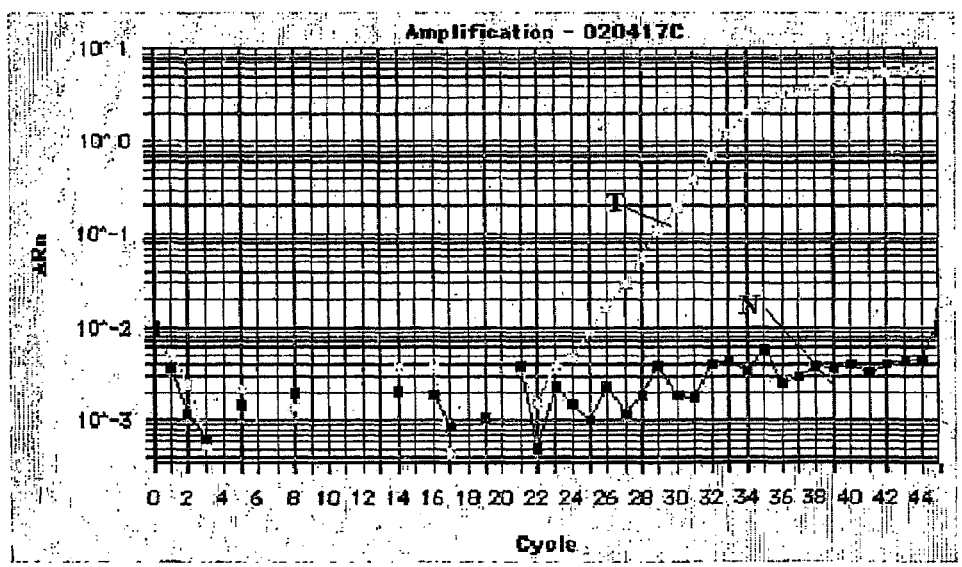
Figure 21:
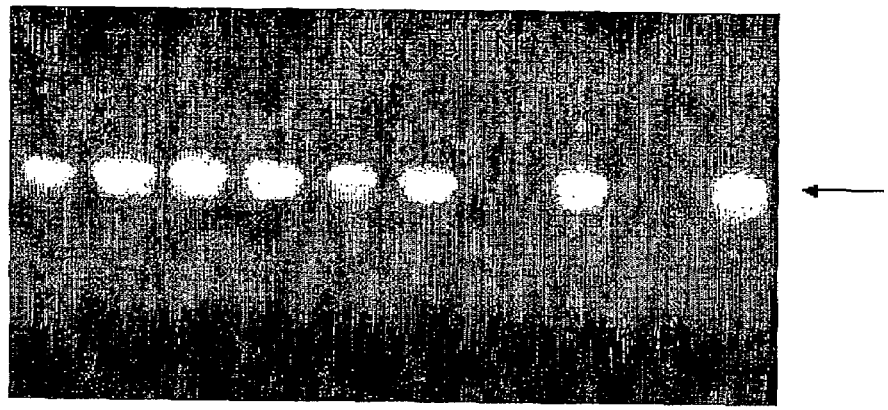
FIG. 21 shows gel electrophoresis of the endpoint PCR of the amplification of the LUMA1 transcript in lung adenocarcinomas and corresponding normal tissue. In tumor T1 and T3 enhanced expression of LUMA1 was seen, in tumor T4 and T5 a strong overexpression of LUMA1 compared to the corresponding normal sample. The PCR products analysed on the agarose gel, were derived from the real time PCR reactions shown in FIG. 16-20.
Figure 22:
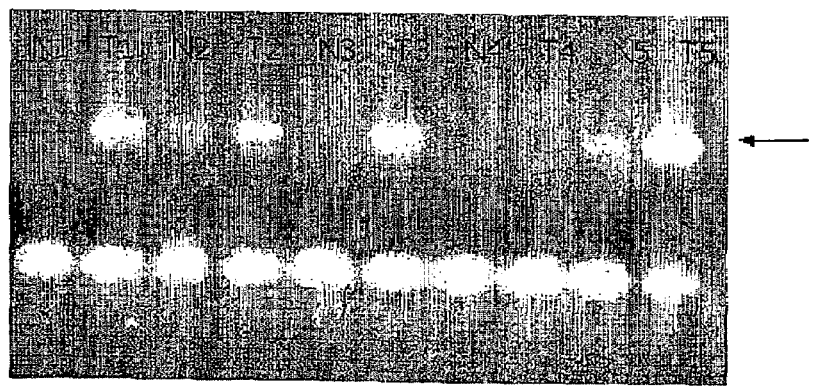
FIG. 22 shows gel electrophoresis of the endpoint PCR of the amplification of the LUMA1 transcript in lung adenocarcinomas and corresponding normal tissue. Whereas in normal sample N1, N3 and N4 no LUMA1 transcript was detectable, in lung adenocarcinoma T1 and T3 expression of LUMA1 transcript was detected. In T4 no amplification was visible. In T2 and T5 an enhanced expression was detected. For amplification of the LUMA1 gene the following primers were used.

The PCR products were directly sequenced or first cloned into the pCR2.1 vector (Invitrogen) and then sequenced. Sequence analysis and database searches were performed with the HUSAR program package (DKFZ Heidelberg). Sequence analysis of the cloned PCR products has demonstrated an extensive splicing of the LUMA1 transcript. One transcript has been identified which was characterized by the absence of exon 3. Another transcript missed exon 3 and 4. In addition, a transcript has been cloned where exon 3, 4 and 5 was spliced out. Splicing out the exons 3 or 4 or 5 or combinations thereof do not change the reading frame and lead to internal deletions in the encoded LUMA1 protein isoforms. In contrast to these splice variants, the differential splicing at exon 7 led to a frameshift. If the complete exon 7 was present in the transcript, the open reading frame almost extended to the 3' end of the transcript. If the first part of exon 7 was spliced out in the resulting transcript a frameshift was generated which lead to a shorter carboxy terminus of the encoded protein. Both exon 7 splice variants were shown to be upregulated in lung adenocarcinomas (FIG. 13-17; FIG. 18-19).

Example 3

Full Length Cloning of LUMA1

Full length cloning of LUMA1 (Rapid Amplification of cDNA Ends)

Full length cloning was performed using SMART™ RACE cDNA Amplification Kit (Clontech) to amplify the 5'end of LUMA1 cDNA.

PCR reaction was prepared as follows: 1 µl dNTP (10 mM), 1 µl 50×TaqAdvantageII (Clontech), 5 µl 10×Buffer, 2,5 µl cDNA, placenta (Clontech)(1 µg/µl), 5 µl Universal Primer Mix (Clontech)(10×), 1 µl Gene specific Primer, reverse (Clontech), 34,5 µl H$_2$O.

```
Universal Primer Mix:
                                        SEQ ID NO: 34
CTAATACGACTCACTATAGGGCAAGCAGTGGTATCAACGCAGAGT,
(0.4 µm), SEQ ID NO: 35
CTAATACGACTCACTATAGGGC,
(0.2 µm)

LUMA1 Gene specific Primer, reverse:
                                        (SEQ ID NO: 36)
GGAGATGGAGCTGTTTGACCTGA
```

Because PCR reaction failed to give a distinct band, nested PCR was performed.

5 µl of primary PCR product were diluted into 245 µl Tricine-EDTA buffer (Clontech) (10 mM Tricine-KOH (pH 8,5), 1 mM EDTA)

PCR reaction was prepared as follows: 1 µl dNTP (10 mM), 1 µl 50×TaqAdvantageII (Clontech), 5 µl 10×Buffer, 5 µl diluted primary PCR product, 1 µl Nested Universal Primer (Clontech)(10×), 1 µl nested Gene specific Primer, reverse (Clontech)(10 µm), 36 µl H$_2$O.

Nested Universal Primer: AAGCAGTGGTATCAACGCAGAGT, SEQ ID NO: 37

LUMA1 nested Gene Specific Primer, Reverse: TGTCAGTTGAACATTTTCTGCC, SEQ ID NO: 38

The following PCR conditions used were to generate full length transcripts:

(94° C. 30 sec 72° C. 3 min)-5 cycles (94° C. 30 sec, 70° C. 30 sec, 72° C. 3 min)-5 cycles (94° C. 30 sec, 68° C. 30 sec, 72° C. 3 min)-27 cycles RACE product was detected in agarose gel electrophoresis. Bands were gel-purified using the High Pure PCR Product Purification Kit (Roche). DNA band was cut from agarose gel (1%) using an ethanol-cleaned scalpel. Agarose gel slice was placed in a tube and transferred for 2 min into liquid nitrogen. The gel slide was placed into a sterile filter microcentrifuge tube and centrifuged for 10 min at 1300 rpm. 500 µl Binding buffer was added to every 100 µl flowthrough and placed in a new sterile filter microcentrifuge tube and centrifuged for 1 min at 1300 rpm Sample was washed two times with 500 µl Washing Buffer and centrifuged for 1 min at 1300 rpm. Flowthrough was discarded. 50 µl Elution Buffer was added to the upper reservoir of the filter tube and centrifuged for 1 min at 1300 rpm. The microcentrifuge tube contained the purified DNA.

Purified DNA was cloned into the pCR-XL-TOPO vector (Invitrogen) and then sequenced. Sequence analysis and database searches were performed with the HUSAR program package (DKFZ Heidelberg). Sequence analysis of the cloned PCR products identified 12 new exons (A, B, C, D, E, F, G, H, I, J, K, L) and new part of exon1 (exon M) and a 5' extension of exon 8 (exon T).

Additional LUMA1 exons were identified with the RACE experiments. The location of LUMA1 exons are indicated in respect to the genomic clone AL359711 (VERSION AL359711.18 GI:13234940/Human DNA sequence from clone RP11-425D10 on chromosome 6, complete sequence) (Acc. No. al359711).

|  |  | bp |
|---|---|---|
| Exon A |  | 16742-16898 |
| Exon B |  | 17967-18132 |
| Exon C |  | 22671-22809 |
| exon is differentially spliced |  |  |
| Exon D |  | 28399-28552 |
| Exon E |  | 30422-32094 |
| Exon F |  | 36503-36732 |
| Exon G |  | 37720-37858 |
| Exon H |  | 39288-39408 |
| Exon I |  | 46143-46290 |
| differentially spliced, present in fetal lung |  |  |
| Exon J |  | 51443-51552 |
| Exon K |  | 58808-58957 |
| Exon L |  | 59836-59889 |
| Exon M | Exon 1 | 60888-61055 |
| Exon N | Exon 2 | 63342-63494 |
| Exon O | Exon 3 | 63739 (63742)-63873 |

-continued

| | | bp |
|---|---|---|
| alternative start of exon at bp 63742, exon is differentially spliced | | |
| Exon P | Exon 4 | 64839-64991 |
| exon is differentially spliced | | |
| Exon Q | Exon 5 | 66427-66636 |
| exon is differentially spliced | | |
| Exon R | Exon 6 | 70867-70987 |
| Exon S | Exon 7 | 75227 (75279)-75354 |
| alternative start of exon at bp 75279, both exon variants are differentially spliced, alternative start of exon leads to a frameshift, complete exon can be spliced out | | |
| Exon T | Exon 8 | 76537 (77287)-77410 |
| alternative start of exon at bp 77287, alternative start of exon leads to a frameshift art of exon leads to a frameshift | | |

Example 4

Generation of Antibodies

LUMA1 peptides were used to produce monoclonal as well as polyclonal antibodies directed against these polypeptides. For LUMA exon 2 the following peptide has been used for immunization (C E L I G E V R T E G I D N M K D L K. to SEQ ID NO: 39) to generate polyclonal antibodies. For the generation of monoclonal antibodies, peptide sequences encoded by the LUMA exon 7b (long variant) have been used (R F L K T N L K G S K I T R C, SEQ ID NO: 40).

A. Production of the Polyclonal Antibodies:

The polyclonal antibodies were purified by affinity chromatography and afterwards used for the detection of the respective polypeptides in patient samples. The procedures were performed as follows:

NZW (New Zealand White) Rabbits were immunized with 100 μg LUMA1 peptides coupled to KLH (ground immunization) in Complete Freunds Adjuvants and boosted 4 times with the same amount of protein in incomplete Freunds Adjuvans at intervals of 2 weeks.

Blood was taken one week after the $2^{nd}$ boost and subjected to ELISA on the immobilized Antigen. One week after the final boost animals were subjected exsanguination. After coagulation the final blood was centrifuged at 4000×g for 10 minutes. The supernatant from this step was centrifuged again at 16600×g for 15 min. The supernatant represented the raw LUMA1 antiserum.

The antiserum was purified in 2 steps. Step 1 represented a conventional Protein A Chromatography. In step 2, the Ig fraction of step 1 was purified by Affinity chromatography on the Antigen immobilized onto SEPHAROSE® (high molecular weight substance for separation by gel filtration of macromolecules). The eluate of step 2 represented the purified LUMA1 antiserum.

The purified antiserum was tested in several dilutions 1/1000-1/1000 000 on the immobilized antigen by peptide ELISA. The specific antibodies were detected by anti Rabbit secondary reagents coupled to horseradish peroxidase (HRP) with a subsequent colorimetric reaction (e.g. TMB).

In a second approach, the purified Antiserum was evaluated by Western Blot with immobilized Antigen subsequently to SDS-PAGE and transfer onto Nitrocellulose.

In a last evaluation step, the antiserum was tested on tissue arrays by Immuno-histochemistry (IHC). In Western Blot Analysis as well as with IHC bound antibodies were visualized with anti Rabbit secondary Reagents conjugated to HRP catalysing a colorimetric reaction.

B. Monoclonal Antibodies

Monoclonal antibodies directed against the peptide sequence (R F L K T N L K G S K I T R C, SEQ ID NO: 40) encoded by the LUMA exon 7b (long variant) were generated as described in Harlow and Lane. Antibodies: A Laboratory Manual, $1^{st}$ Edition, 1988.

Example 5

Immunohistochemical Detection of Expression of LUMA1

Sections of formalin fixed, paraffin embedded tissue samples of the lung were immunocytochemically stained using antibodies specific for LUMA1.

The sections were rehydrated through incubation in xylene and graded ethanol, and transferred to Aqua bidest. Antigen Retrieval was carried out with 10 mM citrate buffer (pH 6.0) Thereafter the slides were heated in a waterbath for 40 min at 95° C. The slides were cooled down to RT for 20 minutes, transferred to washing buffer (PBS/0.1% TWEEN® 20 (polyoxyethylene sorbitan monolauate).

For inactivation of endogenous peroxidase the samples were incubated with 3% H2O2 for 20 min at RT and afterwards washed in PBS/0.1% TWEEN® 20 for 5 to 10 min.

The slides were then incubated with the primary antibodies specific for exon 2 (FIG. 24) and exon 7 (FIG. 25, 26) respectively (2 μg/ml) (for 1 hour at RT, the slides were then rinsed with washing buffer and placed in a fresh buffer bath for 5 min.

Afterwards, the slides were incubated with the secondary antibody (goat anti rabbit (1:500) or goat anti mouse (1:500) for 1 hour at RT. Washing was performed 3 times for 5 minutes. Slides were covered with 200 μl substrate-chromogen solution (DAB) for 10 min. Then slides were washed as before and counterstained for 2 min in a bath of haematoxylin. Residual haematoxylin was rinsed with distilled water, and specimens were mounted and coverslipped with an aqueous mounting medium.

The microscopic examination of the slides revealed that tumor cells showed a specific immunoreactivity with the monoclonal LUMA1 antibody directed against exon 7 encoded sequences. In the tumor cells, a specific staining was visible in the cytoplasm.

Immunochemical analysis of peripheral venous blood, of bone marrow and of lymphocytes by the described methods revealed no immunoreactivity for LUMA1 in samples obtained from normal control individuals. This indicates that disseminated tumour cells that are immunoreactive with LUMA1 can be identified in these samples by specific immunochemical staining with antibodies directed against LUMA1.

Summary of immunohistochemical analysis of lung tumor tissues and corresponding normal tissues employing a monoclonal antibody directed against LUMA1 exon 7.

| Multi tissue array position | case-number | T/N | diagnosis | positivity in epithelium | positivity in connective tissue |
|---|---|---|---|---|---|
| 1 + 2 | 00-13369 | T | alveolarcellcarcinoma | tumorcells 2+ cytoplasmatic | negative |
| 3 + 4 | 00-13369 | N | normal lung | negative | negative |
| 5 + 6 | 00-30716 | T | NSCLC partially squamous | tumor cells 2+ cytoplasmatic | negative |
| 7 + 8 | 00-30716 | N | normal lung | negative | single alveolar macrophages |
| 9 + 10 | 00-24442 | T | NSCLC, NOS | negative | granulocytes, plasmacells 3+ |
| 11 + 12 | 00-24442 | N | normal lung | negative | negative |
| 13 + 14 | 00-25861 | T | NSCLC, partially squamous | tumorcells 1-2+ cytoplasmatic | granulocytes |
| 15 + 16 | 00-25861 | N | normal lung | negative | negative |
| 17 + 18 | 00-22890 | T | transitionalcellcarcinoma | tumorcells 1+ cytoplasmatic | plasmacells 3+ |
| 19 + 20 | 00-22890 | N | purulent pneumonia, alv.-macroph. | bronchus epithelium cytoplasmic | granulocytes |
| 21 + 22 | 00-6335 | T | NSCLC, NOS | negative | granulocytes plasmacells 3+ |
| 23 + 24 | 00-6335 | N | normal lung | missing | missing |
| 25 + 26 | 01-3009 | T | squamous cell carcinoma, G3 | tumorcells 1+ cytoplasmatic | granulocytes, plasmacells 3+ |
| 27 + 28 | 01-3009 | N | normal lung | single pneumocytes | negative |
| 29 + 30 | 01-1437 | T | Adenocarcinoma, G3 | tumorcells 1+ cytoplasmatic | plasmacells 1+ |
| 31 + 32 | 01-1437 | N | normal lung | negative | negative |
| 33 + 34 | 01-20774 | T | dysplasia in bronchial mucosa | n.a. | fibroblasts 1+ |
| 35 + 36 | 01-20774 | N | normal lung | negative | negative |
| 37 + 38 | 01-19729 | T | adenocarcinoma, G2 | negative | negative |
| 39 + 40 | 01-19729 | N | emphysema, blood vessels | negative | negative |
| 41 + 42 | 01-9819 | T | carcinoid | tumorcells 1-2+ cytoplasmatic | plasmacells 2+ |
| 43 + 44 | 01-9819 | N | normal lung | negative | single granulocytes |
| 45 + 46 | 00-13368 | T | Clear cell carcinoma | tumorcells 0-1+ cytoplasmatic | granulocytes 2+ |
| 47 + 48 | 00-13186 | N | lymphat. tissue, blood vessels | n.a. | negative |
| 49 + 50 | 00-13186 | T | adenocarcinoma | negative | negative |
| 51 + 52 | 00-5335 | N | normal lung | negative | negative |
| 53 + 54 | 00-5879 | N | normal lung | negative | negative |
| 55 + 56 | 00-11844 | T | Squamous cell carcinoma, G3 | negative | granulocytes |
| 57 + 58 | 01-545 | N | duodenal mucosa | single epithelium cells | negative |
| 59 + 60 | 01-6112 | N | adipocytes, connective tissue, stomach | n.a. | negative |

T = tumor — malign tumor
N = normal — positive in normal lung

14 lung tumors have been analysed for the expression of the LUMA exon 7 proteinisoform. 8 tumors showed a positive staining. The corresponding normal tissues did not show a staining. In the connective tissue of some lung tumors, a staining of inflammatory cells was detected. The results show that the staining with reagents specific for LUMA1 exon 7 sequences allowed to identify tumor cells in biological samples. The results obtained at the protein level did correlate with the results from the Real time PCR. In both experiments, the LUMA1 exon 7 sequences (RNA sequences and protein sequences) were found to be specifically upregulated in tumor cells. In contrast to the exon 7 sequences, the exon 2 of LUMA did not show an upregulation neither at the RNA nor the protein level in tumor cells. This clearly indicates that only specific LUMA1 splice variants and encoded proteinvariants are tumorspecific.

We claim:

1. An isolated nucleic acid comprising: (a) SEQ ID NO: 1, 3, or 5, or (b) a nucleic acid molecule having a sequence different from the sequence of the cDNA or mRNA of SEQ ID NO: 1, 3, or 5 due to the degeneracy of the genetic code of the cDNA or mRNA, wherein said nucleic acid molecule encodes the amino acid sequence of SEQ ID NO: 2, 4, or 6, respectively.

2. An isolated recombinant vector comprising the nucleic acid molecule of claim 1.

3. The isolated recombinant vector of claim 2 wherein the nucleic acid molecule is operatively linked to regulatory elements allowing transcription and synthesis of a translatable RNA in prokaryotic and/or eukaryotic host cells.

4. An isolated recombinant host cell which contains the recombinant vector of claim 2.

5. The recombinant host cell of claim 4, which is a mammalian cell, a bacterial cell, an insect cell or a yeast cell.

6. An isolated chimeric nucleic acid comprising the isolated nucleic acid according to claim 1.

7. An isolated DNA or RNA that is the full complement of the isolated nucleic acid of claim 1.

8. The isolated nucleic acid according to claim 1, which is detectably labeled.

9. The isolated nucleic acid according to claim 8, wherein the label is selected from the group consisting of a radioisotope, a bioluminescent compound, a chemiluminescent compound, a fluorescent compound, a metal chelate, biotin, digoxygenin and an enzyme.

10. The isolated nucleic acid according to claim 1, which comprises SEQ ID NO: 1.

11. The isolated nucleic acid according to claim 1, which comprises SEQ ID NO: 3.

12. The isolated nucleic acid according to claim 1, which comprises SEQ ID NO: 5.

* * * * *